(12) United States Patent
Ibrahim et al.

(10) Patent No.: US 10,828,092 B2
(45) Date of Patent: Nov. 10, 2020

(54) CARDIAC ABLATION SYSTEMS AND METHODS

(71) Applicant: AtriCure, Inc., Mason, OH (US)

(72) Inventors: Tamer Ibrahim, Danville, CA (US); Michael J. Banchieri, Discovery Bay, CA (US); Dwight P. Morejohn, Davis, CA (US)

(73) Assignee: AtriCure, Inc., Mason, OH (US)

( * ) Notice: Subject to any disclaimer, the term of this patent is extended or adjusted under 35 U.S.C. 154(b) by 333 days.

(21) Appl. No.: 15/669,639

(22) Filed: Aug. 4, 2017

(65) Prior Publication Data

US 2017/0325885 A1    Nov. 16, 2017

Related U.S. Application Data

(63) Continuation of application No. 14/143,420, filed on Dec. 30, 2013, now abandoned, which is a continuation of application No. 12/124,743, filed on May 21, 2008, now Pat. No. 8,628,522.

(60) Provisional application No. 60/939,201, filed on May 21, 2007.

(51) Int. Cl.
*A61B 18/12* (2006.01)
*A61B 18/14* (2006.01)
*A61B 18/00* (2006.01)

(52) U.S. Cl.
CPC ............ *A61B 18/1492* (2013.01); *A61B 2018/00273* (2013.01); *A61B 2018/00291* (2013.01); *A61B 2018/00363* (2013.01); *A61B 2018/00375* (2013.01); *A61B 2018/00577* (2013.01); *A61B 2018/1407* (2013.01)

(58) Field of Classification Search
CPC ...... A61B 18/1492; A61B 2018/00273; A61B 2018/00291; A61B 2018/00363; A61B 2018/00375; A61B 2018/00577; A61B 2018/1407
See application file for complete search history.

(56) References Cited

U.S. PATENT DOCUMENTS

| | | | |
|---|---|---|---|
| 5,440,632 A | 8/1995 | Bacon et al. | |
| 5,666,293 A | 9/1997 | Metz et al. | |
| 5,845,077 A | 12/1998 | Fawcett | |
| 6,023,464 A | 2/2000 | Woundy | |
| 6,308,289 B1 | 10/2001 | Ahrens et al. | |
| 6,351,773 B1 | 2/2002 | Fijolek et al. | |
| 6,393,585 B1 | 5/2002 | Houha et al. | |
| 6,464,700 B1 * | 10/2002 | Koblish | A61B 18/1482 600/374 |
| 6,478,029 B1 | 11/2002 | Boyd et al. | |
| 6,501,750 B1 | 12/2002 | Shaffer et al. | |
| 6,529,910 B1 | 3/2003 | Fleskes | |
| 6,553,568 B1 | 4/2003 | Fijolek et al. | |

(Continued)

FOREIGN PATENT DOCUMENTS

WO    WO 2005/079000    8/2005

*Primary Examiner* — Daniel W Fowler
(74) *Attorney, Agent, or Firm* — Levine Bagade Han LLP

(57) ABSTRACT

Cardiac ablation systems and methods of their use and manufacture involve an ablation mechanism, a stabilizer mechanism, and a cinching mechanism that urges the ablation mechanism toward a patient tissue. Embodiments encompass methods for administering epicardial and endocardial lesions, including box lesions and connecting lesions, to patient tissue.

9 Claims, 88 Drawing Sheets

(56) References Cited

U.S. PATENT DOCUMENTS

| | | |
|---|---|---|
| 6,560,203 B1 | 5/2003 | Beser et al. |
| 6,570,855 B1 | 5/2003 | Kung et al. |
| 6,574,796 B1 | 6/2003 | Roeck et al. |
| 6,577,642 B1 | 6/2003 | Fijolek et al. |
| 6,613,046 B1 | 9/2003 | Jenkins et al. |
| 6,636,485 B1 | 10/2003 | Fijolek et al. |
| 6,654,387 B1 | 11/2003 | Beser et al. |
| 6,658,000 B1 | 12/2003 | Raciborski et al. |
| 6,690,655 B1 | 2/2004 | Miner et al. |
| 6,693,878 B1 | 2/2004 | Daruwalla et al. |
| 6,715,075 B1 | 3/2004 | Loukianov |
| 6,751,299 B1 | 6/2004 | Brown et al. |
| 6,768,722 B1 | 7/2004 | Katseff et al. |
| 6,768,743 B1 | 7/2004 | Borella et al. |
| 6,822,955 B1 | 11/2004 | Brothers et al. |
| 6,831,921 B2 | 12/2004 | Higgins |
| 6,836,806 B1 | 12/2004 | Raciborski et al. |
| 6,857,009 B1 | 2/2005 | Ferreria et al. |
| 6,865,613 B1 | 3/2005 | Millet et al. |
| 6,904,460 B1 | 6/2005 | Raciborski et al. |
| 6,917,675 B2 | 7/2005 | Lazarus et al. |
| 6,952,428 B1 | 10/2005 | Necka et al. |
| 7,007,080 B2 | 2/2006 | Wilson |
| 7,035,270 B2 | 4/2006 | Moore, Jr. et al. |
| 7,039,432 B2 | 5/2006 | Strater et al. |
| 7,058,055 B2 | 6/2006 | Mugica et al. |
| 7,065,047 B2 | 6/2006 | Boxall et al. |
| 7,085,814 B1 | 8/2006 | Gandhi et al. |
| 7,120,139 B1 | 10/2006 | Kung et al. |
| 7,127,049 B2 | 10/2006 | Godse et al. |
| 7,158,543 B1 | 1/2007 | Garakani et al. |
| 7,213,062 B1 | 5/2007 | Raciborski et al. |
| 7,272,846 B2 | 9/2007 | Williams et al. |
| 7,285,090 B2 | 10/2007 | Stivoric et al. |
| 7,293,078 B2 | 11/2007 | Danforth |
| 7,293,282 B2 | 11/2007 | Danforth et al. |
| 7,308,700 B1 | 12/2007 | Fung et al. |
| 7,334,258 B1 | 2/2008 | Ford et al. |
| 7,337,217 B2 | 2/2008 | Wang |
| 7,353,021 B2 | 4/2008 | Ejzak et al. |
| 7,356,841 B2 | 4/2008 | Wilson et al. |
| 7,372,809 B2 | 5/2008 | Chen et al. |
| 7,373,660 B1 | 5/2008 | Guichard et al. |
| 7,415,603 B2 | 8/2008 | Woundy et al. |
| 7,443,883 B2 | 10/2008 | Seiden |
| 7,467,214 B2 | 12/2008 | Chin |
| 7,484,234 B1 | 1/2009 | Heaton et al. |
| 7,496,485 B2 | 2/2009 | Elfadel et al. |
| 7,496,652 B2 | 2/2009 | Pezzutti |
| 7,502,841 B2 | 3/2009 | Small et al. |
| 7,512,969 B2 | 3/2009 | Gould et al. |
| 7,526,538 B2 | 4/2009 | Wilson |
| 7,539,193 B2 | 5/2009 | Pfeffer et al. |
| 7,568,220 B2 | 7/2009 | Burshan |
| 7,600,003 B1 | 10/2009 | Okmianski et al. |
| 7,609,619 B2 | 10/2009 | Naseh et al. |
| 7,617,517 B2 | 11/2009 | Kay |
| 7,647,617 B2 | 1/2010 | Bartfeld et al. |
| 7,693,171 B2 | 4/2010 | Gould |
| 7,710,865 B2 | 5/2010 | Naseh et al. |
| 7,747,772 B2 | 6/2010 | Raciborski et al. |
| 7,769,886 B2 | 8/2010 | Naseh et al. |
| 7,836,092 B2 | 11/2010 | Alaniz et al. |
| 7,839,870 B2 | 11/2010 | Siripunkaw et al. |
| 7,848,234 B2 | 12/2010 | McKinnon, III et al. |
| 7,881,225 B2 | 2/2011 | Siripunkaw et al. |
| 8,041,824 B1 | 10/2011 | Maeng |
| 8,042,132 B2 | 10/2011 | Carney et al. |
| 8,050,194 B2 | 11/2011 | Siripunkaw et al. |
| 8,108,911 B2 | 1/2012 | Datla et al. |
| 8,493,987 B2 | 7/2013 | Siripunkaw et al. |
| 8,914,522 B2 | 12/2014 | Rao et al. |
| 2001/0038690 A1 | 11/2001 | Palmer et al. |
| 2001/0049732 A1 | 12/2001 | Raciborski et al. |
| 2001/0051980 A1 | 12/2001 | Raciborski et al. |
| 2001/0053159 A1 | 12/2001 | Bunn et al. |
| 2002/0010865 A1 | 1/2002 | Fulton et al. |
| 2002/0013948 A1 | 1/2002 | Aguayo et al. |
| 2002/0042819 A1 | 4/2002 | Reichert et al. |
| 2002/0061012 A1 | 5/2002 | Thi et al. |
| 2002/0066033 A1 | 5/2002 | Dobbins et al. |
| 2002/0103931 A1 | 8/2002 | Mott |
| 2002/0106017 A1 | 8/2002 | Dombkowski et al. |
| 2002/0116721 A1 | 8/2002 | Dobes et al. |
| 2002/0143326 A1* | 10/2002 | Foley ............... A61B 18/1492 606/41 |
| 2002/0147819 A1 | 10/2002 | Miyakoshi et al. |
| 2002/0152384 A1 | 10/2002 | Shelest et al. |
| 2002/0165535 A1* | 11/2002 | Lesh ............... A61B 17/2202 606/41 |
| 2003/0014764 A1 | 1/2003 | Saladino et al. |
| 2003/0069965 A1 | 4/2003 | Ma et al. |
| 2003/0106067 A1 | 6/2003 | Hoskins et al. |
| 2003/0200548 A1 | 10/2003 | Baran et al. |
| 2004/0024912 A1 | 2/2004 | Fukao et al. |
| 2004/0037316 A1 | 2/2004 | Choi et al. |
| 2004/0048609 A1 | 3/2004 | Kosaka |
| 2004/0095923 A1 | 5/2004 | Ejzak et al. |
| 2004/0103308 A1 | 5/2004 | Paller |
| 2004/0147912 A1 | 7/2004 | Sinofsky |
| 2004/0153665 A1 | 8/2004 | Browne |
| 2004/0177133 A1 | 9/2004 | Harrison et al. |
| 2004/0179539 A1 | 9/2004 | Takeda et al. |
| 2004/0190699 A1 | 9/2004 | Doherty et al. |
| 2004/0213278 A1 | 10/2004 | Pullen et al. |
| 2004/0226051 A1 | 11/2004 | Carney et al. |
| 2005/0005154 A1 | 1/2005 | Danforth et al. |
| 2005/0034115 A1 | 2/2005 | Carter et al. |
| 2005/0047442 A1 | 3/2005 | Volpe et al. |
| 2005/0055595 A1 | 3/2005 | Frazer et al. |
| 2005/0055708 A1 | 3/2005 | Gould et al. |
| 2005/0060749 A1 | 3/2005 | Hong et al. |
| 2005/0078668 A1 | 4/2005 | Wittenberg et al. |
| 2005/0078688 A1 | 4/2005 | Sharma et al. |
| 2005/0122976 A1 | 6/2005 | Poli et al. |
| 2005/0123001 A1 | 6/2005 | Craven et al. |
| 2005/0204168 A1 | 9/2005 | Johnston et al. |
| 2005/0232304 A1 | 10/2005 | Quigley |
| 2005/0233742 A1 | 10/2005 | Karaoguz et al. |
| 2005/0246757 A1 | 11/2005 | Relan et al. |
| 2006/0009759 A1 | 1/2006 | Chrisitian et al. |
| 2006/0031436 A1 | 2/2006 | Sakata et al. |
| 2006/0031921 A1 | 2/2006 | Danforth et al. |
| 2006/0059092 A1 | 3/2006 | Burshan et al. |
| 2006/0104232 A1 | 5/2006 | Gidwani |
| 2006/0123118 A1 | 6/2006 | Choe et al. |
| 2006/0159100 A1 | 7/2006 | Droms et al. |
| 2006/0173977 A1 | 8/2006 | Ho et al. |
| 2006/0184640 A1 | 8/2006 | Hatch |
| 2006/0191005 A1 | 8/2006 | Muhamed et al. |
| 2006/0206586 A1 | 9/2006 | Ling et al. |
| 2006/0223497 A1 | 10/2006 | Gallagher et al. |
| 2006/0235372 A1 | 10/2006 | Ward |
| 2006/0256799 A1 | 11/2006 | Eng |
| 2006/0271772 A1 | 11/2006 | Woundy et al. |
| 2006/0271946 A1 | 11/2006 | Woundy et al. |
| 2006/0285544 A1 | 12/2006 | Taylor et al. |
| 2007/0011725 A1 | 1/2007 | Sahay et al. |
| 2007/0016762 A1 | 1/2007 | Ho |
| 2007/0130471 A1 | 6/2007 | Walker et al. |
| 2007/0133409 A1 | 6/2007 | McKinnon et al. |
| 2007/0174471 A1 | 7/2007 | Van Rossum |
| 2007/0177526 A1 | 8/2007 | Siripunkaw et al. |
| 2007/0180484 A1 | 8/2007 | Siripunkaw et al. |
| 2007/0183405 A1 | 8/2007 | Bennett |
| 2007/0214265 A1 | 9/2007 | Zampiello et al. |
| 2007/0299496 A1 | 12/2007 | Podmore et al. |
| 2008/0034071 A1 | 2/2008 | Wilkinson et al. |
| 2008/0060064 A1 | 3/2008 | Wynn et al. |
| 2008/0189778 A1 | 8/2008 | Rowley |
| 2008/0209537 A1 | 8/2008 | Wong et al. |
| 2008/0285544 A1 | 11/2008 | Qiu et al. |
| 2009/0005066 A1 | 1/2009 | Florkey et al. |
| 2009/0063833 A1 | 3/2009 | Ho |

(56) References Cited

U.S. PATENT DOCUMENTS

| | | |
|---|---|---|
| 2009/0125958 A1 | 5/2009 | Siripunkaw et al. |
| 2009/0238349 A1 | 9/2009 | Pezzutti |
| 2010/0064356 A1 | 3/2010 | Johnston et al. |
| 2010/0083362 A1 | 4/2010 | Francisco |
| 2011/0026536 A1 | 2/2011 | Siripunkaw et al. |
| 2013/0091534 A1 | 4/2013 | Gilde et al. |
| 2014/0143420 A1 | 5/2014 | Datla et al. |

* cited by examiner

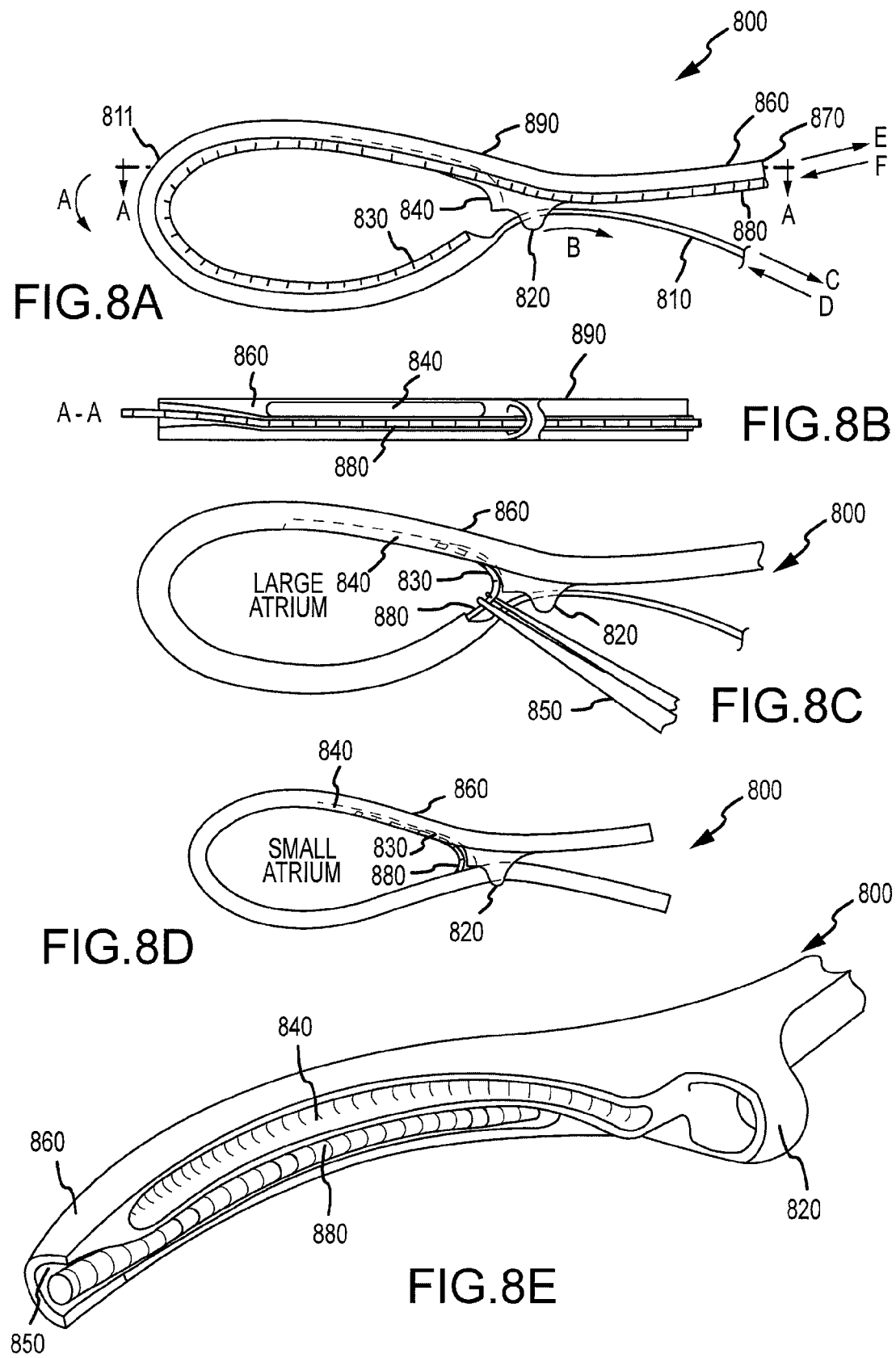

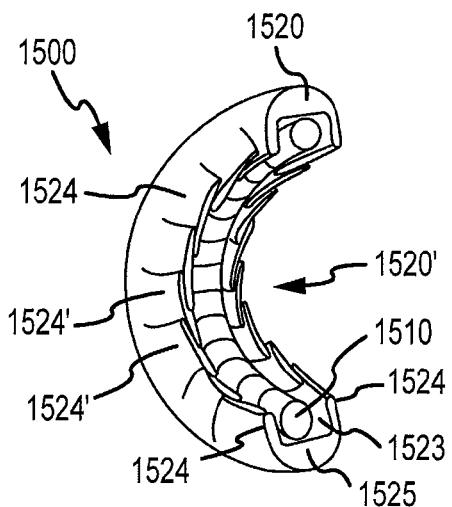
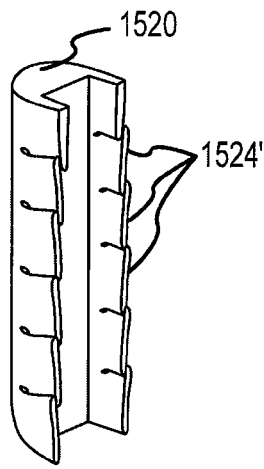
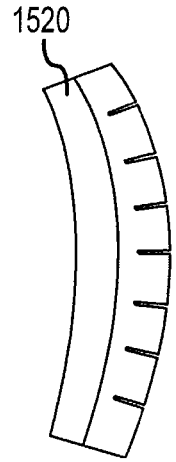
FIG.15A  FIG.15B  FIG.15C
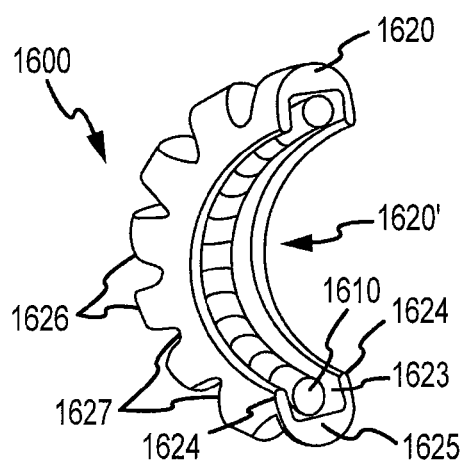
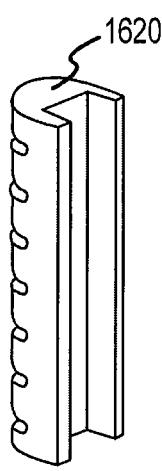
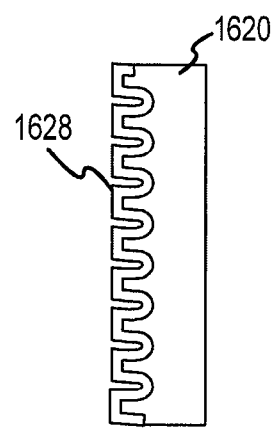
FIG.16A  FIG.16B  FIG.16C

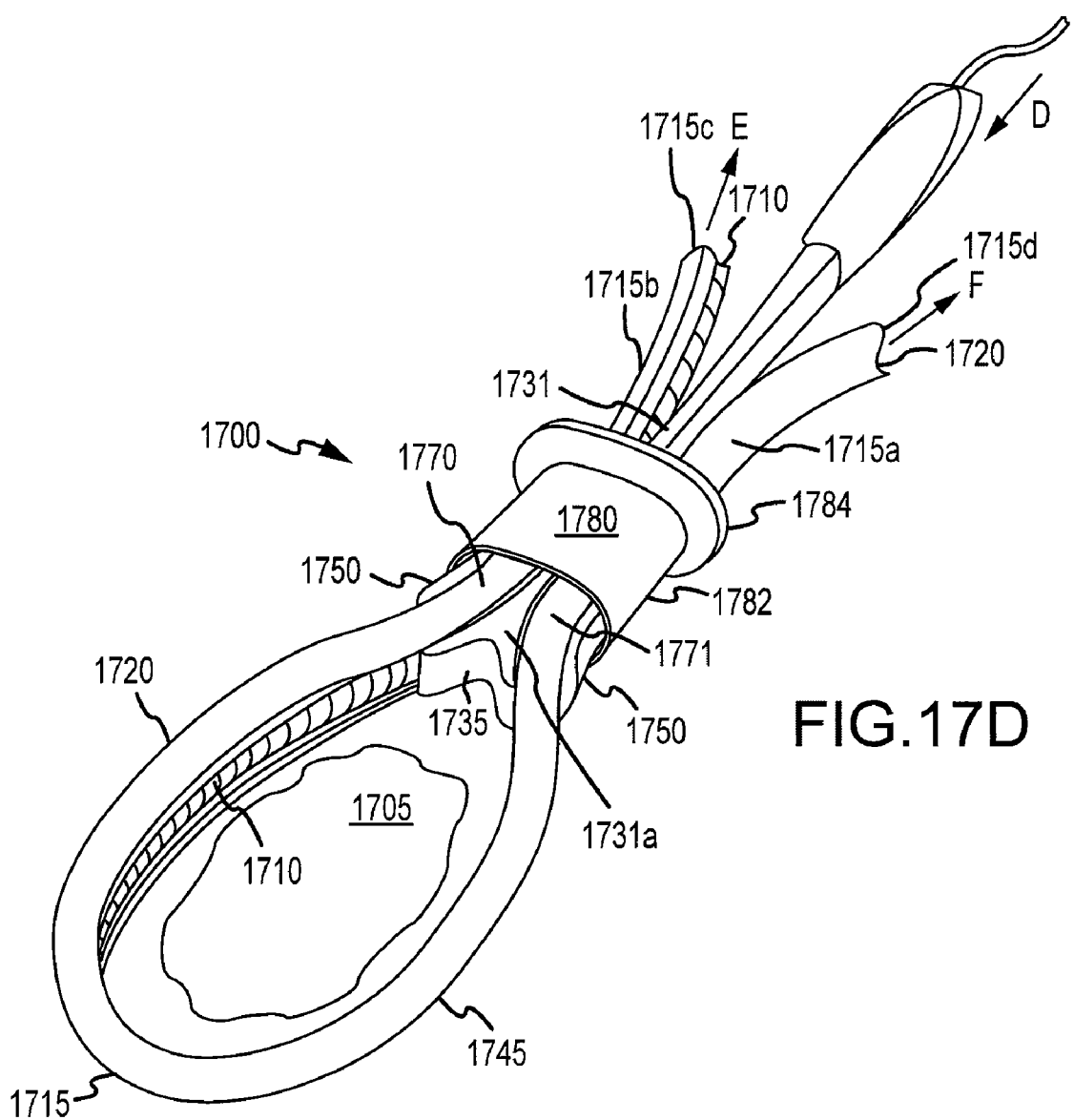
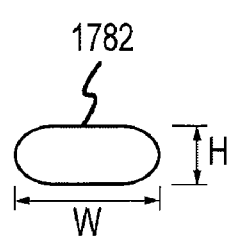
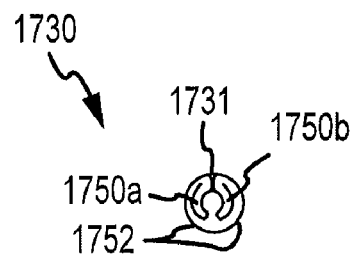
FIG.17D
FIG.17E
FIG.17F

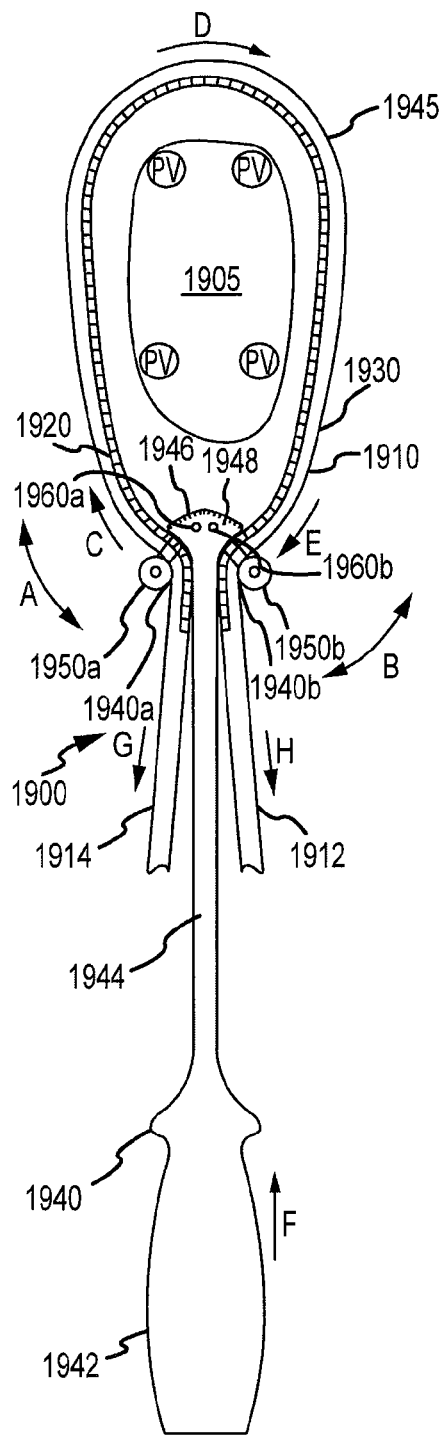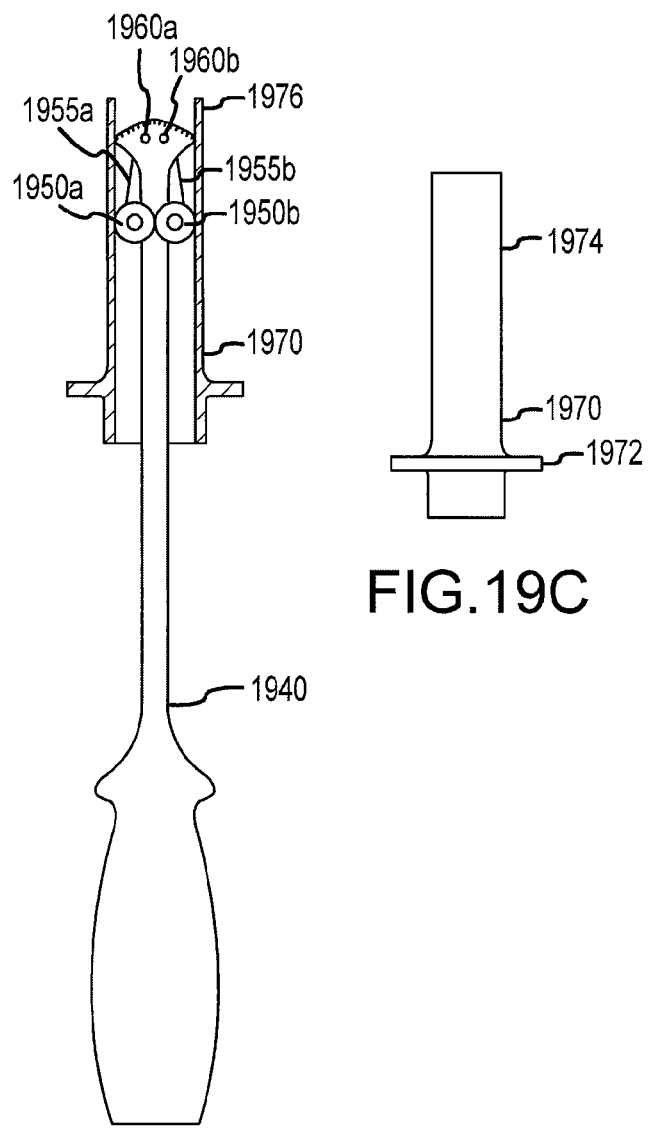
FIG.19A
FIG.19B
FIG.19C

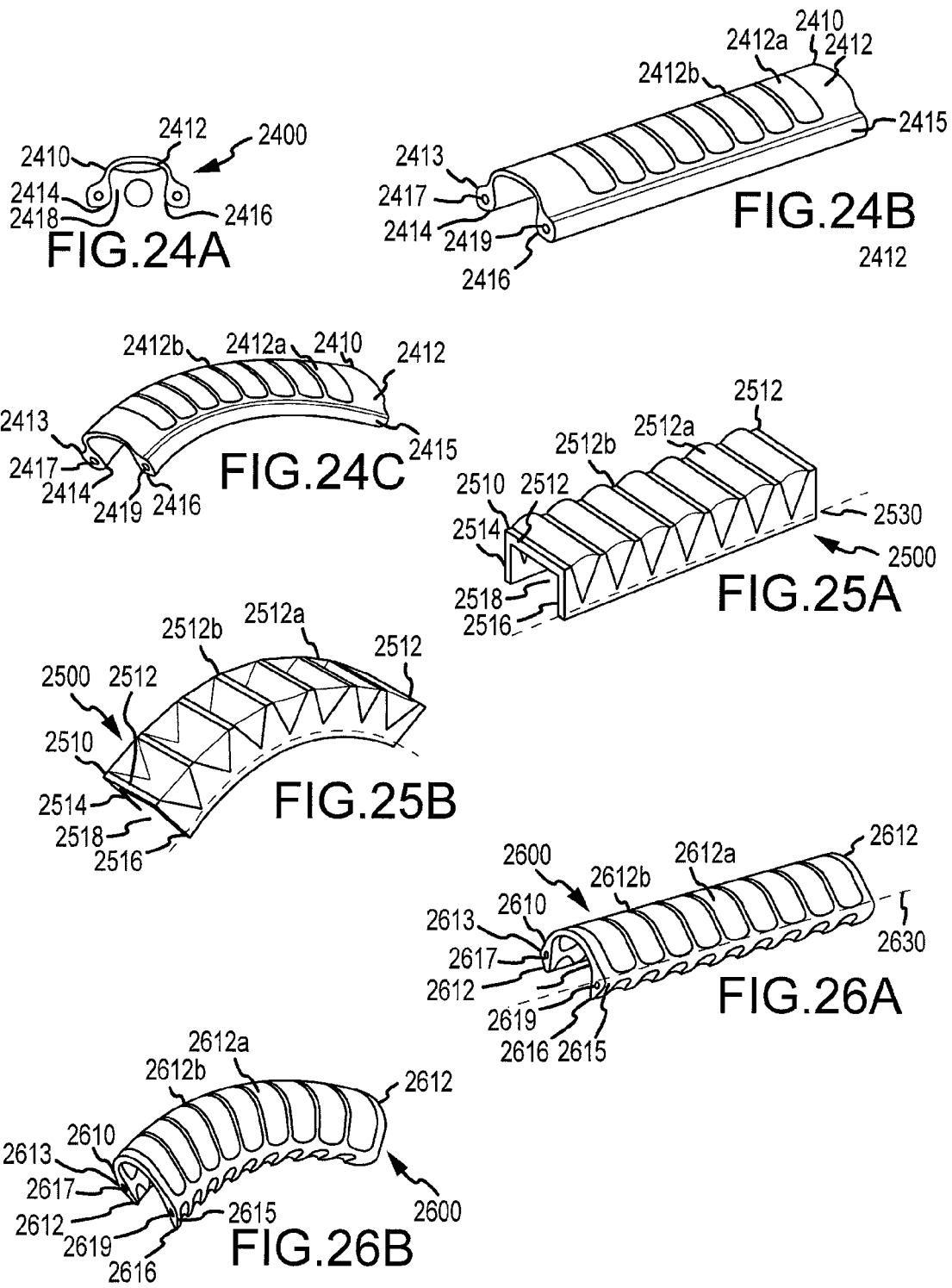

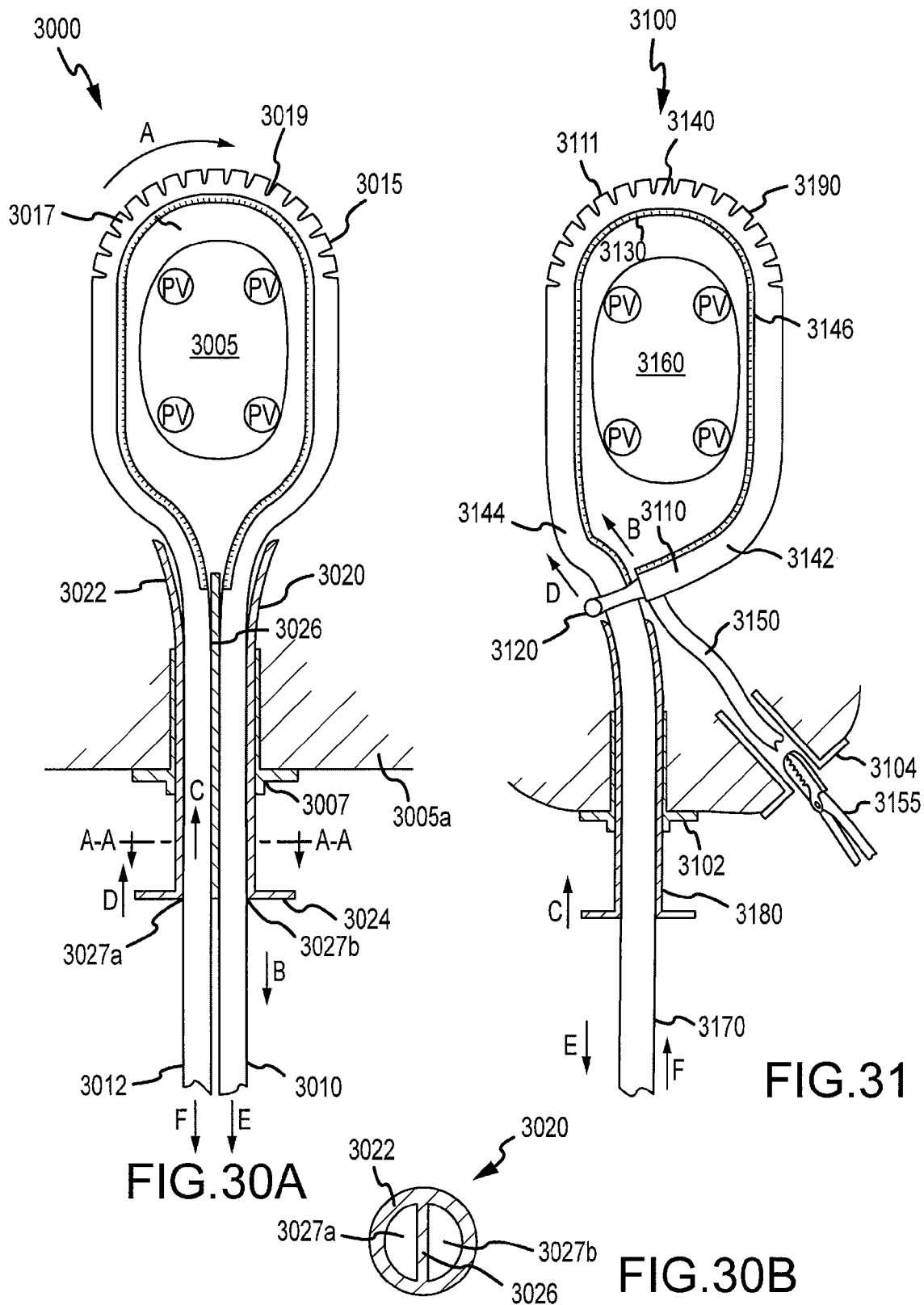

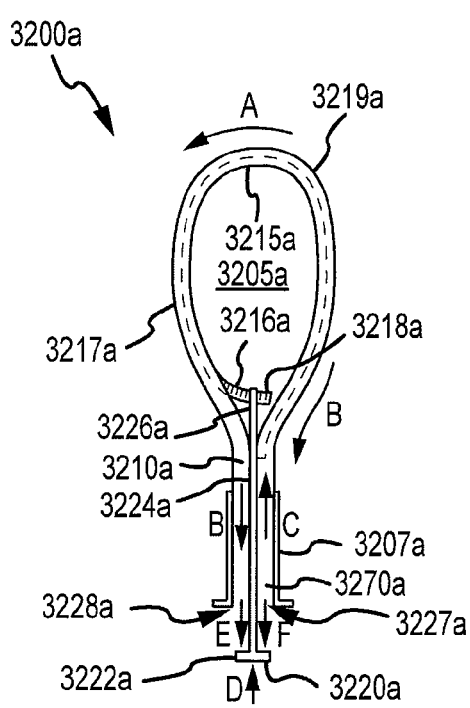
FIG.32A
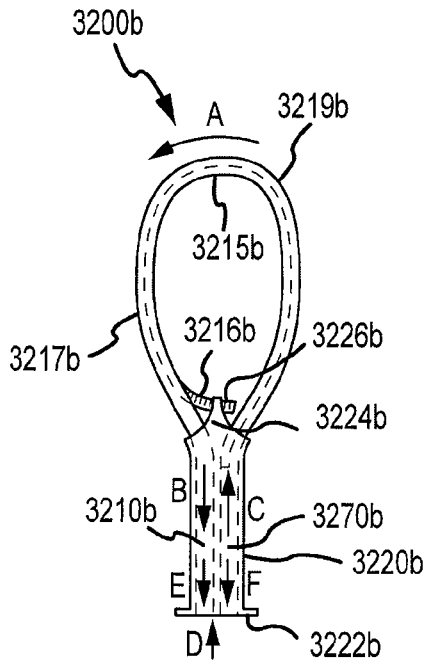
FIG.32B
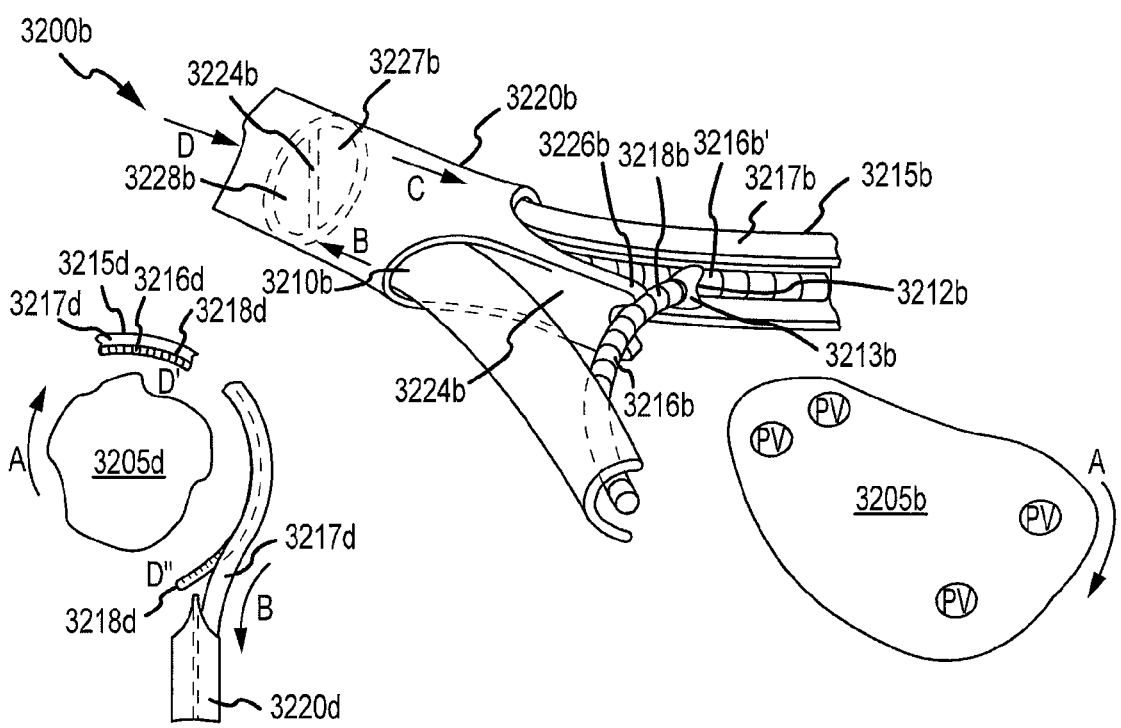
FIG.32C
FIG.32D

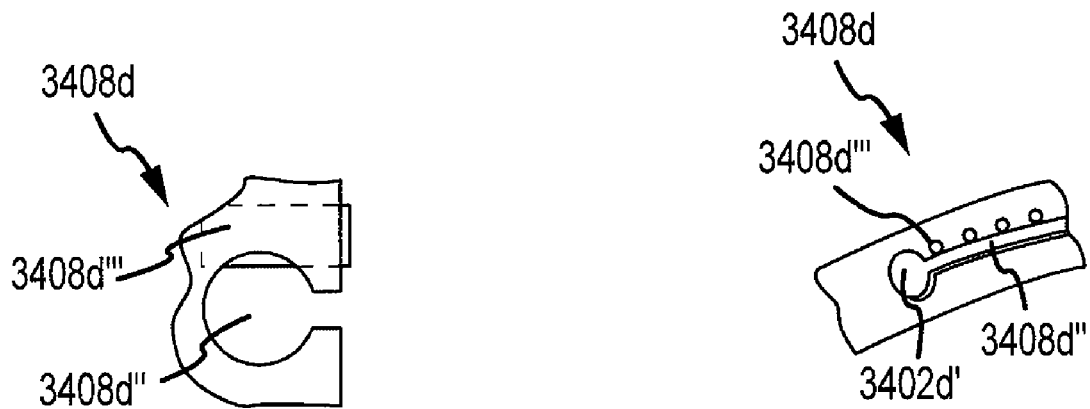
FIG.34D    FIG.34D2
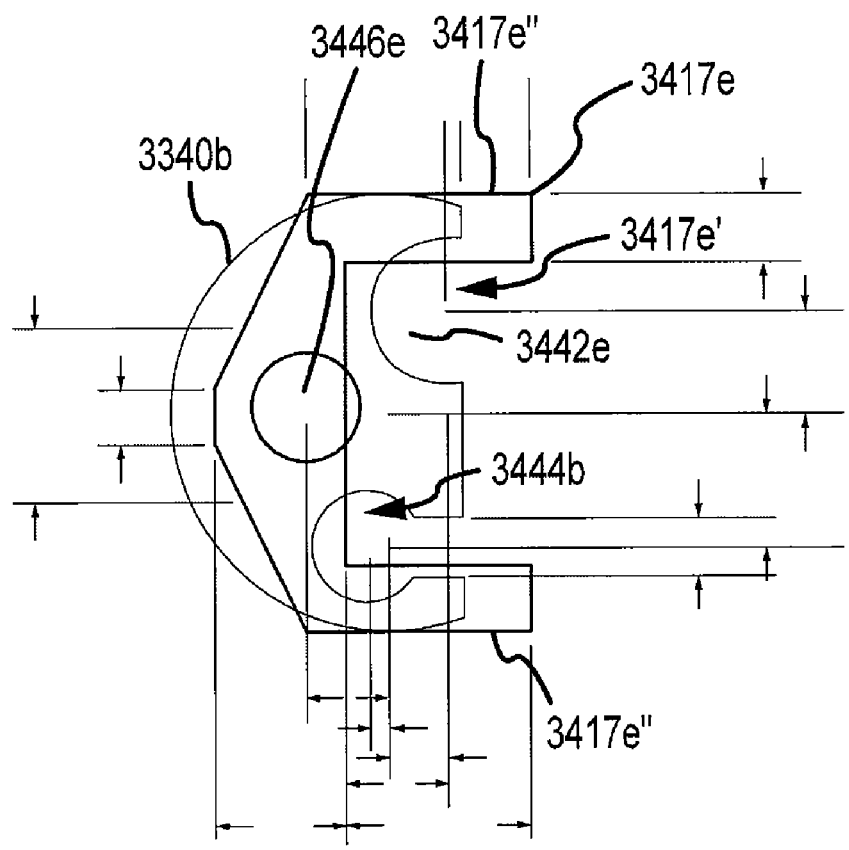
FIG.34E

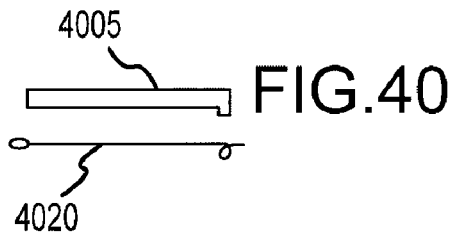
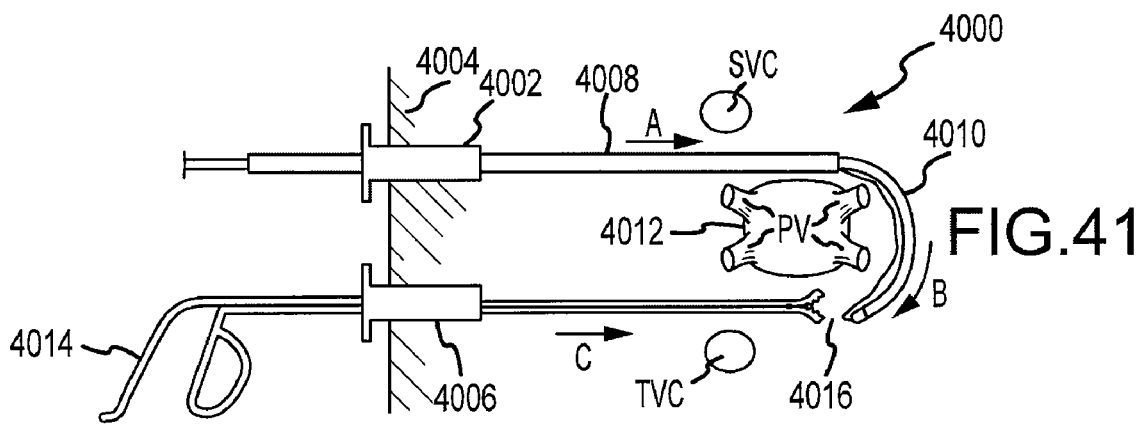
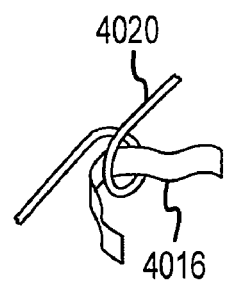
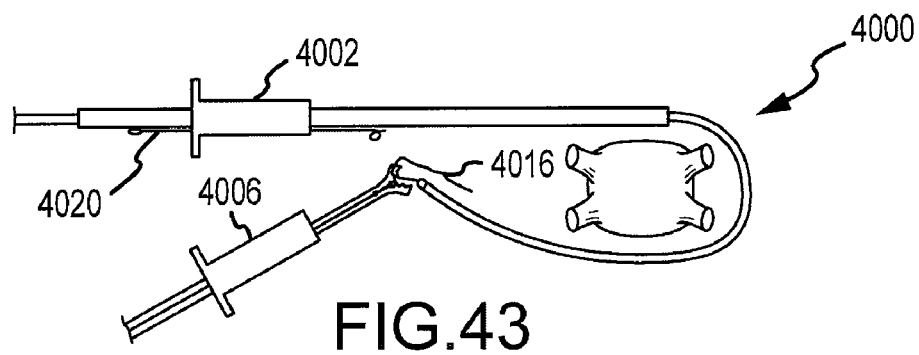

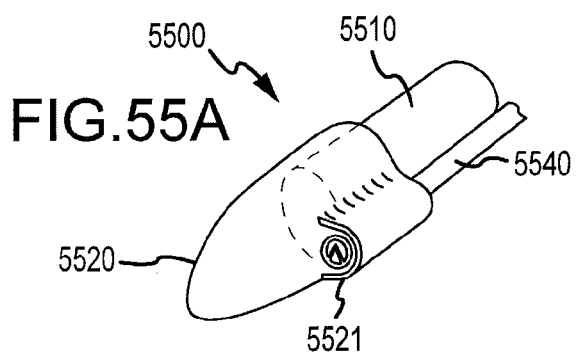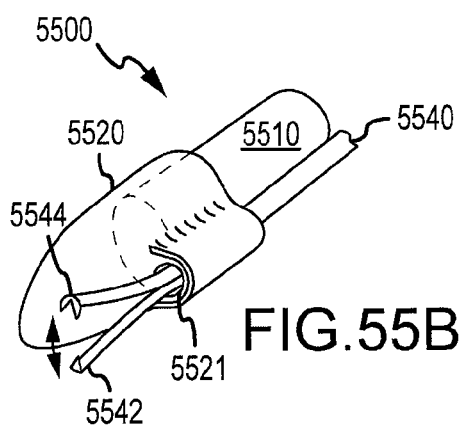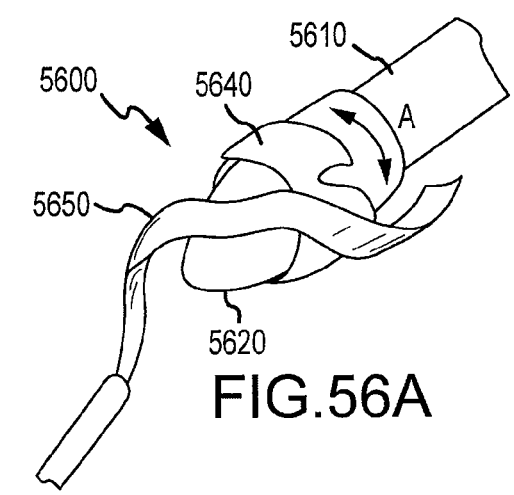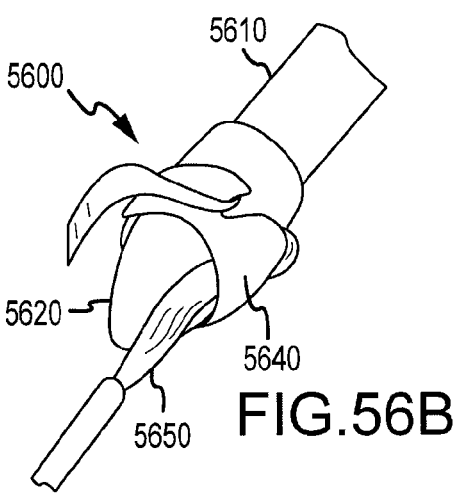

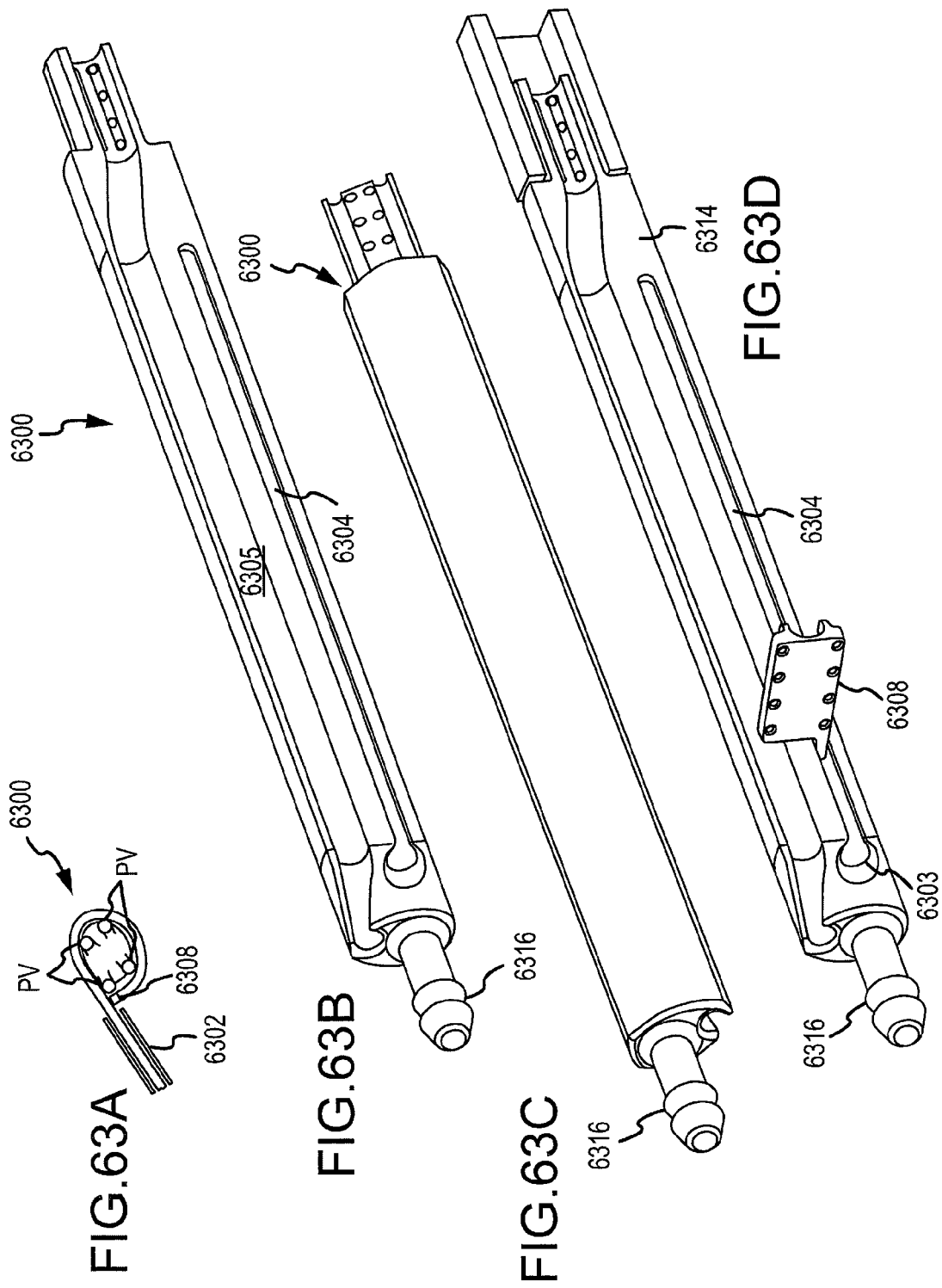

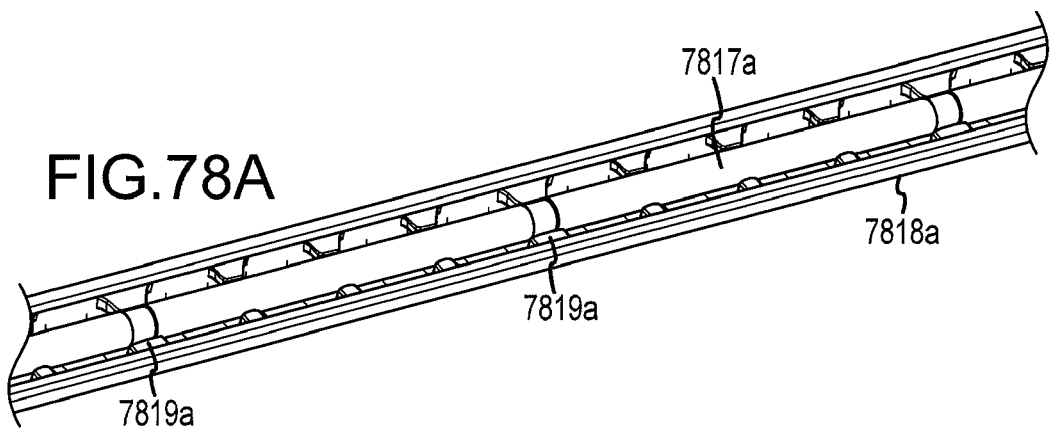
FIG.78A
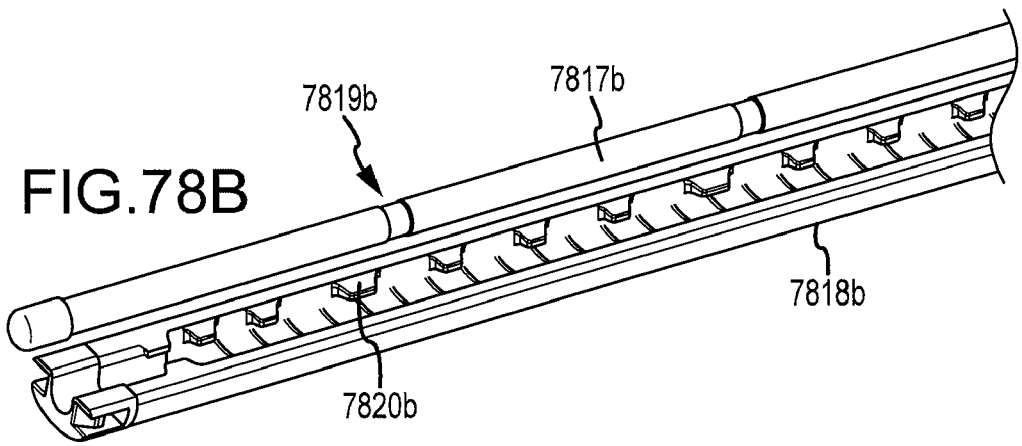
FIG.78B
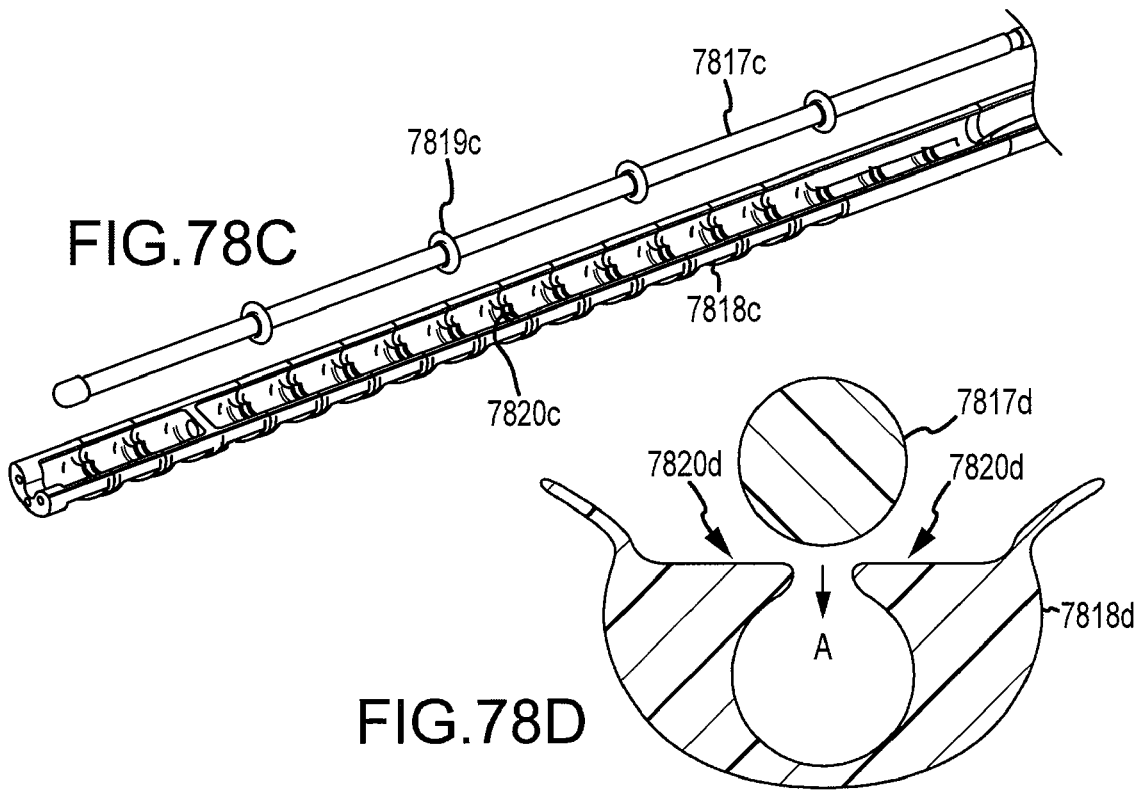
FIG.78C
FIG.78D

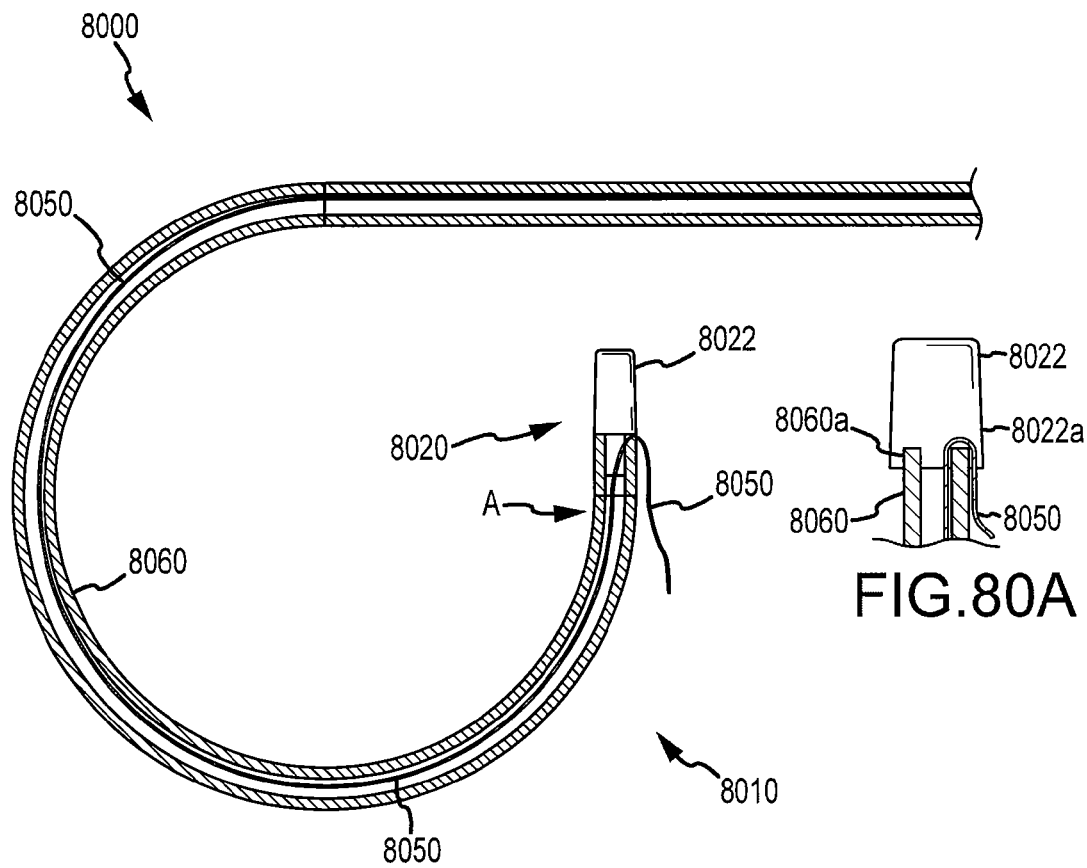
FIG.80A
FIG.80
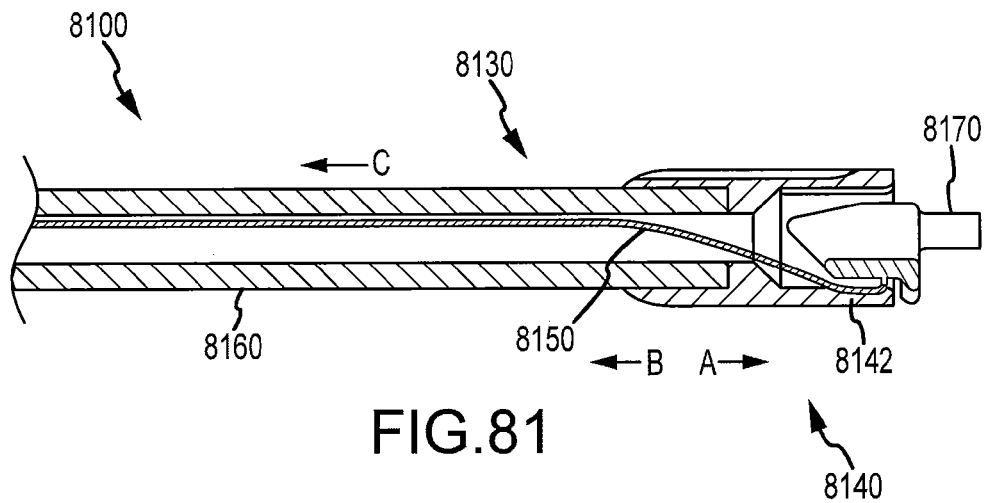
FIG.81

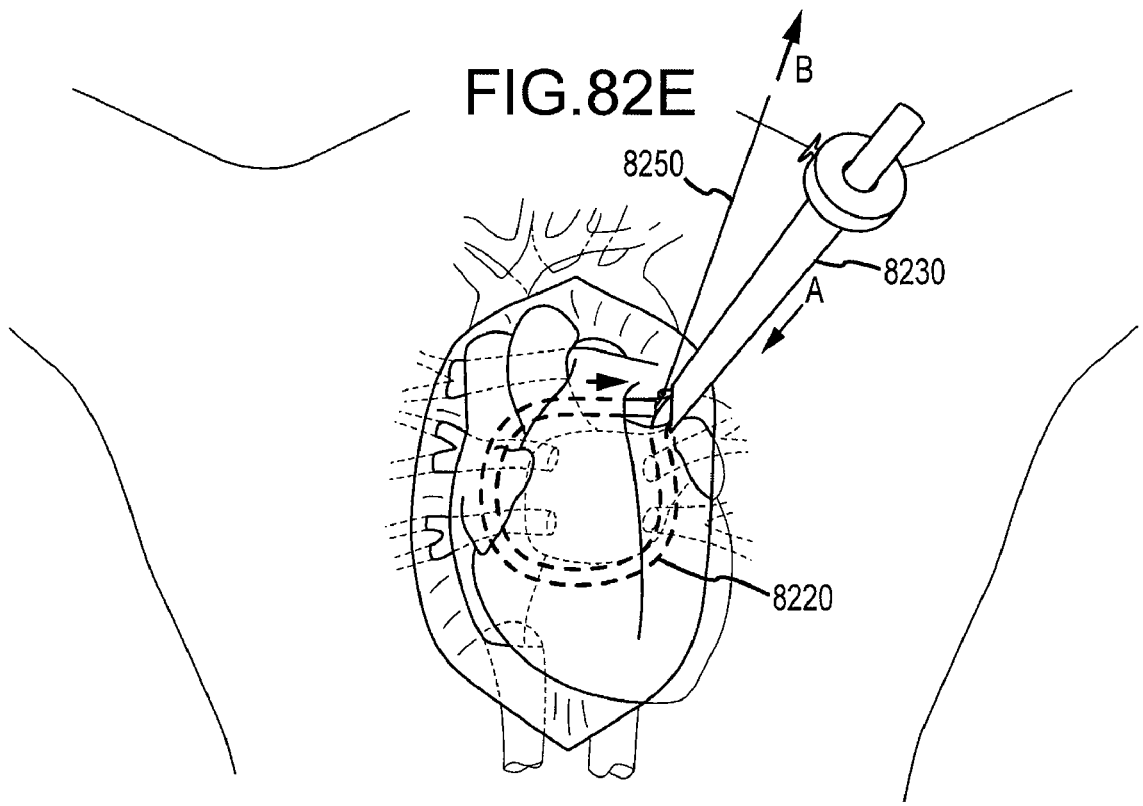
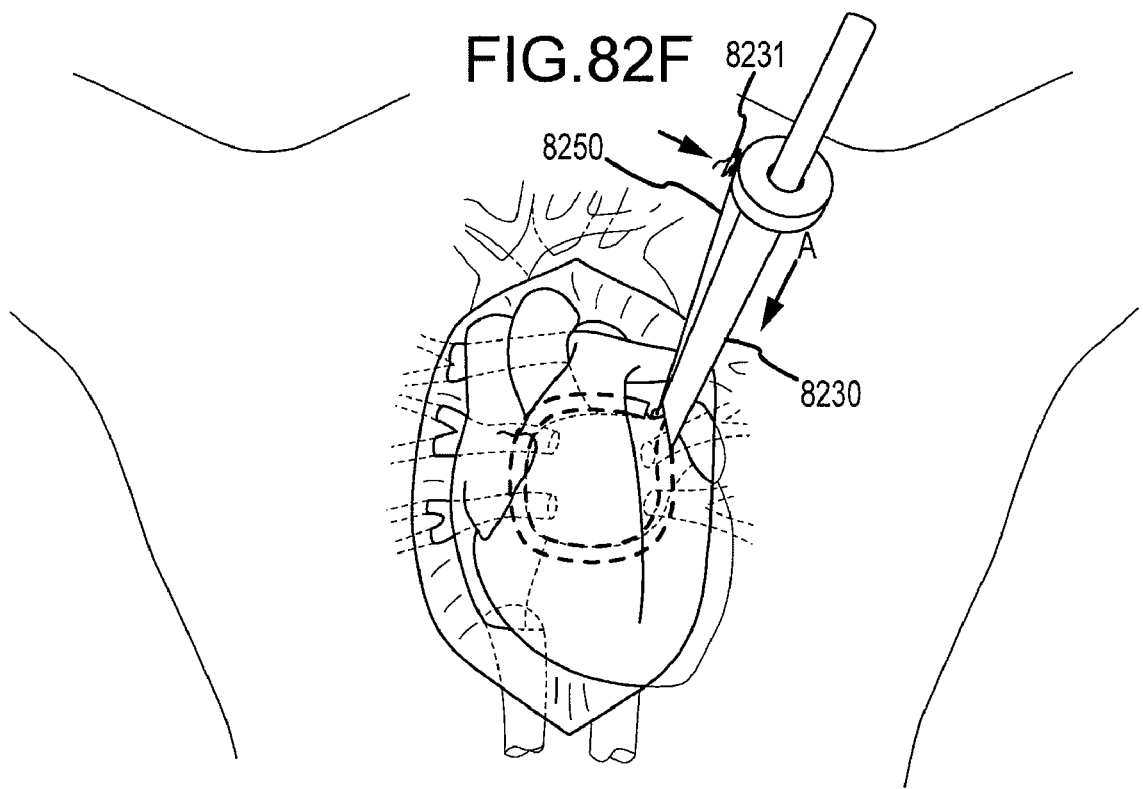

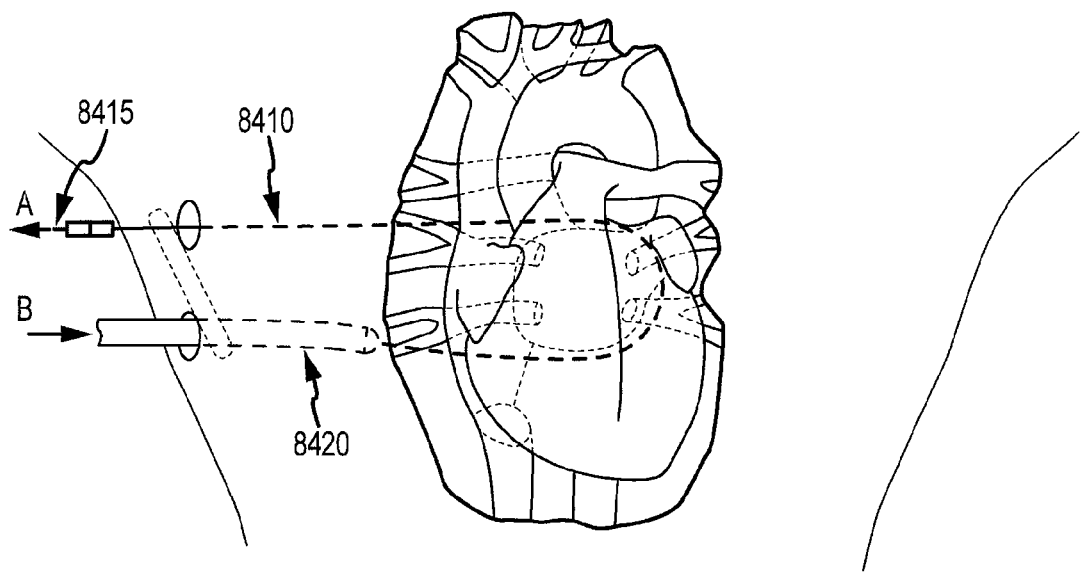
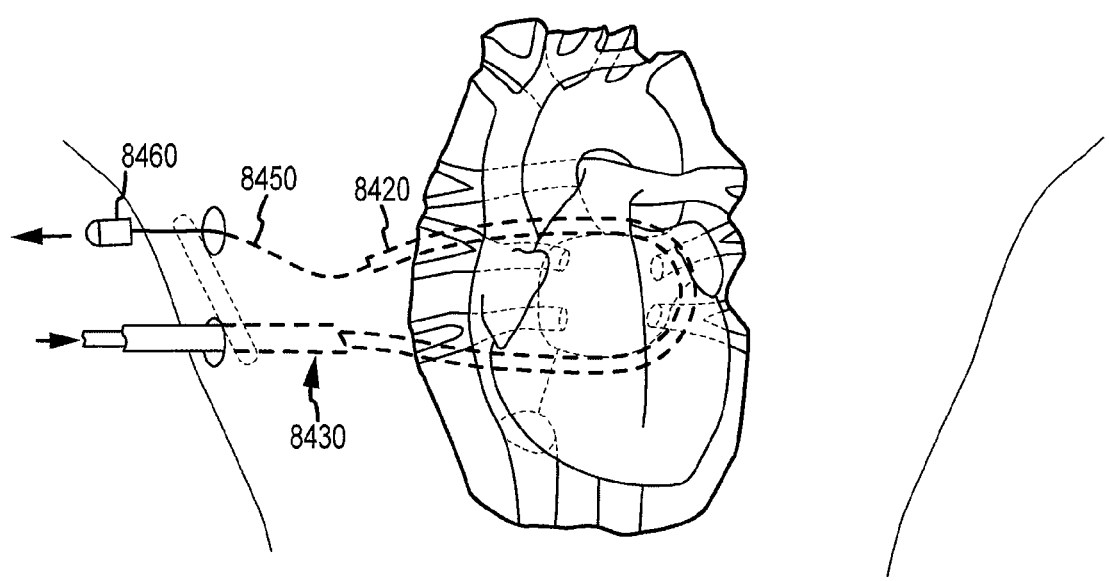

CARDIAC ABLATION SYSTEMS AND METHODS

CROSS-REFERENCES TO RELATED APPLICATIONS

This application is a continuation of U.S. patent application Ser. No. 14/143,420 filed Dec. 30, 2013, which is a continuation of U.S. patent application Ser. No. 12/124,743, filed on May 21, 2008 (now U.S. Pat. No. 8,628,522 issued Jan. 14, 2014), which claims the benefit of U.S. Provisional Patent Application No. 60/939,201 filed May 21, 2007. This application is also related to U.S. Provisional Patent Application No. 61/015,472 filed Dec. 20, 2007. The entire disclosure of each of these filings is incorporated herein by reference for all purposes.

BACKGROUND OF THE INVENTION

Embodiments of the present invention related to medical devices and methods, and in particular to cardiac ablation systems and methods.

Certain cardiac surgical procedures involve administering ablative energy to the cardiac tissue in an attempt to create a transmural lesion on the tissue. However, in some cases such methods may not be optimal due to the formation of incomplete lesions, which do not effectively create a conduction block in the tissue. Hence, there continues to be a need for improved systems and methods that can deliver ablative energy to patient tissue in a uniform and reproducible manner.

Embodiments of the present invention provide solutions to at least some of these outstanding needs.

BRIEF SUMMARY OF THE INVENTION

Advantageously, embodiments of the present invention provide techniques for applying circumferential lesions to the pulmonary vein (PV) ostia to cause conduction block at the junction of the PV and left atrium as well as other blocking lesions. Such techniques are well suited for use with patients presenting with paroxysmal (focal) atrial fibrillation. Exemplary embodiments involve the administration of precisely controlled ablative energy to create reproducible, uniform transmural lesions during cardiac surgery. Such techniques enable rapid and effective ablative lesions in a variety of clinical situations, including endocardial and epicardial ablations. By forming the transmural ablations, surgeons are able to achieve conduction block in the patient.

Embodiments of the present invention include introducer systems and instruments equipped with magnetic elements that facilitate one-sided port introduction and can reduce procedure times significantly, in many cases to less than one hour. Embodiments also provide systems with flexible suction probes or stabilizer mechanisms that can be used in conjunction with cinching mechanisms or delivery tubes, which are well suited for use on any patient tissue or anatomy of any size or shape. Cinching mechanisms facilitate length adjustability for variable atria lesion sizes and box lesion sizes, for example. Hence, it is possible to form a complete box lesion with a single device placement with minimal or no gaps. In some embodiments, techniques involve unilateral 10 mm port access. Systems and methods disclosed herein are also well suited for creating Cox Maze lesions. For example, a single device can be used to create a transmural box lesion and a connecting lesion. In some embodiments, a surgeon or operator can use a cinching mechanism such as a delivery or push tube as a placement wand. Suction stabilizer mechanisms can be operatively associated with cinching mechanisms such as delivery tubes to facilitate length adjustability of a stabilizer mechanism, an ablation mechanism, or both. Improved coupling techniques for introducers and introducer retrievers can vastly improve introducer search times, which often can occupy more than half of the entire procedure time. Introducers, stabilizer and ablation assemblies, and other components of the treatment systems described herein can have curved configurations, such as helical curves, for improved routing into the oblique sinus from a transverse sinus, for example. Embodiments also provide single step continuity, whereby a cinching delivery mechanism can easily be used to snare a distal tape to form a continuous box lesion without the need for repositioning or additional instruments. Advantageously, embodiments of the present invention can be used to create complete lesion sets and reliably produce transmural lesions on a beating heart.

Embodiments also includes ablation systems having an ablation energy source for providing energy to the ablation device. An ablation energy source is typically suited for use with ablation apparatus as described herein using RF energy. With regard to RF ablation, a typical RF ablation system includes a RF generator which feeds current to an ablation device, including those described in this application, containing a conductive electrode for contacting targeted tissue. The electrical circuit can be completed by a return path to the RF generator, provided through the patient and a large conductive plate, which is typically in contact with the patient's back. Embodiments encompass ablation using RF electrodes, including single RF ablation electrodes. Although ablation energy is often described herein in terms of RF energy, it is understood that embodiments are not limited to such ablation modalities, and other kinds of ablation energy sources and ablation devices may be used. Hence, with regard to the ablation techniques disclosed herein, other suitable ablation elements or mechanisms, instead or in addition to an RF electrode, can be used. Embodiments of the present invention therefore encompass any of a variety of ablation techniques, including without limitation infrared lasers, high intensity focused ultrasound (HIFU), microwave, cryoablation (killing or damaging the tissue by freezing), chemical or biological agents, radiation, and the like. In some cases, an ablation mechanism can include an ablation element that transmits or delivers RF energy to patient tissue. Optionally, suitable ablation elements can transmit or deliver infrared laser energy, high intensity focused ultrasound (HIFU) energy, microwave energy, cryoablation energy, chemical agents, biological agents, radiation energy, and the like. Embodiments encompass ablation mechanisms having multiple ablation elements, such as multiple RF electrodes. According to some embodiments, an ablation element may include a monopolar electrode. Relatedly, an ablation element may include a bipolar electrode.

In one aspect, embodiments of the present invention provide systems for administering an ablation treatment to a patient. Systems may include an ablation assembly having a flexible ablation mechanism configured to ablate a tissue of the patient, and a cinching mechanism configured to constrict the ablation member about the patient tissue. Systems may include a stabilizer mechanism that forms a seal with the tissue of the patient. The ablation mechanism may be at least partially disposed within a recess of the stabilizer member. The cinching mechanism can be configured to cinch the ablation assembly about the patient tissue in a circumferential path. In some cases, a system includes an introducer which may be coupled with the ablation assembly. In some cases, the introducer may include a ribbon or tape. A cinching mechanism may include a trocar, a push tube, a roller, a guide or catch, a breakaway tip, a hinge, or any combination thereof. In some cases, an ablation mechanism includes an electrode.

In another aspect, embodiments of the present invention encompass methods for ablating a tissue, such as a cardiac tissue, of a patient. Methods may include placing an ablation assembly near the tissue of the patient, cinching the ablation assembly so as to urge an ablation mechanism toward the tissue, and administering an ablation to the tissue via the ablation mechanism to create a lesion in the tissue. In some cases, methods may include forming a transmural lesion, such as a box lesion or a connecting lesion, in cardiac tissue. For example, methods may include creating a lesion in the form of a closed path. According to some methods, an ablation assembly can be disposed at least partially within a stabilizer assembly, and the method may include forming a seal between the stabilizer assembly and the cardiac tissue. Methods may also involve urging the ablation mechanism toward cardiac tissue with a cinching mechanism.

In some aspects, embodiments encompass systems and methods for treating an epicardial or endocardial tissue of a patient. Exemplary methods may include placing a treatment assembly near the epicardial tissue of the patient, wrapping an ablation mechanism of the treatment assembly about a portion of the epicardial tissue such that the ablation mechanism is disposed near at least one pulmonary vein of the patient, cinching the ablation mechanism toward the epicardial tissue, and delivering an ablative treatment through the ablation mechanism of the ablation assembly toward the epicardial tissue, so as to form a lesion on the epicardial tissue. Some methods may involve creating a seal between the epicardial tissue and a stabilizer mechanism of the treatment assembly. In some cases, the process of placing the ablation mechanism near the epicardial tissue of the patient includes passing the ablation mechanism through a transverse sinus of the patient, through an oblique sinus of the patient, or through both. Methods may include forming or creating a conduction block at a junction of left atrium and a pulmonary vein.

In another aspect, embodiments encompass systems for administering an ablation treatment to a patient tissue. Systems may include a treatment assembly having a stabilizer mechanism and a flexible ablation mechanism configured to ablate a tissue of the patient. Systems may also include a cinching mechanism configured to constrict the ablation mechanism about the patient tissue. A stabilizer mechanism may include a series of undulating projections. In some case, a stabilizer mechanism includes a body coupled with two opposing sidewalls forming a recess. In some cases, an ablation mechanism is at least partially disposed within the recess of the stabilizer mechanism. A stabilizer mechanism may include a memory shape configuration having a bend. According to some embodiments, a sidewall of the stabilizer mechanism may include a first flap and a second flap that can overlap each other when the stabilizer mechanism is in a bent configuration. In some cases, a stabilizer mechanism includes a tension member. Optionally, a tension member may be disposed within, or at least partially within, a sidewall of the stabilizer mechanism. In some embodiments, a tension member can be disposed within a ridge coupled with or on a sidewall of the stabilizer mechanism. In some cases, a tension member includes a tension strap or a tension cord. Optionally, the body of the stabilizer mechanism may include a one or more support ribs. Relatedly, the body of the stabilizer mechanism may include a thin elastic membrane disposed between two adjacent support ribs. In some cases, a body of the stabilizer mechanism includes a channel configured to receive an obturator. A stabilizer mechanism may be coupled with the ablation mechanism via a loop. A stabilizer mechanism may be coupled with the ablation mechanism via a partial loop. A stabilizer mechanism may be coupled with the ablation mechanism via an adhesive or bonding material.

In still another aspect, embodiments of the present invention encompass methods for administering an ablation to a patient. Methods may involve placing a treatment assembly near tissue of the patient. The treatment assembly may include a monopolar ablation mechanism and a stabilizer mechanism that presents a suction zone. Methods may also include adjusting a size of the suction zone, and administering an ablation to the tissue via the monopolar ablation mechanism to create a lesion in the tissue. In some cases, the procedure of adjusting the size of the suction zone includes extending a distal portion of the treatment assembly from a cinching mechanism, or retracting a distal a distal portion of the treatment assembly toward the cinching mechanism. In some cases, a cinching mechanism includes a push tube.

In yet a further aspect, embodiments of the present invention include systems for administering an ablation treatment to a patient tissue. Systems may include a treatment assembly having a stabilizer mechanism and a flexible ablation mechanism configured to ablate a tissue of the patient. Systems may also include a cinching mechanism configured to urge the ablation mechanism toward the patient tissue. A stabilizer mechanism may include an adjustable suction zone. Optionally, a stabilizer mechanism can include a series of undulating projections.

In another aspect, embodiments of the present invention encompass ablation treatment systems that include an ablation assembly having a flexible ablation member configured to deliver an ablation energy to a tissue of the patient, and a stabilizer member configured to create a seal against the tissue of the patient. Such treatment systems can also include a cinching member that engages the ablation assembly and cinches the ablation assembly about the patient tissue in a circumferential path. In some cases, the ablation member comprises an electrode. The cinching member can include a roller, an ablation segment, a delivery tube, or an ablation protection mechanism, or any combination thereof. Embodiments also encompass methods for delivering an ablative energy to a cardiac tissue. An exemplary method includes placing an ablation assembly against the cardiac tissue of the patient, where the ablation assembly has a stabilizer member coupled with an ablation member, securing the stabilizer member with the patient tissue via a vacuum, and administering the ablative energy to the cardiac tissue via the ablation member to create a transmural lesion in the cardiac tissue. Optionally, methods may include cinching, binding, or squeezing the ablation assembly or ablation member about the cardiac tissue. In some methods, a transmural lesion is formed in the shape of a closed path. Some methods involve contacting a cinching device with the ablation assembly, and cinching the ablation device about the cardiac tissue with the cinching device. Some methods involve separating a proximal section of an ablation member from a distal section of the ablation member with an ablation member protection mechanism.

In still a further aspect, embodiments of the present invention include systems and methods for treating an epicardial tissue of a patient. An exemplary method may include placing an ablation system near an epicardial tissue of the patient, and wrapping an ablation assembly of the ablation system about a portion of the epicardial tissue, where the ablation assembly includes a stabilizer member and an ablation member. Methods may also include cinching a loop structure of the ablation assembly against the epicardial tissue, securing the ablation assembly against the epicardial tissue by creating a seal between the stabilizer member and the epicardial tissue, and delivering an ablative energy through the ablation member of the ablation assembly toward the epicardial tissue, so as to form a closed path lesion on the epicardial tissue. Some methods involve passing a distal section of the ablation assembly through a catch disposed on a proximal section of the ablation assembly.

For a fuller understanding of the nature and advantages of the present invention, reference should be had to the ensuing detailed description taken in conjunction with the accompanying drawings.

BRIEF DESCRIPTION OF THE DRAWINGS

FIGS. 8A-8E show aspects of an ablation system having a loop mechanism according to embodiments of the present invention.

FIGS. 15A-15C show aspects of an ablation system with a stabilizer member according to embodiments of the present invention.

FIGS. 16A-16C depict aspects of an ablation system with a stabilizer member according to embodiments of the present invention.

FIGS. 17A-17F show aspects of an ablation system with a cinching mechanism according to embodiments of the present invention.

FIGS. 19A-19F show aspects of ablation systems with a stabilizer member according to embodiments of the present invention.

FIGS. 24A-24C show aspects of ablation systems with a stabilizer member according to embodiments of the present invention.

FIGS. 25A-25B show aspects of ablation systems with a stabilizer member according to embodiments of the present invention.

FIGS. 26A-26B show aspects of ablation systems with a stabilizer member according to embodiments of the present invention.

FIG. 27 shows aspects of an ablation system with a stabilizer member according to embodiments of the present invention.

FIGS. 30A-30B show aspects of ablation systems with a stabilizer member according to embodiments of the present invention.

FIG. 31 shows aspects of an ablation systems with a stabilizer member according to embodiments of the present invention.

FIGS. 32A-32D show aspects of ablation systems with a stabilizer member according to embodiments of the present invention.

FIGS. 34A-34E show aspects of ablation systems with a stabilizer member according to embodiments of the present invention.

FIG. 40 shows aspects of an ablation system with a stabilizer member according to embodiments of the present invention.

FIG. 41 shows aspects of an ablation system with a stabilizer member according to embodiments of the present invention.

FIG. 42 shows aspects of an ablation system with a stabilizer member according to embodiments of the present invention.

FIG. 43 shows aspects of an ablation system with a stabilizer member according to embodiments of the present invention.

FIGS. 55A-55B show aspects of ablation systems with a visualization system according to embodiments of the present invention.

FIGS. 56A-56B show aspects of ablation systems with a visualization system according to embodiments of the present invention.

FIGS. 63A-63F show aspects of ablation systems forming a loop enclosure according to embodiments of the present invention.

FIGS. 78A-78D show aspects of ablation systems with a stabilizer mechanism according to embodiments of the present invention.

FIG. 80 shows aspects of an ablation system with a coupling mechanism according to embodiments of the present invention.

FIG. 80A shows aspects of a coupling mechanism of an ablation system according to embodiments of the present invention.

FIG. 81 shows aspects of an ablation system with a coupling mechanism according to embodiments of the present invention.

FIGS. 82A-82F show aspects of ablation systems with an introducer system according to embodiments of the present invention.

FIGS. 84A-84F show aspects of ablation systems with an introducer system according to embodiments of the present invention.

DETAILED DESCRIPTION OF THE INVENTION

Embodiments of the present invention are well suited for ablating epicardial and other tissue of a patient in need thereof. Exemplary techniques involve placing an ablation system near cardiac tissue of the patient, and can also involve wrapping an ablation assembly of the ablation system about at least a portion of the tissue. The ablation assembly may include a stabilizer member, an ablation member, or both. Techniques can also include cinching or tightening the ablation assembly against the tissue, and optionally securing the ablation assembly against epicardial tissue by creating a seal between a stabilizer member and the tissue. Such approaches also include delivering an ablative energy or procedure through the ablation member to the tissue, so as to form a closed or substantially closed path lesion on the tissue. Embodiments provide various desirable techniques for constricting or tightening an ablation member about or against a patient tissue. Systems and methods can be used to create tissue ablations such as those described in U.S. Pat. Nos. 6,241,754 and 7,115,122, the content of which is incorporated herein by reference.

Figure 1A:
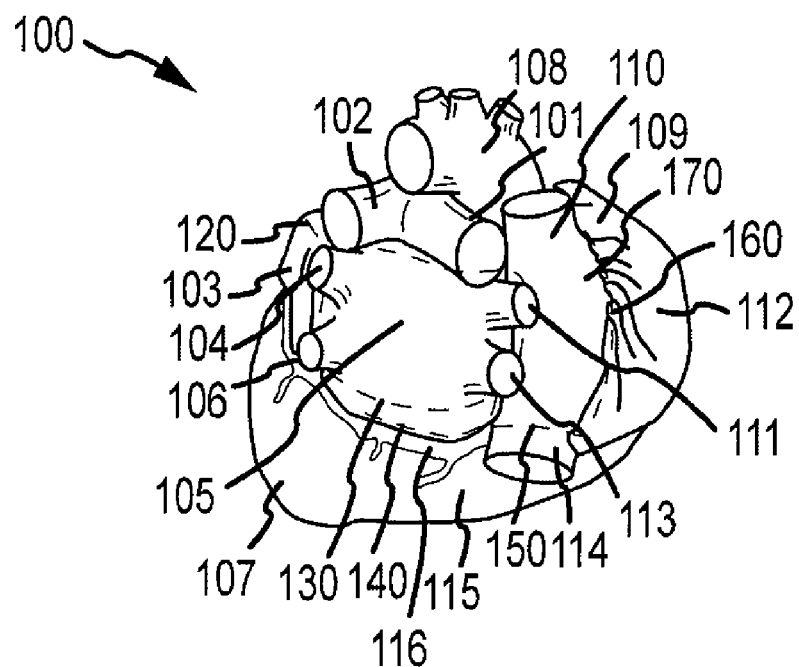
FIG. 1A illustrates exemplary lesion patterns on a patient heart according to embodiments of the present invention.
Figure 1B:
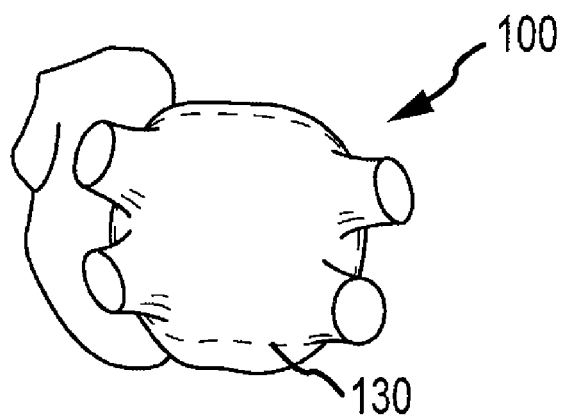
FIG. 1B illustrates aspects of a box lesion according to embodiments of the present invention.

Turning now to the drawings, FIG. 1A illustrates exemplary lesion patterns on a posterior aspect, or base, of a patient heart 100, according to embodiments of the present invention. Patient heart 100 includes a right pulmonary artery 101, a left pulmonary artery 102, a left atrial appendage (LAA) 103, a left superior pulmonary vein (PV) 104, a left atrium (LA) 105, a left inferior pulmonary vein (PV) 106, a left ventricle 107, an aortic arch 108, a right atrial appendage (RAA) 109, a superior vena cava (SVC) 110, a right superior pulmonary vein (PV) 111, a right atrium (RA) 112, a right inferior pulmonary vein (PV) 113, an inferior vena cava (IVC) 114, a right ventricle 115, and a coronary sinus (CS) 116. The dashed lines "- - - -" can represent one or more transmural burn zones on tissue of the heart. For example, lesion 120 represents a left atrial appendage (LAA) connecting lesion, lesion 130 represents a circumferential lesion, or box lesion, about the pulmonary vein (PV) ostia, lesion 140 represents a juxta coronary sinus (CS) lesion, lesion 150 represents a transverse right atrium (RA) lesion, lesion 160 represents an intra-cava lesion, and lesion 1 70 represents a right atrial lesion. FIG. 1B illustrates another view of a circum-pv lesion 130, or box lesion, which can be applied contiguously, or without a break, around the pulmonary veins. In some cases, a circum-pv lesion 130 length can be within a range from about 18.5 cm to about 22 cm. A cardiothoracic surgical procedure may involve a left thoracotomy approach. Some surgical procedures involve shape-biased suction.

Figure 2A:
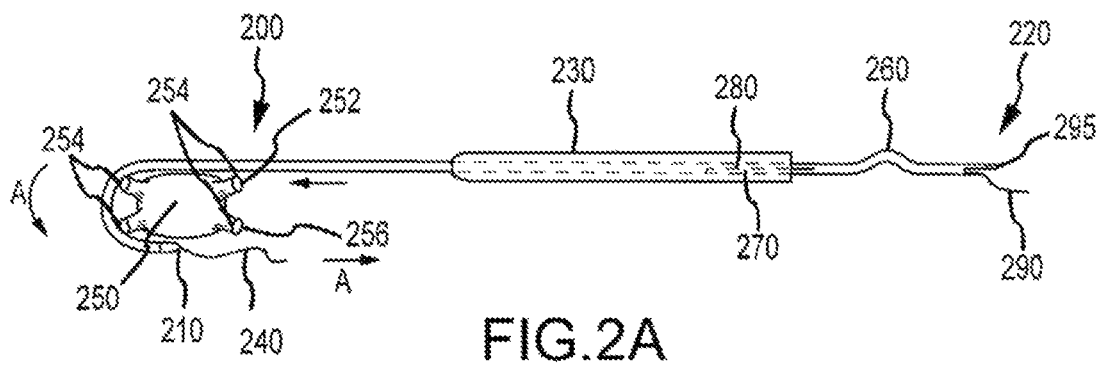
FIGS. 2A-2C illustrate aspects of a spring-loaded free-tip electrode according to embodiments of the present invention.
Figure 2B:
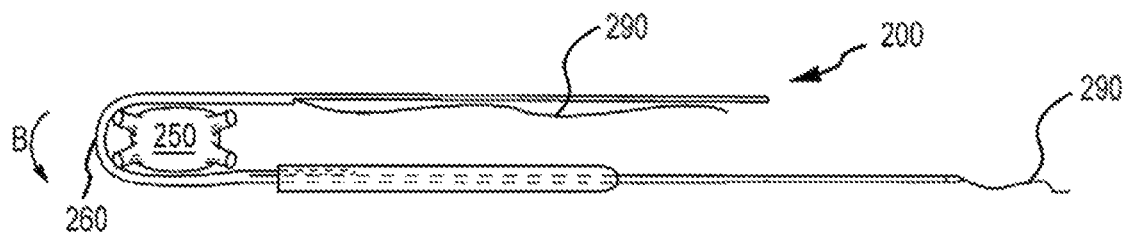
Figure 2C:
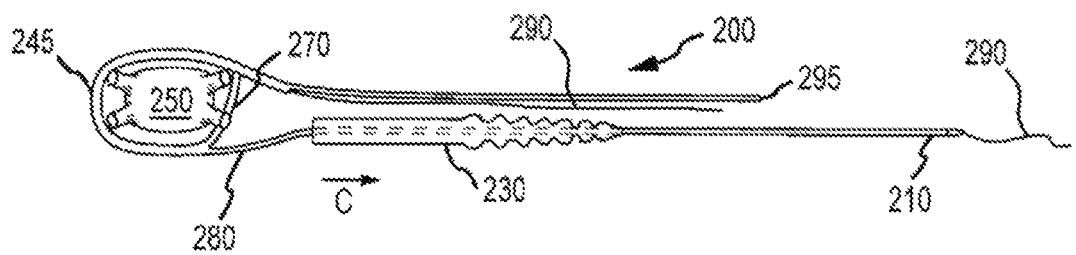

FIGS. 2A-2C illustrate aspects of a spring-loaded free-tip electrode, according to embodiments of the present invention. FIG. 2A shows an ablation system 200 that involves a sheath containing a free tip in a parallel position. System 200 includes a distal end 210, a proximal end 220, a sheath 230, a distal element 240, a tip 270, and a trunk section 280. In some embodiments, system 200 may optionally include a formed or preformed bend or curve 260. Ablation system 200 also includes an ablation member 290 in operative association with a placement or stabilizer member 295. Further, ablation system 200 can include one or more curvable sections or portions than can conform to the shape of any of a variety of tissue surfaces. For example, a curvable portion may be disposed along a length of the ablation system, between a location near distal end 210 and a location near proximal end 220. In some cases, a curvable portion may include a formed bend 260. Tip 270 may be biased to extend laterally or away from trunk section 280, and can be constrained by sheath 230 so as to be aligned in parallel with trunk section 280. In use, an operator or surgeon can advance a distal end 210 of system 200 around a tissue or organ 250 such as a heart, as depicted by A arrows. For example, a surgeon can advance system 200 through or near a transverse pericardial sinus 252, circumferentially around the pulmonary veins 254, and through or near an oblique pericardial sinus 256. The operator can facilitate placement of system 200 by engaging or grasping distal element 240 and maneuvering distal end 210. In some embodiments, distal element 240 includes a string or tape which the operator can grasp with a maneuvering mechanism such as a pair of forceps. Optionally, distal end portion 210 may include a magnetic material or a material that can be attracted by a magnet, such as iron or steel. In some cases, ablation system can be used in conjunction with an introducer obturator system, and discussed elsewhere herein. As depicted in FIG. 2B, ablation system 200 can be further wrapped around tissue 250, as depicted by Barrow, such that bend 260 is disposed at or near the tissue. As shown here, the contour of bend 260 is similar to or conforms with the shape of the tissue 250. Bend 260 can include a molded curve. In some cases, a molded-in curve presents a tight radius. As shown in FIG. 2C, sheath 230 can be partially retracted, withdrawn, or translated longitudinally relative to other elements of the system as indicated by arrow C, and free tip 270 can pop out into a functional position. For example, tip 270 can be biased so that when constraining forces provided by sheath 230 are removed, tip 270 can extend away from trunk 280 and adopt a shape that conforms with or is similar to the shape of tissue 250. Optionally, this shape can be a preformed or memory shape. The shape may present a radius of curvature in a range from 0.25" R to 0.3" R, for example. In some cases, the curvature might be similar to bend 260 such that it also conforms with the shape of the tissue 250. In this way, ablation system 200 forms a loop structure 245 that can be used to administer a circular or closed ablation treatment to the patient. Releasing tip 270 from the stressed or high energy state, and allowing it to adopt a more low energy state, operates to cinch or tighten an ablation element toward the patient tissue. By encircling or enclosing portion of the patient tissue, the operator can apply energy to create closed ablation pattern. If needed or desired, the operator can adjust the shape or overall circumference of loop structure 245, and therefore can adjust the shape or overall circumference of a box lesion that is formed in the tissue. As noted above, ablation system 200 includes an ablation member 290 in operative association with a placement or stabilizer member 295. Placement member 295 can assist in holding ablation member 290 against or near tissue 250 so as to enhance lesion formation. In some embodiments, ablation member 290 includes a radiofrequency cable, and placement member 295 includes a suction tube. Ablation system 200 is well suited for use in creating transmural ablations that extend through or affect the entire thickness of a tissue wall, for example.

Figure 3A:
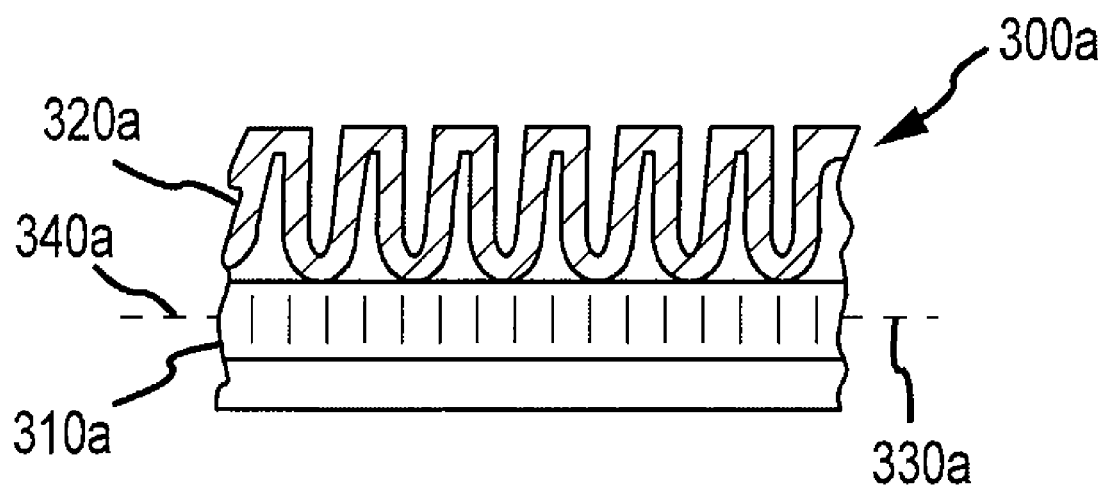
FIGS. 3A-3B show aspects of a flexible backbone configuration according to embodiments of the present invention.
Figure 3B:
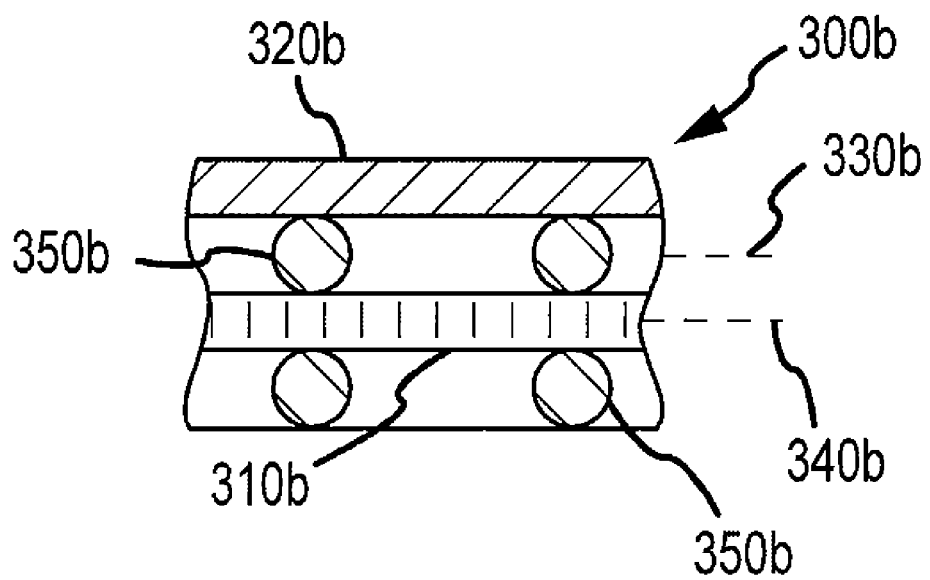

As noted above, an ablation system can have a plurality of curvable or deformable portions or sections. Curvable sections can facilitate the placement of the ablation system on the tissue. FIGS. 3A and 3B show aspects of a flexible backbone configuration according to embodiments of the present invention. FIG. 3A shows a side-view cross-section of a curvable section 300a of an ablation system according to some embodiments. Curvable section 300a includes an ablation member 310a, such as an electrode, in operative association with a placement or stabilizer member 320a. In this embodiment, curvable section 300a presents a flex center-line 330a which is co-axially aligned with the ablation member 310a. For example, a central longitudinal axis 340a of ablation member 310a can be aligned with flex center-line 330a of curvable section 300a. In some cases, the bending center of mass of the curvable section can be aligned with the bending center of mass of the ablation member. Stabilizer member or backbone 320a can include or provide a suction mechanism that allows a surgeon to securely apply the ablation system to a patient tissue. As seen here, the cross-section of stabilizer member 320a presents a serpentine or accordion-like configuration. The profile of the stabilizer member presents a series of undulating, or rising and falling, wave-like projections. The undulating accordion-like configuration allows the stabilizer to be placed against or near any of a variety of curved or irregular surfaces without inducing or increasing distortion or buckling in the stabilizer, as discussed elsewhere herein. Relatedly, the accordion-like configuration can prevent or inhibit distortion or buckling in a molded bend portion of a stabilizer member. Such distortion or buckling can lead to the development of air gaps along the length of the stabilizer member, between the stabilizer member and the patient tissue. Hence, the buckling may prevent a desired seal from forming between the stabilizer member and the patient tissue. The corrugated profile of stabilizer member 320a can reduce the amount of residual stress that may otherwise be created when the stabilizer member is bent. The application of increasing amounts of suction can help to offset of overcome the effects of such residual stress. Hence, relatively little or no suction may be needed to conform the stabilizer with a curved tissue surface when the stabilizer member 320a is sufficiently flexible, and this corrugated profile can significantly contribute to such flexibility. In general, is it often desirable to avoid or minimize deformations in the sealing members, whether induced by motion or inherent in the shape of the stabilizer, so that a seal can be created and also so that the seal can be maintained when 'gross scale' pushing or tugging movements on the system are incidentally produced during a procedure. In some cases, a curvable portion having a first flexibility over the length of the curvable portion can include a molded curve that has a flexibility over the length of the molded bend, where the length of the curvable portion is greater than the length of the molded bend, and the flexibility over the length of the curvable portion is greater than the flexibility over the length of the molded bend.

FIG. 3B shows a side-view cross-section of a curvable section 300b of an ablation system according to some embodiments. Curvable section 300b includes an ablation member 310b, such as an electrode, in operative association with a placement or stabilizer member 320b. In this embodiment, curvable section 300b presents a flex center-line 330b which is axially offset with the ablation member 310b. For example, a central longitudinal axis 340b of ablation member 310b can parallel or substantially parallel to, but axially offset from, flex center-line 330b of curvable section 300b. As shown here, curvable section 300b includes one or more attachment members 350b, such as o-rings, which couple ablation member 310b with stabilizer member 320b. In some embodiments, an attachment member includes silicone retention loop. An attachment member can include a partial ring that is coupled with the ablation member and the stabilizer member. For example, an attachment member can include one half of an o-ring, or a 210 degree section of an o-ring. In some cases, the o-ring may contact the tissue during treatment. Due to current spread, convective heat, and wedge effects, an ablation system can deliver ablative treatment to patient tissue even where an ablation member is separated from the patient tissue by an attachment member. Stabilizer member 320b can include a suction mechanism that allows a surgeon to securely apply the ablation system to a patient tissue.

Figure 4A:
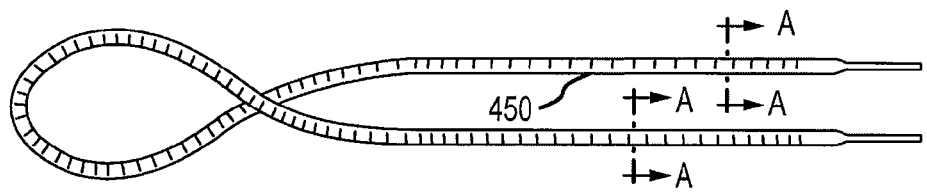
FIGS. 4A-4E show aspects of an obturator ablation system according to embodiments of the present invention.
Figure 4B:
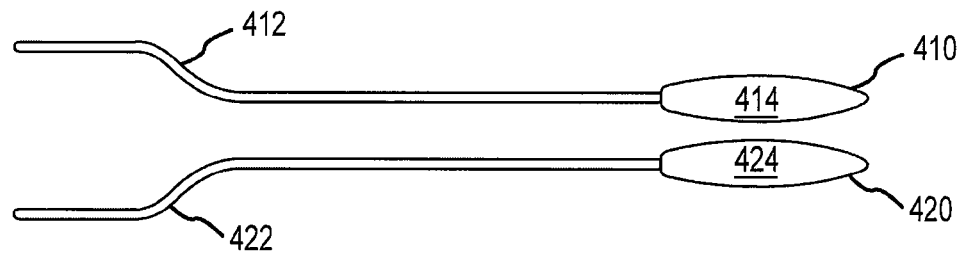
Figure 4C:
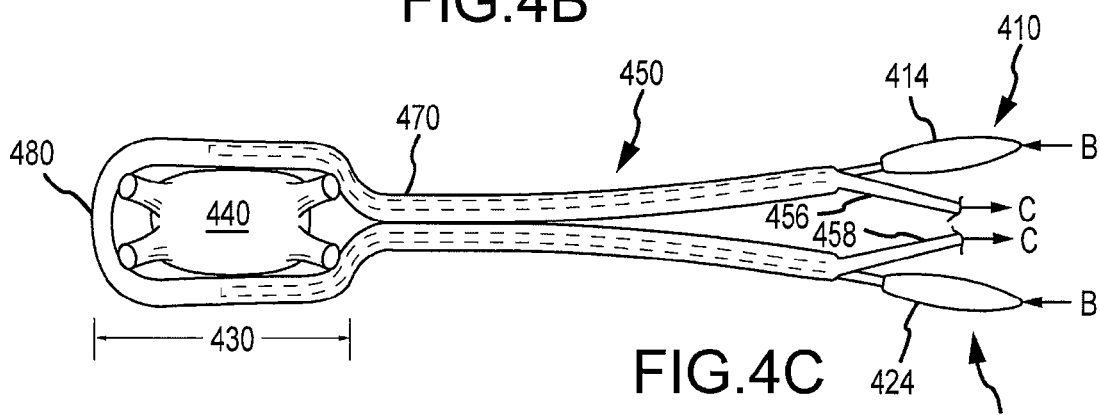

FIGS. 4A-4E show aspects of an obturator ablation system according to embodiments of the present invention. In some cases, an obturator system can include an overwrapped mold with double obturators. An obturator ablation system can also include an ablation member and a stabilizer member. As shown in FIG. 4A, an obturator system component 450 can present a standard shape, and a curved length can provide a "push-pull" ability. The hash marks indicate the location or presence of an ablation member, such as an electrode, on that side of the system. As shown in FIG. 4B, in some embodiments obturator system 450 includes a pair of curved obturators or stylets 410, 420 which an operator can slide into a receptacle or hole of a stabilizer member of the obturator system. Preformed obturators 410, 420 can have proximal handles 414, 424, and can present opposing distal bends or molded shapes 412, 422. Typically, the obturators or stylets are more rigid than the stabilizer member. Thus, the preformed stylets are inserted into a flexible stabilizer member, the stabilizer member conforms with the shape of the stylets. As shown in FIG. 4C, an obturator can be advanced into a stabilizer member to a depth so as to curve or form the flexible stabilizer or suction member into close proximity with itself at location 470. In some cases, location 470 may be disposed on the side of the left atrium (LA) nearest to a thoracotomy. The obturator ablation system can be used within a patient in accordance with the techniques described in U.S. Provisional Patent Application No. 61/015,472 filed Dec. 20, 2007, the contents of which are incorporated herein by reference for all purposes. It is further understood that in some cases the obturators can be inserted one at a time into the stabilizer after the stabilizer is routed around the tissue. Obturators 410, 420 can be advanced or retracted relative to the stabilizer member to shorten or lengthen the length 430 of a loop or race track structure 480. For example, an operator can advance the obturators toward the patient tissue by grasping and pushing handles 414, 424 in the direction indicated by arrows B. Similarly, the operator can fix or retract the stabilizer member relative to the obturators by grasping and holding or pulling end portions 456, 458 of the stabilizer member as indicated by arrows C. In this way, the operator can slide the obturators deeper into the stabilizer member so as to adjust the configuration of loop structure 480. When the configuration of loop structure 480 is adjusted as desired or needed and the ablation member is placed at or near the tissue, the operator can transmit ablative energy through the obturator ablation system to create a box lesion at tissue 440.

Figure 4D:
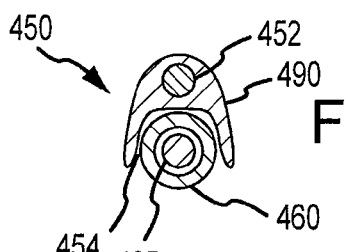
Figure 4E:
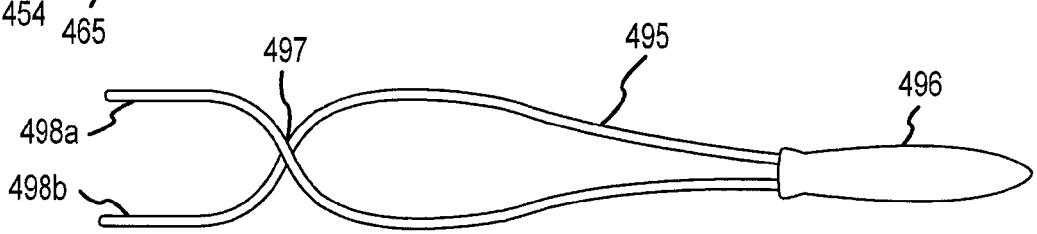

FIG. 4D shows a cross-section view of a portion A-A of FIG. 4A. As depicted here, a stabilizer member 490 of ablation system 450 includes a hole, receptacle, or channel 452 that is configured to receive an obturator, and a recess or receptacle 454 that is configured to receive an ablation member or mechanism 460 which may include an electrode 465. In some cases, electrode 465 is exposed at one or more locations. Ablation member or mechanism 460 may include or be coupled with an intermittent loop, such as an o-ring, that is attached to or coupled with member 490 and holds electrode 465 in a desired orientation. According to the embodiment shown in FIG. 4E, an obturator 495 can present a double shish kabob configuration having a single handle 496, or alternatively two handles, and two preformed tongs 498a, 498b. Such a configuration can have pivots where tongs cross 497 or at another spot or in multiple spots to provide a spreading or clamping action at the pulmonary veins. Pivoted designs can enable the operator to squeeze the obturators 495 together to produce a similar motion at tongs 498a and 498b inside the body. Multiple pivots may give a 'motion vs. distance traveled' advantage or a lower profile outside the body. According to some embodiments, an unpivoted design can produce the opposite motion at the tongs such that a spreading motion of obturators 495 outside the body produce a squeezing motion at the tongs.

Figure 5A:
FIGS. 5A-5G show aspects of an obturator ablation system according to embodiments of the present invention.
Figure 5B:
Figure 5C:
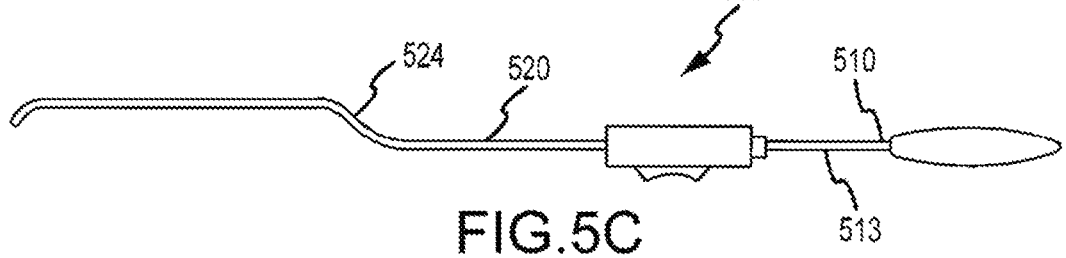
Figure 5D:
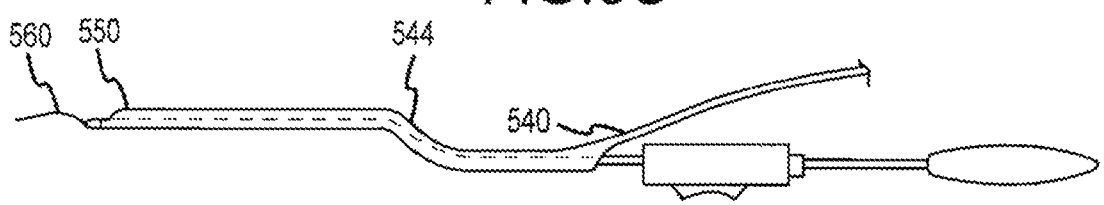
Figure 5E:
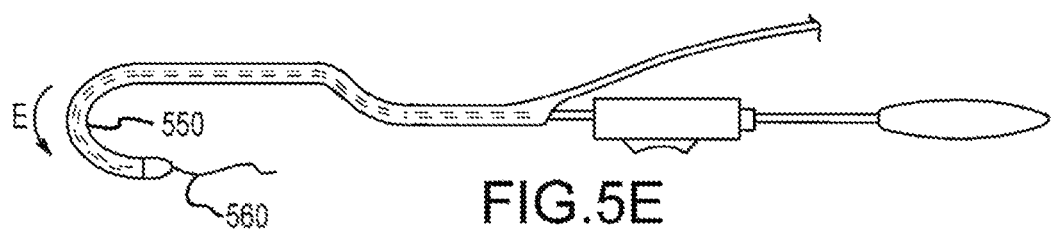
Figure 5F:
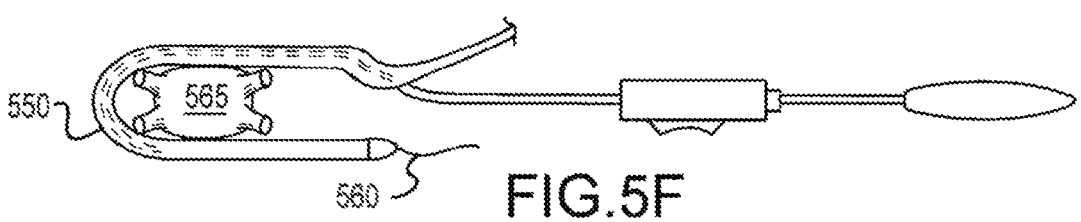
Figure 5G:
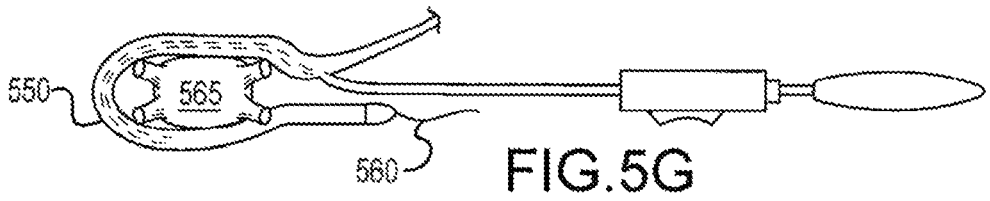

FIGS. 5A-5G show aspects of an obturator ablation system according to embodiments of the present invention. Such systems can involve a stationary curve based on a steerable sheath and an obturator. FIG. 5A illustrates an obturator 510 having a handle 512 coupled with a tong 513. As shown here, preformed tong 513 includes a preformed bend 514. FIG. 5B illustrates a steerable sheath 520 having a handle 522 and a flexible casing 524. The flexible casing may include a preformed curve or bend 526. As depicted in FIG. 5C, an operator can construct the obturator assembly 500 by inserting obturator tong 513 into sheath 520. Typically, the obturator tong is more rigid than the sheath casing. Accordingly, the shape of casing 524 can conforms with the shape of the bent tong, so as to provide a complementary bend 524 in the casing. In some cases, both an obturator and a steerable sheath can be provided in a pre-assembled configuration. As depicted in FIG. 5D, an ablation system can slide over the combined sheath and obturator, so as to create a bend 544 in the ablation system. The ablation system 540 can be inserted across the left atrium of a patient's heart. An operator can facilitate placement of ablation system 540 by engaging or grasping distal element 560 and maneuvering a system distal end 550. In some embodiments, distal or grasping element 560 includes a string or tape which the operator can grasp with a maneuvering mechanism such as a pair of forceps. FIG. 5E shows that distal end 550 can be advanced or steered as depicted by arrow E. In this way, ablation system 540 can be further wrapped around a patient tissue 565, such that the bend is disposed at or near the tissue. As shown here, the contour of the bend is similar to or conforms with the shape of the tissue 565. As shown in FIG. 5F, it is possible to slide the device around a curve, for example around a tissue 550, as depicted by arrows F. According to FIG. 5G, a distal end of the assembly or system can be pushed in to make or enhance tissue contact. The obturator can be pushed or manipulated to move the curve against one or more PV s. The obturator ablation system can be used within a patient in accordance with the techniques described in U.S. Provisional Patent Application No. 61/015,472 filed Dec. 20, 2007, the contents of which are incorporated herein by reference for all purposes.

Figure 6A:
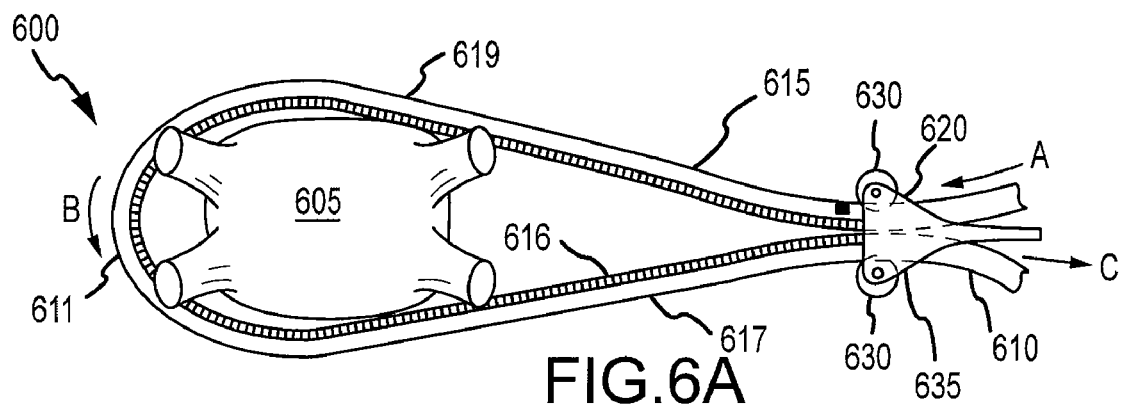
FIGS. 6A-6D illustrate aspects of an ablation system having a cinching device according to embodiments of the present invention.

FIGS. 6A-6D illustrate aspects of an ablation system according to embodiments of the present invention. FIG. 6A shows that an ablation system 600 can be wrapped around a patient tissue 605, such as a heart or other cardiovascular tissue, and a distal end 610 of the system can be pulled or passed through a cinching device 620. Ablation system 600 includes a flexible ablation assembly 615 and a cinching device 620. Ablation assembly 615 can be used to deliver energy to the patient tissue 605 in order to ablate the tissue. In some embodiments, ablation assembly 615 includes an ablation member 616, such as an electrode, coupled with a stabilizer member or backbone 617. In some embodiments, ablation assembly 615 might include any suitable ablation mechanism designed to deliver different forms of energy, including, but without limitation to, RF, thermoelectric, cryogenic, microwave, laser, ultrasound or the like. In some embodiments, stabilizer member 617 includes a flexible backbone member coupled with the ablation member. An operator can use cinching device 620 to help increase or modulate the amount of contact between ablation member 616 and the patient tissue 605. Cinching device 620 may come in many different configurations and is not limited to those depicted in the figures. As shown here, cinching device 620 can include two rollers 630, coupled with a support or support plate 635. In some embodiments, support 635 may include one or more support plates. In some embodiments, cinching device 620 may include a plurality of rollers 630. Optionally, cinching device 620 may include a first support and a second support plate, and a plurality of rollers disposed at least partially therebetween. Accordingly, support plates can provide support to the rollers. In some cases, elements of cinching device 620 may include insulating or non-conducting materials.

In use, an operator can pass or place ablation assembly 615 through cinching device 620 between rollers 630 a first time, as indicated by arrow A. The ablation assembly can then be wrapped around the patient tissue 605 as indicated by arrow B, and distal end 610 of the ablation assembly can then be pulled back or passed through cinching device 620 between rollers 630 a second time, as indicated by arrow C. As shown here, an intermediate portion 611 of ablation assembly 615 can thus be wrapped around patient tissue 605, which may include a heart or other cardiovascular tissue, and distal end 610 of the ablation assembly 615 can be pulled or placed through cinching device 620 such that ablation assembly 615 forms a loop structure 619.

Figure 6B:
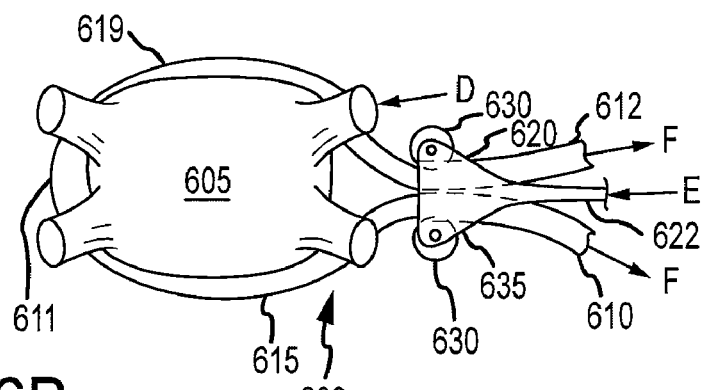
Figure 6C:
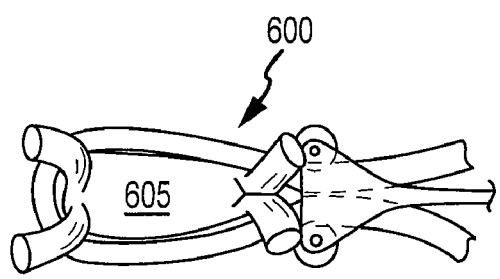
Figure 6D:
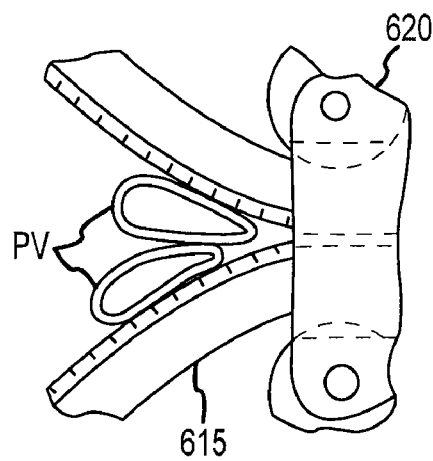

As depicted in FIG. 6B, a loop structure around the patient tissue can be tightened by a cinching procedure, for example by advancing the cinching device toward the tissue. Loop structure 619, which typically includes intermediate portion 611, can be tightened around the patient tissue 605 by advancing the cinching device 620 along the ablation assembly 615, as indicated by arrow D. For example, an operator can grasp or control a handle or pull rod 622 of cinching device 620 so as to move the handle toward the tissue as indicated by arrow E. Relatedly, an operator can grasp or control section 610 or section 612 of ablation assembly 615, or both, so as to positionally fix ablation assembly 615 or provide an opposing force to the handle operation described above, as indicated by arrow F. FIGS. 6C and 6D depict the ablation system 600 after the cinching device 620 has been advanced even further along ablation assembly 615 toward the tissue, so as to increase contact between ablation assembly 615 and patient tissue 605. Hence, when the operator has position cinching device 620, the system is ready to have energy applied through the ablation member 616 of ablation assembly 615, toward patient tissue 605. The operator can position ablation assembly 615 to make contact with selected parts of patient tissue 605 such that when ablative energy is transmitted through the ablation assembly, it is possible to create an approximately circular or closed ablation pattern or lesion on the tissue. In this way, energy can be applied by the ablation system to the tissue, as indicated by FIGS. 6C and 6D. The position of cinching device 620 relative to ablation assembly 615 can be adjusted by the operator. For example, the cinching device may be advanced or retracted to differing degrees in order to increase or decrease an amount of contact between the ablation assembly and the patient tissue. As shown in FIG. 6D cinching device 620 may pinch portions of the patient tissue if used or designed improperly due to improper positional placement, application of excessive force, or the like, as depicted by the cross sections of the compressed pulmonary veins. In some cases, the device may temporarily flatten a portion of the vessel walls together at the area where they join the atrial heart chamber so that a transmural lesion can be produced. According to some embodiments, the stabilizer placement may be preferably only on the atrial walls encircling the PV s, although this may not always be the case. If the suction stabilizer includes a portion of the root of one or more vessels as the stabilizer enters the cinching device, a continuous lesion may still be achieved by flattening the vessel walls together. For example, cinching device 620 may impinge upon pulmonary veins (PV) of the patient, so as to pinch or squeeze them to a teardrop or collapsed shape. In some cases, if the cinching device is not placed sufficiently close to the patient tissue or if the loop structure does not sufficiently encircle the patient tissue, a discontinuous gap will occur in the tissue lesion after the ablative energy is applied. In some embodiments, a deeply transmural technique can offset or minimize what could otherwise be significant gaps in an ablation pattern when released. According to some embodiments, a transmural lesion can be defined as a lesion that extends all the way through a tissue wall. In some cases, a transmural lesion guarantees a break in the propagation an the aberrant electrical signal. According to some embodiments, a surgical procedure can involve forming a lesion that is both transmural and continuous. If the device must cross the vessel even just partially, it may be desirable to collapse the walls to create transmurality across the double wall thicknesses. It may also be desirable to stay off the PV's proper but to create a lesion on the atria close to their 'roots'.

Figure 7A:
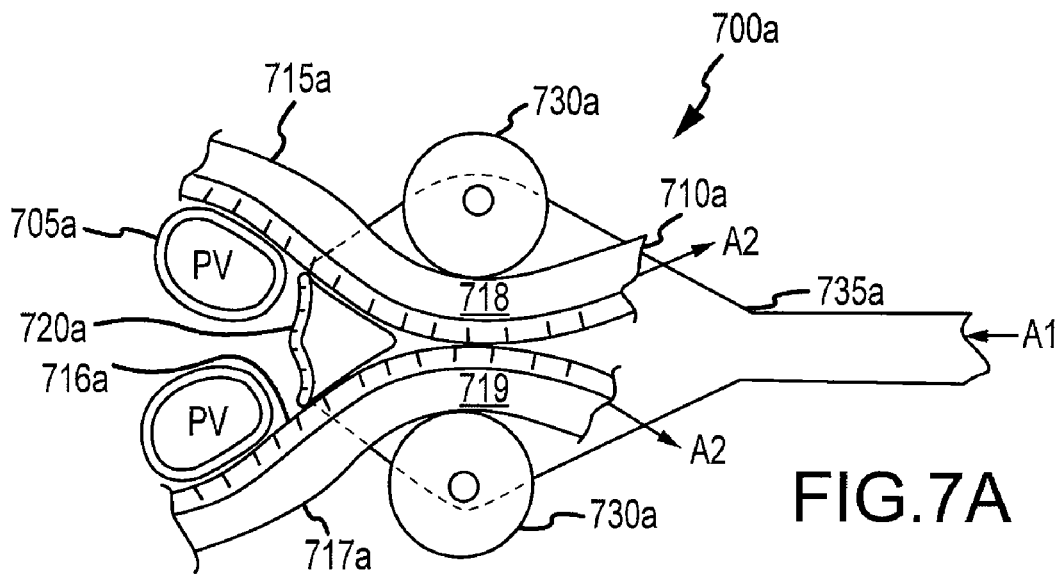
FIGS. 7A-7C show aspects of ablation system having a cinching device with guides according to embodiments of the present invention.
Figure 7B:
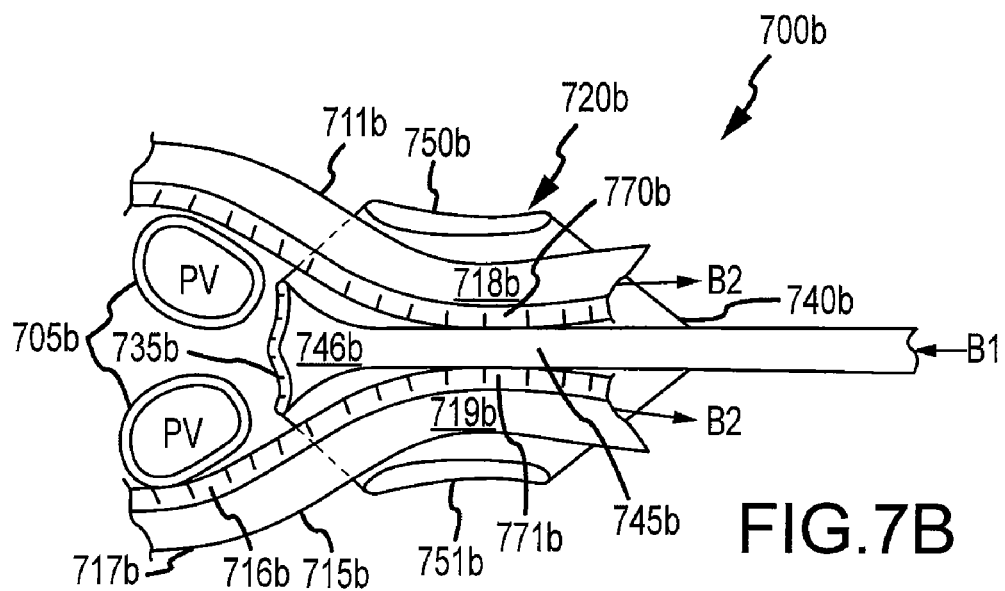
Figure 7C:
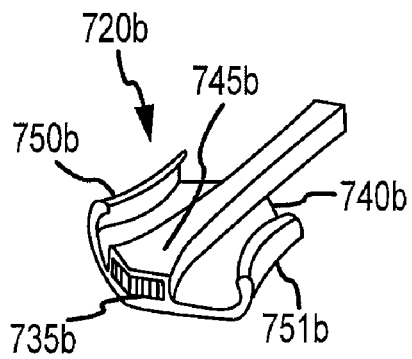

FIGS. 7A-7C show aspects of ablation systems according to embodiments of the present invention. An ablation system 700*a* is depicted in FIG. 7A. Ablation system 700 includes an ablation assembly 715*a* and a cinching device 710*a*. Ablation assembly 715*a* includes an ablation member 716*a* and a stabilizer member 717 *a*. Cinching device 710*a* includes or is coupled with an ablation segment 720*a* such as a corner electrode. Cinching device 710*a* includes a support 735*a* and one or more rollers 730*a*. Ablation segment 720*a* can be coupled with support 735*a* as part of cinching device 710*a*. Ablation segment 720*a* may be positioned on support 735*a* toward a distal end of cinching device 710*a*, so that when an operator or surgeon advances cinching device 710*a* towards pulmonary veins (PV) of patient tissue 705*a*, ablation segment 720*a* can make contact with the atria adjacent to the pulmonary veins. In some embodiments, ablation segment 720*a* can be used to help insure or increase the likelihood that the ablation system ablates the patient tissue 705*a* in an approximate or complete circle or closed path around the patient tissue. Ablation segment 720*a* can be designed to bridge the gap between opposing sides of ablation element 716*a*, so that a loop structure is formed in more of a smooth circumferential path and in less of a teardrop shaped path. Ablation segment 720*a* can thus be used to bridge a gap that might otherwise exist between ablation member 715*a* and patient tissue 705*a*. In some embodiments, ablation member 716*a* may be coupled with ablation segment 720*a*. In some embodiments, the ablation segment or member may include a material that is capable of transmitting different forms of energy, including but not limited to RF, thermoelectric, cryogenic, microwave, laser, ultrasound, or the like. In some embodiments, ablation segment 720*a* can be positioned in order to inhibit the ablation assembly 715*a* from pinching the patient tissue 705*a* as depicted in FIG. 6D.

In some embodiments, the ablation segment 720*a* may be shaped in order to maximize contact with the patient tissue 705*a*. In some embodiments, the ablation segment 720*a* may be shaped in order to minimize or reduce any pinching of the patient tissue 705*a*. Ablation segment 720*a* may be rigid in some embodiments. Ablation segment 720*a* may be flexible in some embodiments. Ablation segment 720*a* may make contact with the ablation member 716*a*. Optionally, ablation segment 720*a* may not make contact with the ablation member 716*a*. Cinching device 710*a* can be advanced in a direction toward the patient tissue 705*a* as indicated by arrow A1, to increase the amount of contact between ablation member 717*a* and the patient tissue 705*a* or to help secure the position of ablation member 717*a* relative to patient tissue 705*a*. Similarly, by advancing cinching device 710*a* in this direction, an operator can increase the amount of contact between ablation segment 720*a* and the patient tissue 705*a* or help secure the position of ablation segment 720*a* relative to patient tissue 705*a*. The operator can also establish or apply an opposing force by grasping or pulling sections 718*a*, 719*a* of ablation assembly 715*a* in an opposing direction, as indicated by arrows A2. The operator can position ablation assembly 715*a* to make contact with selected parts of patient tissue 705*a* such that when ablative energy is transmitted through the ablation assembly, it is possible to create an approximately circular or closed ablation pattern or lesion on the tissue. In this way, energy can be applied by the ablation system to the tissue. The position of cinching device 710a relative to ablation assembly 715a can be adjusted by the operator. For example, the cinching device may be advanced or retracted to differing degrees in order to increase or decrease an amount of contact between the ablation assembly and the patient tissue. Ablation segment 720a in combination with ablation member 716a can form a continuous circumferential loop that can be used to ablate a circumferential lesion on the patient tissue.

As shown in FIGS. 7B and 7C, an ablation system 700b can include a cinching device 720b and an ablation assembly 715b. Cinching device 720b can include one or more guides 750b, and can be used in operative association with an ablation assembly 715b having an ablation member 716b and a stabilizer member 717b. Cinching device 720b can also include an ablation member protection mechanism 745b which can be disposed between portions 770b and 771b of ablation member 716b. Hence, it is possible to avoid contact between different portions of an ablation member such as an electrode. One or more guides 750b, 751b of cinching device 720b may include a flat or curved retaining wall perpendicularly attached to, or formed along with, a support 740b of cinching device 720b. In some embodiments, one or more guides 750b, 751b may have a curved top edge. The shape of guides 750b, 751 b can be designed in order to help facilitate positioning an ablation assembly 715b around the patient tissue 705b by keeping distal 771b and proximal 770b segments of the ablation member 716b close to each other. In an embodiment with two or more guides, the guides may be located on opposite sides of a support plate of cinching device 720b. In one method for using the cinching device 720b with guides, ablation assembly 715b can be passed through the cinching device along one guide 750b and then wrapped around the patient tissue 705b. The ablation assembly 715b can then be pulled through cinching device 720b in the opposed direction, passing along another guide 751b. The guides may be made of or include various semi-rigid or rigid materials. Cinching device 720b can be advanced in a direction toward the patient tissue 705b as indicated by arrow B1, to increase the amount of contact between the ablation member 717b and the patient tissue 705b or to help secure the position of ablation member 717b relative to patient tissue 705b. Similarly, by advancing cinching device 720b in this direction, an operator can increase the amount of contact between ablation segment 735b and the patient tissue 705b or help secure the position of ablation segment 735b relative to patient tissue 705b. The operator can also establish or apply an opposing force by grasping or pulling sections 718b, 719b of ablation assembly 715b in an opposing direction, as indicated by arrows B2.

In some embodiments, as cinching device 720b is advanced towards the patient tissue 705b, a loop structure 711b of the ablation assembly 715b is reduced in diameter or otherwise contracted. As shown in FIG. 7B, in some embodiments, an ablation member protection mechanism 745b can be utilized along with the cinching device 720b. Cinching device 720b can include ablation member protection mechanism 745b disposed between guides 750b, 751b. Ablation member protection mechanism 745b can act to keep a first segment 770a and a second segment 771b of the ablation member from making contact with each other. Ablation member protection mechanism 745b may either be fixed or integral to cinching device 720b or separate from cinching device 720b. In some embodiments, an ablation segment 735b may be attached with cinching device 720b, such as with a first or distal section 746b of ablation member protection mechanism 745b. Ablation segment 735b can be utilized to increase the amount of contact between the ablation assembly 715b and the patient tissue 705b. Ablation segment 735b can also be utilized to reduce pinching of the patient tissue 705b that might otherwise occur if ablation segment 735b were not disposed between opposing segments of ablation member 716b. The operator can position ablation assembly 715b to make contact with selected parts of patient tissue 705b such that when ablative energy is transmitted through the ablation assembly, it is possible to create an approximately circular or closed ablation pattern or lesion on the tissue. In this way, energy can be applied by the ablation system to the tissue. The position of cinching device 720b relative to ablation assembly 715b can be adjusted by the operator. For example, the cinching device may be advanced or retracted to differing degrees in order to increase or decrease an amount of contact between the ablation assembly and the patient tissue. Ablation segment 735b in combination with ablation member 716b can form a continuous circumferential loop that can be used to ablate a circumferential lesion on the patient tissue. FIG. 7C shows a perspective view of cinching device 720b which includes ablation member protection mechanism 745b, guides 750b, 751b, and ablation segment 735b.

FIGS. 8A-8E show aspects of an ablation system according to embodiments of the present invention. FIG. 8A shows ablation system 800 having a distal end 810 and a belt loop 820. Optionally, the ablation system may include a peel out electrode 830. Distal end 810 of system 800 is disposed through belt loop 820. FIG. 8B shows a cross-section view of a portion A-A of FIG. 8A. As depicted in FIG. 8C, ablation system 800 can be disposed about a large atria. Similarly, as depicted in FIG. 8D, ablation system 800 can be disposed about a small atria. According to FIG. 5E, ablation system 800 can have a receiving slot 840 adapted to receive peel out electrode 830. With a more detailed reference now to FIG. 8A, ablation system 800 includes a flexible ablation member 880, which may have a peel out portion or electrode 830, an encircling mechanism or catch 820 such as a belt loop, a hook, a closable clasp, or the like, and a flexible stabilizer member or bracing 860 having a distal end 810, a proximal end 870, and a recessed receiving slot or receptacle 840. The combination of the ablation member and the stabilizer member can collectively be referred to as an ablation assembly 890. In use, an operator may treat a patient by wrapping a loop structure 811 of the ablation system around pulmonary veins of a patient. This may involve passing flexible bracing distal end 810 circumferentially around the tissue as indicated arrow A, and through belt loop 820 as indicated by arrow B. The operator may expand or contract ablation system 800 by manipulating the flexible stabilizer member distal end 810. Moving distal end 810 in direction C results in contraction of loop structure 811 of ablation system 800 in a cinching fashion. Moving distal end 810 in direction D results in expansion of loop structure 811 of ablation system 800. Stabilizer member 860 may be made of or include any suitable flexible material, such as a silicone, polyurethane, polycarbonate, another suitable polymer, or combination of polymers or the like.

In some embodiments of use, a surgeon or operator can pass stabilizer member distal end 810 through catch 820, and expand or contract ablation system 800 by manipulating the flexible bracing proximal end 870. Moving proximal end 870 in direction E results in contraction of loop structure 811 of ablation system 800 in a cinching fashion. Moving proximal end 870 in direction F results in expansion of loop structure 811 of ablation system 800. FIG. 8B depicts a cross-section portion A-A of ablation assembly 890 as shown in FIG. 8A. As shown here, receiving slot 840 is located adjacent to ablation member 880. In some cases, receiving slot 840 might be located on either side of ablation member 880. Receiving slot 840 is adapted to receive a distal section or peel out portion 830 of ablation member 880.

As shown in FIG. 8C, a surgeon or operator can detach or separate peel out portion 830 from stabilizer member 860 and insert portion 830 into receiving slot 840, by grasping and manipulating the peel out portion with a positioning device 850. In some cases, a portion of the stabilizer member which is separated from the peel out portion can be inserted through catch 820. A positioning device such as a forceps or grasper can be introduced into the patient via a minimally invasive incision. Positioning device 850 may be used by the operator to detach peel out section 830 from flexible bracing 860 and to insert the detached section of peel out section 830 into receiving slot 840 so that ablation member 880 approximately encircles tissue of a heart. An operator can administer ablative energy through the ablation member to produce a circular or closed ablation pattern or lesion on the patient tissue. Positioning device 850 may include opposable jaws, forceps, clamps or any combination or other suitable means that can be used by surgeon or operator to grasp or hold distal portion 830 of ablation member 880. Positioning device 850 may also be used to position ablation system 800 on the heart or reposition ablation system 800 to perform ablation in multiple locations on a heart. With continued reference to FIG. 8C, a surgeon or operator can use positioning device 850 to insert peel out distal section 830 into receiving slot 840 on the opposite side of flexible stabilizer bracing 860. Ablation system 800 can be used to produce a circular, elliptical, or closed ablation pattern or lesion on a large atria. As shown in FIG. 8D, ablation system 800 may be used to produce an ablation pattern or lesion on a small atria. Because the atria is smaller, a longer section of flexible stabilizer member 860 may be moved though catch 820 in order to snugly fit the ablation assembly around the atria. This may involve a longer section of distal ablation member 830 being inserted into receiving slot 840. By administering ablative energy through the ablation system and to the heart, an operator can use ablation system 800 to produce a circular, elliptical, or closed ablation pattern or lesion on the small atria.

FIG. 8E provides a partial view of ablation system 800. Catch 820 is shown without the distal end of flexible bracing 810 inserted therein. In this embodiment, ablation member section 880 is partial recessed or disposed within a receptacle or slot 850 flexible bracing 860. Receiving slot 840 is shown without a distal section of peel out electrode 830 inserted therein. Ablation member 880 may include one or more mechanisms for providing various types of ablation energy, including RF, thermoelectric, cryogenic, microwave, laser, ultrasound or the like. In one embodiment, ablation may be achieved or enhanced by delivery of one or more drugs to the tissue, and drug delivery can be carried out by any of the systems disclosed herein. Drug delivery can be achieved through mechanical surface contact, chemical reaction or a particular feature set like fine, short 'needle-like' structures that penetrate the surface, for example. Drug delivery may also be enhanced by the surface pressure of the device, the heat generated, the RF energy itself or even the changed physiology of the tissue of the lesion (e.g. via apoptosis, desiccation, cytolysis, etc).

Figure 9A:
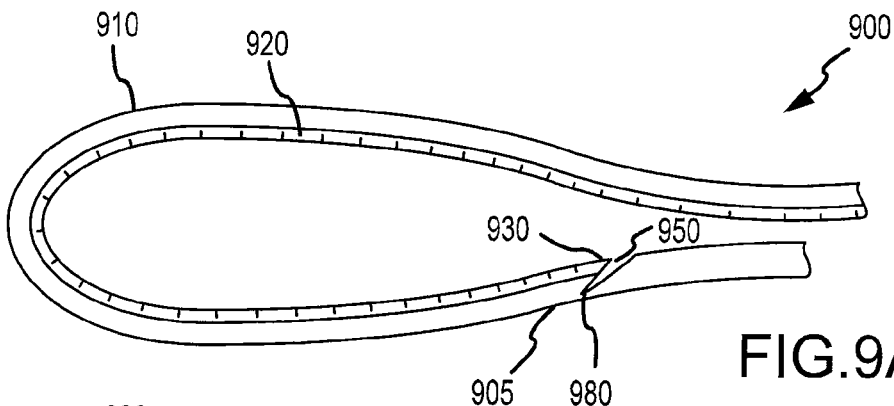
FIGS. 9A-9D show aspects of an ablation system having a flexible device with a breakaway tip according to embodiments of the present invention.
Figure 9B:
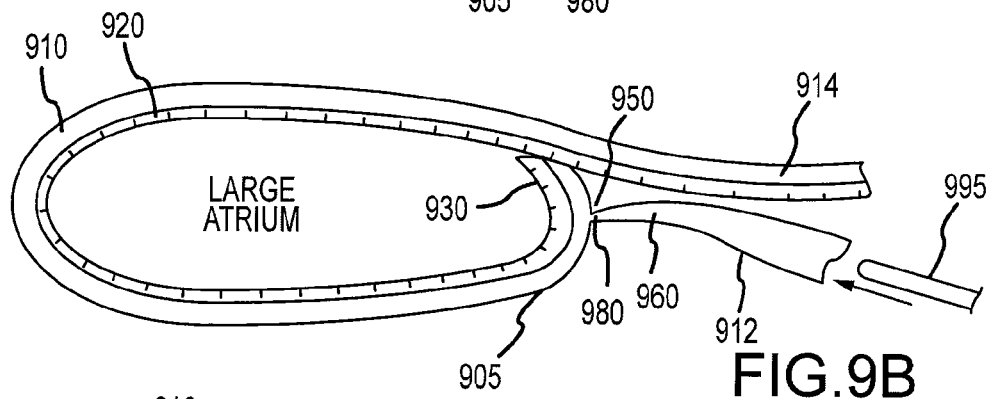
Figure 9C:
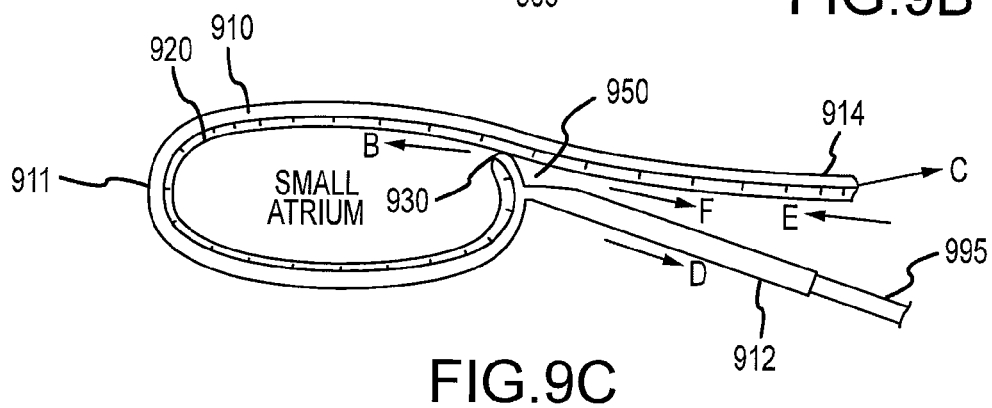

Referring now to FIG. 9A, in some embodiments an ablation system 900 includes a flexible device which includes an encircling mechanism 905 having a breakaway tip 930, a slit 950, and a living hinge 980. Ablation system 900 also includes an ablation member 920 in operative association with a stabilizer member. As shown in FIG. 9B, ablation system 900 can be extended around a large atrium of a patient. In use, a surgeon can insert a stiffening probe 995 into a distal end 912 of stabilizer member 910. By manipulating distal end 912 of stabilizer member 910, or by adjusting proximal end 914 of stabilizer member 910 relative to encircling mechanism 905, an operator can activate hinge 980 and move breakaway tip 930 toward the atrium. This pushing action causes breakaway tip 930 to move away from a portion 960 of the stabilizer member that is located on the opposing side of slit 950. Hence, breakaway tip 930 can bridge a gap that may exist between the ablation member and the tissue surface of the atrium, thereby allowing the ablation member to approximately encircle the tissue. In some cases, slit 950 extends about halfway through a cross section of the stabilizer member. An operator can transmit ablative energy through the ablation member to the tissue, so as to produce an approximately circular, elliptical, or closed ablation pattern or lesion. As shown in FIG. 9C, an operator can use ablation system 900 to apply ablative energy to a small atrium, in a similar fashion. Stiffening probe 995 can be pushed farther toward the heart, in the direction indicated by arrow A, which can cause the expansion of a wider angle defined by slit 950, as hinge 980 opens further and breakaway tip 930 moves more distally along ablation member 920, as indicated by arrow B. Hence, breakaway tip 950 can move closer to the atrium, and ablation member 920 can snugly fit against the atrium. In some cases, it may be desirable to move proximal end 914 of the stabilizer member in the direction indicated by arrow C, which can also effectively move breakaway tip 930 more distally along ablation member 920, as indicated by arrow B. Optionally, the surgeon or operator can move distal portion 912 in the direction indicated by arrow D, or proximal portion 914 in the direction indicated by arrow E, so as to move the breakaway tip more proximally along the ablation member, as indicated by arrow F. In this way, by manipulating aspects of the system such as the distal end or the proximal end of a stabilizer member, an operator can adjust the size of a loop structure 911 provided by the ablation system. In some instances, the ablation member may be adjusted to contact epicardial tissue directly adjacent to the base or ostia of one or more pulmonary veins. In some instances, the ablation member may be adjusted so that a gap exists between the ablation member and the pulmonary veins.

Figure 9D:
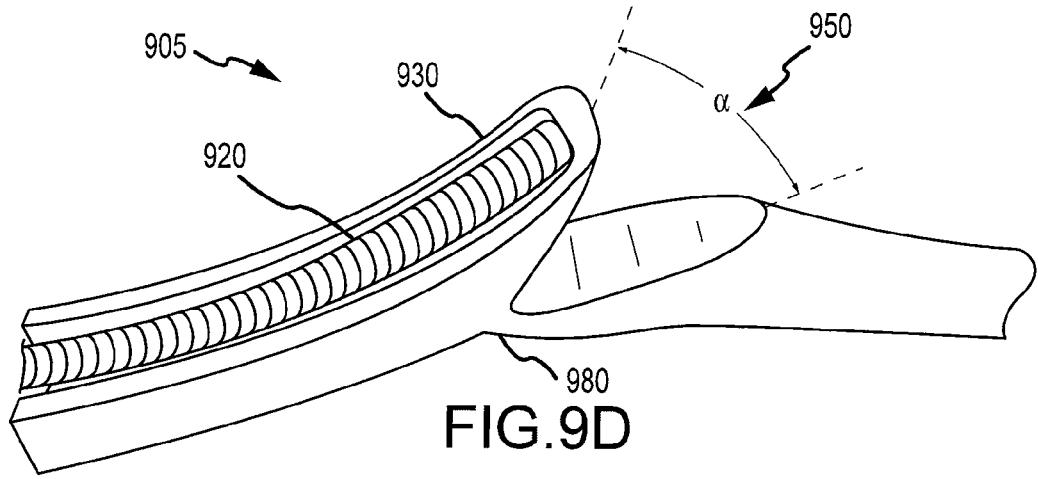

FIG. 9D provides a close-up view of encircling mechanism 905 of the ablation system, which includes breakaway tip 930, slit 950, and living hinge 980. In some embodiments, ablation member 920 extends to the distal end or nearly to the distal end of breakaway tip 930. By manipulating aspects of the system, such the distal end or the proximal end of an ablation assembly, an operator can adjust an angle α of defined by slit 950. Hence, it is possible to conform the ablation member with a contour presented by a patient tissue. When the ablation member is placed at or near the tissue, ablative energy can be transmitted through the ablation member to the tissue, thus ablating at least a portion of the tissue to form one or more lesions.

Figure 10A:
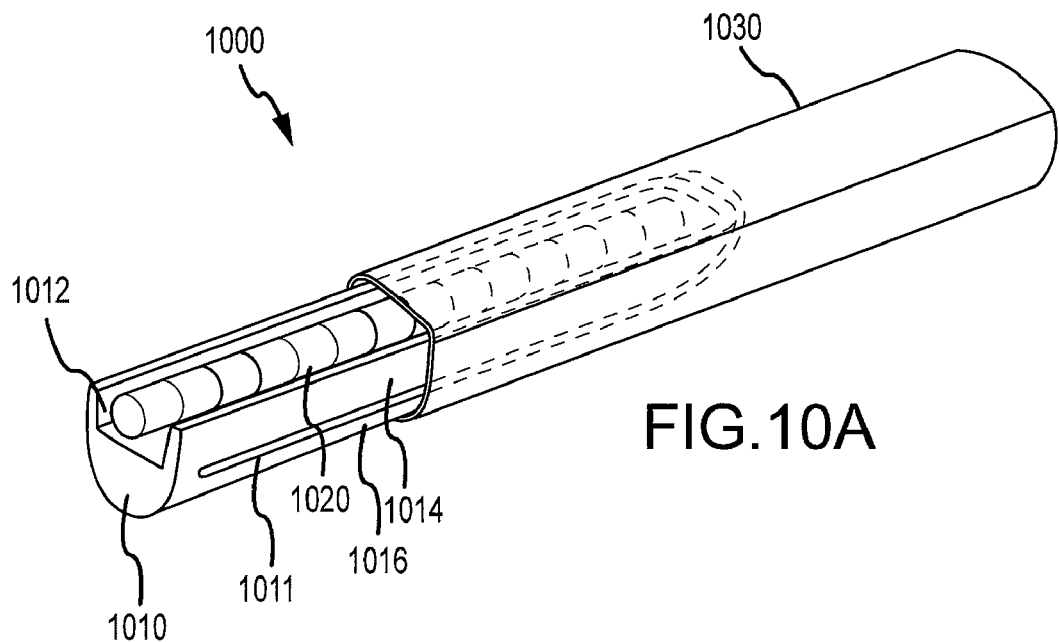
FIGS. 10A-10F show aspects of an ablation system with a stabilizer mechanism according to embodiments of the present invention.
Figure 10B:
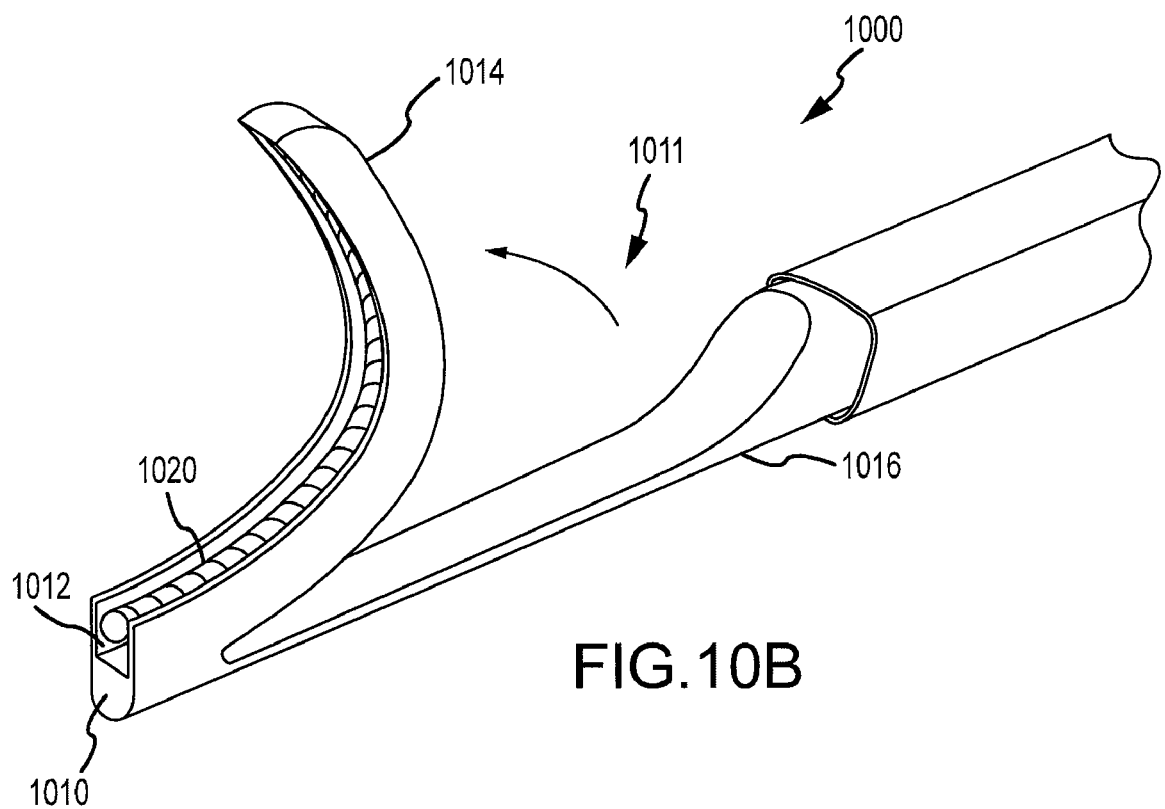
Figure 10C:
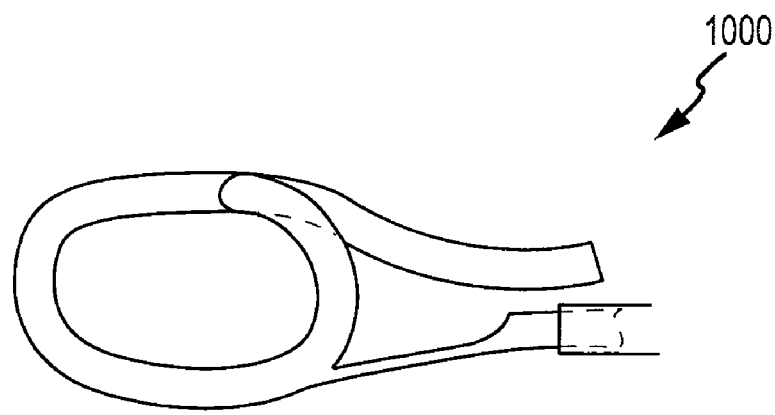
Figure 10D:
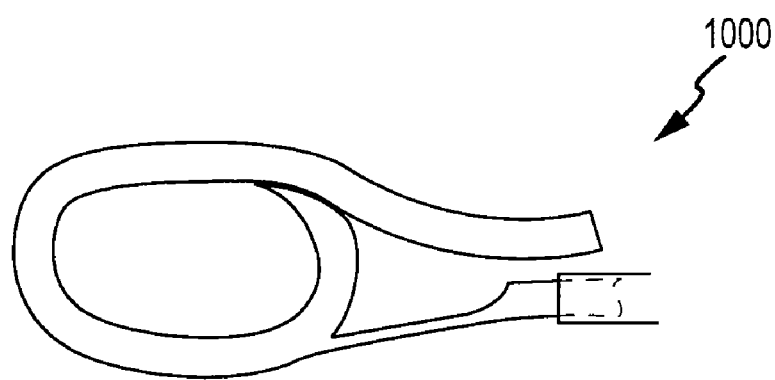
Figure 10E:
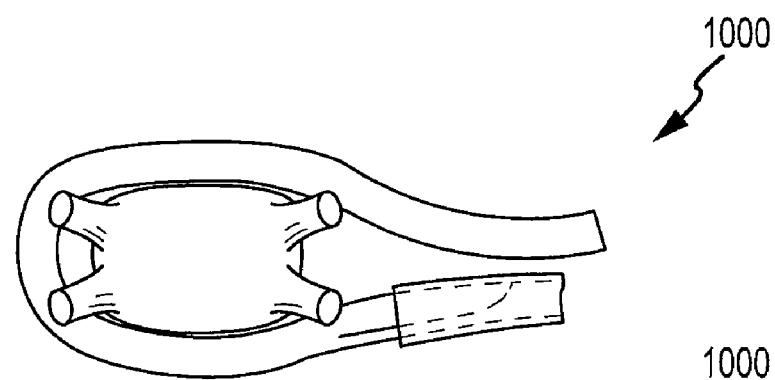
Figure 10F:
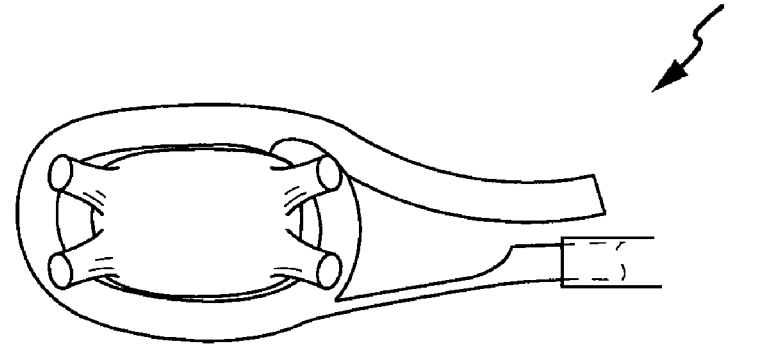

FIGS. 10A to 10F show partial views of an ablation system 1000 according to embodiments of the present invention. As shown in FIG. 10A, ablation system 1000 includes a stabilizer member 1010 having a slit 1011, and an ablation member 1020 disposed within a recess 1012 of the stabilizer member. The stabilizer member also includes a breakaway tip portion 1014 and a trunk portion or tether band 1016, whereby the breakaway tip is separated from the trunk portion by slit 1011. Trunk portion 1016 may be reinforced with a braid or ribbon material. The ablation system also includes a retractable sleeve 1030, which can act to constrain or keep breakaway tip 1014 in close proximity with trunk 1016. Stabilizer member 1010 can be constructed so that breakaway tip 1014 is biased to separate or extend laterally from trunk 1016. Hence, as shown in FIG. 10B, when the retractable sleeve is moved to fully expose slip 1011, breakaway tip 1014 can move or spring away from trunk 1016, as indicated by arrow A. In this way, breakaway tip 1014 can adopt a natural or relaxed configuration, whereas breakaway tip 1014 may be stressed or constrained when housed within the retractable sleeve. Breakaway tip provides a preformed spring loaded free tip that can be releasably contained in the sleeve. FIG. 10C represents an overlapped configuration and FIG. 10D represents a concentric positioning that remains in the same plane. As shown in FIG. 10E, an operator can wrap ablation system 1000 around a patient tissue or organ 1050 when the sleeve is in an advanced position and breakaway tip is in the constrained configuration. As shown in FIG. 10F, an operator can retract the sleeve in a distal direction, and the breakaway tip can relax toward the heart tissue, and thus the ablation member can form a circumferential loop or closed path about the patient tissue. In this way, an ablation element can be cinched or tightened toward the patient tissue. In some embodiments, an operator can keep the retractable sleeve in a fixed position when applying ablative energy through the ablation member to the patient tissue. As shown here, an operator can slide the retractable sleeve longitudinally along a distal length of the stabilizer member.

As shown in FIGS. 10E and 10F, an operator can use ablation system 1000 to apply ablative energy to cardiac tissue. The retractable sleeve can be pulled further away from the heart, which can allow the breakaway tip to release and adopt its low energy configuration or memory shape. Hence, the breakaway tip can more closer to the atrium, and in a cinching fashion the ablation element is moved toward the patient tissue. As the ablation member is brought snugly against the heart, the desired contact or proximity between the ablation member and the cardiac tissue is achieved. In some instances, the ablation member may be adjusted to contact epicardial tissue directly adjacent to the base or ostia of one or more pulmonary veins. In some instances, the ablation member may be adjusted so that a gap exists between the ablation member and the pulmonary veins. When the ablation member is placed at or near the tissue, ablative energy can be transmitted through the ablation member to the tissue, thus ablating at least a portion of the tissue to form one or more lesions. Such lesions may be formed in the shape of a loop, and ellipse, a circle, or some other closed path configuration. Exemplary techniques also encompass the application of ablative energy or treatment to create a circumferential lesion or box lesion.

Figure 11A:
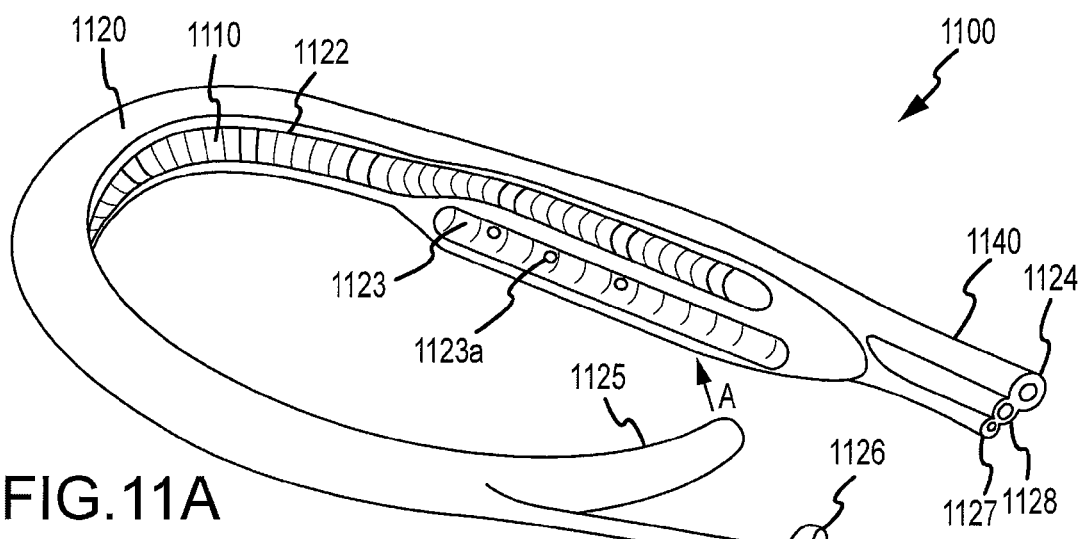
FIGS. 11A-11C show aspects of an ablation system with a stabilizer member according to embodiments of the present invention.
Figure 11B:
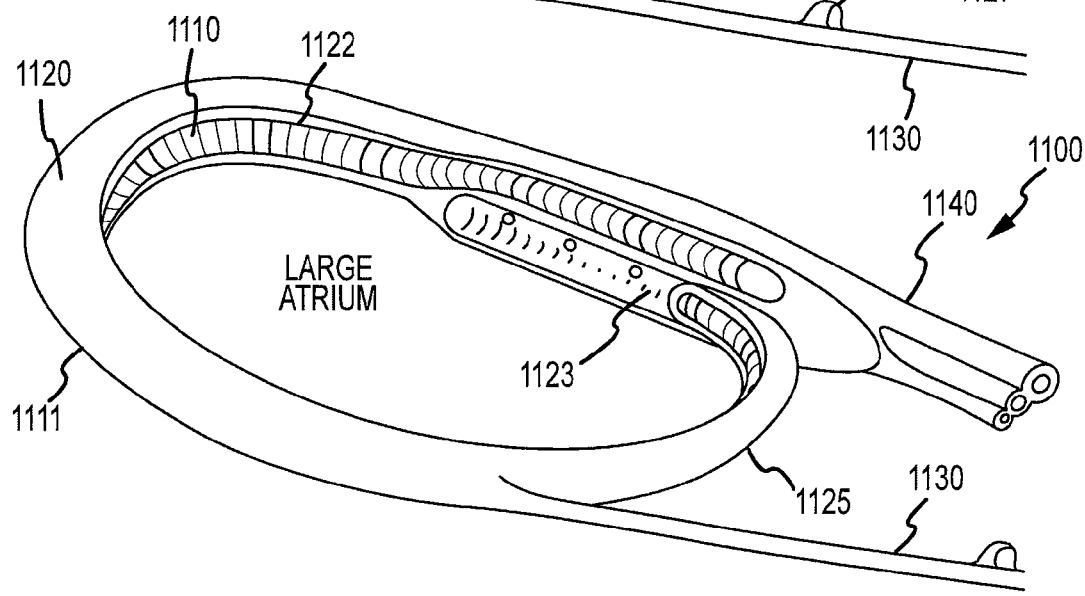
Figure 11C:
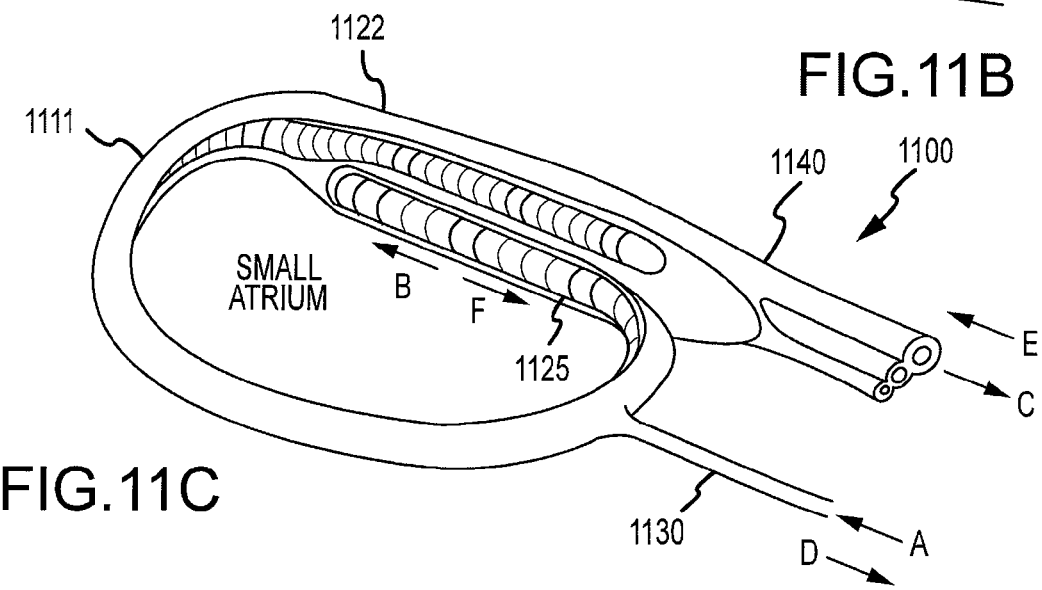

FIGS. 11A to 11C illustrate aspects of an ablation system according to embodiments of the present invention. As shown in FIG. 11A, ablation system 1100 includes an ablation member 1110 in operative association with a stabilizer member 1120. Ablation member 1110 extends through a first port 1124 of stabilizer member, along a first recess 1122 of stabilizer member 1120. Stabilizer member 1120 includes a breakaway tip 1125, and a catch 1126 that is configured to releasably hold the breakaway tip. Breakaway tip 1125 may present a portion of an ablation assembly that is free to move or extend away from an adjacent portion of a stabilizer member. The breakaway tip may include a distal end of an ablation member that is partially housed by a stem section of a stabilizer member. In use, an operator may disengage the breakaway tip from the catch, so that the breakaway tip extends toward a second recess 1123 of stabilizer member 1120, as indicated by arrow A. Stabilizer member 1120 may include one or more pressure lines 1127, 1128, which can be constructed in fluid communication with second recess 1123 via one or more ports 1123a, or with first recess via one or more ports (not shown), or with both the first recess and the second recess. The pressure in the pressure lines can be adjusted so as to provide a positive or negative pressure to the tissue via the ports and recesses. For example, in use an operator may apply a vacuum via a pressure line so as to help seal first recess 1122 with a patient tissue. Similarly, an operator may apply a vacuum via a pressure line so as to help seal second recess 1123 with a patient tissue, or with breakaway tip 1125, or both.

As shown in FIG. 11B, ablation system 1100 can be extended around a large atrium of a patient. In use, a surgeon can manipulate a distal end 1130 of stabilizer member 1120, a proximal end 1140 of stabilizer member 1120, or both. By manipulating distal end 1130 of stabilizer member 1120, or by adjusting proximal end 1140 of stabilizer member 1120, an operator can move breakaway tip 1125 toward the atrium. In this way, an operator can urge breakaway tip 1125 to bridge a gap that may exist between ablation member 1110 and the tissue surface of the atrium, thereby allowing the ablation member to approximately encircle the tissue. As shown here, a distal portion of breakaway tip 1125 inserts into or is placed in close proximity with first recess 1123. An operator can transmit ablative energy through the ablation member toward the tissue, so as to produce an approximately circular, elliptical, or closed ablation pattern or lesion. As shown in FIG. 11C, an operator can use ablation system 1100 to apply ablative energy to a small atrium, in a similar fashion. Distal section 1130 can be pushed farther toward the heart, in the direction indicated by arrow A, which can cause breakaway tip 1125 to move more distally along ablation member 1110, as indicated by arrow B. Hence, breakaway tip 1125 can move closer to the atrium, and ablation member 1110 can snugly fit against the atrium. In some cases, it may be desirable to move proximal end 1140 of the stabilizer member in the direction indicated by arrow C, which can also effectively move breakaway tip 1125 more distally along ablation member 1110, as indicated by arrow B. Optionally, the surgeon or operator can move distal portion 1130 in the direction indicated by arrow D, or proximal portion 1140 in the direction indicated by arrow E, so as to move the breakaway tip more proximally along the ablation member, as indicated by arrow F. In this way, by manipulating aspects of the system such as the distal end or the proximal end of a stabilizer member, an operator can adjust the size of a loop structure 1111 provided by the ablation system. In some instances, the ablation member may be adjusted to contact epicardial tissue directly adjacent to the base or ostia of one or more pulmonary veins. In some instances, the ablation member may be adjusted so that a gap exists between the ablation member and the pulmonary veins. When the ablation member is placed at or near the tissue, ablative energy can be transmitted through the ablation member to the tissue, thus ablating at least a portion of the tissue to form one or more lesions. Such lesions may be formed in the shape of a loop, an ellipse, a circle, or some other closed path or circumferential configuration.

Figure 12A:
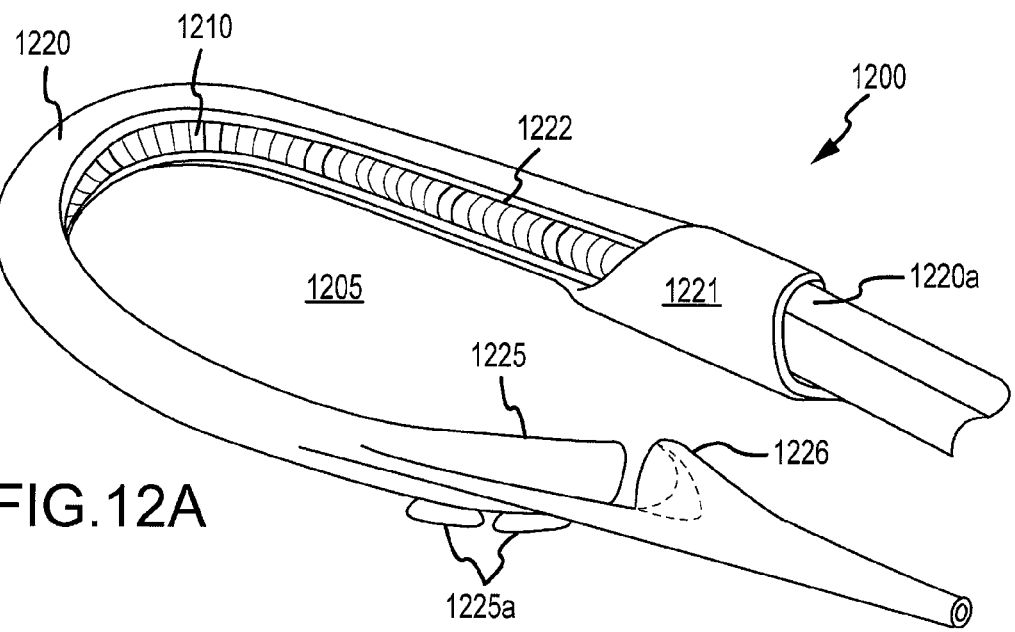
FIGS. 12A-12C show aspects of an ablation system with a stabilizer member according to embodiments of the present invention.
Figure 12B:
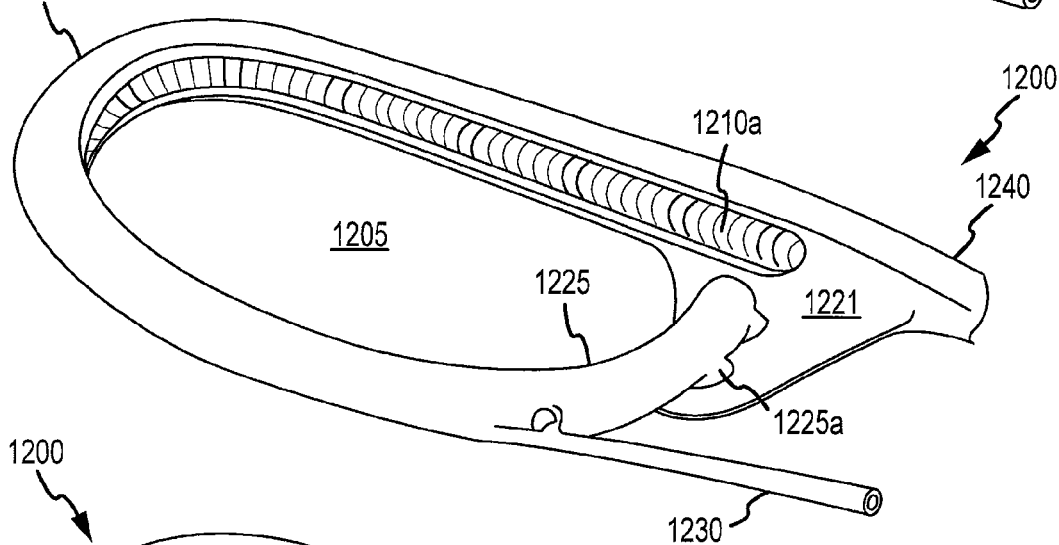
Figure 12C:
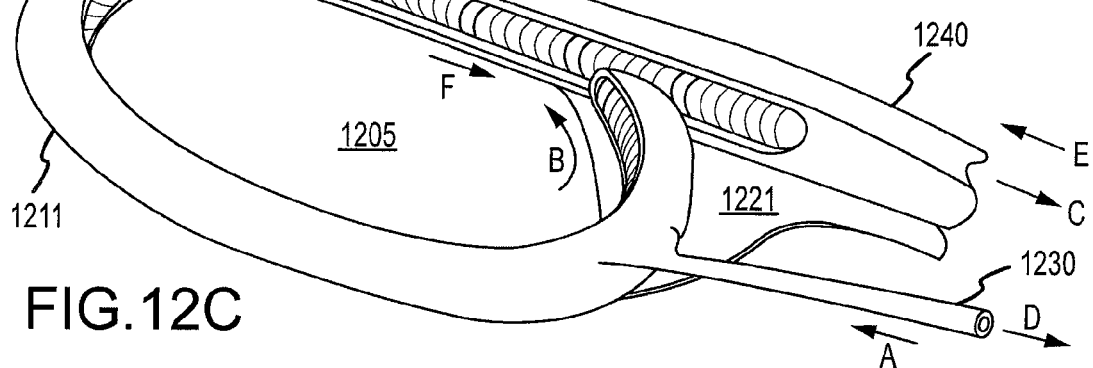

FIGS. 12A to 12C illustrate aspects of an ablation system according to embodiments of the present invention. As shown in FIG. 12A, ablation system 1200 includes an ablation member 1210 in operative association with a stabilizer member 1220. Ablation member 1210 extends along a recess 1222 of stabilizer member 1220. Stabilizer member 1220 includes a breakaway tip 1225, and a catch 1226 that is configured to releasably hold the breakaway tip. For example, the catch may include a recessed portion or cap that can hold the breakaway tip, and from which the breakaway tip may be released so as to extend toward a proximal portion of the ablation assembly. Breakaway tip 1225 may present a portion of an ablation assembly that is free to move or extend away from an adjacent portion of a stabilizer member. The breakaway tip may include a distal end of an ablation member that is partially housed by a stem section of a stabilizer member, and may include one or more connection mechanisms 1225a, such as suction cups. Stabilizer member 1220 may also include a flexible platform 1221 that can be wrapped around the body 1220a of the stabilizer member as shown in FIG. 12A, or that can be unwrapped and extended away from the body of the stabilizer member, as shown in FIGS. 12B and 12C. In some embodiments, the platform is wrapped around the stabilizer member body when the ablation assembly is inserted into the patient via a port. In use, an operator may disengage breakaway tip 1225 from catch 1226, unwrap platform 1221 from body 1220a, and engage breakaway tip 1225 with platform 1221. For example, the breakaway tip can be suctioned onto or coupled with the platform with a connection mechanism.

As shown in FIG. 12B, ablation system 1200 can be extended around a tissue or organ 1205 of a patient. In use, a surgeon can manipulate a distal portion 1230 of stabilizer member 1220, a proximal portion 1240 of stabilizer member 1220, or both. By manipulating distal portion 1230 of stabilizer member 1220, or by adjusting proximal portion 1240 of stabilizer member 1220, an operator can move breakaway tip 1225 toward the patient organ or tissue. In this way, an operator can urge breakaway tip 1225 to bridge a gap that may exist between ablation member 1210 and the tissue surface, thereby allowing the ablation member to approximately encircle the tissue. As shown here, a distal portion of breakaway tip 1225 can be moved toward a proximal portion 1210a of the ablation member. When making such adjustments of the ablation assembly, the connection mechanism may or may not maintain contact with the platform.

As shown in FIG. 12C, distal section 1230 can be moved in the direction indicated by arrow A, which can cause breakaway tip 1225 to move more distally along ablation member 1210 or to move closer to proximal portion 1210a of ablation member, as indicated by arrow B. Hence, breakaway tip 1225 can move closer to the patient tissue, and ablation member 1210 can snugly fit against the tissue. In some cases, it may be desirable to move proximal end 1240 of the stabilizer member in the direction indicated by arrow C, which can also effectively move breakaway tip 1225 more distally along ablation member 1210 or closer to proximal portion 1210a of ablation member, as indicated by arrow B. Optionally, the surgeon or operator can move distal portion 1230 in the direction indicated by arrow D, or proximal portion 1240 in the direction indicated by arrow E, so as to move the breakaway tip more proximally along the ablation member, as indicated by arrow F. In this way, by manipulating aspects of the system such as the distal end or the proximal end of a stabilizer member, an operator can reposition the connection mechanism on the platform so as to adjust the size or shape of a loop structure 1211 provided by the ablation system. In some instances, the ablation member may be adjusted to contact epicardial tissue directly adjacent to the base or ostia of one or more pulmonary veins.

In some instances, the ablation member may be adjusted so that a gap exists between the ablation member and the pulmonary veins. When the ablation member is placed at or near the tissue, ablative energy can be transmitted through the ablation member to the tissue, thus ablating at least a portion of the tissue to form one or more lesions. Hence, an operator can transmit ablative energy through the ablation member toward the tissue, so as to produce an approximately circular, elliptical, or circumferential or closed ablation pattern or lesion. It is understood that in some embodiments, aspects of distal portion 1230 and proximal portion 1240 may be reversed, as compared with the operational or configurations described above.

Figure 13A:
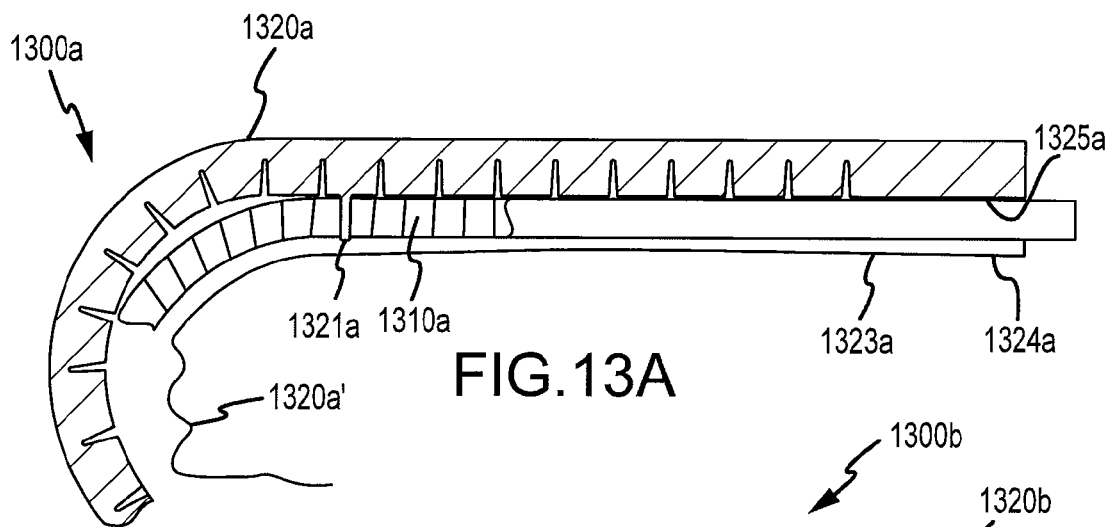
FIGS. 13A-13C show aspects of an ablation system with a stabilizer member according to embodiments of the present invention.
Figure 13B:
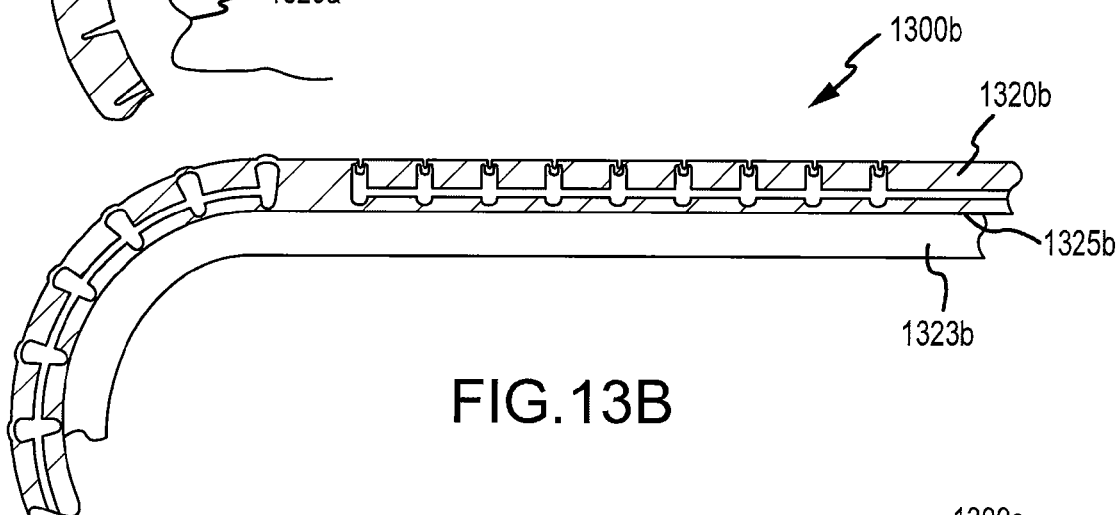
Figure 13C:
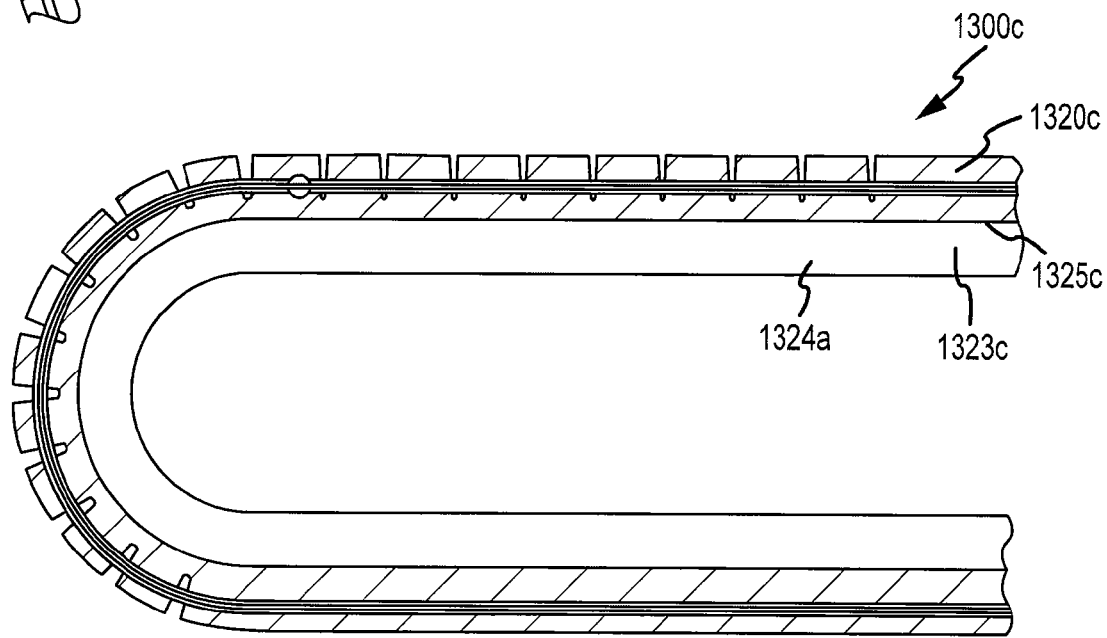

FIGS. 13A to 13C show aspects of an ablation system according to embodiments of the present invention. Exemplary ablation systems provide a flexible stabilizer member that can adhere to a tissue surface via the application of a vacuum or suction pressure, while at the same time exhibiting little or no bowing or buckling in sidewalls of the stabilizer member itself. As shown in the FIG. 13A cross section, ablation system 1300a includes an ablation member 1310a in operative association with a stabilizer member 1320a. Ablation member 1310a extends along a recess of stabilizer member 1320a, disposed at least partially between a sidewalls 1324a and an opposing sidewall (not shown) of the stabilizer member. Recess 1323a is formed by the opposing sidewalls and body 1325a of stabilizer member 1320a. The stabilizer shape is similar to the stabilizer shape shown in FIG. 14A but has notches cut into the inside top wall to enable bending in the direction shown, which can be assisted by the application of a vacuum inside the suction stabilizer when it is attached to tissue, as discussed elsewhere herein. Stabilizer member 1320a can include or be coupled with, for example with a glue or adhesive, one or more loops 1321a which secure ablation member 1310a relative to stabilizer member 1320a. In some cases, such accordion features or loops help to relieve strain or residual stress when the ablation system undergoes bending or flexing. As depicted is this illustration, the natural bending plane of the stabilizer is at the outside of the curve of the stabilizer which can be at odds with the natural bending plane of the electrode which lies at a significantly smaller radius in the curve. In a curved state, this could result in much tension and stretching of the outside edge of the stabilizer and compression of the electrode and bowing and buckling of the skirt of the stabilizer along the inside edge of the curve as shown at 1320a', which may negatively impact the ability of the stabilizer member to adhere to a tissue surface contour due to deformation of the skirt edge. Such distortion or buckling can lead to the development of air gaps along the length of the stabilizer member, between the stabilizer member and the patient tissue. Other embodiments shown display more ability to conform easily to a curved surface. In some embodiments, a vacuum in the suction chamber inside the stabilizer and surrounding the electrode can assist in the bending. The cross-section of stabilizer member 1320a presents a configuration with a smooth outside surface and deeply notched inside surface. The profile of the stabilizer member presents a series of rising and falling wave-like cuts or notches into the inner surface of the upper wall. The notched configuration allows the stabilizer to be placed against or near any of a variety of curved or irregular surfaces and curve more readily than if it did not have these features. Relatedly, the cut or notched features, depending on the gap of the feature, can prevent or inhibit curving in a portion of a stabilizer member as the adjacent walls of the notches may contact each other, acting as motion limiters. In FIG. 13A this is depicted as all gaps are shown nearly closed. If curved portion of 1320a were straightened, the gaps or notches in this section would open up to allow vacuum within. A suction skirt can also assist in creating dependable suction inside a seal surface or flat floor of a lumen of a push tube for the portion of a suction stabilizer that remains inside the push tube while a procedure is performed, as described herein with reference to FIG. 72.

As shown in the FIG. 13B cross section, ablation system 1300b includes a stabilizer member 1320b, which has a recess 1323b that can at least partially receive an ablation member. Three-sided recess 1323b is formed by body 1325b of stabilizer member 1320b, by side wall 1324b, and by another side wall (not shown in the section view) opposing side wall 1324b. FIG. 13B shows two bladder features 1301b, 1302b that include individual chambers 1303b, 1304b connected by a lumen. A first bladder feature 1301b is in a straight section of the stabilizer and a second bladder feature 1302b is in the curved section. The two bladders can be separately inflated/deflated with air or saline through separate lumen paths to assist in producing the desired stabilizer curves. As shown in FIG. 13B, the straight section can be deflated or under negative pressure while the curved one is inflated. The thin, flexible, accordionated outer wall 1305b, 1306b of each individual chamber has enough length to it so that it becomes relatively straight when the chamber is inflated, unlike the thin but unaccordionated inner or bottom wall of each chamber, causing the stabilizer to curve as the chambers inflate. The center of mass of the suction stabilizer can be configured to coincide with the center of mass of the probe when assembled.

As shown in FIG. 13C, ablation system 1300c includes a stabilizer member 1320c, which has a recess 1323c that can at least partially receive an ablation member. Recess 1323c is formed by opposing sidewalls and body 1325c of stabilizer member 1320c. The opposing sidewalls can include sidewall 1324c and another side wall (not shown in the section view) opposing sidewall 1324c. A steel or NiTi wire or ribbon can be fixed or coupled with the distal end of the stabilizer. In use, the distal end can be deflected by pushing, pulling, or otherwise manipulating the wire at the proximal end. As shown in FIG. 13C, the ablation system can include a bond spot 1340c where two ribbons are attached to the stabilizer. The bond spot is shown toward the center of a flexible portion, indicated by the extents of the notched backside of the stabilizer. The stabilizer is shown with only one curve developed, making the stabilizer off-center with regard to the relative length of the two straight sections. If the curve shown were relaxed and the other one simultaneously formed (to the right of the 'bond spot') the curve would effectively translate down the length of the stabilizer, or alternately, the curve could stay in the same place on the anatomy and the stabilizer could translate lengthwise around the anatomy by translating its curve. The way the curve is formed is through the interaction of tension in the cable (or lack thereof) and the length of the stabilizer as measured along its natural bending plane (which is inside, or below, the ribbon). When a ribbon is tensioned by pulling on the end (not shown) and pushing on the end of the stabilizer (not shown), the notches collapse and the stabilizer straightens. When the ribbon is relaxed, it allows the stabilizer to curve and the ribbon end (not shown) slides into the end of the stabilizer (not shown) as it may need more length to lie around the curve.

Figure 14A:
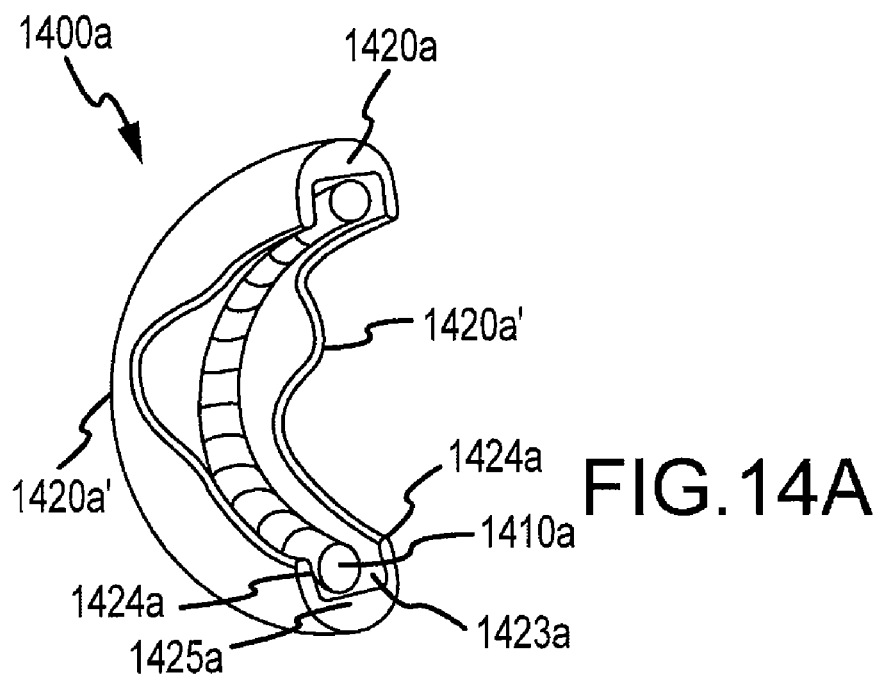
FIGS. 14A-14B show aspects of an ablation system with a stabilizer member according to embodiments of the present invention.
Figure 14B:
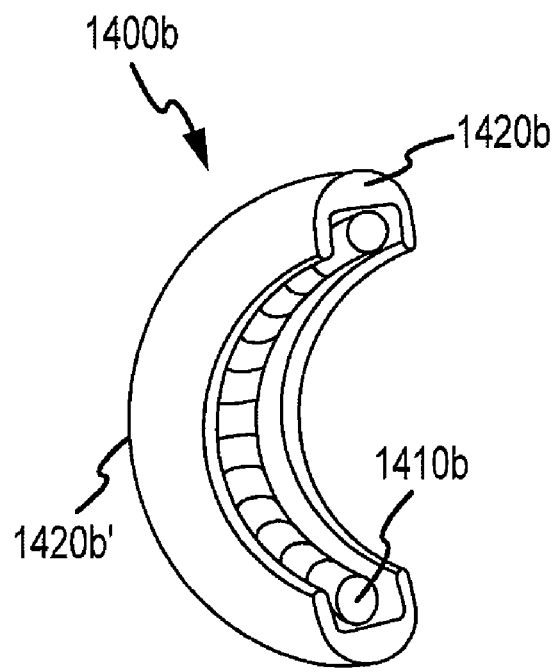

FIG. 14A depicts an ablation system 1400a having a stabilizer member 1420a that at least partially houses an ablation member 1410a. As shown here, when stabilizer member 1420a bends it may form a bow or buckle 1420a'. In some cases, such bowing or buckling may be undesirable because it can lead to a loss of a contact seal or suction between a stabilizer member and a patient tissue. FIG. 14B depicts an ablation system 1400b having a stabilizer member 1420b that at least partially houses an ablation member 1410b. In some embodiments, ablation member 1410b is disposed within a recess 1423a which is formed by opposing sidewalls 1424a and body 1425a of stabilizer member 1420a. As shown here, stabilizer member 1420b includes a section 1420b' that exhibits little or no bowing or buckling when the stabilizer member bends. For example, section 1420b' may be heat treated or formed, or provided with a shape memory, so that when the ablation system is bent, section 1420b' presents a curved shape that conforms to a tissue contour and does not fold or collapse, or otherwise warp. In some cases, if a stabilizer member has an overly rigid curve or form it may be difficult to insert the stabilizer member through a tube or catheter. If the curve is too rigid, it can cause friction as the stabilizer member passes through the tube. In some cases, the rigid curve may prevent the stabilizer member from passing through the tube. FIGS. 15A to 15C depict an ablation system 1500 having a stabilizer member 1520 that at least partially houses an ablation member 1510 within sidewalls 1524 of the stabilizer member. In some embodiments, ablation member 1510 is disposed within a recess 1523 which is formed by opposing sidewalls 1524 and body 1525 of stabilizer member 1520. As shown here, stabilizer member 1520 includes a section 1520' that exhibits little or no bowing or buckling when the stabilizer member bends. For example, section 1520' includes sidewall flaps 1524' which can overlap when the stabilizer member bends. Hence, when the ablation system is bent, section 1520' presents a curved shape that conforms to a tissue contour and does not fold or collapse, or otherwise warp. FIG. 15B shows the ablation system in a straightened configuration, where sidewall flaps are slightly overlapped. These flaps can allow a stabilizer member to bend when the member is passed through a tube, so that the member does not create excessive friction. In some cases, the stabilizer member will not have a shape memory for a curve or arc. The formation of the flaps allow the stabilizer member to bend, to seal with a patient tissue, and to expand and contract against variations in the contour of the patient tissue. FIG. 15C shows an original molded configuration of a stabilizer member according to embodiments of the present invention.

FIGS. 16A to 16C depict an ablation system 1600 having a stabilizer member 1620 that at least partially houses an ablation member 1610 within sidewalls 1624 of the stabilizer member. In some embodiments, ablation member 1610 is disposed within a recess 1623 which is formed by opposing sidewalls 1624 and body 1625 of stabilizer member 1620. As shown here, stabilizer member 1620 includes a section 1620' that exhibits little or no bowing or buckling when the stabilizer member bends. For example, section 1620' includes a flexible spine or backbone having alternating protrusions 1626 and indentions 1627 that allow section 1620' to flex through a range of motion when the stabilizer member bends. Hence, when the ablation system is bent, section 1620' presents a curved shape that conforms to a tissue contour and does not fold or collapse, or otherwise warp. FIG. 16B illustrates stabilizer member 1620 in a straightened configuration. The flexible spine 1628 of the stabilizer member presents a serpentine profile, as shown in the cross section of FIG. 16C. Hence, the center of mass can be moved toward the recess opening, and can be aligned with the center of the probe. When something like a beam bends, the outside of that beam stretches and the inside compresses. But the middle of the beam is doing neither; it is the area of least stress and no length change. According to embodiments of the present invention, one configuration is to have the stabilizer neutral bending plane be aligned with the electrode neutral bending plane to minimize stress when it bends. This may also mean that the electrode and stabilizer are not changing overall length relative to each other whether straight or bent. In FIGS. 16B and C, the stabilizer, which also happens to be easily moldable in this shape, has a bending plane right about where the electrode lies.

Figure 17A:
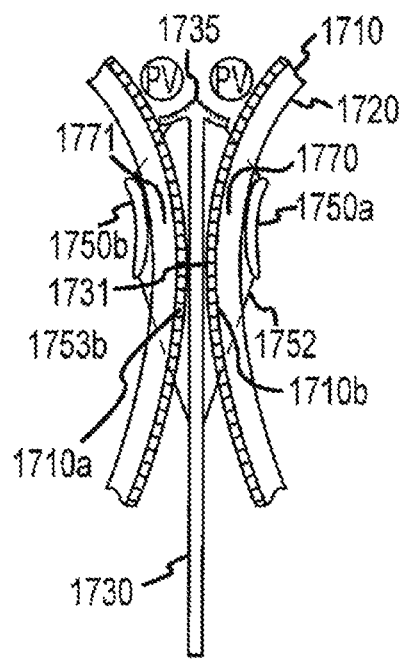
Figure 17B:
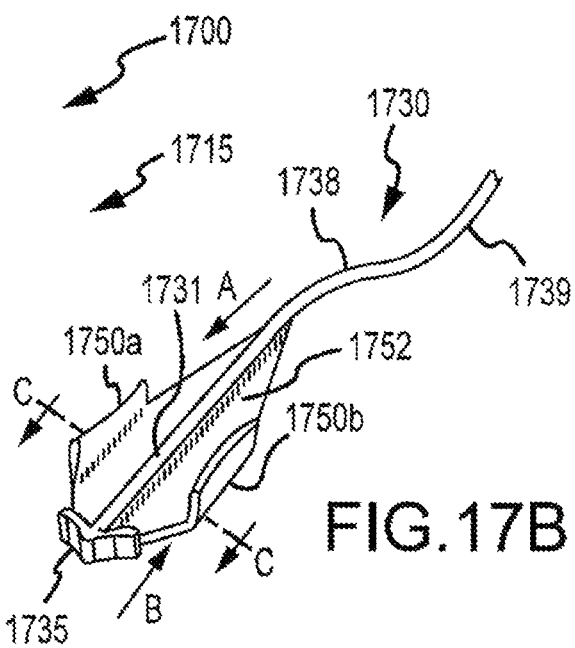
Figure 17C:
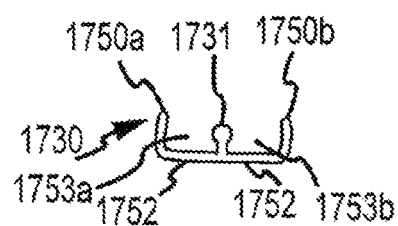

FIGS. 17 A to 17F show aspects of an ablation system 1700 according to embodiments of the present invention. As depicted in FIG. 17 A, ablation system 1700 includes an ablation assembly 1715 having a stabilizer member 1720 in operative association with an ablation member 1710. Ablation system 1700 also includes a cinching device 1730. Cinching device 1730 can have one or more guides 1750a, 1750b, and can be used in operative association with an ablation assembly 1715 having an ablation member 1710 and a stabilizer member 1720. Cinching device 1730 can also include an ablation member protection mechanism 1731 which can be disposed between portions 1770 and 1771 of ablation assembly 1715. Hence, it is possible to avoid contact between different portions of an ablation member such as an electrode, where the ablation member protection mechanism is disposed between adjacent portions of the ablation member. One or more guides 1750a, 1750b of cinching device 1730 may include a flat or curved retaining wall perpendicularly attached to, or formed along with, a support 1752 of cinching device 1730. Accordingly, cinching device 1730 can present a pair of channels 1753a, 1753b that can receive the ablation assembly. For example, channel 1753a is disposed between guide 1750a and ablation member protection mechanism 1731, and channel 1753b is disposed between guide 1750b and ablation member protection mechanism 1731. This feature is also illustrated in FIG. 17C, which depicts a cross section of cinching device corresponding to C-C of FIG. 17B. In some embodiments, one or more guides 1750a, 1750b may have a curved top edge. The shape of guides 1750 can be designed in order to help facilitate positioning an ablation assembly 1715 around or against a patient cardiac tissue, which may include one or more pulmonary veins PV, by keeping distal 1715a and proximal 1715b segments of the ablation member close to each other, as shown in FIG. 17D. In an embodiment with two or more guides, the guides may be located on opposite sides of a support plate of cinching device 1730.

In one method for using the cinching device 1730 with guides, ablation assembly 1715 can be passed through the cinching device along one guide 1750a as depicted by arrow A in FIG. 17B and wrapped around the patient tissue. The ablation assembly can then be pulled through cinching device 1730 in the opposed direction as indicated by arrow B, passing along another guide 1750b. The guides may be made of or include various semi-rigid or rigid materials. Cinching device 1730, which may be used as a pusher or a guide handle, can be advanced in a direction toward the patient tissue 705b as indicated by arrow D, so as to decrease the circumference of a loop structure 1745 formed by ablation assembly 1715, and to increase the amount of contact between the ablation member 1710 and the patient tissue 1705 or to help secure the position of ablation member 1710 relative to patient tissue 1705. Similarly, by advancing cinching device 1730 in this direction, an operator can increase the amount of contact between an ablation segment 1735 of the cinching device and the patient tissue 1705 or help secure the position of the ablation segment relative to the patient tissue. The operator can also establish or apply an opposing force by grasping or pulling proximal and distal sections 1715c, 1715d of ablation assembly 1715 in an opposing direction, as indicated by arrows E and F, respectively.

In some embodiments, as cinching device 1730 is advanced towards the patient tissue 1705, a loop structure 1745 of the ablation assembly 1715 is reduced in diameter or otherwise contracted. As shown in FIGS. 178 and 17D, for example, in some embodiments an ablation member protection mechanism 1731 can be utilized along with the cinching device 1730. Cinching device 1730 can include ablation member protection mechanism 1731 disposed toward the center of device 1730, optionally between guides 1750a, 1750b. Ablation member protection mechanism 1731 can operate to keep a first segment 1710a and a second segment 1710b of the ablation member from making contact with each other. Ablation member protection mechanism 1731 may either be fixed or integral to cinching device 1730 or separate from cinching device 1730. In some embodiments, an ablation segment 1735, which may include an electrode or an energy transmission element, can be attached with cinching device 1730. For example, ablation segment 1735 can be coupled with or part of a first or distal section 1731 a of ablation member protection mechanism 1731. Ablation segment 1735 can be utilized to increase the amount of contact between the ablation assembly 1715 and the patient tissue 1705. Ablation segment 1735 can also be utilized to reduce pinching of the patient tissue 1705 that might otherwise occur if ablation segment 1735 were not disposed between opposing segments of ablation member 1710. The operator can position ablation assembly 1715 to make contact with selected parts of patient tissue 1705 such that when ablative energy is transmitted through the ablation assembly, it is possible to create an approximately circular or closed ablation pattern or lesion on the tissue. In this way, energy can be applied by the ablation system to the tissue. The position of cinching device 1730 relative to ablation assembly 1715 can be adjusted by the operator. For example, the cinching device may be advanced or retracted to differing degrees in order to increase or decrease an amount of contact between the ablation assembly and the patient tissue. Ablation segment 1735 in combination with ablation member 1710 can form a continuous or closed circumferential loop that can be used to ablate a circumferential lesion on the patient tissue. In FIG. 178 ablation segment 1735 may have 'arrowhead' shape as shown or another configuration, perhaps a 'U' shape as if to scoop up the vessel tissue as it advances against the tissue instead of trying to part the two pulmonary vessels or ablate partway between them by physical separation by the arrowhead-like shape. Ablation segment 1735 may also have a flat shape, a convex shape, a concave shape, or any other desired shape so as to contact or manipulate tissue. In some embodiments, ablation segment includes a flexible material that conforms readily with the tissue.

FIG. 17B shows a perspective view of cinching device 1730 which includes ablation member protection mechanism 1731, guides 1750a, 1750b, ablation segment 1735, and handle 1739. In some cases, handle 1739 of cinching device 1730 may include a bent or offset portion 1738. As shown in FIG. 17F, in some embodiments cinching device 1730 can be folded or rolled into a compact configuration. FIG. 17F corresponds to the view presented in FIG. 17C, except that in FIG. 17F the device is folded. Device 1730 includes ablation member protection mechanism 1731, guides 1750*a*, 1750*b*, and support 1752. As illustrated in FIG. 17D, in some cases the ablation system may also include a trocar 1780 having a sleeve 1782 coupled with a flange 1784. In use, an operator may place the ablation assembly and cinching device through the trocar, such that the trocar assists in keeping the ablation assembly snugly situated within channels 1753*a*, 1753*b* of the cinching device. FIG. 17E shows a cross section of trocar sleeve 1782. In some cases, trocar sleeve 1782*a* can have a first dimension W that is about 25 mm, and a second dimension H that is about 10 mm.

Figure 18A:
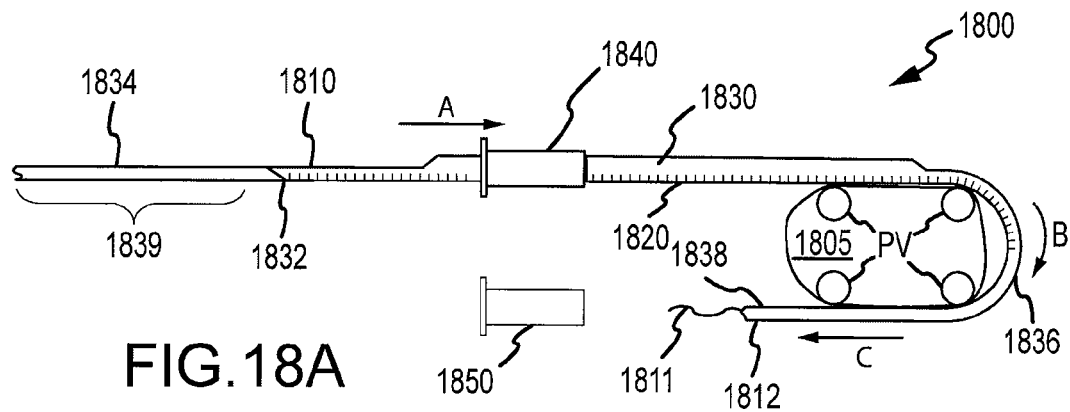
FIGS. 18A-18E show aspects of ablation systems with a stabilizer member according to embodiments of the present invention.
Figure 18B:
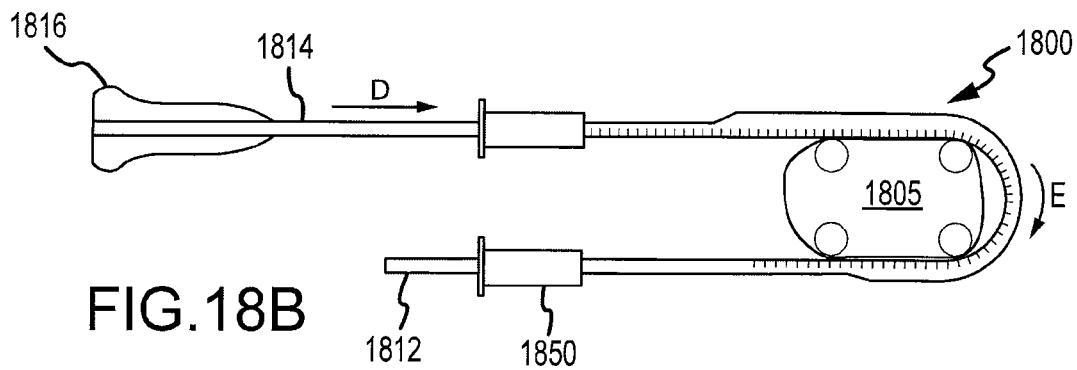

FIGS. 18A to 18E show aspects of an ablation system according to embodiments of the present invention. As depicted in FIG. 18A, an ablation system 1800 includes an ablation assembly 1810 having an ablation member 1820 coupled with a stabilizer member 1830, a first port 1840, and a second port 1850. Ablation member 1820 can include an electrode and stabilizer member 1830 can include a bladder, according to some embodiments. In use, an operator can advance a distal portion 1812 of the ablation assembly through first port 1840 as indicated by arrow A, around a patient tissue 1805 as indicated by arrow B, and toward second port 1850 as indicated by arrow C. The patient tissue can encompass cardiac tissue which may also include one or more pulmonary veins (PV). Stabilizer member 1830 includes a proximal living hinge 1832 disposed toward a proximal portion 1834 of the stabilizer member, and a distal living hinge 1836 disposed toward a distal portion 1838 of the stabilizer member. Stabilizer member 1830 may also include a stiff tube section 1839 disposed toward distal portion 1838. FIG. 18B shows another view of ablation system 1800, which can include a proximal handle 1816 disposed toward a proximal end 1814 of the ablation assembly. In use, an operator can move handle 1816 toward the patient tissue as indicated by arrow D, such that the ablation assembly continues to advance around the patient tissue as indicated by arrow E. Consequently, distal end 1812 of the ablation assembly can be advanced through second port 1850.

Figure 18C:
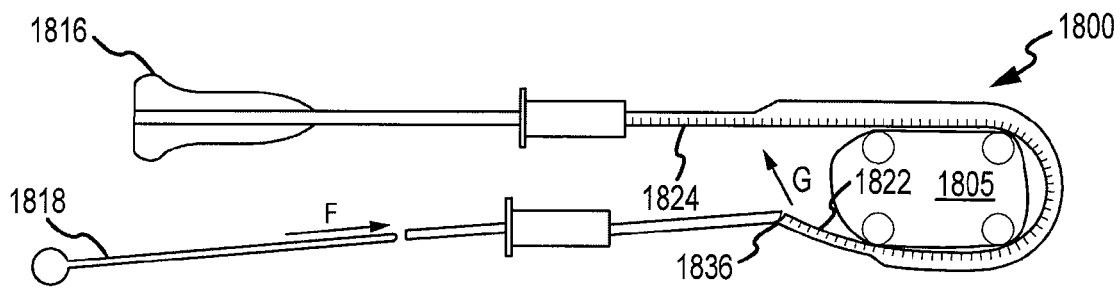
Figure 18D:
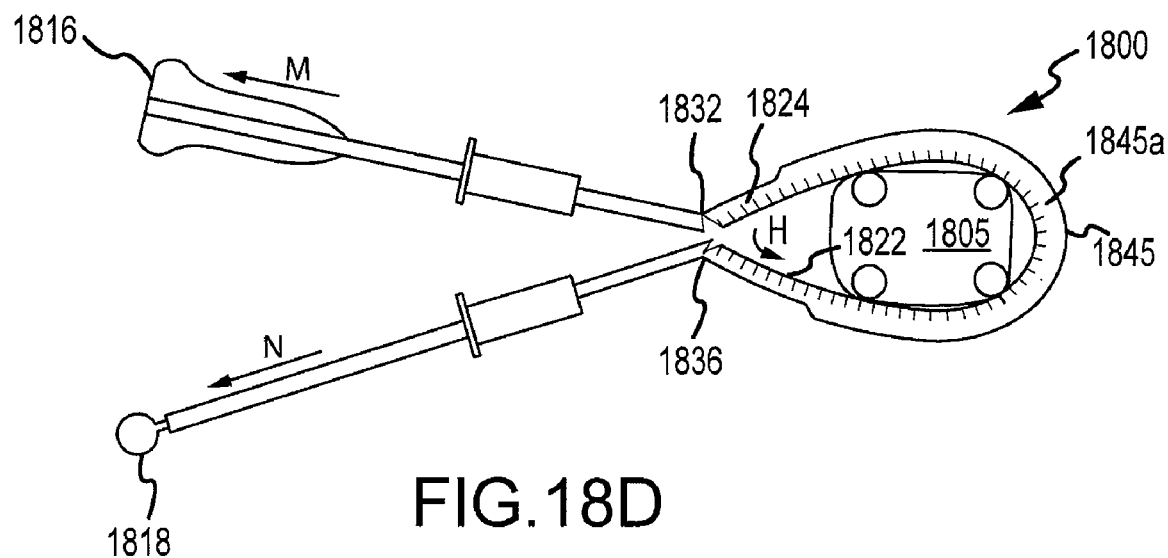
Figure 18E:
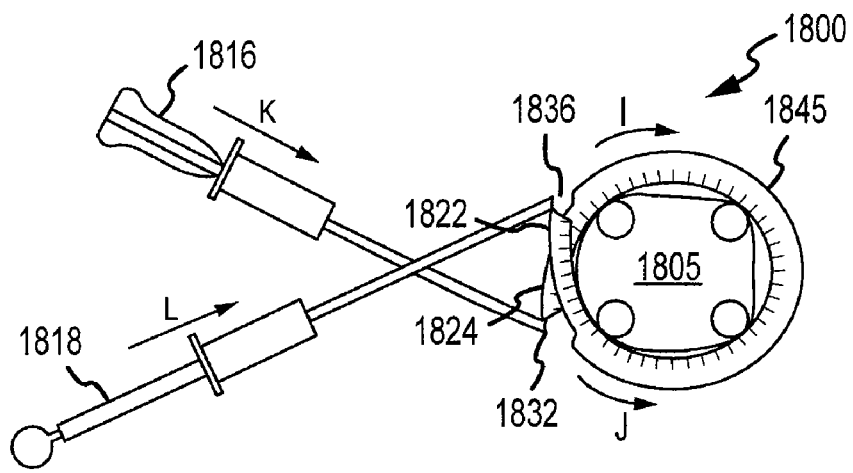

FIG. 18C provides an illustration of ablation system 1800. In use, an operator can contact distal end 1812 of the ablation assembly with a distal handle or obturator 1818. For example, distal handle 1818 or stiffening probe can be advanced into a recess, channel, or other lumen or passage of the distal end 1812, as indicated by arrow F. An operator can manipulate the distal handle so as to activate distal living hinge 1836, thereby bringing a distal section 1822 of the ablation member toward a proximal section 1824 of the ablation member, as indicated by arrow G. As shown in FIG. 18D, an operator can also manipulate proximal handle 1816 so as to activate proximal living hinge 1832, thereby bringing proximal section 1824 of the ablation member toward distal section 1822 of the ablation member, as indicated by arrow H. Hence, the operator can form a loop structure 1845 with the ablation assembly, about the patient tissue. Optionally, the operator may move proximal handle 1816 away from the tissue as indicated by arrow M, or distal handle 1818 away from the tissue as indicated by arrow N, so as to bring a distal portion 1845*a* of the loop structure snug against the patient tissue, as indicated by arrow 0. In some cases, an operator can manipulate proximal handle 1816, distal handle 1818, or both, as depicted in FIG. 18E, so as to further activate proximal living hinge 1832, distal living hinge 1836, or both, so as to dilate or contract loop structure 1845. For example, ablation member distal portion 1822 can be moved along the loop structure in a first direction as indicated by arrow 1, for example by moving distal handle 1818 in the direction indicated by arrow L, and ablation member proximal portion 1824 can be moved along the loop structure in a second opposing direction as indicated by arrow J, for example by moving proximal handle 1816 in the direction indicated by arrow K. In this way, an operator can cinch the ablation member about the tissue. The loop structure can be adjusted so that the ablation member maintains continuous contact the tissue. The operator can transmit ablation member to the tissue via the ablation member, so as to form a closed path ablation or lesion on the tissue. Handle 1818 can be easily withdrawn through second port 1850. Accordingly, embodiments of the present invention provide techniques that include port access in addition to open sternotomy, as well as techniques that can be used to form a complete loop for lesion formation. Further, such embodiments may provide ease of vision and maneuverability, and can be easily manufactured.

Figure 19D:
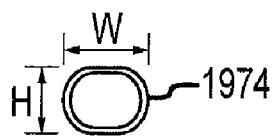

FIGS. 19A to 19E show aspects of an ablation system according to embodiments of the present invention. As depicted in FIG. 19A, an ablation system 1900 can include an ablation assembly 1910 having an ablation member 1920 and a stabilizer member 1930. Ablation member 1920 can include an electrode and stabilizer member 1930 can include a bladder, according to some embodiments. Ablation system 1900 also includes a cinching member 1940 having a proximal handle 1942, an intermediate shaft 1944, and a distal ablation segment or tip electrode 1946. Cinching member 1940 also includes one or more collapsible rollers or guides 1950*a*, 1950*b*. As shown here, guides 1950*a*, 1950*b* are in an expanded configuration, and are coupled with a distal support 1948 of the cinching member. Optionally, guides 1950*a*, 1950*b* can be coupled with distal support 1948 via pivots 1960*a*, 1960*b*, respectively, such that guide 1950*a* can move in an arc as indicated by arrow A, and guide 1950*b* can move in an arc as indicated by arrow B. Cinching member 1940 presents a first passage or channel 1940*a* disposed between first guide 1950*a* and distal support 1948, and a second passage or channel 1940*b* disposed between second guide 1950*b* and distal support 1948. In use, an operator can advance a distal portion 1912 of the ablation assembly through first passage 1940*a* as indicated by arrow C, around a patient tissue 1905 as indicated by arrow D, and through second passage 1940*b* as indicated by arrow E. An operator can adjust the positioning or tightness of a loop structure 1945 formed by the ablation assembly, by advancing cinching member 1940 toward the patient tissue as indicated by arrow F, by pulling a proximal section 1914 of the ablation assembly away from the patient tissue as indicated by arrow G, and by pulling distal section 1912 of the ablation assembly away from the patient tissue as indicated by arrow H.

Figure 19F:
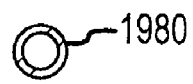
Figure 19E:
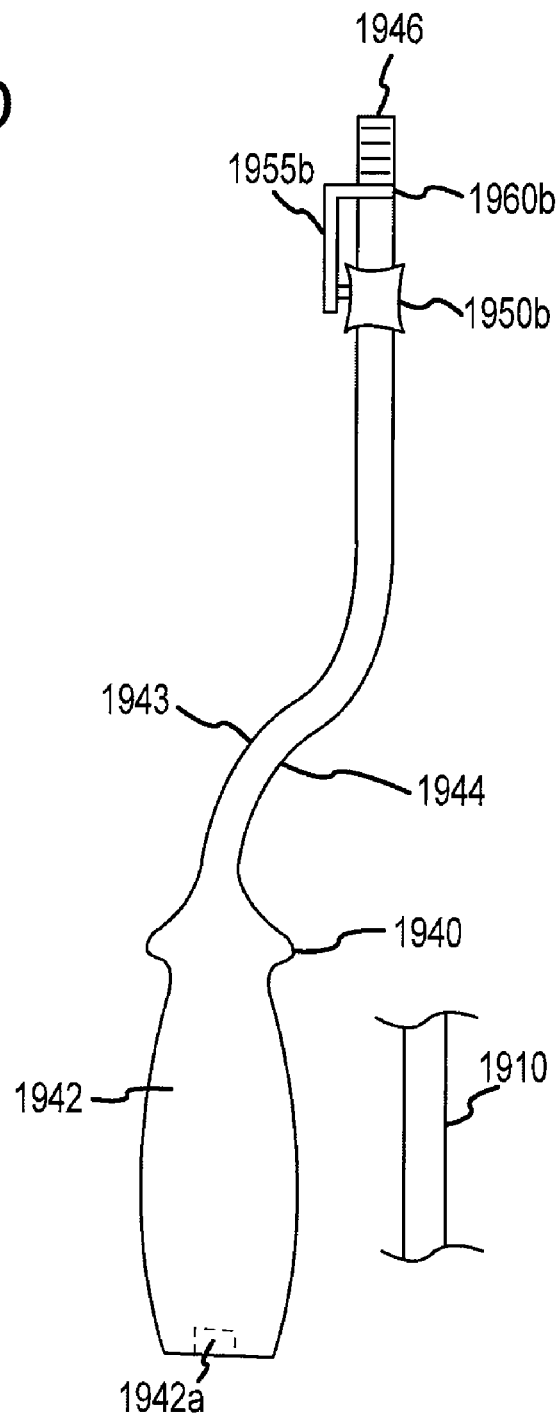

FIG. 198 illustrates cinching member 1940 partially disposed within a trocar 1970. Guides 1950*a*, 1950*b* of the cinching member are in a collapsed or low profile configuration, and are disposed toward the proximal end or handle of the cinching member. Optionally, guides 1950*a*, 1950*b* can be collapsed such that they are disposed toward the distal end of the cinching member (not shown). First guide 1950*a* is coupled with first pivot 1960*a* via a first arm 1955*a*. Second guide 1950*b* is coupled with second pivot 1960*b* via a second arm 1955*b*. In some embodiments, the arms can include a biasing mechanism, such as a spring or an elastomer, such that the guides are biased toward an open or laterally extended configuration. Due to the pivotable nature of the guides, they can swing in or collapse to allow the cinching member or device to fit inside of the trocar. Guides can be collapsed in either a forward orientation or a reverse orientation, which allows cinching member to be easily passed into and out of the trocar. For example, the guides shown in FIG. 19C extend toward the proximal end of the cinching member. If the guide member is passed through the trocar such that the guides extend beyond a distal end 1976 of the trocar, guides 1950*a*, 1950*b* can expand laterally toward an open or extended configuration. When the operator pulls cinching member 1940 back through the trocar, the guides can adopt a collapsed configuration such that they extend toward the distal end of the cinching member. FIG. 19C shows trocar 1970 having a flange section 1972 and a shaft section 1974. FIG. 190 shows a cross section of shaft section 1974. In some embodiments, shaft section 1974 has a first dimension W of about 25 mm, and a second dimension H of about 10 mm. FIG. 19E shows another view of cinching member 1940 according to embodiments of the present invention. Second guide 950*b* is coupled with second pivot 1960*b* via a second arm 1955*b*. As depicted here, intermediate shaft 1944 includes an offset bend or S-curve 1943. Such a bend configuration in the intermediate shaft of the cinching member can allow an operator to grasp and pull an ablation assembly 1910 that is disposed at or near the intermediate shaft 1944 or handle 1942, without interfering with the shaft or handle. In some cases, handle 1942 includes a plug in 1942*a* for providing energy to tip electrode or distal ablation segment 1946. FIG. 19F shows a cross section of a trocar 1980 according to some embodiments. In some instances, trocar 1980 can have a diameter of about 10 mm.

FIGS. 20A-B, 21A-B, 22A-B, 23A-B, 24A-C. 25A-B, 26A-B, and 27 generally show various embodiments of a stabilizer that can bend along the same plane as the electrode yet keep a suction space open around the electrode, that can keep a large surface of tissue exposed to both tissue and electrode, and that can be easily manufactured. For example, the stabilizer can have proportions that are wider than tall, and provide support to keep suction chamber from collapsing under vacuum.

Figure 20A:
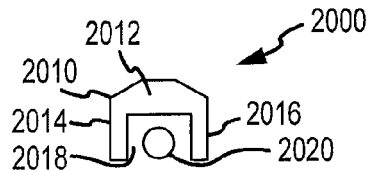
FIGS. 20A-20B show aspects of ablation systems with a stabilizer member according to embodiments of the present invention.
Figure 20B:
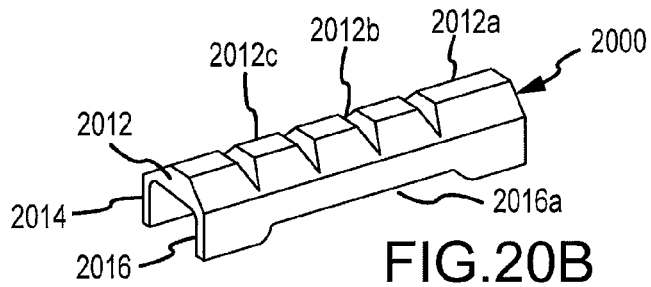

FIGS. 20A and 20B illustrate aspects of an ablation assembly according to embodiments of the present invention. As seen in the cross section view of FIG. 20A, ablation assembly 2000 includes a stabilizer member 2010 having a body 2012 and opposing sidewalls 2014, 2016. Stabilizer member 2010 presents a channel or recess 2018 that is bordered by body 2012 and sidewalls or side bars 2014, 2016. Ablation assembly 2000 also includes an ablation member 2020 disposed at least partially within channel 2018. As seen in the perspective view of FIG. 20B, an outer surface 2012*a* of stabilizer member body 2012 includes a plurality of notches 2012*b* and teeth 2012*c*. Optionally, the sidewalls may include a depression or section where the length of the sidewall is reduced. For example, sidewall 2016 can include a depression 2016*a*. This carve-out portion 2016*a* presents a reduced height:width ratio for the stabilizer member cross section.

Figure 21A:
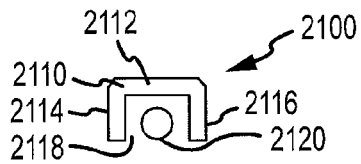
FIGS. 21A-21B show aspects of ablation systems with a stabilizer member according to embodiments of the present invention.
Figure 21B:
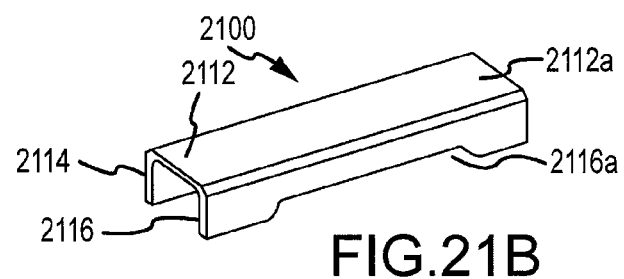

FIGS. 21A and 21B illustrate aspects of an ablation assembly according to embodiments of the present invention. As seen in the cross section view of FIG. 21A, ablation assembly 2100 includes a stabilizer member 2110 having a body 2112 and opposing sidewalls 2114, 2116. Stabilizer member 2110 presents a channel or recess 2118 that is bordered by body 2112 and sidewalls or side bars 2114, 2116. Ablation assembly 2000 also includes an ablation member 2120 disposed at least partially within channel 2118. As seen in the perspective view of FIG. 21B, an outer surface 2012*a* of stabilizer member body 2012 provides a flat profile. Optionally, the sidewalls may include a depression or section where the length of the sidewall is reduced. For example, sidewall 2116 can include a depression 2116*a*. This carve-out portion 2116*a* presents a reduced height:width ratio for the stabilizer member cross section.

Figure 22A:
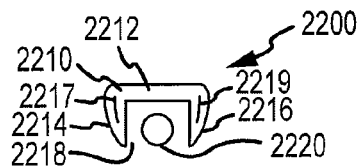
FIGS. 22A-22B show aspects of ablation systems with a stabilizer member according to embodiments of the present invention.
Figure 22B:
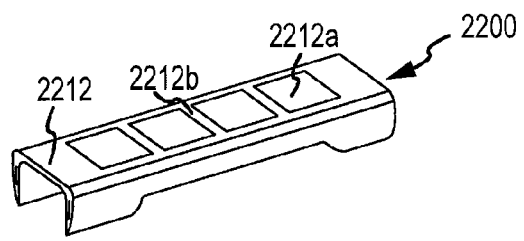

FIGS. 22A and 22B illustrate aspects of an ablation assembly according to embodiments of the present invention. As seen in the cross section view of FIG. 22A, ablation assembly 2200 includes a stabilizer member 2210 having a body 2212 and opposing sidewalls 2214, 2216. Stabilizer member 2210 presents a channel or recess 2218 that is bordered by body 2212 and sidewalls or side bars 2214, 2216. Ablation assembly 2200 also includes an ablation member 2220 disposed at least partially within channel 2218. As seen in the perspective view of FIG. 22B, an outer surface 2212*a* of stabilizer member body 2212 includes a plurality of molded thin elastic windows 2212*a* that are substantially coplanar with the profile of body 2210. Outer surface 2212*a* also includes a plurality of support ribs 2212*b*. Optionally, the sidewalls may include a depression or section where the length of the sidewall is reduced. For example, sidewall 2216 can include a depression 2216*a*. This carve-out portion 2216*a* presents a reduced height:width ratio for the stabilizer member cross section. Sidewalls 2214, 2216 can also include or be coupled with tension straps 2217, 2219, respectively. As shown here, the tension straps are disposed within the sidewalls. Tension straps can operate to provide additional torsional rigidity to the stabilizer member. And while rigidity in torsion can be enhanced by these straps, the straps can also function to keep the trimmed-down, reduced-mass stabilizer from stretching under tension. A braided or woven strap may not detract from the flexibility of the stabilizer and can provides strength in tension. According to some embodiments, it is desirable to minimize the degree to which the stabilizer stretches, as this can also minimize the degree to which tension is transferred to the electrode.

Figure 23A:
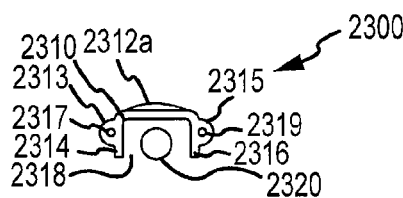
FIGS. 23A-23B show aspects of ablation systems with a stabilizer member according to embodiments of the present invention.
Figure 23B:
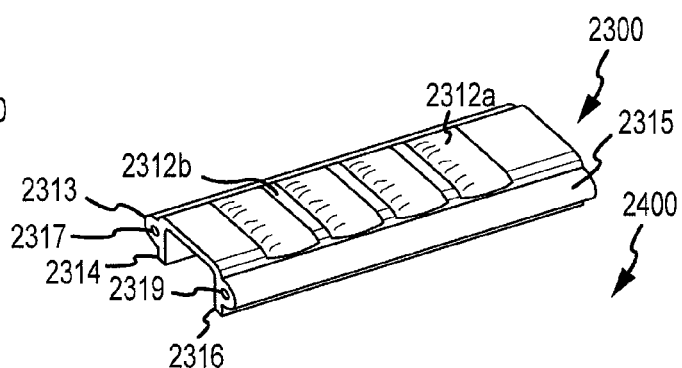

FIGS. 23A and 23B illustrate aspects of an ablation assembly according to embodiments of the present invention. As seen in the cross section view of FIG. 23A, ablation assembly 2300 includes a stabilizer member 2310 having a body 2312 and opposing sidewalls 2314, 2316. Stabilizer member 2310 presents a channel or recess 2318 that is bordered by body 2312 and sidewalls or side bars 2314, 2316. Ablation assembly 2300 also includes an ablation member 2320 disposed at least partially within channel 2318. As seen in the perspective view of FIG. 23B, an outer surface 2312*a* of stabilizer member body 2312 includes a plurality of molded thin elastic windows 2312*a* that extend or puff away from the recess 2318, and a plurality of support ribs 2312*b*. Sidewalls 2314, 2216 can include ridges 2313, 2315 which contain or are coupled with tension cords 2317, 2319, respectively. As shown here, the tension cords are disposed within the sidewall ridges. In some embodiments, ridges 2313, 2315 are disposed at a neutral bending plane. Accordingly, the center of mass of the stabilizer member can be aligned with the probe.

FIGS. 24A to 24C illustrate aspects of an ablation assembly according to embodiments of the present invention. As seen in the cross section view of FIG. 24A, ablation assembly 2400 includes a stabilizer member 2410 having a body 2412 and opposing sidewalls 2414, 2416. Stabilizer member 2410 presents a channel or recess 2418 that is bordered by body 2412 and sidewalls or side bars 2414, 2416. Ablation assembly 2400 also includes an ablation member 2420 disposed at least partially within channel 2418. As seen in the perspective view of FIG. 24B, an outer portion 2412*a* of stabilizer member body 2412 includes a plurality of molded thin elastic windows 2412*a* that extend or are biased inward toward the recess 2418, and a plurality of support ribs 2412*b*. Sidewalls 2414, 2416 can include ridges 2413, 2415 which contain or are coupled with tension cords 2417, 2419, respectively. As shown here, the tension cords are disposed within the sidewall ridges. As seen in FIG. 24C, the stabilizer member can be bent under tension. The stabilizer member can have elastic features on the backbone.

FIGS. 25A and 25B illustrate aspects of an ablation assembly according to embodiments of the present invention. As seen in the perspective view of FIG. 25A, ablation assembly 2500 includes a stabilizer member 2510 having a body 2512 and opposing sidewalls 2514, 2516. Stabilizer member 2510 presents a channel or recess 2518 that is bordered by body 2512 and sidewalls or side bars 2514, 2516. An outer portion 2512*a* of stabilizer member body 2512 includes a plurality of molded thin elastic windows 2512*a* that extend or are biased away from the recess 2518, and a plurality of support ribs 2512*b*. Ablation assembly 2500 presents a low neutral bending zone 2530. According to some embodiments, the upper portion of the stabilizer flexes easily, and doesn't compress the lower section to compensate, it just bends it. FIG. 25B shows ablation assembly 2500 in a bent or curved configuration. As seen in FIG. 25B, the stabilizer member can be bent under tension. Elastic membrane windows 2512*a* are drawn taut, and in some cases can stretch when the ablation assembly bends. The stabilizer member shown here can have some extra material built in or included in the backbone so as to reduce or modulate the elasticity.

FIGS. 26A and 26B illustrate aspects of an ablation assembly according to embodiments of the present invention. As seen in the perspective view of FIG. 26A, ablation assembly 2600 includes a stabilizer member 2610 having a body 2612 and opposing sidewalls 2614, 2616. Stabilizer member 2610 presents a channel or recess 2618 that is bordered by body 2612 and sidewalls or side bars 2614, 2616. An outer portion 2612*a* of stabilizer member body 2612 includes a plurality of molded thin elastic windows 2612*a* that extend or puff away from the recess 2618, and a plurality of support ribs 2612*b*. Sidewalls 2614, 2616 can include ridges 2613, 2615 which contain or are coupled with tension cords 2617, 2619, respectively. As shown here, the tension cords are disposed within the sidewall ridges. Ablation assembly 2600 presents a bend plane 2630 that is low, at the level of the tension cords. FIG. 26B shows ablation assembly 2600 in a bent or curved configuration. As seen in FIG. 26B, the stabilizer member can be bent under tension. Elastic membrane windows 2612*a* are drawn taut, and in some cases can stretch when the ablation assembly bends. The stabilizer member can have elastic features on the backbone. Material under the bending plane is compressing/shortening in length. The small flexible portions do not resist that and are small enough to not bow or buckle away from tissue so much that an air gap is created which can lead to loss of suction. As the stabilizer is passed or dragged through tissue planes, the thin soft bubbles fold into soft scale-like flaps that protect tissue from potential damage caused by the stiffer vertical ribs. In FIG. 27, the 3-4 bubbles on the right side are pushed into this shape by tissue.

Figure 28A:
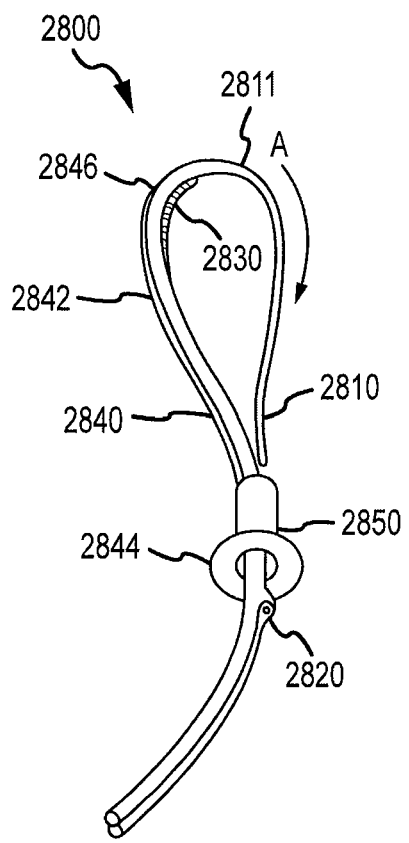
FIGS. 28A-28C show aspects of ablation systems with a stabilizer member according to embodiments of the present invention.
Figure 28B:
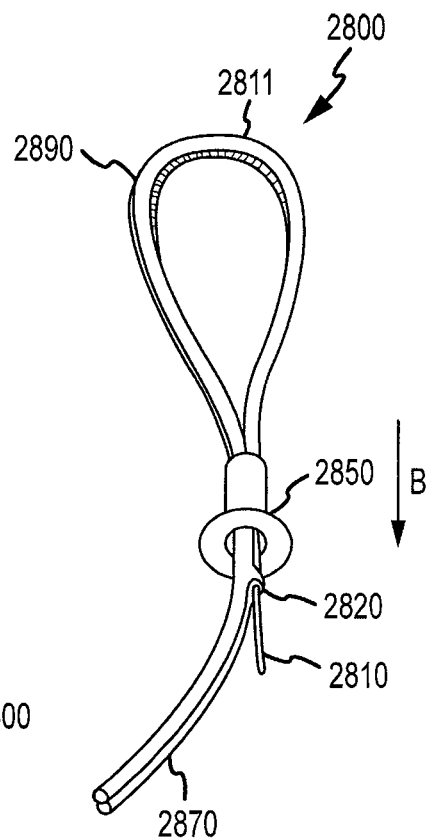
Figure 28C:
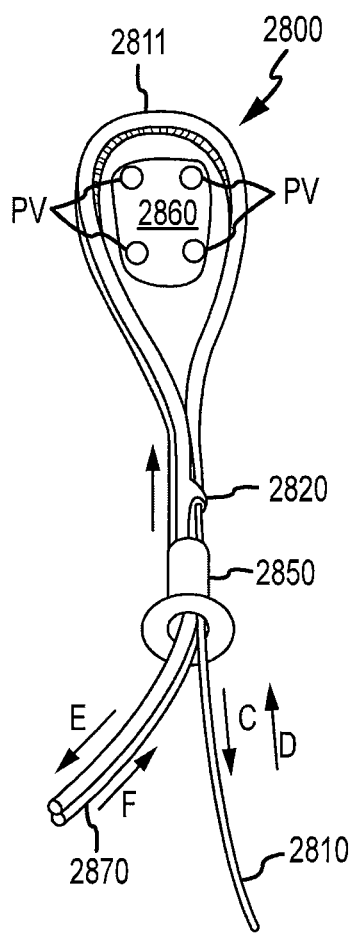

FIGS. 28A to 28C show aspects of an ablation system according to embodiments of the present invention. FIG. 28A shows ablation system 2800 having a distal end 2810, a catch or belt loop 2820, an ablation member 2830, a stabilizer member 2840, a trocar 2850, and a proximal end 2870. In some embodiments, trocar or introducer 2850 can have an inside diameter of about 10 mm. The trocar can present a stiff tube that is placed through the body wall that the entire ablation system or portions thereof are passed through. FIG. 28B shows another view of ablation system 2800, where distal end 2810 is disposed in trocar 2850 and catch 2820. As depicted in FIG. 28C, ablation system 2800 can be disposed about a patient tissue, such as a heart 2860 and pulmonary veins (PV). With a more detailed reference now to FIG. 28A, ablation system 2800 includes a flexible ablation member 2830, an encircling mechanism or catch 2820 such as a belt loop, a hook, a closable clasp, or the like, and a flexible stabilizer member or bracing 2840 having a distal end 2842, a proximal end 2844, and a recessed receiving slot or receptacle 2846. Ablation member 2830 is disposed at least partially within receptacle 2846. The combination of the ablation member and the stabilizer member can collectively be referred to as an ablation assembly 2890. In use, an operator may treat a patient by wrapping a loop structure 2811 of the ablation system around pulmonary veins of a patient. This may involve passing distal end 2810 circumferentially around the tissue as indicated arrow A, and through trocar 2850 and catch 2820 as indicated by arrow B in FIG. 28B. In this way, the ablation system can form a lasso about the patient tissue. The operator may expand or contract loop structure 2811 of ablation system 2800 by manipulating distal end 2810, proximal end 2870, or trocar 2850. Moving distal end 2810 in direction C, as shown in FIG. 28C, results in contraction of loop structure 2811 of ablation system 2800 in a cinching fashion. Moving distal end 2810 in direction D results in expansion of loop structure 2811 of ablation system 2800. In this way, the operator can adjust the sizing of loop structure 2811 to accommodate any of a variety of anatomical configurations in the patient tissue. As shown here, loop structure 2811 can be adjusted to settle securely and snugly around the pulmonary veins. Stabilizer member 2840 may be made of or include any suitable flexible material, such as a silicone, polyurethane, polycarbonate, another suitable polymer, or combination of polymers or the like.

In some embodiments of use, a surgeon or operator can pass stabilizer member distal end 2810 through catch 2820, and expand or contract ablation system 2800 by manipulating the proximal end 2870. Moving proximal end 2870 in direction E results in contraction of loop structure 2811 of ablation system 2800 in a cinching fashion. Moving proximal end 2870 in direction F results in expansion of loop structure 2811 of ablation system 2800. Catch 2820 is typically formed so that it can receive distal end 2810 and maintain the position of a portion of distal end 2810 relative to a portion of proximal end 2870. Catch 2820 may include a loop, a hook, an aperture, an eyelet, a channel, a recess, or the like. As shown in FIGS. 28A to 28C, catch 2820 can be integral with proximal end 2870. In some embodiments, catch 2820 is coupled with proximal end 2870. In some embodiments, a catch is coupled with or integral to distal end 2810, and adapted to receive proximal end 2870 therethrough.

As shown in FIG. 28C, a surgeon or operator can advance catch 2820 through trocar 2850, so that catch 2820 is disposed on a distal side of trocar 2850. Ablation member 2830 may include one or more mechanisms for providing various types of ablation energy, including RF, thermoelectric, cryogenic, microwave, laser, ultrasound or the like. An operator can administer ablative energy through the ablation member to produce a circular or closed ablation pattern or lesion on the patient tissue. Accordingly, embodiments encompass techniques wherein distal end 2810 is threaded or passed through catch 2820.

Figure 29A:
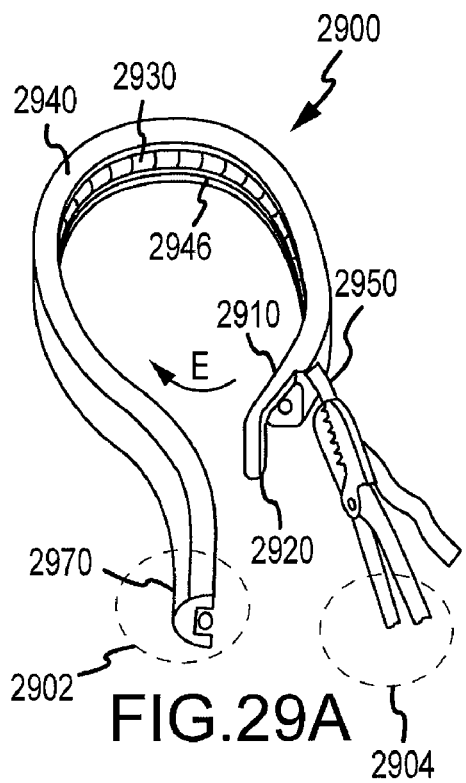
FIGS. 29A-29C show aspects of ablation systems with a stabilizer member according to embodiments of the present invention.
Figure 29B:
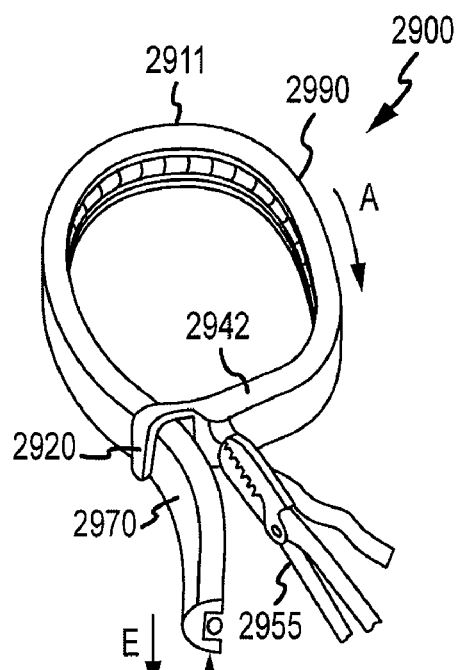
Figure 29C:
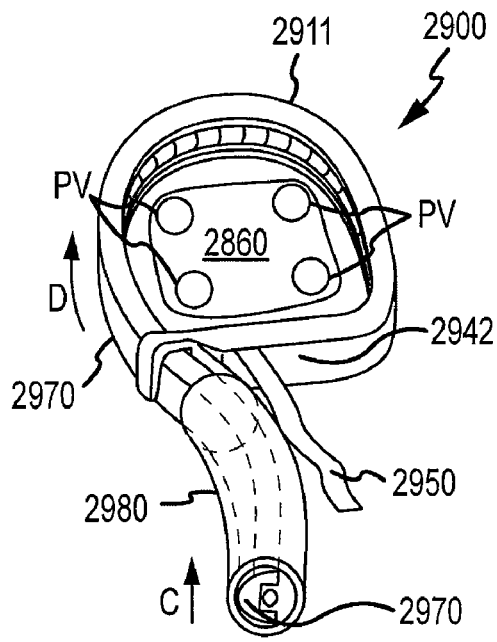

FIGS. 29A to 29C show aspects of an ablation system according to embodiments of the present invention. FIG. 29A shows ablation system 2900 having a distal end 2910, a catch or belt loop 2920, an ablation member 2930, a stabilizer member 2940, a distal or grasping element 2950, and a proximal end 2970. A pair of forceps can be used to grab the distal element. Ablation system 2900 can be introduced toward a patient tissue via a first port 2902, and the forceps 2955 can be introduced toward the ablation system via a second port 2904. FIG. 29B shows another view of ablation system 2900, where distal end 2910 is attached with proximal end 2970 via catch 2920. A pair of forceps can be used to hook the catch over the proximal end. As depicted in FIG. 29C, ablation system 2900 can be disposed about a patient tissue, such as a heart 2960 and pulmonary veins (PV), and can include a sleeve 2980. Proximal end 2970 can be pulled in one direction, and sleeve 2980 can be pushed in an opposing direction, so as to tighten the ablation assembly about a patient tissue. With a more detailed reference now to FIGS. 29A and 29B, ablation system 2900 includes a flexible ablation member 2930, an encircling mechanism or catch 2920 such as a belt loop, a hook, a closable clasp, or the like, and a flexible stabilizer member or bracing 2940 having a distal end 2942, a proximal end 2970, and a recessed receiving slot or receptacle 2946. Ablation member 2930 is disposed at least partially within receptacle 2946. The combination of the ablation member and the stabilizer member can collectively be referred to as an ablation assembly 2990. In use, an operator may treat a patient by wrapping a loop structure 2911 of the ablation system around pulmonary veins of a patient. This may involve passing distal end 2910 circumferentially around the tissue as indicated arrow A, and securing catch 2920 with proximal end 2970.

The operator can facilitate placement of system 2900 by engaging or grasping distal element 2950 and maneuvering distal end 2942. In some embodiments, distal element 2950 includes a string or tape which the operator can grasp with a maneuvering mechanism or positioning device 2955, such as a pair of forceps. FIGS. 29A and 29B show that distal end 2942 can be advanced or steered as depicted by arrow B. In this way, ablation system 2900 can be further wrapped around the patient tissue, so as to encircle or lasso the tissue. Positioning device 2955 can be introduced into the patient via a minimally invasive incision. Positioning device 2955 may be used by the operator to grasp distal element 2950 and maneuver distal end 2942 as desired. As shown in FIG. 29C, an operator can advance sleeve 2980 along proximal end 2970 toward distal end 2942 as indicated by arrow C, so as to force catch 2920 along proximal end 2970 toward distal end 2942 as indicated by arrow D, and thereby cinch or contract loop structure 2911. Hence, the loop structure can conform with anatomical features of the heart 2860, so as to provide enhanced lesion continuity. Conversely, an operator may allow loop structure 2911 to expand or relax by moving sleeve in a direction opposite of arrow C. In this way, the operator can adjust the sizing of loop structure 2911 to accommodate any of a variety of anatomical configurations in the patient tissue. As shown here, loop structure 2911 can be adjusted to settle securely and snugly around the pulmonary veins. Stabilizer member 2940 may be made of or include any suitable flexible material, such as a silicone, polyurethane, polycarbonate, another suitable polymer, or combination of polymers or the like.

In some embodiments of use, a surgeon or operator can pass stabilizer member distal end 2910 through catch 2920, and expand or contract ablation system 2900 by manipulating the proximal end 2970. Moving proximal end 2970 in direction E results in contraction of loop structure 2911 of ablation system 2900 in a cinching fashion. Moving proximal end 2970 in direction F results in expansion of loop structure 2911 of ablation system 2900. Catch 2920 is typically formed so that it can receive proximal end 2944 and maintain the position of a portion of distal end 2910 relative to a portion of proximal end 2970. Catch 2920 may include a loop, a book, an aperture, an eyelet, a channel, a recess, or the like. As shown in FIGS. 29A to 29C, catch 2820 can be integral with distal end 2942. In some embodiments, catch 2920 is coupled with distal end 2942. In some embodiments, a catch is coupled with or integral to proximal end 2970, and adapted to receive distal end 2942 therethrough.

Ablation member 2930 may include one or more mechanisms for providing various types of ablation energy, including RF, thermoelectric, cryogenic, microwave, laser, ultrasound or the like. An operator can administer ablative energy through the ablation member to produce a circular or closed ablation pattern or lesion on the patient tissue. Positioning device 2955 may include opposable jaws, forceps, clamps or any combination or other suitable means that can be used by surgeon or operator to grasp or hold distal element 2950. Positioning device 2955 may also be used to position ablation system 2900 on the heart or reposition ablation system 2900 to perform ablation in multiple locations on a heart.

FIGS. 30A and 30B show aspects of an ablation system according to embodiments of the present invention. Ablation system 3000 can be wrapped around a patient tissue 3005 of a patient 3005a, such as a heart or other cardiovascular tissue, as indicated by arrow A. A distal end 3010 of the system can be pulled or passed through a cinching device 3020, as indicated by arrow B. Ablation system 3000 can include a flexible ablation assembly 3015, a cinching device 3020, and a trocar 3007. Ablation assembly 3015 can be used to deliver energy to the patient tissue 3005 in order to ablate the tissue. In some embodiments, ablation assembly 3015 includes an ablation member 3016, such as an electrode, coupled with a stabilizer member or backbone 3017. In some embodiments, ablation assembly 3015 might include any suitable ablation mechanism designed to deliver different forms of energy, including, but without limitation to, RF, thermoelectric, cryogenic, microwave, laser, ultrasound or the like. In some embodiments, stabilizer member 3017 includes a flexible backbone member coupled with the ablation member. An operator can use cinching device 3020 to help increase or modulate the amount of contact between ablation member 3016 and the patient tissue 3005. FIG. 30B shows a cross-section view of cinching device 3020, corresponding to the A-A line depicted in FIG. 30A. Cinching device 3020 may come in many different configurations and is not limited to those depicted in the figures. As shown here, cinching device 3020 can include a tubular member 3022, a proximal flange, 3024, and an internal divider 3026. Cinching device 3020 can define a first lumen or passage 3027a and a second lumen or passage 3027b. In some cases, elements of cinching device 3020 may include insulating or non-conducting materials.

In use, an operator can pass or place ablation assembly 3015 through first passage 3027a of cinching device 3020, as indicated by arrow C. The ablation assembly can then be wrapped around the patient tissue 3005 as indicated by arrow A, and distal end 3010 of the ablation assembly can then be pulled back or passed through second passage 3027b of cinching device 3020, as indicated by arrow B. As shown here, the ablation member can thus be wrapped around patient tissue 3005, which may include a heart or other cardiovascular tissue, and distal end 3010 of the ablation assembly can be pulled or placed through cinching device 3020 such that ablation assembly 3015 forms a loop structure 3019.

Loop structure 3019 can be tightened around the patient tissue by a cinching procedure, for example by advancing the cinching device toward the tissue as indicated by arrow D. For example, an operator can grasp or control flange 3024 of cinching device 3020 so as to move the cinching device toward the tissue as indicated by arrow D. Relatedly, an operator can grasp or control distal section 3010 of the ablation assembly, a proximal section 3012 of the ablation assembly, or both, so as to positionally fix ablation assembly 3015 or provide an opposing force to the cinching operation described above, as indicated by arrows E and F. Cinching device 3020 can be advanced along ablation assembly 3015 toward or away from the tissue, so as to increase or decrease contact between ablation assembly 3015 and patient tissue 3005. When the assembly is in the desired location, energy can be applied through the ablation member 3016 of ablation assembly 3015, toward patient tissue 3005. The operator can position ablation assembly 3015 to make contact with selected parts of patient tissue 3005 such that when ablative energy is transmitted through the ablation assembly, it is possible to create an approximately circular or closed ablation pattern or lesion on the tissue. In this way, energy can be applied by the ablation system to the tissue. The position of cinching device 3020 relative to ablation assembly 3015 can be adjusted by the operator. For example, the cinching device may be advanced or retracted to differing degrees in order to increase or decrease an amount of contact between the ablation assembly and the patient tissue. As the stabilizer is dragged around the path around the heart from a port access, drag can be minimized or reduced if two sides of the stabilizer are pulled at once as in FIG. 30A.

FIG. 31 shows aspects of an ablation system according to embodiments of the present invention. Ablation system 3100 has a distal end 3110, a catch or belt loop 3120, an ablation member 3130, a stabilizer member 3140, a distal or grasping element 3150, and a proximal end 3170. A pair of forceps can be used to grab the distal element. Ablation system 3100 can be introduced toward a patient tissue via a first port or trocar 3102, and the forceps 3155 can be introduced toward the ablation system via a second port or trocar 3104. Distal end 3110 can be attached with proximal end 3170 via catch 3120. A pair of forceps can be used to hook the catch over the proximal end. Ablation system 3100 can be disposed about a patient tissue, such as a heart 3160 and pulmonary veins (PV), and can include a push tube 3180. Proximal end 3170 can be pulled in one direction, and sleeve 3180 can be pushed in an opposing direction, so as to tighten the ablation assembly about a patient tissue. With a more detailed reference now to FIG. 31, ablation system 3100 includes a flexible ablation member 3130, an encircling mechanism or catch 3120 such as a belt loop, a hook, a closable clasp, or the like, and a flexible stabilizer member or bracing 3140 having a distal end 3142, a proximal end 3144, and a recessed receiving slot or receptacle 3146. Ablation member 3130 is disposed at least partially within receptacle 3146. The combination of the ablation member and the stabilizer member can collectively be referred to as an ablation assembly 3190. In use, an operator may treat a patient by wrapping a loop structure 3111 of the ablation system around pulmonary veins of a patient. This may involve passing distal end 3110 circumferentially around the tissue as indicated arrow A, and securing catch 3120 with proximal end 3170.

The operator can facilitate placement of system 3100 by engaging or grasping distal element 3150 and maneuvering distal end 3142. In some embodiments, distal element 3150 includes a string or tape which the operator can grasp with a maneuvering mechanism or positioning device 3155, such as a pair of forceps. Distal end 3142 can be advanced or steered as depicted by arrow B. In this way, ablation system 3100 can be further wrapped around the patient tissue, so as to encircle or lasso the tissue. Positioning device 315 5 can be introduced into the patient via a minimally invasive incision. Positioning device 3155 may be used by the operator to grasp distal element 3150 and maneuver distal end 3142 as desired. An operator can advance sleeve 3180 along proximal end 3170 toward distal end 3142 as indicated by arrow C, so as to force catch 3120 along proximal end 3170 toward distal end 3142 as indicated by arrow D, and thereby cinch or contract loop structure 3111. Conversely, an operator may allow loop structure 3111 to expand or relax by moving sleeve in a direction opposite of arrow C. In this way, the operator can adjust the sizing of loop structure 3111 to accommodate any of a variety of anatomical configurations in the patient tissue. As shown here, loop structure 3111 can be adjusted to settle securely and snugly around the pulmonary veins. Stabilizer member 3140 may be made of or include any suitable flexible material, such as a silicone, polyurethane, polycarbonate, another suitable polymer, or combination of polymers or the like.

In some embodiments of use, a surgeon or operator can pass stabilizer member distal end 3110 through catch 3120, and expand or contract ablation system 3100 by manipulating the proximal end 3170. Moving proximal end 3170 in direction E results in contraction of loop structure 3111 of ablation system 3100 in a cinching fashion. Moving proximal end 3170 in direction F results in expansion of loop structure 3111 of ablation system 3100. Catch 3120 is typically formed so that it can receive proximal end 3144 and maintain the position of a portion of distal end 3110 relative to a portion of proximal end 3170. Catch 3120 may include a loop, a hook, an aperture, an eyelet, a channel, a recess, or the like. Catch 3120 can be integral with distal end 3142. In some embodiments, catch 3120 is coupled with distal end 3142. In some embodiments, a catch is coupled with or integral to proximal end 3170, and adapted to receive distal end 3142 therethrough.

Ablation member 3130 may include one or more mechanisms for providing various types of ablation energy, including RF, thermoelectric, cryogenic, microwave, laser, ultrasound or the like. An operator can administer ablative energy through the ablation member to produce a circular or closed ablation pattern or lesion on the patient tissue. Positioning device 3155 may include opposable jaws, forceps, clamps or any combination or other suitable means that can be used by surgeon or operator to grasp or hold distal element 3150. Positioning device 3155 may also be used to position ablation system 3100 on the heart or reposition ablation system 3100 to perform ablation in multiple locations on a heart.

FIGS. 32A to 32D show aspects of ablation systems according to embodiments of the present invention. An ablation system can be wrapped around a patient tissue, such as a heart or other cardiovascular tissue, as indicated by arrow A. A distal end of the system can be pulled or passed through a cinching device, as indicated by arrow B. As illustrated in FIG. 32A, an ablation system 3200a can include a flexible ablation assembly 3215a, a cinching device 3220a, and a trocar 3207a. Ablation assembly 3215a can be used to deliver energy to the patient tissue in order to ablate the tissue. In some embodiments, ablation assembly 3215a includes an ablation member 3216a, such as an electrode, coupled with a stabilizer member or backbone 3217a. In some embodiments, ablation assembly 3215a might include any suitable ablation mechanism designed to deliver different forms of energy, including, but without limitation to, RF, thermoelectric, cryogenic, microwave, laser, ultrasound or the like. In some embodiments, stabilizer member 3017a includes a flexible backbone member coupled with the ablation member. An operator can use cinching device 3020a to help increase or modulate the amount of contact between ablation member 3016a and the patient tissue. As shown here, cinching device 3220a can include a proximal flange 3222a, a central portion or moveable center blade 3224a, and a distal portion 3226a which is adapted to contact the ablation member. Cinching device 3220a, in combination with trocar 3207a, can define a first lumen or passage 3227a and a second lumen or passage 3228a. In some cases, elements of cinching device 3220a may include insulating or non-conducting materials.

In use, an operator can pass or place ablation assembly 3215a through first passage 3227a of cinching device 3220a, as indicated by arrow C. The ablation assembly can then be wrapped around the patient tissue as indicated by arrow A, and distal end 3210a of the ablation assembly can then be pulled back or passed through second passage 3228a of cinching device 3220a, as indicated by arrow B. As shown here, the ablation member can thus be wrapped around patient tissue, which may include a heart or other cardiovascular tissue. Distal end 3210a of the ablation assembly, proximal end 3270a of the ablation assembly, or both, can be pulled or otherwise positioned such that ablation assembly 3215a forms a loop structure 3219a about the patient tissue.

Loop structure 3219a can be tightened around the patient tissue by a cinching procedure, for example by advancing the cinching device toward the tissue as indicated by arrow D. For example, an operator can grasp or control flange 3222a of cinching device 3220a so as to move the cinching device toward the tissue as indicated by arrow D. Relatedly, an operator can grasp or control distal section 3210a of the ablation assembly, a proximal section 3270a of the ablation assembly, or both, so as to positionally fix ablation assembly 3215a or provide an opposing force to the cinching operation described above, as indicated by arrows E and F. Accordingly, an operator can engage a distal ablation tip 3218a with distal portion 3226a, the distal ablation tip 3218a has been separated from stabilizer member 3217a. Cinching device 3220a can be advanced along ablation assembly 3215a toward or away from the tissue, so as to increase or decrease contact between ablation assembly 3215a and patient tissue 3205a. When the assembly is in the desired location, energy can be applied through the ablation member 3216a of ablation assembly 3215a, toward patient tissue 3205a. The operator can position ablation assembly 3215a to make contact with selected parts of patient tissue 3205a such that when ablative energy is transmitted through the ablation assembly, it is possible to create an approximately circular or closed ablation pattern or lesion on the tissue. In this way, energy can be applied by the ablation system to the tissue. The position of cinching device 3220a relative to ablation assembly 3215a can be adjusted by the operator. For example, the cinching device may be advanced or retracted to differing degrees in order to increase or decrease an amount of contact between the ablation assembly and the patient tissue.

As illustrated in FIG. 32B, an ablation system 3200b can include a flexible ablation assembly 3215b and a cinching device 3220b. Ablation assembly 3215b can be used to deliver energy to the patient tissue in order to ablate the tissue. In some embodiments, ablation assembly 3215b includes an ablation member 3216b, such as an electrode, coupled with a stabilizer member or backbone 3217b. As shown here, cinching device 3220b can include a proximal flange 3222b, a central portion or center blade 3224b, and a distal portion 3226b which is adapted to contact the ablation member. As shown in FIG. 32C, cinching device 3220b can define a first lumen or passage 3227b and a second lumen or passage 3228b. A cross-section of these passages may present a "double-D" profile, and the cinching device 3220b can be manufactured via an extrusion procedure.

In use, an operator can pass or place ablation assembly 3215b through first passage 3227b of cinching device 3220b, as indicated by arrow C. The ablation assembly can then be wrapped around the patient tissue as indicated by arrow A, and distal end 3210b of the ablation assembly can then be pulled back or passed through second passage 3228b of cinching device 3220b, as indicated by arrow B. As shown here, the ablation member can thus be wrapped around patient tissue, which may include a heart or other cardiovascular tissue. Distal end 3210b of the ablation assembly, proximal end 3270b of the ablation assembly, or both, can be pulled or otherwise positioned such that ablation assembly 3215b forms a loop structure 3219b about the patient tissue.

Loop structure 3219b can be tightened around the patient tissue by a cinching procedure, for example by advancing the cinching device toward the tissue as indicated by arrow D. For example, an operator can grasp or control flange 3222b of cinching device 3220b so as to move the cinching device toward the tissue as indicated by arrow D. Relatedly, an operator can grasp or control distal section 3210b of the ablation assembly, a proximal section 3270b of the ablation assembly, or both, so as to positionally fix ablation assembly 3215b or provide an opposing force to the cinching operation described above, as indicated by arrows E and F. Accordingly, an operator can engage a distal ablation tip 3218a with distal portion 3226a, the distal ablation tip 321 Sa has been separated from stabilizer member 3217a. This separated portion of ablation member 3216b can be urged toward or against a more proximal section 3216b' of the ablation member, so as to form a more circular or circumferential loop structure. As shown here, distal ablation tip 321 Sb can be disposed in close proximity with a more proximal section of the ablation member. In some cases, distal ablation tip 321b8 includes or is coupled with a distal guide 3213b having a recess 3212b that is contoured to receive the more proximal section of the ablation member.

Cinching device 3220b can be advanced along ablation assembly 3215b toward or away from the tissue, so as to increase or decrease contact between ablation assembly 3215b and patient tissue 3205b. The operator can position ablation assembly 3215b and ablation member 3216b to make contact with selected parts of patient tissue 3205b such that when ablative energy is transmitted through the ablation assembly, it is possible to create an approximately circular or closed ablation pattern or lesion on the tissue. The position of cinching device 3220b relative to ablation assembly 3215b can be adjusted by the operator. For example, the cinching device may be advanced or retracted to differing degrees in order to increase or decrease an amount of contact between the ablation assembly or the ablation member and the patient tissue.

As shown in FIG. 32D, as an ablation assembly 3215d is advanced about a patient tissue 3205d, in the direction indicated by arrow A, a distal ablation tip 3218d of an ablation member 3216d remains associated with a stabilizer member 3217d. This is shown at section D'. Then, as ablation assembly 3215d is advanced further about the tissue, and into a cinching device 3220d, in the direction indicated by arrow B, the changing curvature of the stabilizer member, from a concave bend to a convex bend, facilitates the separation of distal ablation tip 3218d from stabilizer member 3217d. This is shown at section D".

Figure 33A:
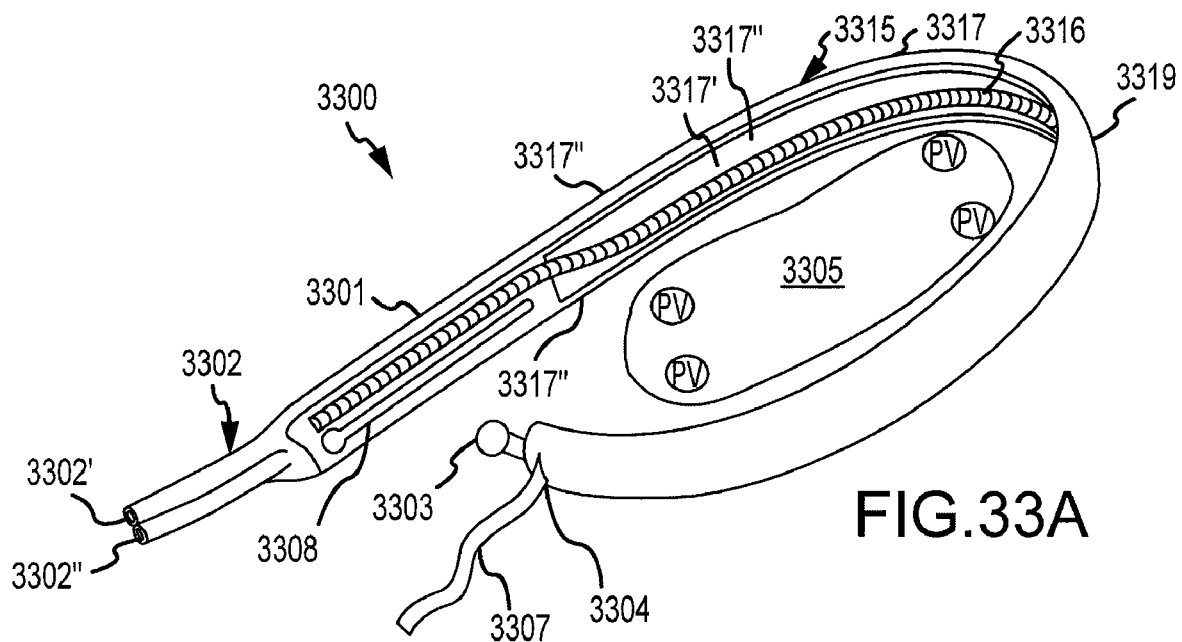
FIGS. 33A-33J show aspects of ablation systems with a stabilizer member according to embodiments of the present invention.
Figure 33B:
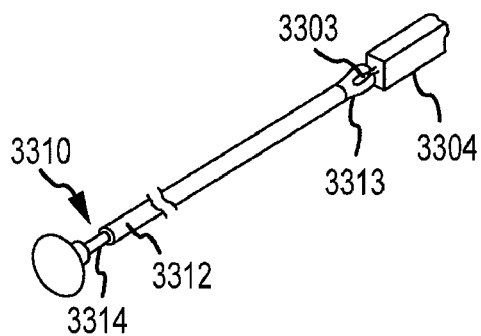

FIGS. 33A to 33J illustrate aspects of ablation systems according to embodiments of the present invention. As shown in FIG. 33A, an ablation system 3300 presents a proximal section or end 3302 and a distal section or end 3304. Ablation system 3300 includes an ablation assembly 3315 having an ablation member 3316 and a stabilizer member 3317. Proximal section 3302 includes a first lumen 3302' configured to receive the ablation member, and a second lumen 3302" configured to fluidly couple the stabilizer member with a suction source. In some embodiments, ablation system 3300 can present a "U" or loop shaped configuration, which can be placed near or applied to a path which surrounds or travels about the pulmonary veins (PV) of a patient tissue 3305. Distal section 3304 may include a distal element 3307 such as a ribbon, or the like. In use, an operator can facilitate placement of the ablation system by grasping distal element 3307 and maneuvering a system distal end 3304. In some embodiments, distal or grasping element 3307 includes a string or tape which the operator can grasp with a maneuvering mechanism such as a pair of forceps. Ablation system 3300 can be cinched about the pulmonary veins, so as to form an oval or loop shape. For example, a distal engagement member 3303 such as a ball disposed on distal end 3304 of system 3300 can be advanced toward a proximal engagement member 3308, such as slot or channel, disposed on a more proximal section 3301 of system 3300. In some cases, distal engagement member 3303 can be urged toward slot 3308 by an operator using an introducer instrument 3310, as shown in FIG. 33B. When distal engagement member 3303 engages proximal engagement member 3308, the distal engagement member can be moved along the proximal engagement member, either distally or proximally, so as to respectively tighten or loosen a loop enclosure or structure 3319 formed by the ablation system. In some cases, the proximal engagement member includes a track which has a shape that is complementary to the shape of the distal engagement member. In some cases, the position of distal engagement member 3303 along proximal engagement member 3308 can be incrementally adjusted, so as to achieve any desired loop structure circumference. Patients may present tissues of varying dimensions and sizes, and it may be desirable to configure ablation system 3300 so as to provide discrete stopping points or attraction points for distal engagement member 3303 along a length of proximal engagement member 3308. This allows an operator to select from a multiplicity of stable connection points, so as to form loop closures or ovals which are customized or dimensioned for a particular patient's anatomy.

Figure 33C:
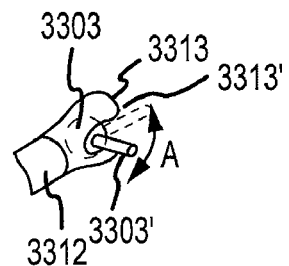

FIGS. 33B and 33C show aspects of an introducer instrument 3310 according to embodiments of the present invention. Introducer instrument 3310 can include an sleeve 3312, and an obturator 3314 which can be inserted into the sleeve. Sleeve 3312 may have a distal catch 3313 adapted to releasably couple with a distal engagement member 3303 of an ablation system. For example, a distal catch or introducer tip can be used to grasp a distal engagement member or conductive ball. In use, an operator may insert the obturator into the sleeve in a distal direction or fashion, such that the distal end of the obturator forces the distal engagement member out or away from the distal catch. Distal catch 3313 may include a recess 3313' that allows a stem 3303' of ball 3303 to swing or rotate, as indicated by arrow A, which allows ball 3303 to be directed toward or injected into slot 3308.

Figure 33D:
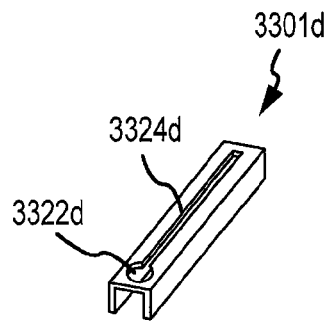
Figure 33E:
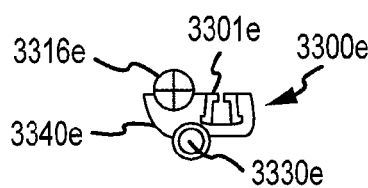
Figure 33F:
Figure 33G:
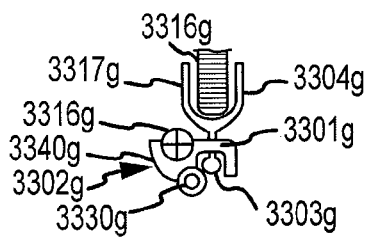
Figure 33H:

FIG. 33D shows features of a proximal engagement member 3301d according to embodiments of the present invention. Proximal engagement member 3301d includes a circular aperture 3322d and an elongate track 3324d. In some embodiments, proximal engagement member 3301d presents a keyhole and slot configuration. FIG. 33E shows a cross-section of a proximal portion of an ablation system 3300e, including a body 3340e, a proximal engagement member 3301 e, an ablation member 33 1 6e, and a vacuum lumen 3330e. Body 3340e can be made of molded silicone, for example, and proximal engagement member 3301e can be made of a harder material such as polycarbonate or polypropylene, for example. FIG. 33F shows a cross-section of a proximal portion body 3340f according to embodiments of the present invention. Body 3340f can be made of molded silicone, for example. FIG. 33G shows a cross-section of an ablation assembly 3300g, which includes a distal end 3304g and a proximal end 3302g. Distal end 3304g includes an ablation member 3316g disposed within a stabilizer member 3317g, and a distal engagement member 3303g. Proximal end 3302g includes a body 3340g, a proximal engagement member 3301g, an ablation member 3316g, and a vacuum or fluid lumen 3330g such as an air tube. Body 3340e can be made of molded silicone, for example. FIG. 33H shows a cross-section of a proximal portion body 3340h according to embodiments of the present invention. Body 3340h can be made of molded silicone, for example.

Figure 33I:
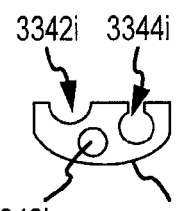
Figure 33J:
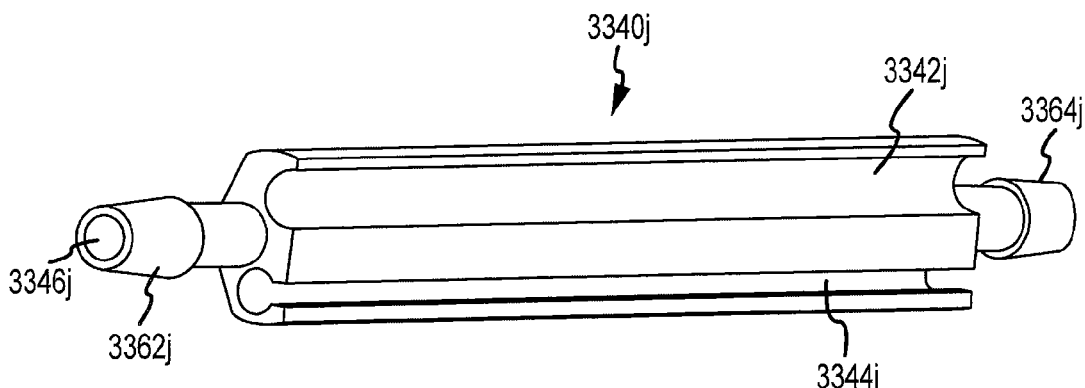

FIG. 33J shows a proximal section body 3340j according to embodiments of the present invention. Proximal section body 3340j includes an ablation member engagement section 3342j such as a recess or channel configured to receive an ablation member, a proximal engagement member 3344j such as a recess or channel configured to receive a distal engagement member, and a lumen or passage 3346j. As shown here, body 3340j includes a proximal barb fitting 3362j and a distal barb fitting 3364j. FIG. 33I shows a cross-section of a proximal section body 3 340i according to embodiments of the present invention. Proximal section body 3340i includes an ablation member engagement section 3342i such as a recess or channel configured to receive an ablation member, a proximal engagement member 3344i such as a recess or channel configured to receive a distal engagement member, and a lumen or passage 3346i. Hence, the proximal engagement member can present a track or slot that allows the operator to adjust the size of the loop structure, and to change the shape of the loop structure, for example from a teardrop shape to a more circular shape. The distal engagement member can include a conductive element, such as a stainless steel ball. The proximal engagement member may present discrete stopping points for the distal engagement member.

Proximal section 3302 includes a first lumen 3302' configured to receive the ablation member, and a second lumen 3302" configured to fluidly couple the stabilizer member with a suction or fluid source. FIG. 33A shows that ablation system 3300 can be disposed about four pulmonary veins (PV), so as to form a loop enclosure. As shown in FIG. 33J, proximal section body 3340j can include a proximal section channel or slot 3344*j* which is configured to receive a distal engagement member, and an ablation member path 3342*j* which is configured to receive an ablation member. In use, an operator can move wrap or place the ablation system about a patient tissue, and insert the distal engagement member into slot 3344*j*. By adjusting the position of the distal engagement member distally or proximally along the length of slot 3344*j*, the operator can respectively tighten or loosen a loop enclosure formed by the ablation system so as to form loops of various circumferences or configurations.

As shown in FIG. 33A, stabilizer member 3317 can include an interface 3317' that is configured to contact the patient tissue. Often, interface 3317' presents a concave channel 3317''' with two opposing sidewalls 3317''. Ablation member 3316 can be at least partially disposed within the concave channel, between the two sidewalls. The concave channel can be in fluid communication with second lumen 3302''. Accordingly, a fluid or vacuum can be applied to a patient tissue via the second lumen and concave channel. For example, the sidewalls may create a seal with the tissue, and a vacuum can be applied through the concave channel so as to suction the stabilizer member against the patient tissue. As shown in FIG. 33J, the fluid or vacuum can be applied through lumen or passage 3346*j* and through luers or fittings 3346*j*, 3364*j* which collectively provide a conduit between the proximal portion second lumen and the concave channel. In this way, an operator can create any desired pressure or material through the concave channel to the tissue.

Figure 34A:
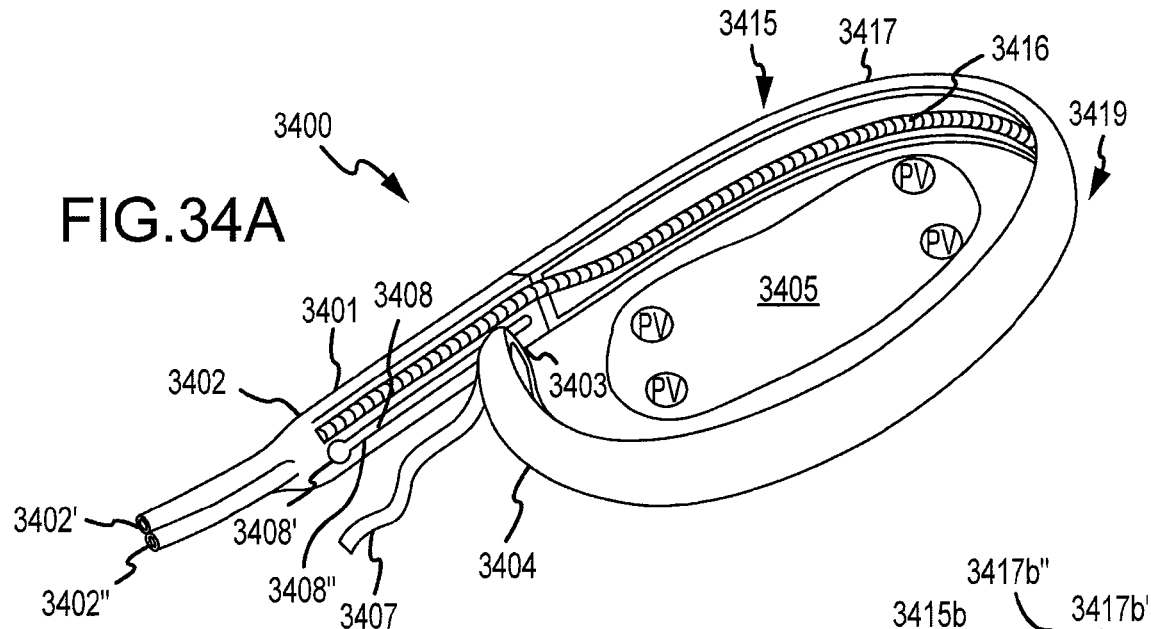

FIGS. 34A to 34E illustrate aspects of ablation systems according to embodiments of the present invention. As shown in FIG. 34A, an ablation system 3400 presents a proximal section or end 3402 and a distal section or end 3404. Ablation system 3400 includes an ablation assembly 3415 having an ablation member 3416 and a stabilizer member or bladder 3417. Proximal section 3402 includes a first lumen 3402' configured to receive the ablation member, and a second lumen 3402'' configured to fluidly couple the stabilizer member with a suction source. In some embodiments, ablation system 3400 can present a "U" or loop shaped configuration, which can be placed near or applied to a path which surrounds or travels about the pulmonary veins (PV) of a patient tissue 3405. Distal section 3404 may include a distal element 3407 such as a ribbon, or the like. In use, an operator can facilitate placement of the ablation system by grasping distal element 3407 and maneuvering a system distal end 3404. In some embodiments, distal or grasping element 3407 includes a string or tape which the operator can grasp with a maneuvering mechanism such as a pair of forceps. Ablation system 3400 can be cinched about the pulmonary veins, so as to form an oval or loop shape. For example, a distal engagement member such as a ball disposed on distal end 3404 of system 3400 can be advanced toward a proximal engagement member 3408, which may include a keyhole 3408' and slot 3408'', disposed on a more proximal section 3401 of system 3400. When the distal engagement member engages proximal engagement member 3408, the distal engagement member can be moved along the proximal engagement member, either distally or proximally, so as to respectively tighten or loosen a loop enclosure or structure 3419 formed by the ablation system. In some cases, the proximal engagement member includes a track which has a shape that is complementary to the shape of the distal engagement member. In some cases, the position of distal engagement member 3403 along proximal engagement member 3408 can be incrementally adjusted, so as to achieve any desired loop structure circumference. Patients may present tissues of varying dimensions and sizes, and it may be desirable to configure ablation system 3400 so as to provide discrete stopping points or attraction points for distal engagement member 3403 along a length of proximal engagement member 3408. This allows an operator to select from a multiplicity of stable connection points, so as to form loop closures or ovals which are customized or dimensioned for a particular patient's anatomy.

Figure 34B:
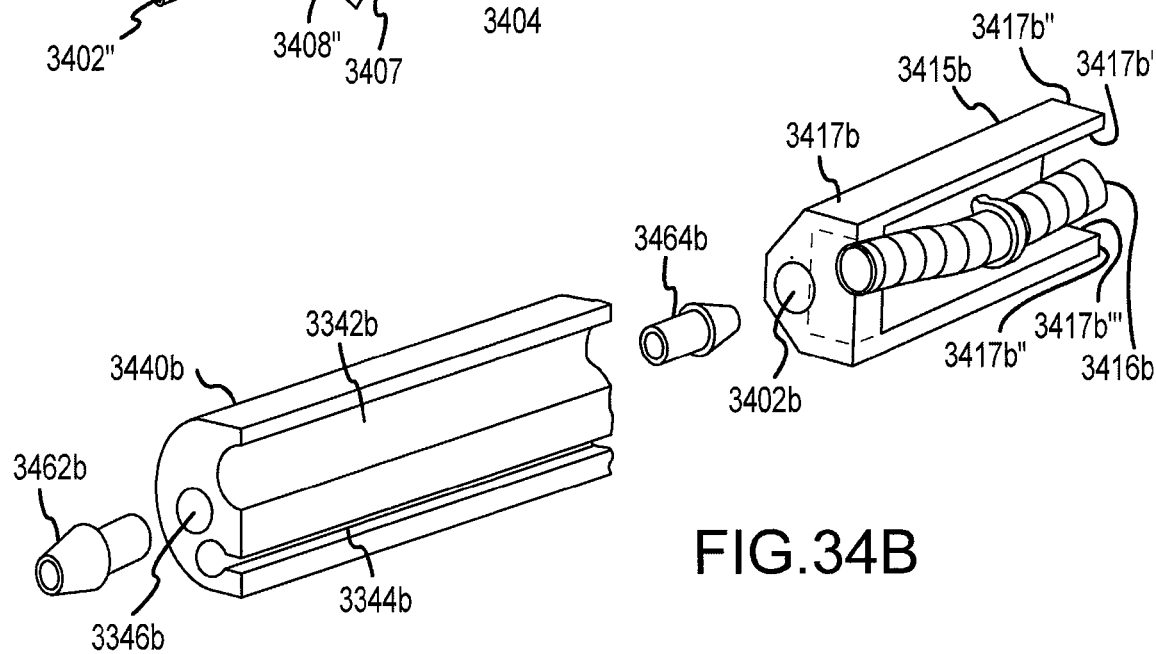

FIG. 34B shows aspects of proximal section body 3440*b*, couplings or fittings 3462*b*, 3464*b*, and ablation assembly 3415*b*, according to embodiments of the present invention. Ablation assembly 3415 includes a stabilizer member 3417*b* and an ablation member 3416*b*. Stabilizer member 3417*b* can include an interface 3417*b*' that is configured to contact the patient tissue. Often, interface 3417*b*' presents a concave channel 3417*b*''' with two opposing sidewalls 3417*b*''. Ablation member 3416*b* can be at least partially disposed within the concave channel, between the two sidewalls. The concave channel can be in fluid communication with a proximal lumen 3402*b* of the stabilizer member. Accordingly, a fluid or vacuum can be applied to a patient tissue via the proximal lumen and concave channel. For example, the sidewalls may create a seal with the tissue, and a vacuum can be applied through the concave channel so as to suction the stabilizer member against the patient tissue.

Proximal section body 3340*b* can include an ablation member engagement section 3342*b* such as a recess or channel configured to receive an ablation member, a proximal engagement member 3344*b* such as a recess or channel configured to receive a distal engagement member, and a lumen or passage 3346*b*. As shown here, body 3340*j* includes a proximal fitting 3362*b* and a distal fitting 3364*b*. FIG. 34A shows that ablation system 3400 can be disposed about four pulmonary veins (PV), so as to form a loop enclosure. As shown in FIG. 34B, proximal section body 3340*b* can include a proximal section channel or slot 3344*b* which is configured to receive a distal engagement member, and an ablation member path 3342*b* which is configured to receive an ablation member. In use, an operator can move wrap or place the ablation system about a patient tissue, and insert the distal engagement member into slot 3344*b*. By adjusting the position of the distal engagement member distally or proximally along the length of slot 3344*b*, the operator can respectively tighten or loosen a loop enclosure formed by the ablation system so as to form loops of various circumferences or configurations. A fluid or vacuum can be applied through lumen or passage 3346*b* and through luers or fittings 3346*b*, 3364*b* which collectively provide a conduit between the proximal portion second lumen and the concave channel. In this way, an operator can create any desired pressure or material through the concave channel to the tissue.

Figure 34C:
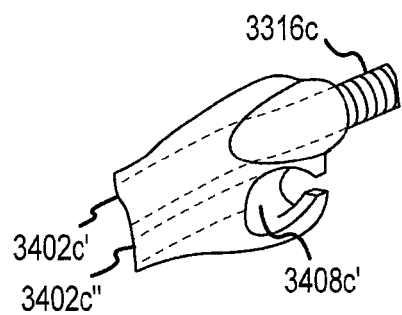

FIG. 34C shows a coupling section 3401*c*' that can be connected with a proximal section body. Coupling section 3401*c*' can include a first lumen 3402' configured to couple with a first lumen of the proximal section body, and a second lumen 3402'' configured to couple with a second lumen of the proximal section body. As shown here, first lumen 3402' may be configured to receive an ablation member 3416*c* therethrough. Coupling section 3401 *c*' can also include a proximal engagement member 3408*c*' that is configured to receive a distal engagement member. FIG. 34D1 shows a partial cross-section view of a proximal engagement member 34084, and FIG. 34D2 shows a partial perspective view of the proximal engagement member 3408*d*, according to embodiments of the present invention. Proximal engagement member 3408*d* may include a keyhole 3408*d*', a slot 3408'', and a plurality of position detents 3408*d*''' which can act to inhibit motion of a distal engagement member along the proximal engagement member. In some cases, a position detent may include a silicone plug. In use, an operator can use the position detents to incrementally adjust the position of the distal engagement member along a length of the proximal engagement member, so as to achieve any desired loop closure circumference. Patients may present tissues of varying dimensions and sizes, and it may be desirable to configure an ablation system so as to provide discrete stopping points or resistance points along a length of the proximal engagement member. This allows an operator to select from a multiplicity of stable connection points, so as to form loop closures or ovals which are customized or dimensioned for a particular patient's anatomy. FIG. 34E shows a cross-section view of a stabilizer member 3417e juxtaposed with a cross-section view of a proximal section body 3440e. As depicted here, stabilizer member 3417e includes an opposing pair of side walls 3417e" and a channel 3417e' disposed therebetween. Proximal section body 3440e includes an ablation member engagement section 3442e such as a recess or channel configured to receive an ablation member, a proximal engagement member 3444b such as a recess or channel configured to receive a distal engagement member, and a lumen or passage 3446e.

Figure 35A:
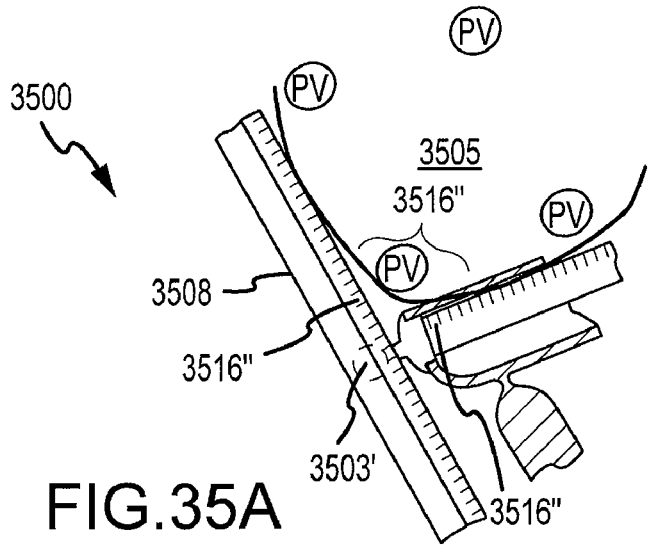
FIGS. 35A-35G show aspects of ablation systems with a stabilizer member according to embodiments of the present invention.
Figure 35B:
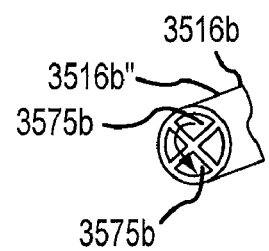
Figure 35C:
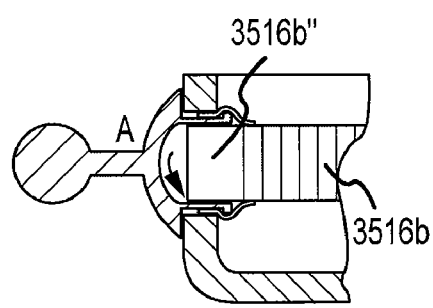
Figure 35D:
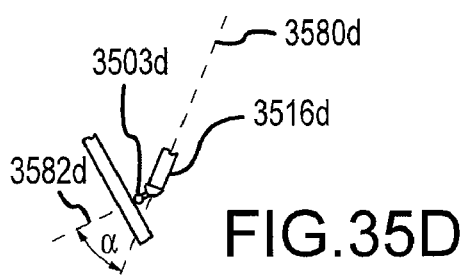
Figure 35E:
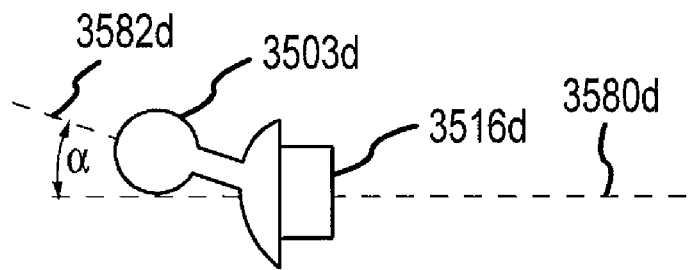
Figure 35F:
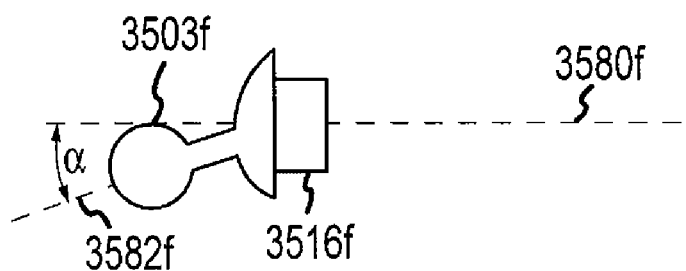
Figure 35G:
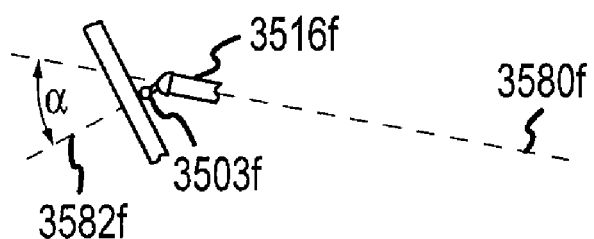
Figure 36A:
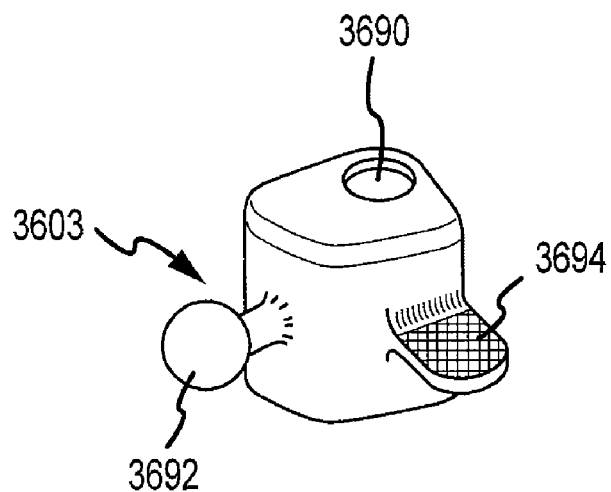
FIGS. 36A-36C show aspects of ablation systems with a stabilizer member according to embodiments of the present invention.
Figure 36B:
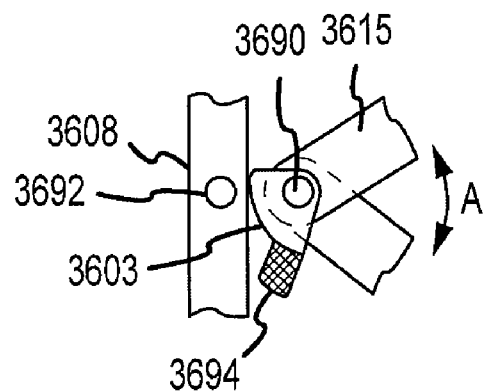
Figure 36C:
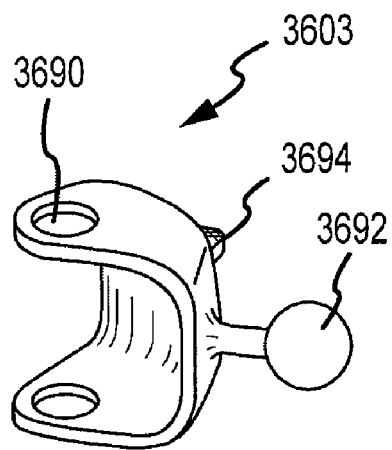

FIG. 35A shows an associative cooperation between a distal engagement member 3503 and a proximal engagement member 3508 of an ablation system 3500, according to embodiments of the present invention. As shown here, a gap 3516' may exist between a distal tip 3516" and a proximal section 3516''' of an ablation member 3516, when the system is wrapped about a patient tissue 3505. In some embodiments, the distal engagement member may include a bridge element 3503' that spans gap 3516' and provides electrical or ablative conductivity across gap 3516' between distal tip 3516" and a proximal section 3516'''. As shown in FIGS. 35B and 35C, an ablation member 3516b can include one or more lumens 3575b having openings at a distal tip 3516". In use, a cooling fluid can be passed through lumens 3575b, such that the fluid exits one lumen and enters another lumen as indicated by arrow A. FIGS. 35D and 35E depict a distal section of an ablation system that presents an offset angle a between a longitudinal axis 3580d define by an ablation member 3516d and a longitudinal axis 3582d defined by a distal engagement member 3503d. FIGS. 35F and 35G depict a distal section of an ablation system that presents an offset angle a between a longitudinal axis 3580f define by an ablation member 3516f and a longitudinal axis 3582f defined by a distal engagement member 3503f. Such offset angles can enhance or facilitate the cooperative association between a distal engagement member and a proximal engagement member. For example, the offset angle can make it easier to couple the distal engagement member with the proximal engagement member. [notes indicate:

FIGS. 36A to 36C shows aspects of a distal engagement member 3603 according to embodiments of the present invention. As shown in these figures, distal engagement member 3603 can include a pivot mechanism 3690, such as an aperture, a pin, a hinge, or the like, that allows the distal engagement member and an ablation assembly 3615 to pivot relative to each other. Distal engagement member 3603 can include a ball 3692 which can be inserted into a slot of a proximal engagement member 3608. Distal engagement member 3603 can also include a grasping tab 3694. In use, an operator may grasp the grasping tab with forceps or another grasping mechanism, and manipulate the position of the distal engagement member along a length of the proximal engagement member. As the distal engagement member slides along the length of the proximal engagement member, the ablation assembly and the distal engagement member can pivot relative to each other, as indicated by arrow A in FIG. 36A. Hence, the pivoting or hinge mechanism can allow an ablation assembly to be cinched or otherwise expanded or contracted, so as to form a loop structure about a patient tissue.

Figure 37A:
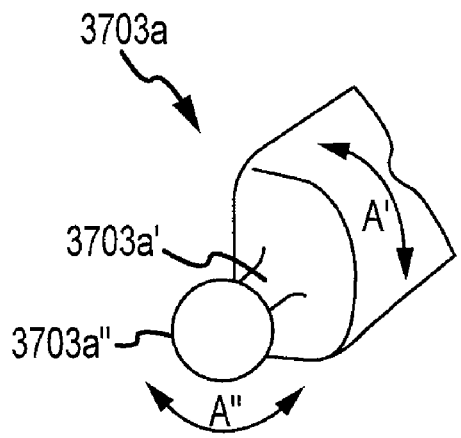
FIGS. 37A-37C show aspects of ablation systems with a stabilizer member according to embodiments of the present invention.
Figure 37B:
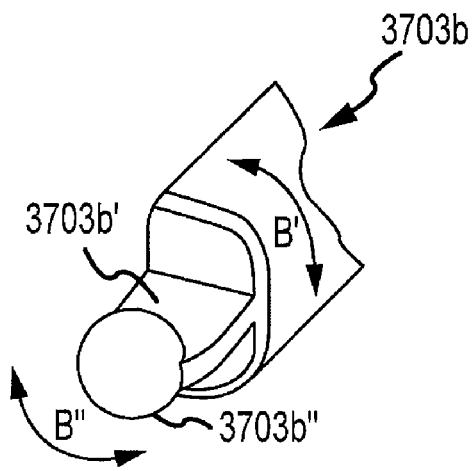
Figure 37C:
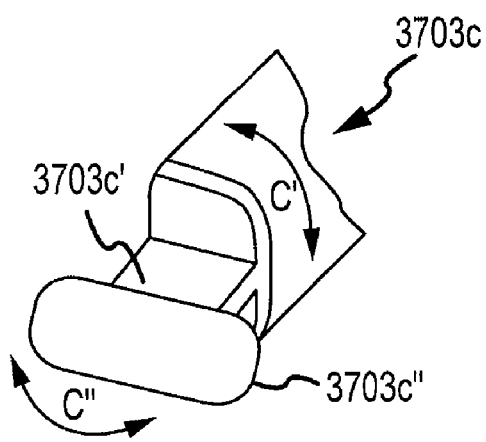

FIG. 37A shows a distal engagement member 3703a according to embodiments of the present invention. Distal engagement member 3703a includes a cylindrical stern 3703a' and a spherical head 3703a". FIG. 37B shows a distal engagement member 3703b according to embodiments of the present invention. Distal engagement member 3703b includes a flat or planar stern 3703b' and a spherical head 3703b". FIG. 37C shows a distal engagement member 3703c according to embodiments of the present invention. Distal engagement member 3703c includes a flat or planar stern 3703c' and a cylindrical head 3703c". These different configurations can allow a distal section of the ablation assembly or stabilizer member to roll or swing to varying degrees. For example, distal engagement member 3703a of FIG. 37A allows for substantial roll as indicated by arrow A', and for substantial swing as indicated by arrow A". Distal engagement member 3703b of FIG. 37B allows for little or no roll as indicated by arrow B', and for substantial swing as indicated by arrow B". Distal engagement member 3703c of FIG. 37C allows for little or no roll as indicated by arrow C', and for little or no swing as indicated by arrow C". In some embodiments, the long axis of 3703c" may be something other than 90° to the long axis of the stabilizer to help establish a desired angle of mating.

Figure 38A:
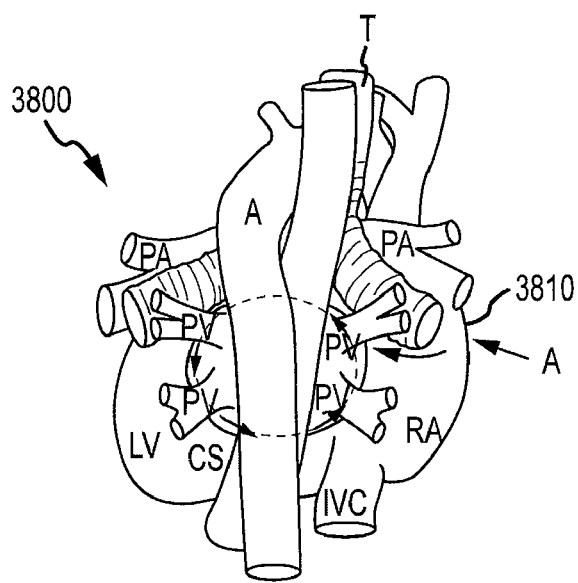
FIGS. 38A-38B show aspects of ablation systems with a stabilizer member according to embodiments of the present invention.
Figure 38B:
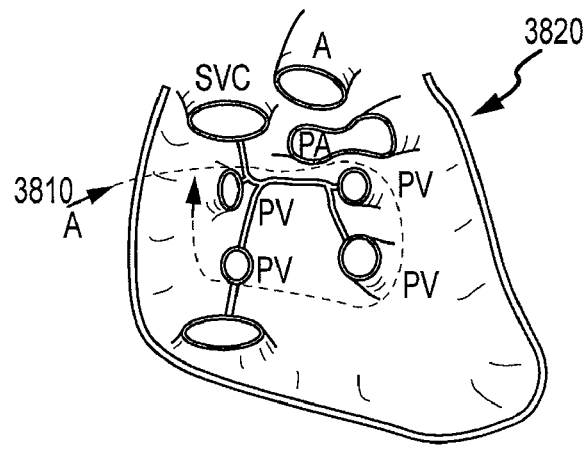
Figure 39:
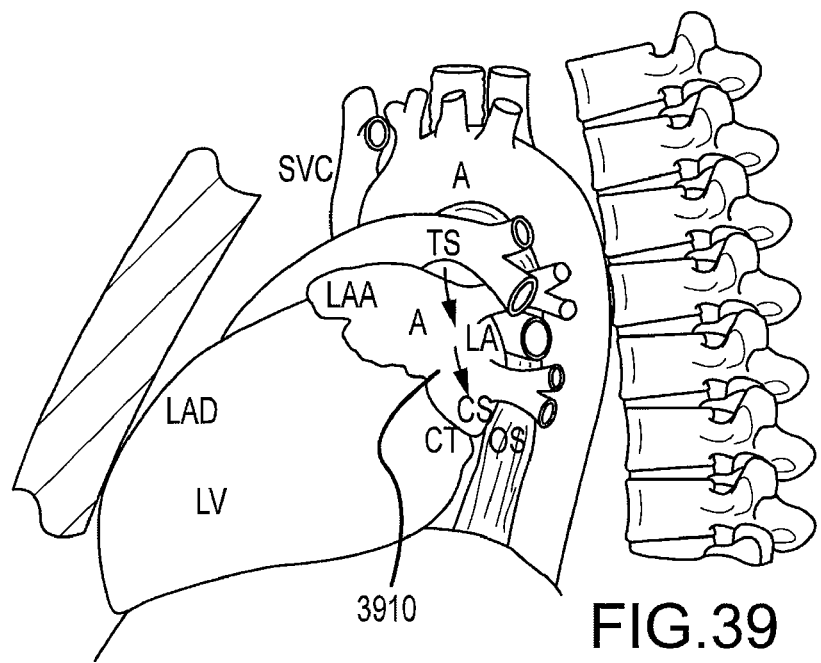
FIG. 39 shows aspects of an ablation system with a stabilizer member according to embodiments of the present invention.

FIG. 38A shows a posterior view of a patient heart 3800. An ablation system insertion path 3810 is shown by arrows A. In an exemplary procedure, an operator can advance an ablation system along ablation system insertion path 3810, so as to place the ablation system in the desired location for ablating the patient tissue. FIG. 38B shows an anterior view of a posterior pericardial lining 3820 of a patient. In FIG. 38B, the heart is swung out 1800 relative to the view shown in FIG. 38A. Ablation system insertion path 3810 is shown by arrows A. In an exemplary procedure, an operator can advance an ablation system along ablation system insertion path 3810, so as to place the ablation system in the desired location for ablating the patient tissue. FIG. 39, provides a left lateral view of a patient. Arrows A indicate an ablation system insertion path 3910. In an exemplary procedure, an operator can advance an ablation system along ablation system insertion path 3910, so as to place the ablation system in the desired location for ablating the patient tissue.

Figure 44:
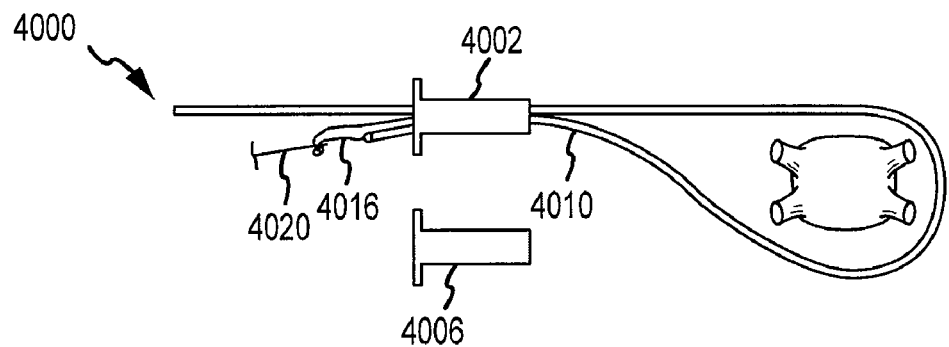
FIG. 44 shows aspects of an ablation system with a stabilizer member according to embodiments of the present invention.

FIGS. 40 to 51 illustrate aspects of an exemplary method for inserting an ablation system 4000 into a patient. FIG. 40 shows a pusher 4005 and a tape hook 4020 according to embodiments of the present invention. As shown in FIG. 41, an operator can place a first trocar 4002 and a second trocar 4006 into a patient 4004. A guide tube 4008 may be disposed through first trocar 4002. In some cases, a guide tube may include an internal obturator. An operator can advance an ablation assembly 4010 through trocar 4002 and guide tube 4008, between a pulmonary vein (PV) and a superior vena cava (SVC) of the patient, and about the heart 4012 as indicated by arrows A and B. The operator can also advance a grasping mechanism 4014 through second trocar, between a pulmonary vein (PV) and an inferior vena cava (IVC), as indicated by arrow C. As depicted in FIG. 43, the operator can also advance tape hook 4020 through first trocar, and can grasp a distal grasping element 4016 of the ablation system. The operator can manipulate the grasping mechanism so as to move the distal grasping element toward the tape hook. In some cases, the operator can retract guide tube 4008 from first trocar 4002 prior to or subsequent to inserting the tape hook. In some cases, trocar 4002 can provide access through an oblique or transverse sinus. Similarly, trocar 4006 can provide access to or through an oblique or transverse sinus. FIG. 42 shows how distal grasping element 4016 can be coupled with or snagged by tape hook 4020. As illustrated in FIG. 44, the operator can retract tape hook 4020 through first trocar 4002, thereby drawing or retrieving distal grasping element 4016 and a distal section of ablation assembly 4010 through first trocar 4002 as well. In some cases, the proximal end of the bladder can be advanced further through push tube from the outside to allow it to slide around the anatomy as the distal end is pulled out.

Figure 45:
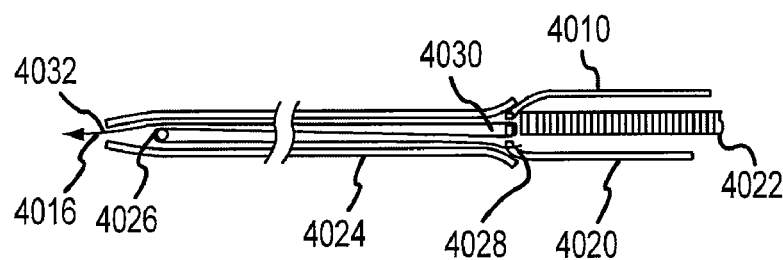
FIG. 45 shows aspects of an ablation system with a stabilizer member according to embodiments of the present invention.
Figure 46:
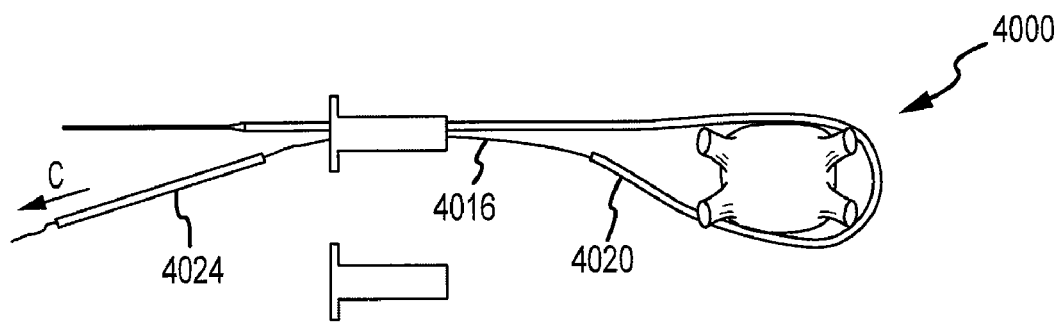
FIG. 46 shows aspects of an ablation system with a stabilizer member according to embodiments of the present invention.
Figure 47:
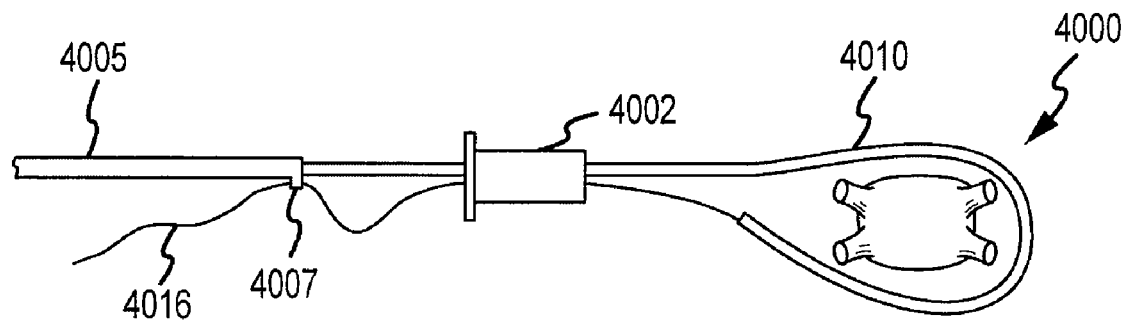
FIG. 47 shows aspects of an ablation system with a stabilizer member according to embodiments of the present invention.
Figure 48:
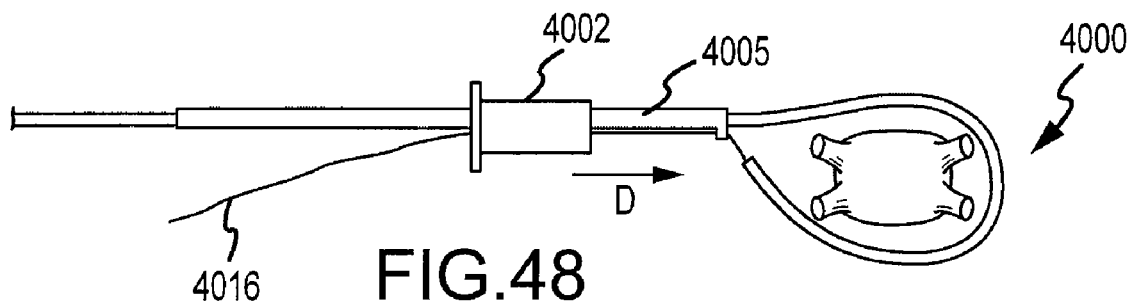
FIG. 48 shows aspects of an ablation system with a stabilizer member according to embodiments of the present invention.
Figure 49:
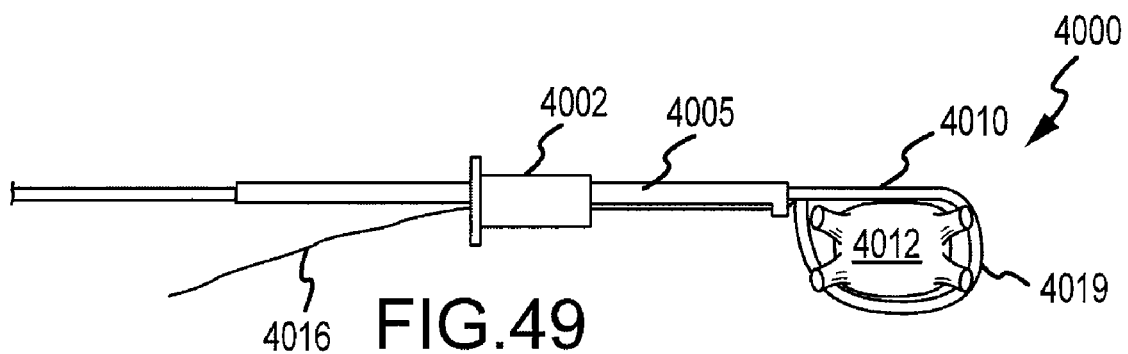
FIG. 49 shows aspects of an ablation system with a stabilizer member according to embodiments of the present invention.
Figure 50:
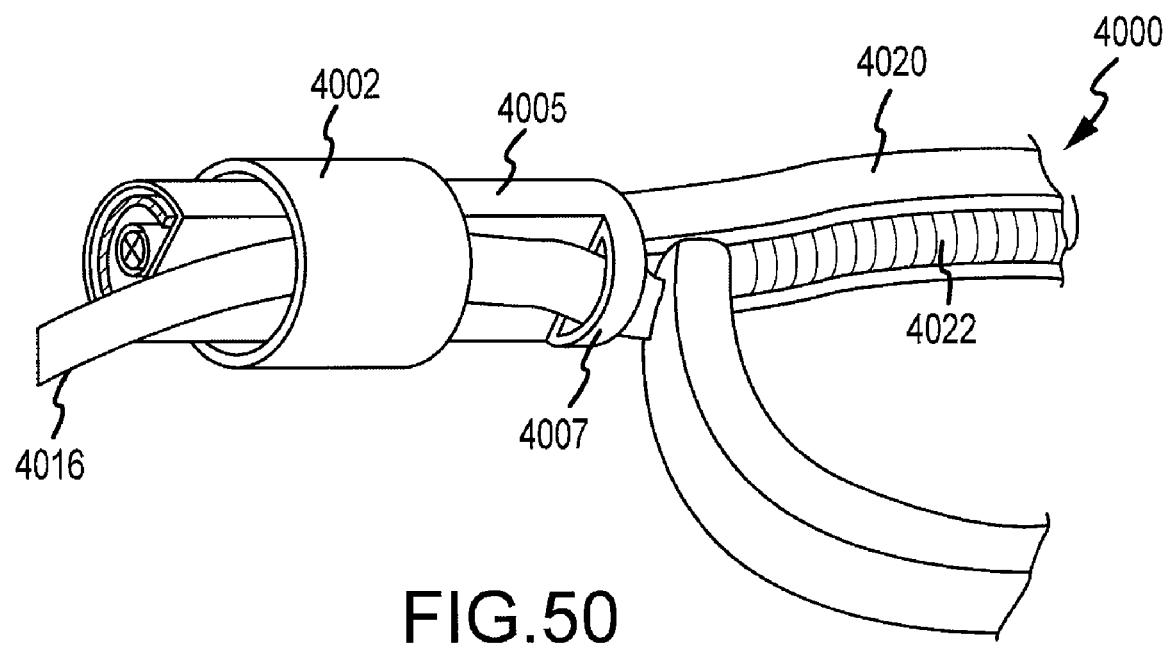
FIG. 50 shows aspects of an ablation system with a stabilizer member according to embodiments of the present invention.
Figure 51:
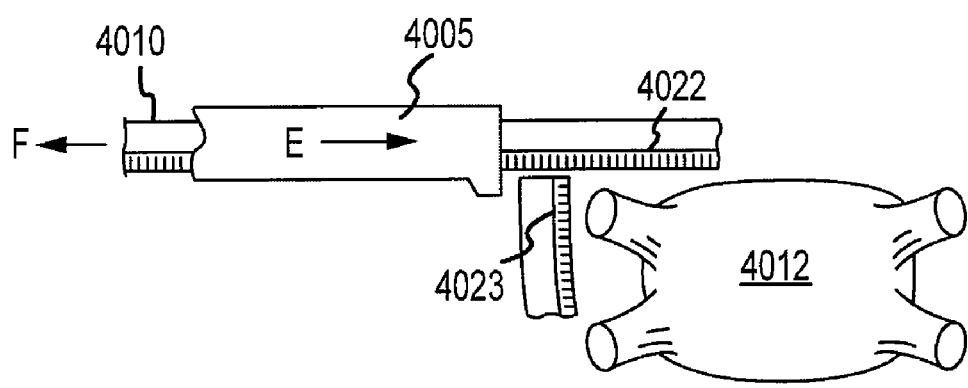
FIG. 51 shows aspects of an ablation system with a pusher according to embodiments of the present invention.

FIG. 45 provides a close up view of a distal section of ablation assembly 4010. As shown here, ablation assembly 4010 includes a bladder or stabilizer member 4020, an ablation member 4022, an introducer 4024 having a pin 4026, and distal grasping element 4016. Distal grasping element 4016 can be anchored with stabilizer member 4020, for example at attachment point 4028. The distal grasping element can be disposed around the pin and back through the bladder at point 4030, and through a distal aperture 4032 of introducer 4024. In use, an operator can pull on distal grasping element 4016 so as to push introducer 4024 onto stabilizer member 4020, for example by urging pin 4026 toward stabilizer member 4020. In some cases, introducer 4024 has a preformed or preset shape. In some cases, introducer can have a bias toward a curve or arc shape. According to some embodiments, the action of pulling on the tape keeps introducer and stabilizer forced together but releasing the grasp on the tape and pulling the introducer away from stabilizer can separate the two and the tape slides around pin in introducer and through slot in end of stabilizer. As shown in FIG. 46, introducer 4024 can be pulled along distal grasping element 4016, away from stabilizer member 4020, in the direction indicated by arrow C. FIG. 47 shows that distal grasping element can be threaded through a loop 4007 of pusher 4005. An operator can advance pusher 4005 through first trocar 4002 in a direction D, as depicted in FIG. 48. The operator can adjust the position of pusher 4005 along ablation assembly 4010 so as to tighten or loosen a loop structure 4019 of the ablation assembly about the patient tissue 4012, as shown in FIG. 49. A close up view of pusher 4005, pusher loop 4007, first trocar 4002, distal grasping element 4016, stabilizer member 4020, and ablation member 4022 is illustrated in FIG. 50. An operator can snug up or cinch a distal section 4023 of ablation member 4022 against patient tissue 4012 by moving pusher 4005 toward the tissue as indicated by arrow E, by pulling ablation assembly 4010 proximally through pusher 4005 away from the tissue, or both, as depicted in FIG. 51.

Figure 52:
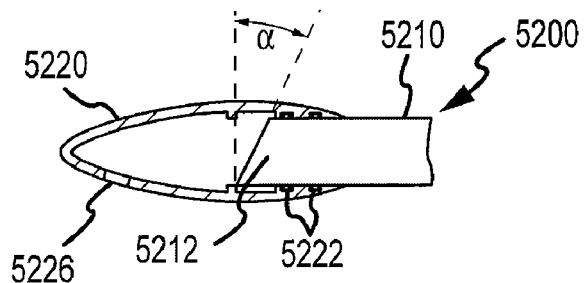
FIG. 52 shows aspects of an ablation system with a visualization system according to embodiments of the present invention.

FIG. 52 shows a cross-section of a visualization system 5200 which can be used for providing or enhancing device placement visualization. For example, such visualization can be carried out in conjunction with a tissue ablation treatment. Visualization system 5200 can include a scope 5210 and a cap or sheath 5220. In some embodiments, the terms cap and sheath may be used interchangeably. Scope 5210 includes a distal end 5212, which in some cases is beveled at an angle a. In some embodiments, angle a can be within a range from about 30 degrees to about 45 degrees. Scope 5210 can be a straight scope, a rigid scope, or both, for example. In some embodiments, scope 5210 includes an endoscope. Sheath 5220 can include a tip having a bullet shape, a cone shape, a dome shape, and the like. In some embodiments, sheath 5220 may present an asymmetric shape. Optionally, a sheath may be shaped for optimized visualization of a tissue. Often, sheath 5220 includes a clear or transparent portion through which a lens of scope 5210 can visualize the surrounding environment. In this way, sheath 5220 can operate to expand the visualization capacity, or the field of view, of scope 5210. In use, sheath 5220 can be advanced into or against tissue, and can separate tissue. Accordingly, tissue which presses on sheath 5220, or is otherwise near sheath 5220, can be visualized. Sheath 5220 can allow a user or operator to visualize an increased amount of tissue, or an increased surface area of tissue, as compared to a similar scope which does not include sheath 5220. In some cases, an operator can use visualization system 5200 for orientation purposes, for treatment purposes, for therapeutic purposes, and the like. Sheath 5220 allows an operator to gain an enhanced awareness of an operating space within a patient's body. For example, an operator may use visualization system 5200 to determine how close a particular instrument or device is to a pulmonary vein. Such techniques can be helpful when applying a treatment to a site that is near, but not on, a pulmonary vein.

Sheath 5220 may include a stop 5224. In use, stop 5224 typically contacts distal end 5212 of scope 5210 when sheath 5220 is disposed on scope 5210. The location or position of stop 5224 on sheath 5220 can be selected so as to control or adjust the distance between a distal end, or some other visualization portion, of sheath 5220, and a lens of scope 5210. Different scopes may have different focal lengths, and selection of a desired stop 5224 configuration can allow sheath 5220 to provide a particular viewing effect on a patient's tissue. For example, by placing stop 5224 at a certain distance from a distal end or viewing portion of sheath 5220, it may be possible to allow an operator to view tissue which contacts the distal end or viewing portion of sheath 5220 with a maximum clarity or distinctness, so that the tissue is in focus.

Sheath 5220 can protect a lens of scope 5210 from unwanted contact with fluid. Toward this end, sheath 5220 may include one or more sealing mechanism 5222. For example, sealing mechanism 5222 may include an o-ring. Sheath 5220 may be releasably attached with scope 5210. For example, it may be possible to snap together, and to snap apart, sheath 5220 and scope 5210. In some cases, sheath 5220 includes an attachment mechanism 5226, which can be used to attach or couple visualization system 5200 with another device or implement. This attachment or coupling can be a releasable attachment. In use, sheath 5220 of visualization system 5200 allows an operator to visualize an operating space within a patient. When an operator views a device or implement to which the operator wishes to couple with visualization system 5200, the operator can utilize attachment mechanism 5226 so as to couple visualization system 5200 with the desired device or implement. For example, attachment mechanism 5226 can include a magnet, and the device or implement can include a material which is attracted to the magnet. The operator can advance or place the magnet near the device or implement, so as to create a releasable coupling between the magnet and the device or implement.

Figure 53:
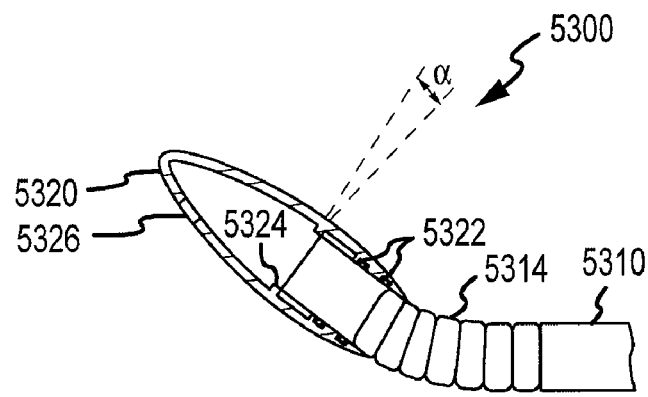
FIG. 53 shows aspects of an ablation system with a visualization system according to embodiments of the present invention.

FIG. 53 shows a cross-section of a visualization system 5300 which can be used for providing or enhancing device placement visualization. For example, such visualization can be performed in conjunction with a tissue ablation treatment. Visualization system 5300 can include a scope 5310 and a sheath 5320. Scope 5310 includes a distal end 5312, which in some cases is not beveled at an angle a. In some embodiments, angle a can be about 0 degrees. Scope 5310 can also include a flexible zone or portion 5314. Scope 5310 can be a curved scope, a flexible scope, or both, for example. In some embodiments, scope 5310 includes an endoscope. Sheath 5320 can include a tip having a bullet shape, a cone shape, a dome shape, and the like. In some embodiments, sheath 3220 may present an asymmetric shape. Optionally, a sheath may be shaped for optimized visualization of a tissue. Often, sheath 5320 includes a clear or transparent portion through which a lens of scope 5310 can visualize the surrounding environment. In this way, sheath 5320 can operate to expand the visualization capacity, or the field of view, of scope 5310. In use, sheath 5 3 20 can be advanced into or against tissue, and can separate tissue. Accordingly, tissue which presses on sheath 5320, or is otherwise near sheath 5320, can be visualized. Sheath 5320 can allow a user or operator to visualize an increased amount of tissue, or an increased surface area of tissue, as compared to a similar scope which does not include sheath 5320. In some cases, an operator can use visualization system 5300 for orientation purposes, for treatment purposes, for therapeutic purposes, and the like. Sheath 5320 allows an operator to gain an enhanced awareness of an operating space within a patient's body. For example, an operator may use visualization system 5300 to determine how close a particular instrument or device is to a pulmonary vein. Such techniques can be helpful when applying a treatment to a site that is near, but not on, a pulmonary vein.

Sheath 5320 may include a stop 5324. In use, stop 5324 typically contacts distal end 5312 of scope 5310 when sheath 5320 is disposed on scope 5310. The location or position of stop 5324 on sheath 5320 can be selected so as to control or adjust the distance between a distal end, or some other visualization portion, of sheath 5320, and a lens of scope 5310. Different scopes may have different focal lengths, and selection of a desired stop 5324 configuration can allow sheath 5320 to provide a particular viewing effect on a patient's tissue. For example, by placing stop 5324 at a certain distance from a distal end or viewing portion of sheath 5320, it may be possible to allow an operator to view tissue which contacts the distal end or viewing portion of sheath 5320 with a maximum clarity or distinctness, so that the tissue is in focus.

Sheath 5320 can protect a lens of scope 5310 from unwanted contact with fluid. Toward this end, sheath 5320 may include one or more sealing mechanism 5322. For example, sealing mechanism 5322 may include an o-ring. Sheath 5320 may be releasably attached with scope 5310. For example, it may be possible to snap together, and to snap apart, sheath 5320 and scope 5310. In some cases, sheath 5320 includes an attachment mechanism 5326, which can be used to attach or couple visualization system 5300 with another device or implement. This attachment or coupling can be a releasable attachment. In use, sheath 5320 of visualization system 5300 allows an operator to visualize an operating space within a patient. When an operator views a device or implement to which the operator wishes to couple with visualization system 5300, the operator can utilize attachment mechanism 5326 so as to couple visualization system 5300 with the desired device or implement. For example, attachment mechanism 5326 can include a magnet, and the device or implement can include a material which is attracted to the magnet. The operator can advance or place the magnet near the device or implement, so as to create a releasable coupling between the magnet and the device or implement.

Figure 54:
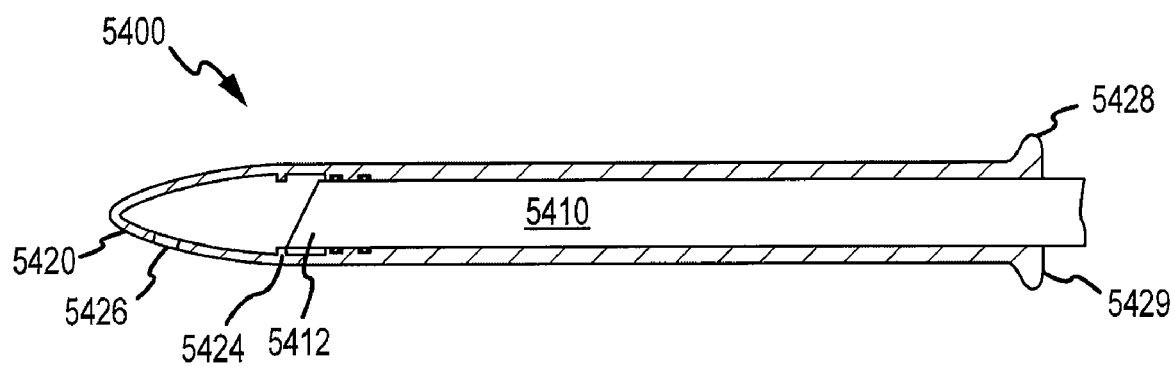
FIG. 54 shows aspects of an ablation system with a visualization system according to embodiments of the present invention.

FIG. 54 shows a cross-section of a visualization system 5400 which can be used for providing or enhancing device placement visualization. For example, such visualization can be performed in conjunction with a tissue ablation treatment. Visualization system 5400 can include a scope 5410 and a sheath 5420. Scope 5410 includes a distal end 5412, which in some cases is not beveled at an angle a. In some embodiments, angle a can be about 30 degrees to about 45 degrees. Scope 5310 can be a straight scope, a rigid scope, or both, for example. In some embodiments, scope 5410 includes an endoscope. Sheath 5420 can include a tip having a bullet shape, a cone shape, a dome shape, and the like. In some embodiments, sheath 3420 may present an asymmetric shape. Optionally, a sheath may be shaped for optimized visualization of a tissue. Often, sheath 5420 includes a clear or transparent portion through which a lens of scope 5410 can visualize the surrounding environment. In this way, sheath 5420 can operate to expand the visualization capacity, or the field of view, of scope 5410. In use, sheath 5420 can be advanced into or against tissue, and can separate tissue. Accordingly, tissue which presses on sheath 5420, or is otherwise near sheath 5420, can be visualized. Sheath 5420 can allow a user or operator to visualize an increased amount of tissue, or an increased surface area of tissue, as compared to a similar scope which does not include sheath 5420. In some cases, an operator can use visualization system 5420 for orientation purposes, for treatment purposes, for therapeutic purposes, and the like. Sheath 5420 allows an operator to gain an enhanced awareness of an operating space within a patient's body. For example, an operator may use visualization system 5400 to determine how close a particular instrument or device is to a pulmonary vein. Such techniques can be helpful when applying a treatment to a site that is near, but not on, a pulmonary vein. Sheath 5420 can be moved relative to scope 5410 or relative to body tissue. In some cases, sheath 5420 can be rotated relative to scope 5410 or relative to body tissue. An operator may effect such movement via a handle 5428 of sheath 5420.

Sheath 5420 may include a stop 5424. In use, stop 5424 can contact distal end 5412 of scope 5410 when sheath 5420 is disposed on scope 5410. The location or position of stop 5424 on sheath 5420 can be selected so as to control or adjust the distance between a distal end, or some other visualization portion, of sheath 5420, and a lens of scope 5410. Different scopes may have different focal lengths, and selection of a desired stop 5424 configuration can allow sheath 5420 to provide a particular viewing effect on a patient's tissue. For example, by placing stop 5424 at a certain distance from a distal end or viewing portion of sheath 5420, it may be possible to allow an operator to view tissue which contacts the distal end or viewing portion of sheath 5420 with a maximum clarity or distinctness, so that the tissue is in focus.

Sheath 5420 can protect a lens of scope 5410 from unwanted contact with fluid. Toward this end, as shown here the length of sheath 5420 can be such that fluid is not present at a proximal end 5429 of sheath 5420. Sheath 5420 may be releasably attached with scope 5410. For example, it may be possible to snap together, and to snap apart, sheath 5420 and scope 5410. In some cases, sheath 5420 includes an attachment mechanism or instrument mount 5426, which can be used to attach or couple visualization system 5400 with another device or implement. This attachment or coupling can be a releasable attachment. In use, sheath 5420 of visualization system 5400 allows an operator to visualize an operating space within a patient. When an operator views a device or implement to which the operator wishes to couple with visualization system 5400, the operator can utilize attachment mechanism 5426 so as to couple visualization system 5400 with the desired device or implement. For example, attachment mechanism 5426 can include a magnet, and the device or implement can include a material which is attracted to the magnet. The operator can advance or place the magnet near the device or implement, so as to create a releasable coupling between the magnet and the device or implement. In some embodiments, all or part of sheath 5420 can be constructed of a flexible material, such as an elastomer. In some embodiments, sheath 5420 is rigid. Similarly, scope 5410 may be flexible or rigid. In some embodiments, a distal end of sheath 5420 is rigid, and a proximal end of sheath 5420 is flexible.

FIGS. 55A and 55B show aspects of a visualization system 5500 which can be used for providing or enhancing device placement visualization. For example, such visualization can be performed in conjunction with a tissue ablation treatment. Visualization system 5500 can include a scope 5510 and a sheath 5520. Scope 5510 and sheath 5520 can include any feature or component of the scopes and sheaths discussed herein, for example the scopes and sheaths depicted in FIGS. 52 to 54. As shown here, sheath 5520 can include an attachment mechanism channel 5521 adapted to receive an attachment mechanism such as a grasping device 5540. Grasping device 5540 can include a pair of spring loaded jaws 5542, 5544. When pushed against a spring force as depicted in FIG. 55B, grasping device 5540 can protrude out of channel 5521, and jaws 5542, 5544 can open or separate. When retracted as depicted in FIG. 55A, jaws 5542, 5544 close together, and grasping device 5540 withdraws into channel 5521. In use, an operator can advance grasping device 5540 out of sheath 5520 and place open jaws 5542, 5544 on a desired item to be grasped. The operator can then withdrawn grasping device 5540 into sheath 5520, thereby clamping jaws 5542, 5544 on the item.

In some embodiments, an operator can push grasping device 5540 against a spring force so that grasping device 5540 protrudes out of sheath channel 5521, thereby opening the jaws. The jaws can be used to grasp a hook, or a fabric, or a component on a device or introducer for a device which the operator wishes to grasp. Often, the operator may grasp a distal end of such a device or introducer. Accordingly, visualization system 5500 can be used in a minimally invasive surgical procedure by an operator to find a device, attach to the device, and then to manipulate or retract the device.

FIGS. 56A and 56B show aspects of a visualization system 5600 which can be used for providing or enhancing device placement visualization. For example, such visualization can be performed in conjunction with a tissue ablation treatment. Visualization system 5600 can include a scope 5610 and a sheath 5620. Scope 5610 and sheath 5620 can include any feature or component of the scopes and sheaths discussed herein, for example the scopes and sheaths depicted in FIGS. 52 to 54. As shown here, the visualization system can include a grasping device 5640, such as a fin or wedge. In use, an operator can place grasping device 5640 near a distal grasping element or introducer tape 5650, and rotate the grasping device as indicated by arrow A. In this way, the grasping device can securely attach with the distal grasping element. As shown in FIG. 56A, when tape 5650 comes into view grasping device 5650 can be rolled to snag tape on a hook or fin of the device, which can then be rolled back to produce a roll of tape. As shown in FIG. 56B, grasping device 5650 can include a wedging shape that holds the tape under tension. Accordingly, visualization system 5600 can be used in a minimally invasive surgical procedure by an operator to find a device, attach to the device, and then to manipulate or retract the device.

Figure 57:
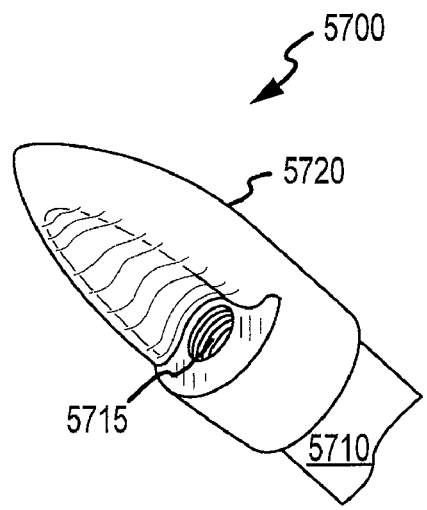
FIG. 57 shows aspects of an ablation system with a visualization system according to embodiments of the present invention.

FIG. 57 shows aspects of a visualization system 5700 which can be used for providing or enhancing device placement visualization. For example, such visualization can be performed in conjunction with a tissue ablation treatment. Visualization system 5700 can include a scope 5710 and a sheath 5720. Scope 5710 and sheath 5720 can include any feature or component of the scopes and sheaths discussed herein, for example the scopes and sheaths depicted in FIGS. 52 to 54. As shown in FIG. 57, a concave shape of sheath 5720 can facilitate use of a working channel 5715 of scope 5710. In some cases, sheath 5720 can operate to protect a lens contained therein.

Figure 58A:
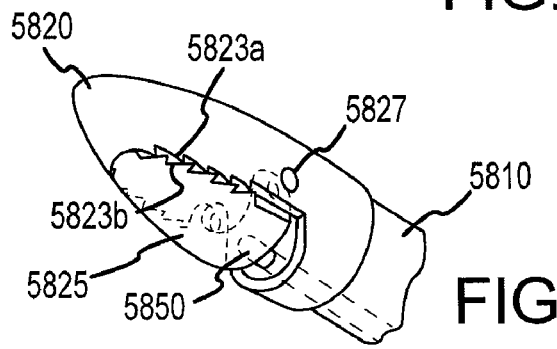
FIGS. 58A-58C show aspects of ablation systems with a visualization system according to embodiments of the present invention.
Figure 58B:
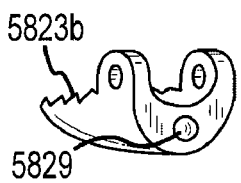
Figure 58C:
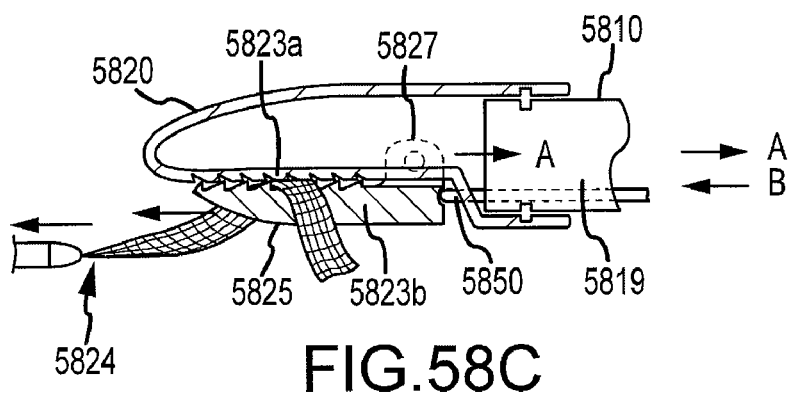

FIGS. 58A-58C illustrate aspects of a visualization system 5800 which can be used for providing or enhancing device placement visualization. For example, such visualization can be performed in conjunction with a tissue ablation treatment. Visualization system 5800 can include a scope 5810 and a sheath or cap 5820. Scope 5810 and sheath or cap 5820 can include any feature or component of the scopes and sheaths or caps discussed herein, for example the scopes and sheaths depicted in FIGS. 52 to 54. As shown in FIG. 58A, the body of sheath or cap 5820 includes a grasping portion 5823a, and a jaw 5825 of sheath or cap 5820 includes a corresponding or complementary grasping portion 5823b. The body of sheath or cap 5820 is coupled with jaw 5825 via a hinge or pivot 5827, as depicted in FIG. 58C. According to FIGS. 58A-58C, a pocket, pivot, or attachment point 5829 of jaw 5825 can be aligned with a working channel 5819 of scope 5810, and a push pull mechanism or axial member 5850 can be disposed in working channel 5819. When axial member 5850 is advanced distally through working channel 5819, for example, the distal section of axial member 5850 can contact and transmit force to jaw divot 5829, thereby closing the bringing the grasping portions 5823a, 5823b toward each other. In some embodiments, this configuration may be well suited for use with an angled scope, as compared to a forward looking scope, due to the desired field of view provided by sheath or cap 5820. In use, push pull mechanism 5850 can be pulled or retracted as indicated by arrow A so as to open jaw 5825. An operator can manipulate jaw 5825 and the body of cap or sheath 5820 about a tape or distal end of a device or introducer. Push pull mechanism 5850 can then be pushed or advanced as indicated by arrow B so as to close jaw 5825, thereby grasping the tape, device, introducer, or other implement 5824.

Figure 59A:
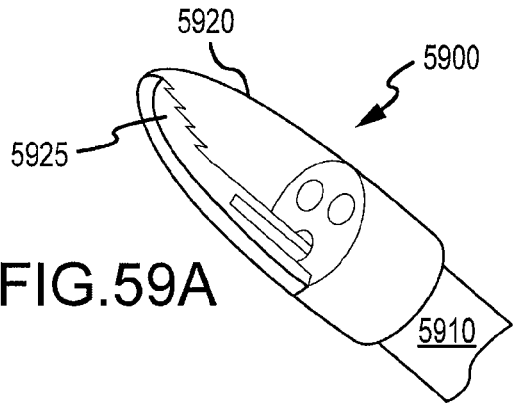
FIGS. 59A-59D show aspects of ablation systems with a visualization system according to embodiments of the present invention.
Figure 59B:
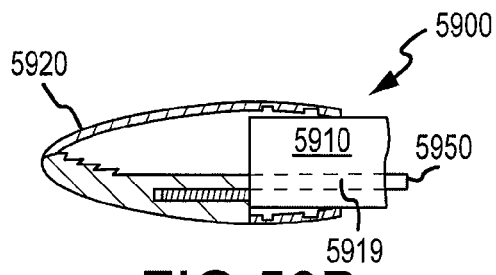

FIGS. 59A-59D illustrate aspects of a visualization system 5900 which can be used for providing or enhancing device placement visualization. For example, such visualization can be performed in conjunction with a tissue ablation treatment. Visualization system 5900 can include a scope 5910 and a sheath 5920. Scope 5910 and sheath 5920 can include any feature or component of the scopes and sheaths discussed herein, for example the scopes and sheaths depicted in FIGS. 52 to 54. According to FIG. 59A, sheath 5920 includes a retractable underslung jaw 5925, shown here in a closed or retracted position. FIG. 59B provides a cross section side view of visualization system 5900. Jaw 5925 can have a push pull mechanism 5950 attached thereto, and disposed within a working channel 5919 of scope 5910.

Figure 59C:
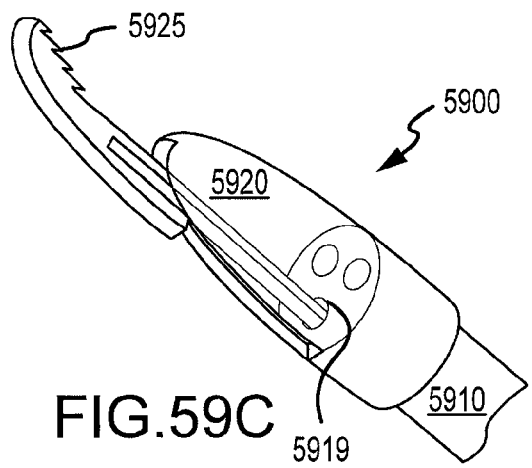
Figure 59D:
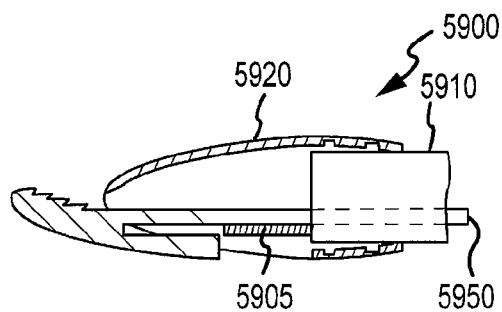

In use, push pull mechanism 5950 can be advanced so as to open jaw 5925, as shown in FIGS. 59C and 59D. An operator can manipulate jaw 5925 so as to snag a tape or distal end of a device or introducer. Push pull mechanism 5950 can then be retracted so as to close jaw 5925, thereby firmly grasping the tape, device, introducer, or other implement. In some embodiments, visualization system 5900 includes an anti-roll guidance rib 5905. In some embodiments, the body of sheath 5920 includes a toothed configuration which is complementary to the toothed configuration of jaw 5925.

Figure 60A:
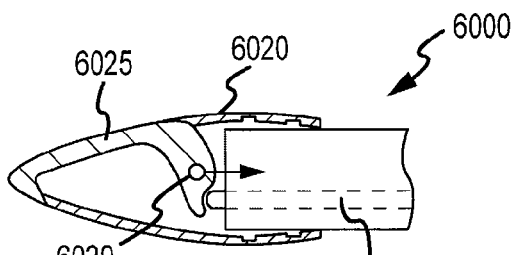
FIGS. 60A-60B show aspects of ablation systems with a visualization system according to embodiments of the present invention.
Figure 60B:
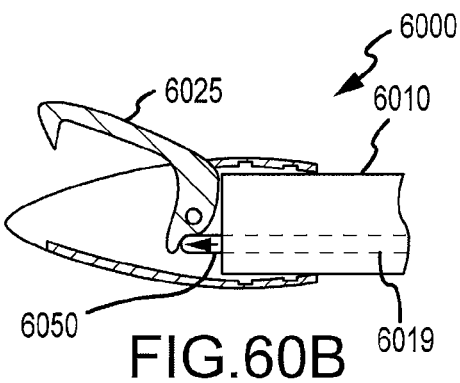

FIGS. 60A and 60B illustrate aspects of a visualization system 6000 which can be used for providing or enhancing device placement visualization. For example, such visualization can be performed in conjunction with a tissue ablation treatment. Visualization system 6000 can include a scope 6010 and a sheath 6020. Scope 6010 and sheath 6020 can include any feature or component of the scopes and sheaths discussed herein, for example the scopes and sheaths depicted in FIGS. 52 to 54. According to FIG. 60A, sheath 6020 includes a pivoting overhung toothed jaw 6025, shown here in a closed or retracted position. Jaw 6025 can have an activating mechanism 6050 or a similar axial member attached thereto, and disposed within a working channel 6019 of scope 6010.

In use, sheath 6020 includes a pivot 6029 that is configured to provide a neutral jaw position under tension, such that there is no tendency for jaw 6025 to open. Activating mechanism 6050 can be advanced distally, as shown in FIG. 60B, so as to swing jaw 6025 about pivot 6029, toward an open configuration. In this configuration, jaw 6025 is disposed outside of the external cone or dome shaped contour of the sheath body. An operator can manipulate jaw 6025 so as to snag a tape or distal end of a device or introducer. Activating mechanism 6050 can then be retracted so as to allow jaw 6025 to close, thereby firmly grasping the tape, device, introducer, or other implement. In some embodiments, the body of sheath 6020 includes a toothed configuration which is complementary to the toothed configuration of jaw 6025.

Many of the visualization system embodiments disclosed herein include a scope having a working channel, and an activating mechanism or push pull rod which can sit at least partially within the working channel. An operator can cause the activating mechanism to retract or advance, so as to open and close a distal grasping mechanism of the visualization system. In exemplary embodiments, the visualization system includes a sheath having a bullet, dome, cone, or similar profile. For example, a sheath may present a flat top bullet profile, or a truncated cone profile. In some cases, a sheath may present a bulged profile or a mushroom profile. Typically, sheath includes a rounded or blunted distal section, so as to not avoid cutting tissue when placed within a patient's body. In some cases, a sheath is integrated with the scope. In some cases, the sheath can be releasably attached with the scope. Often, a scope includes a working channel, and the visualization system includes an activating mechanism that can be disposed at least partially within the working channel. Activating mechanisms can be operated to manipulate grasping members or mechanisms of the visualization system. Often, a sheath, a grasping mechanism, an activating mechanism, or any combination thereof, can be configured such that the activating mechanism can be aligned within the working channel when the sheath is coupled with the scope. In addition to grasping or attaching mechanisms, any of a variety of other tools may be disposed on or coupled with the sheath body, and activated or controlled via an activating mechanism housed at least partially within a working channel of the scope.

Figure 61A:
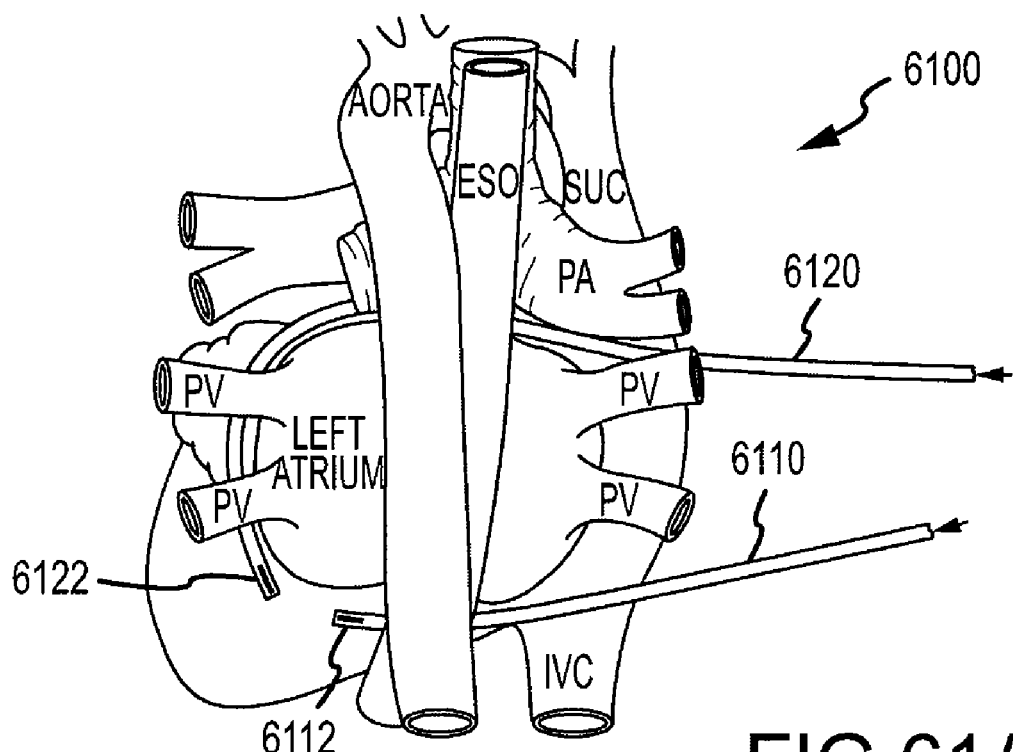
FIGS. 61A-61B show aspects of ablation systems with a visualization system according to embodiments of the present invention.
Figure 61B:
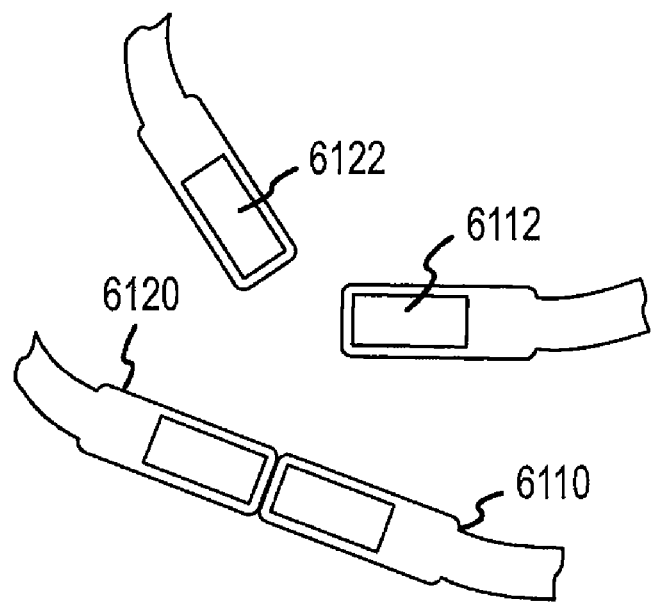

FIGS. 61A and 61B illustrate how an ablation system can be used in a tissue environment of a patient. An ablation system 6100 includes a visualization system 6110 having a probe or scope. Ablation system 6100 also includes a device 6120, which may have an introducer. As with any of the visualization systems disclosed herein, visualization system 6110 can include a magnetically or mechanically attaching mechanism, whereby a distal end of visualization system 6110 can be attached or coupled with a distal end of device 6120. Such configurations can be used in a minimally invasive surgical procedure, so as to position or manipulate an ablation mechanism within the body of a patient. For example, visualization system 6110 can be used to move an ablation device about a patient's pulmonary veins (PV). As shown in FIG. 61A, device 6120 can be advanced within a patient, such that the device enters a first cavity such as a transverse sinus. Similarly, visualization system 6110 can be advanced within a patient, such that the visualization system enters a second cavity such as an oblique sinus. According to some embodiments, device 6120 can be advanced through an oblique sinus and visualization system 6110 can be advanced through a transverse sinus. Optionally, device 6120 or visualization system 6110 can be introduced via a subzyphoid incision or approach. In use, features of the ablation system can be used to encircle a single PV, or a desired set of multiple PVs. The distal end of the device, the distal end of the visualization system, or both, can be manipulated so as to couple one with the other. For example, the device may include a first magnet 6122 and the visualization system may include a second magnet 6110. As shown in FIG. 61B, the magnets can have self aligning faces, and the distal ends of device 6120 and visualization system 6110 can have rounded or blunted edges. Typically, a magnet has a dipolar magnetic field, and therefore opposite ends of magnets are attracted to each other. Due to the self aligning configuration, the magnetic dipole of first magnet 6122 tends to align or orient itself with the opposed polarity of the magnetic dipole of the second magnet. In use, when an operator determines that the distal ends of device 6120 and visualization system 6110 are coupled, the operator can manipulate the ablation system to a position as desired. In some cases, an operator can determine that the distal ends are coupled by visual confirmation. In some cases, an operator can hear or feel the distal ends snap together.

Figure 62A:
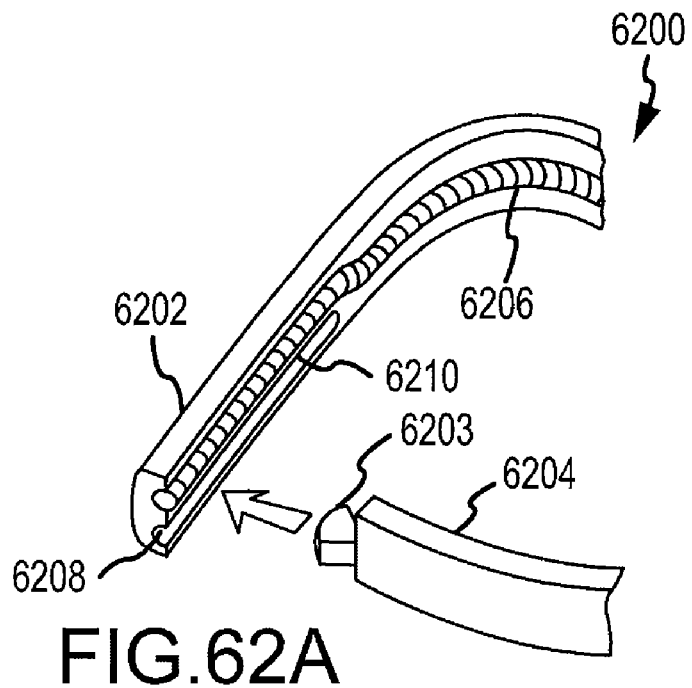
FIGS. 62A-62E show aspects of ablation systems forming a loop closure according to embodiments of the present invention.

FIG. 62A illustrates aspects of an ablation system 6200 having a magnetic loop closure, according to embodiments of the present invention. Ablation system 6200 includes a proximal end 6202 and a distal end 6204. Ablation system 6200 also includes an ablation electrode 6206 and a magnet or magnet array 6208. In some embodiments, ablation system 6200 can present a "U" shaped configuration, which can be placed near or applied to a path which surrounds or travels about the pulmonary veins of a patient. Ablation system 6200 can be cinched about the pulmonary veins, so as to form an oval shape. For example, a magnet 6203 disposed on distal end 6204 of system 6200 can be advanced toward magnet or magnet array 6208. In some cases, magnet 6203 is urged toward magnet 6208 by an operator using an instrument. When magnet 6203 couples with magnet 6208, magnet 6203 can be moved along magnet 6208, either distally or proximally, so as to respectively tighten or loosen the loop enclosure formed by the ablation system. In some cases, the body of ablation system 6200 includes a track 6210 which has a shape that is complementary to the shape of magnet 6203. In some cases, the attractive force between magnet 6203 and magnet 6208 provides a self cinching effect. In some cases, magnet 6208 includes an array of magnets, such that the position of magnet 6203 along magnet 6208 can be incrementally adjusted, so as to achieve any desired loop closure circumference. Patients may present tissues of varying dimensions and sizes, and it may be desirable to configure ablation system 6200 so as to provide discrete stopping points or attraction points along a length of magnet 6208. This allows an operator to select from a multiplicity of stable connection points, so as to form loop closures or ovals which are customized or dimensioned for a particular patient's anatomy.

Figure 62B:
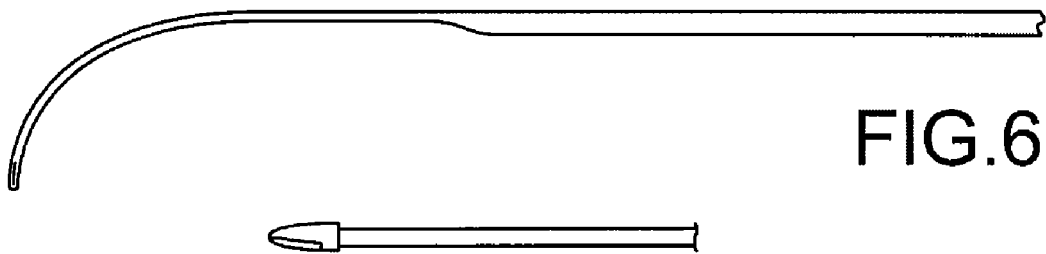
Figure 62C:
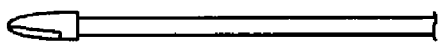
Figure 62D:
Figure 62E:
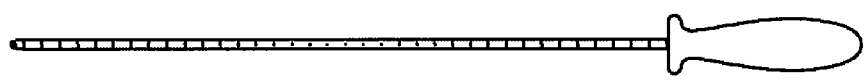

FIGS. 62B to 62E show aspects of ablation device introducers and scopes or probes, according to embodiments of the present invention. FIG. 62B shows that a magnet or other attachment mechanism can be disposed at or toward a distal end of a device introducer. FIG. 62C shows that a magnet or other attachment mechanism can be disposed at or toward a distal end of a scope. The position of the magnet or attachment mechanism may be offset. According to FIG. 62D, a magnet or attachment mechanism can be disposed at or toward a distal end of a probe. In some cases, a probe may be malleable. In some embodiments, the terms "probe", "scope", and "visualization system" may be used interchangeably. According to FIG. 62E, a magnet or attachment mechanism can be disposed at or near a distal end of an oversheath. As noted above, the position of a magnet or attachment mechanism may be offset. In some cases, offsetting the position of the magnet or attachment mechanism can provide an operator with an optimized field of view, depending on the geometric configuration of a visualization system.

Figure 63E:
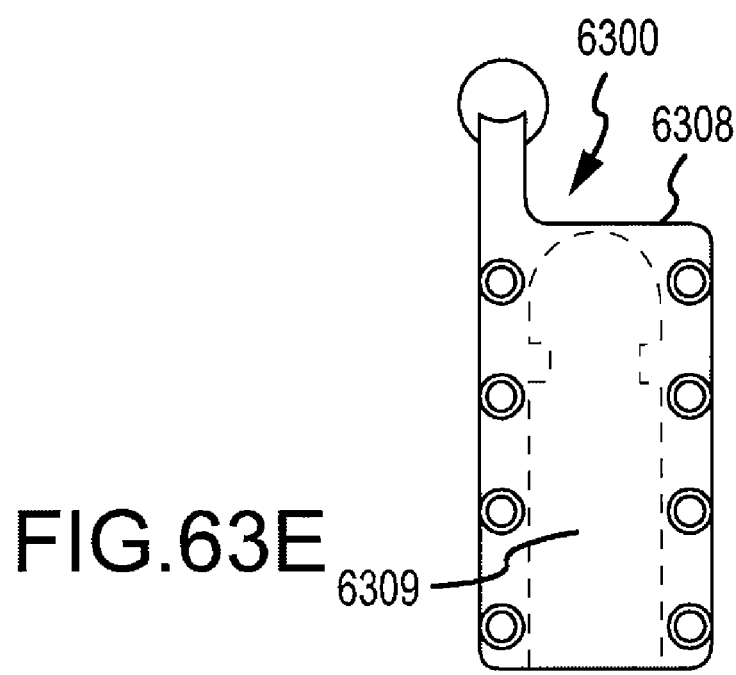
Figure 63F:
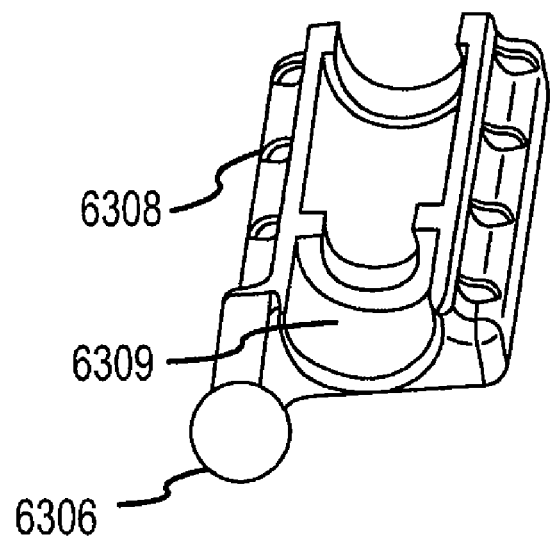

FIGS. 63A to 63F show an ablation system 6300 according to embodiments of the present invention. As depicted here, ablation system 6300 can present a keyhole slot and ball configuration. FIG. 63A shows ablation system 6300 disposed about four pulmonary veins (PV), so as to form a loop enclosure. Ablation system 6300 can include a push sheath 6302. Ablation system 6300 can be used to form an oval shaped lesion on a patient tissue with an ablation probe of the system. As seen in FIGS. 63B and 63D, ablation system 6300 can include a proximal end channel or slot 6304, which is configured to receive a ball 6306 of a suction chamber terminator 6308, and an electrode path 6305, which is configured to receive an electrode. In use, an operator can move wrap or place the ablation system about a patient tissue, and insert ball 6306 of suction chamber 6308 into keyhole 6303 and slot 6304. By advancing ball 6306 distally or proximally along the length of slot 6304, the operator can respectively tighten or loosen a loop enclosure formed by the ablation system, so as to form loops of various circumferences. Suction chamber terminator 6308, for example as shown in FIGS. 63E and 63F, may include a metallic conductor. Terminator 6308 can include a receptacle 6309 adapted to receive a distal electrode tip. Accordingly, ablation system 6300 can create a continuous lesion along the oval or loop. As shown in FIG. 63D, suction chamber terminator 6308 can be perpendicular or substantially perpendicular to slot 6304, for example after the ablation system is routed around the pulmonary veins. The coupling between the chamber terminator and the slot can be characterized by multiple discrete stabilization points. In some cases, the coupling can be characterized by an interference fit or a press fit, whereby the relative positions of the chamber terminator and the slot are maintained without additional attachment mechanisms. As shown in FIG. 63D, ablation assembly 6300 can include a suction chamber 6312, disposed on a distal end of an electrode support 6314. In some embodiments, suction chamber 6312 presents a more flexible configuration, whereas electrode support 6314 presents a more rigid configuration. The suction chamber can be configured to provide an oval shape which can be applied to a patient tissue. For example, suction chamber 6312 can be placed on or about the pulmonary veins of a patient. Suction chamber or bladder 6312 can be maintained in position relative to the patient tissue via a mechanical stabilization, via a vacuum, or a combination thereof. Typically, suction chamber 6312 is coupled with suction chamber terminator 6308. According to FIGS. 63B, 63C, and 63D, ablation system 6300 may also include a vacuum luer or fitting 6316 which can transit a vacuum from a vacuum source to suction bladder 6312.

FIGS. 64, 65, 66A, 66B, and 66C illustrate aspects of ablation systems which can form oval, teardrop, or other loop enclosure configurations, according to embodiments of the present invention. According to FIG. 64, an ablation system 6400 can include a distal portion 6410 and a proximal portion 6420, which can be coupled by a trocar 6430. An operator can cinch or uncinch a loop structure 6440 by sliding trocar 6430 along the distal and proximal portions, as indicated by arrow A. In use, distal portion 6410 can be looped around the pulmonary veins (PV) of a patient, and placed through trocar 6430 which is loaded on proximal portion 6420, so as form loop structure 6440. The trocar can be adjusted so as to cinch the loop structure about the pulmonary veins of the patient to the desired circumference or configuration, and press an electrode against the patient tissue.

Figure 65:
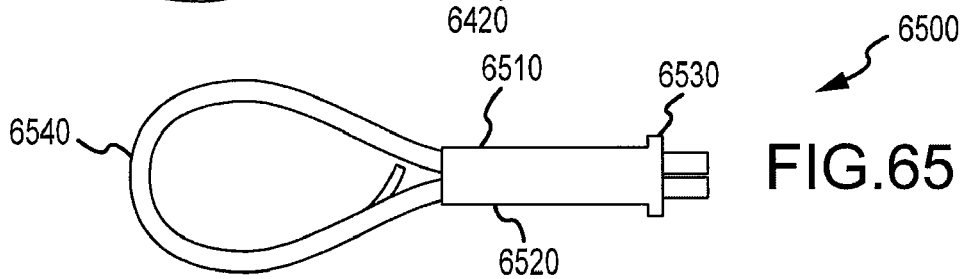
FIG. 65 shows aspects of an ablation system relating to oval, teardrop, or other loop enclosure configurations according to embodiments of the present invention.

According to FIG. 65, an ablation system 6500 can include a distal portion 6510 and a proximal portion 6520, which can be coupled by a trocar 6540. An operator can cinch or uncinch a loop structure 6540 by sliding trocar 6530 along the distal and proximal portions, as indicated by arrow A. In use, distal portion 6510 can be looped around the pulmonary veins (PV) of a patient, and placed through trocar 6530 which is loaded on proximal portion 6520, so as form loop structure 6540. The trocar can be adjusted so as to cinch the loop structure about the pulmonary veins of the patient to the desired circumference or teardrop configuration, and press an electrode against the patient tissue. As shown here, trocar 6530 can present a divided configuration so as to separate the proximal and distal portions. Trocar 6530 can include an extension which urges an electrode tip against the patient tissue. For example, an operator can use the trocar to push the tip of an ablation probe or electrode forward, out of a suction stabilizer or bladder, so as to form a continuous loop. Thus, a tear drop shape defined by the electrode can be made more circular, as the electrode tip is pushed out of the suction bladder and against or closer to the patient tissue. Similar features and configurations are disclosed herein at, for example, FIGS. 32A to 32D.

Figure 66A:
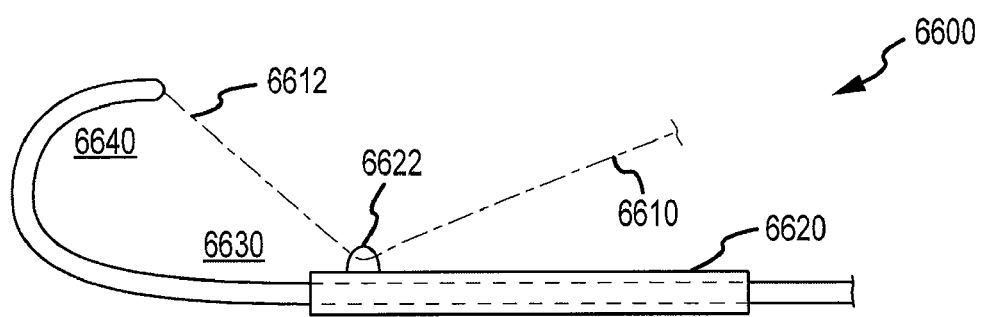
FIGS. 66A-66C show aspects of ablation systems relating to oval, teardrop, or other loop enclosure configurations according to embodiments of the present invention.
Figure 66B:
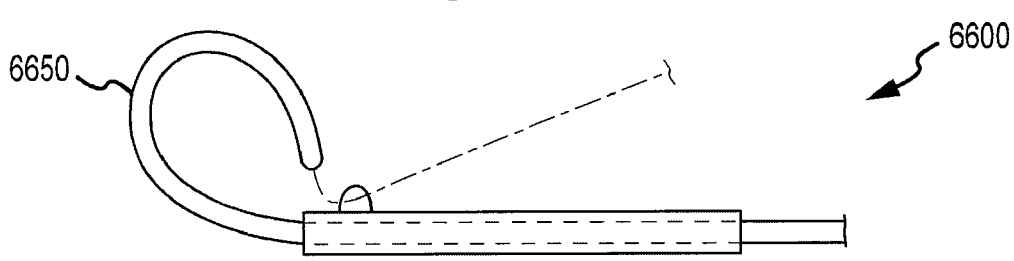
Figure 66C:
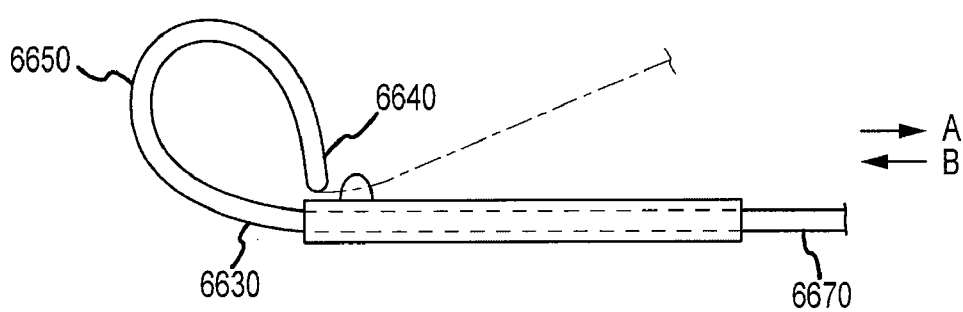

According to FIGS. 66A to 66C, an ablation system 6600 can include a pull tape and pusher configuration. As shown in FIG. 66A, ablation system 6600 includes a pull tape 6610 and a pusher 6620 having a pusher loop 6622. Ablation system 6600 also includes a proximal portion 6630 and a distal portion 6640. Tape 6610 can include a fabric, an elastomer, or the like. A distal end 6612 of tape 6610 is attached with distal portion 6640. In use, an operator can advance tape 6610, and thus distal portion 6640, along a desired path through a patient's anatomy. The tape can then be threaded through pusher loop 6622 of pusher 6620. Hence, this threading action can be performed while the ablation system is inside the chest cavity of a patient. Optionally, this threading can be done while the ablation system 6600 is outside of the patient's body. The operator can pull the tape through the loop to the extent desired, so as to urge distal portion 6640 toward proximal portion 6630, as depicted in FIGS. 66B and 66C. In this way, the ablation system can be positioned circumferentially about the anatomical features of the heart, such that a continuous lesion can be formed. Further, the operator can advance pusher mechanism 6620 distally toward distal portion 6640, or relative to a suction chamber, so as to cinch the ablation system about the pulmonary veins of the patient, and reduce the circumference of a looping structure 6650. According to some embodiments, the operator can hold pusher mechanism 6620 in a fixed position while adjusting the proximal end 6670 of the ablation assembly so as to adjust the loop size. For example, proximal end 6670 can be pulled or withdrawn away from pusher mechanism 6620 as indicated by arrow A, so as to downsize the loop. Similarly, proximal end 6670 can be advanced into or toward pusher mechanism 6620 as indicated by arrow B, so as to increase the loop size. As shown in FIG. 66C, distal portion 6640 can be urged against proximal portion 6630 to as to form an orthogonal connection therewith. Similar features and configurations are disclosed herein at, for example, FIGS. 50 and 51.

Figure 64:
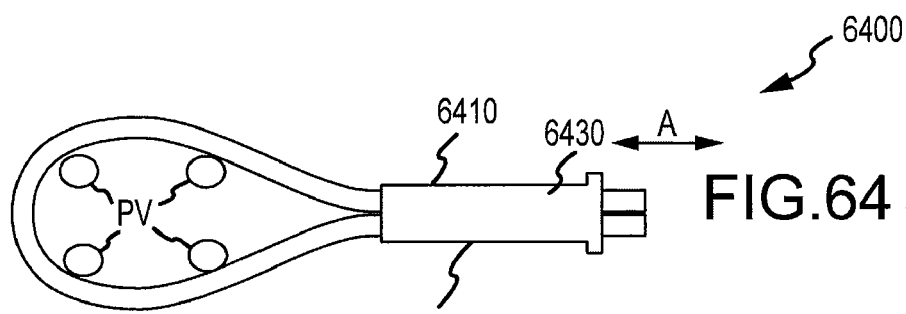
FIG. 64 shows aspects of an ablation system relating to form oval, teardrop, or other loop enclosure configurations according to embodiments of the present invention.

Thus, FIG. 64 presents an embodiment wherein both an electrode and a suction member can be shaped in an oval or teardrop configuration. FIG. 65 present an embodiment wherein an electrode can be cinched toward a circular configuration, and a suction member can be shaped in an oval or teardrop configuration. FIGS. 66A-66C present an embodiment wherein an electrode and a suction member can be cinched toward a circular configuration. In some cases, a suction member or bladder may not include suction apertures along the entire length of the bladder. That is, a suction bladder may contain suction apertures along only a partial length of the bladder. For example, a suction bladder of the ablation system shown in FIG. 64 may only include suction apertures on a circumferential portion that extends from a five o'clock position, clockwise, to a one o'clock position. Relatedly it may be desirable to omit suction apertures from the pointed region of the teardrop shape.

Figure 67:
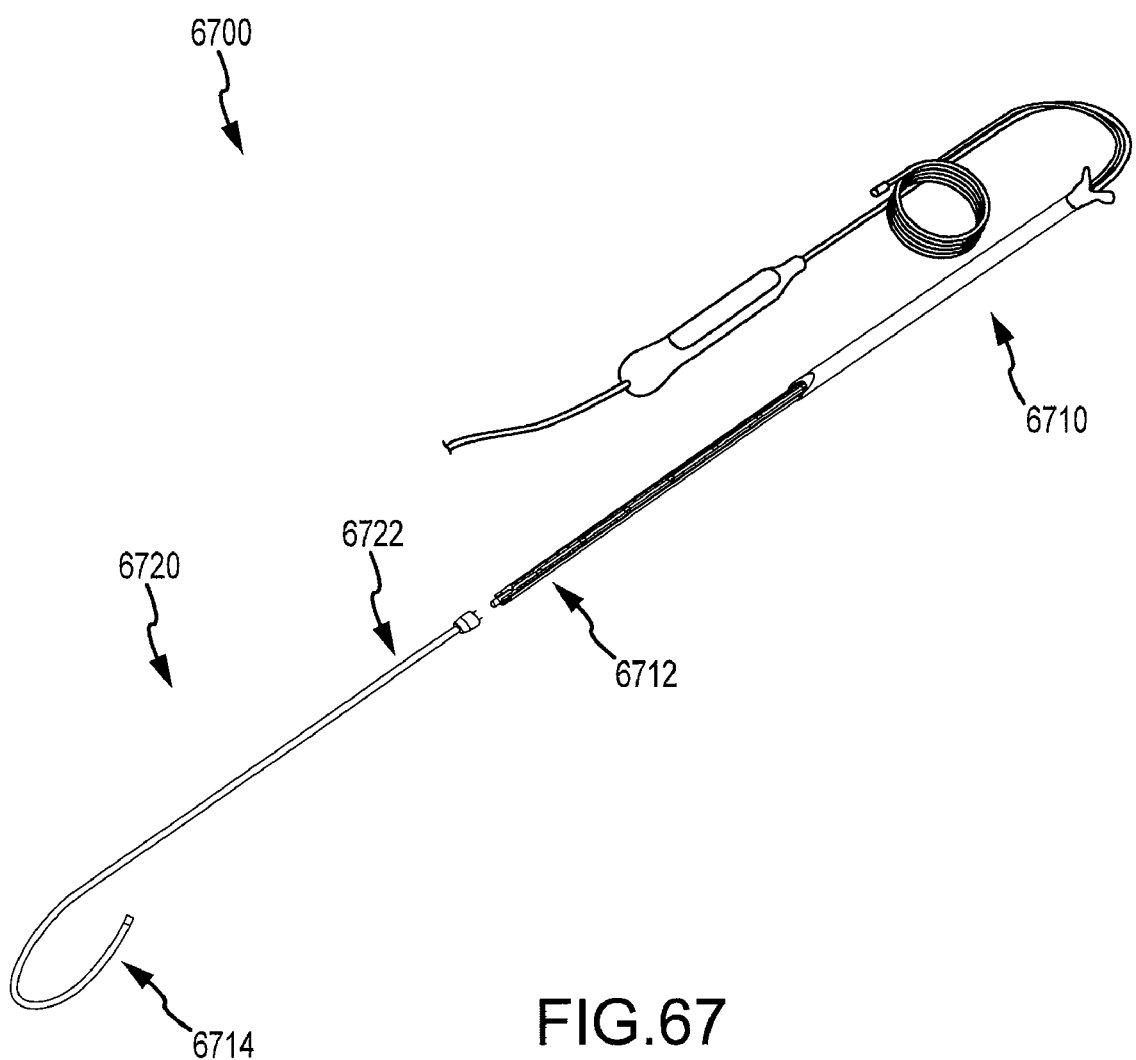
FIG. 67 shows aspects of an ablation system with an introducer according to embodiments of the present invention.

FIG. 67 illustrates an exemplary treatment system 6700 according to embodiments of the present invention. Treatment system 6700 includes a treatment device or ablation assembly 6710 releasably coupled with an introducer 6720. For example, a proximal portion 6722 of introducer 6720 can be releasably coupled with a distal portion 6712 of treatment device 6710. A distal portion 6714 of introducer 6714 can include a magnet or a coupling device that can be used to navigate the treatment system within the patient's anatomy, for example as described in U.S. Patent Application No. 61/015,472 filed Dec. 20, 2007, the content of which is incorporated herein by reference. Treatment device 6710 may include a flexible ablation member or mechanism, a stabilizer member or mechanism, and a cinching mechanism such as a trocar or push tube. Optionally, treatment system 6700 can include or be used in conjunction with one or more obturators or additional introducers.

Figure 68A:
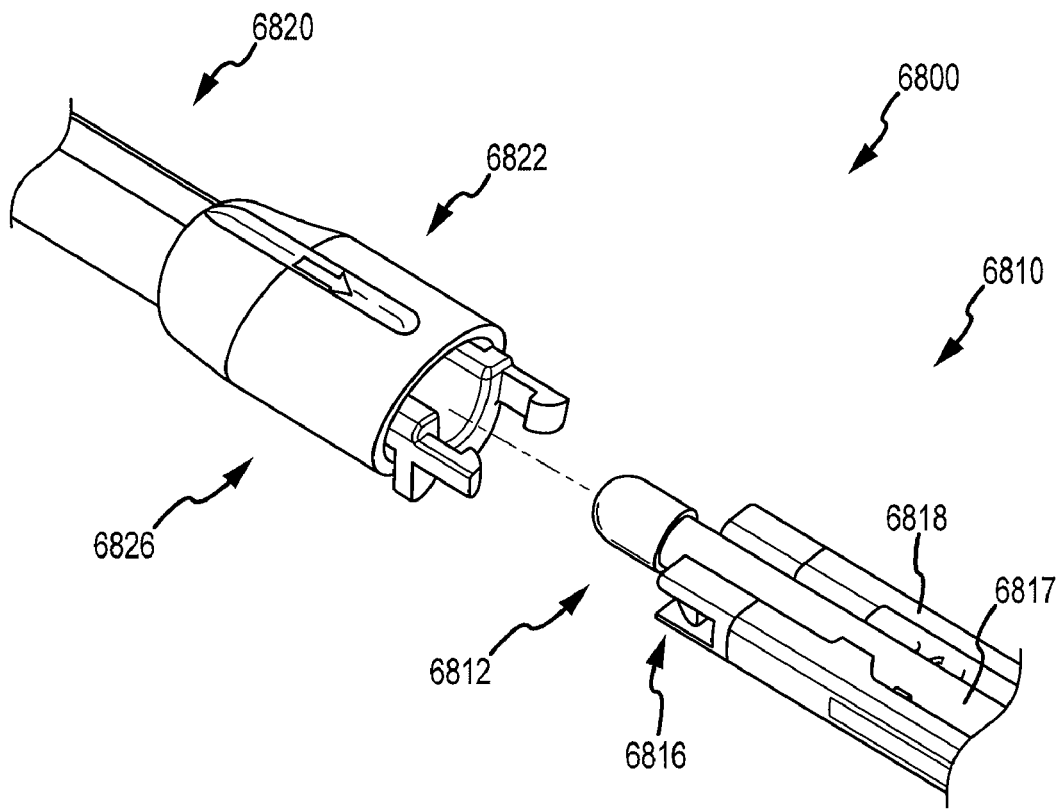
FIGS. 68A-68B show aspects of ablation systems with an introducer according to embodiments of the present invention.
Figure 68B:
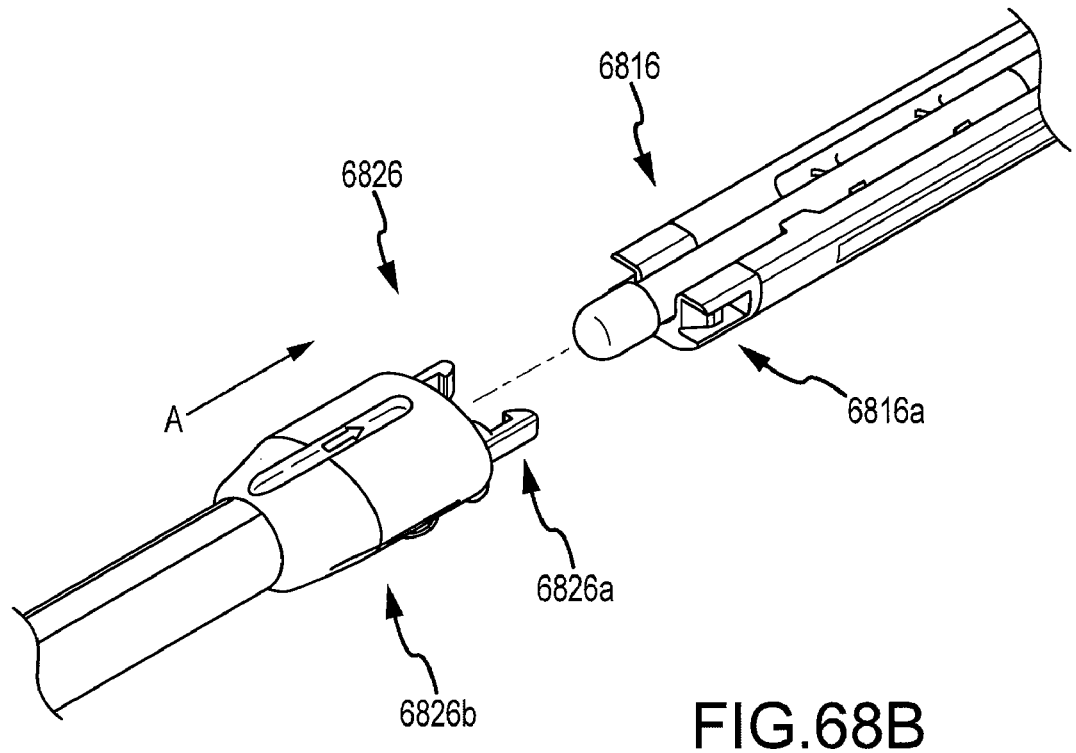

FIG. 68A shows aspects of an exemplary treatment system 6800 according to embodiments of the present invention. Treatment system 6800 includes a treatment device or ablation assembly 6810 releasably coupled with an introducer 6820. For example, a proximal portion 6822 of introducer 6820 can be releasably coupled with a distal portion 6812 of treatment device 6810. Treatment device 6810 may include a flexible ablation member or mechanism 6817, a stabilizer member or mechanism 6818, and a cinching mechanism. Distal portion 6812 of the treatment device includes a treatment device coupling mechanism 6816, and proximal portion 6822 of the introducer includes an introducer coupling mechanism 6826. As depicted in FIG. 68B, treatment device coupling mechanism 6816 may include one or more female snap features 6816a that are configured to receive or couple with one or more male features 6826a of introducer coupling mechanism 6826. Optionally, the introducer coupling mechanism may also include a sleeve or clasp 6826b that can be translated or moved along a length of the introducer, as indicated by arrow A so as to help secure a coupling between snap features 6816a and 6826a. For example, sleeve 6826b can be moved toward the treatment device so as to keep a male feature 6826a engaged with a female feature 6816a. Additional features of exemplary introducers are discussed elsewhere herein, for example with reference to FIGS. 79-81.

Figure 69:
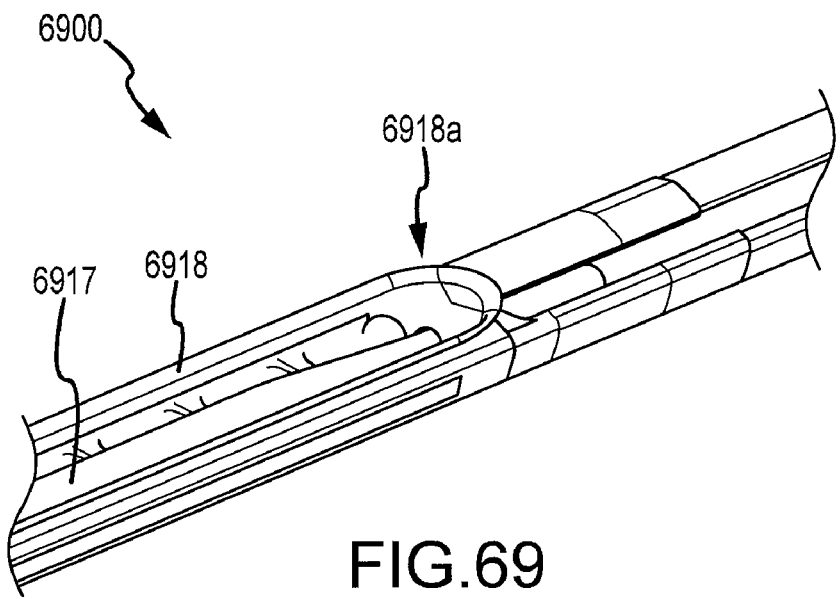
FIG. 69 shows aspects of an ablation system with a stabilizer mechanism according to embodiments of the present invention.
Figure 70:
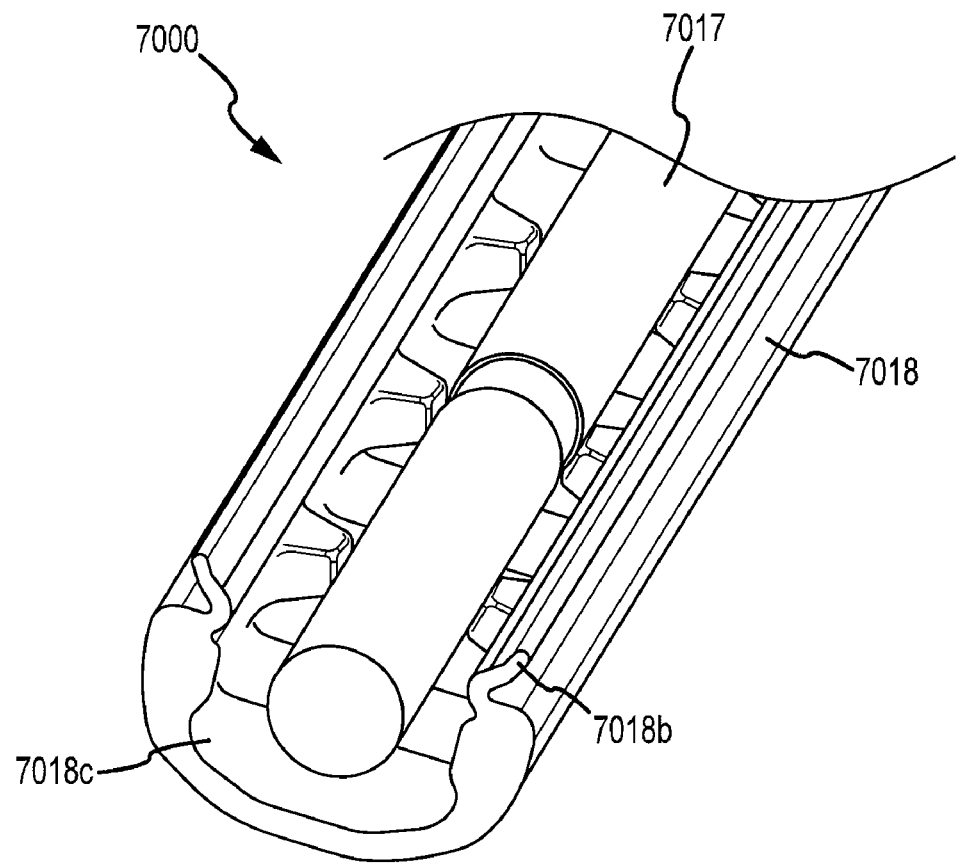
FIG. 70 shows aspects of an ablation system with a stabilizer mechanism according to embodiments of the present invention.
Figure 71:
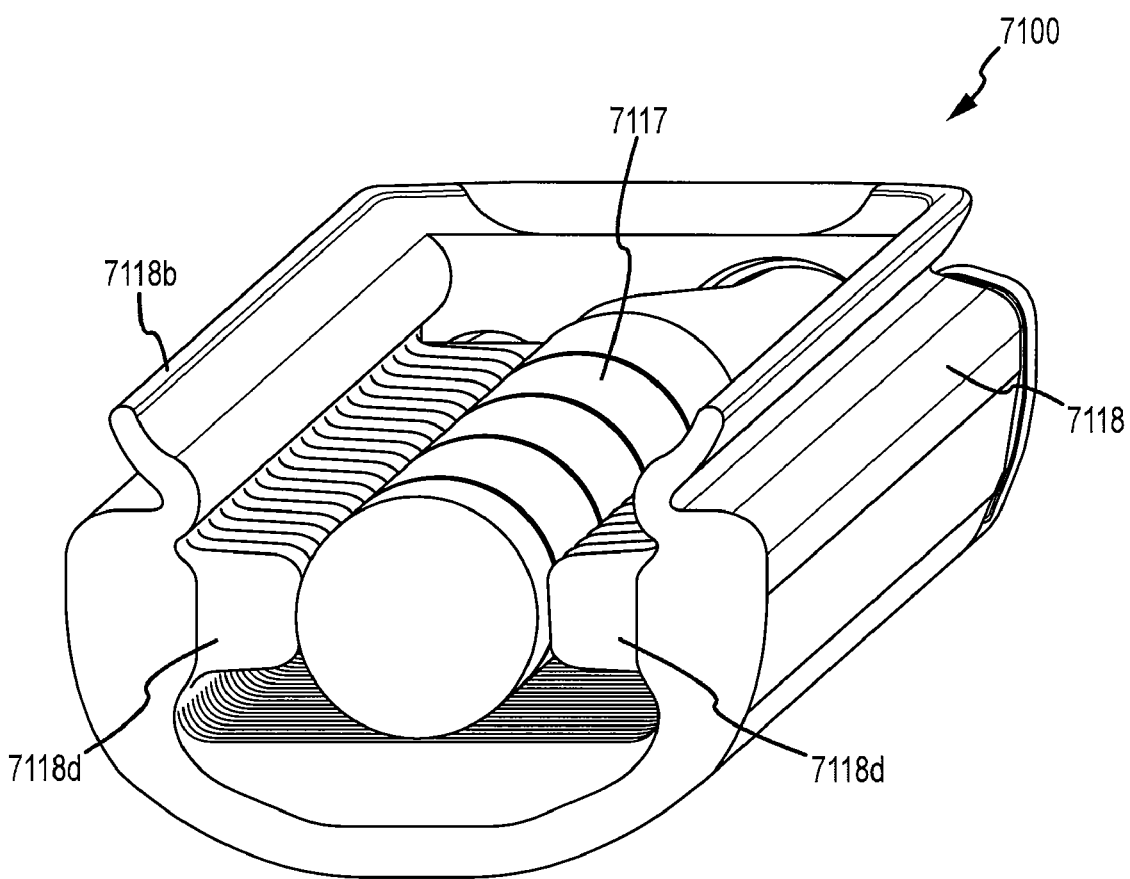
FIG. 71 shows aspects of an ablation system with a stabilizer mechanism according to embodiments of the present invention.

FIG. 69 depicts features of an exemplary treatment system 6900 according to embodiments of the present invention. Treatment system 6900 can include an ablation mechanism 6917 and a stabilizer mechanism 6918. As shown here, stabilizer mechanism 6918 may include a proximal skirt termination 6918a. FIG. 70 depicts features of an exemplary treatment system 7000 according to embodiments of the present invention. Treatment system 7000 can include an ablation mechanism 7017 and a stabilizer mechanism 7018. As shown here, stabilizer mechanism 7018 may include a skirt 7018b configured to contact the tissue of a patient, which can help form a suction area 7018c. FIG. 71 depicts features of an exemplary treatment system 7100 according to embodiments of the present invention. Treatment system 7100 can include an ablation mechanism 7117 and a stabilizer mechanism 7118. As shown here, stabilizer mechanism 7118 may include a skirt 7118b configured to contact the tissue of a patient. Stabilizer mechanism 7118 may also include a coupling mechanism having coupling arms 7118d that are configured to couple with, secure, or otherwise contact the ablation mechanism.

Figure 72:
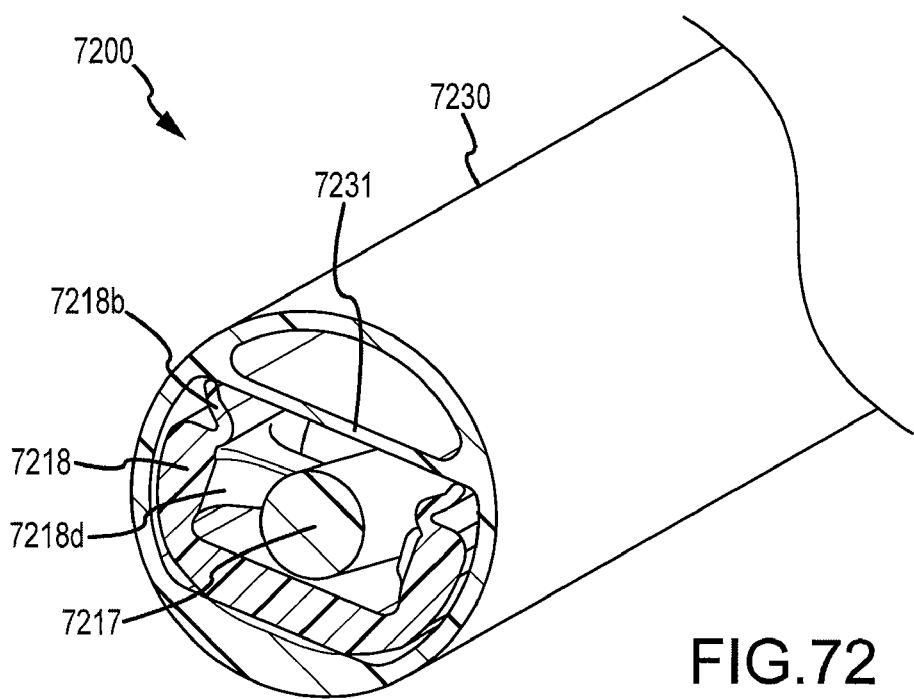
FIG. 72 shows aspects of an ablation system with a stabilizer mechanism according to embodiments of the present invention.
Figure 73:
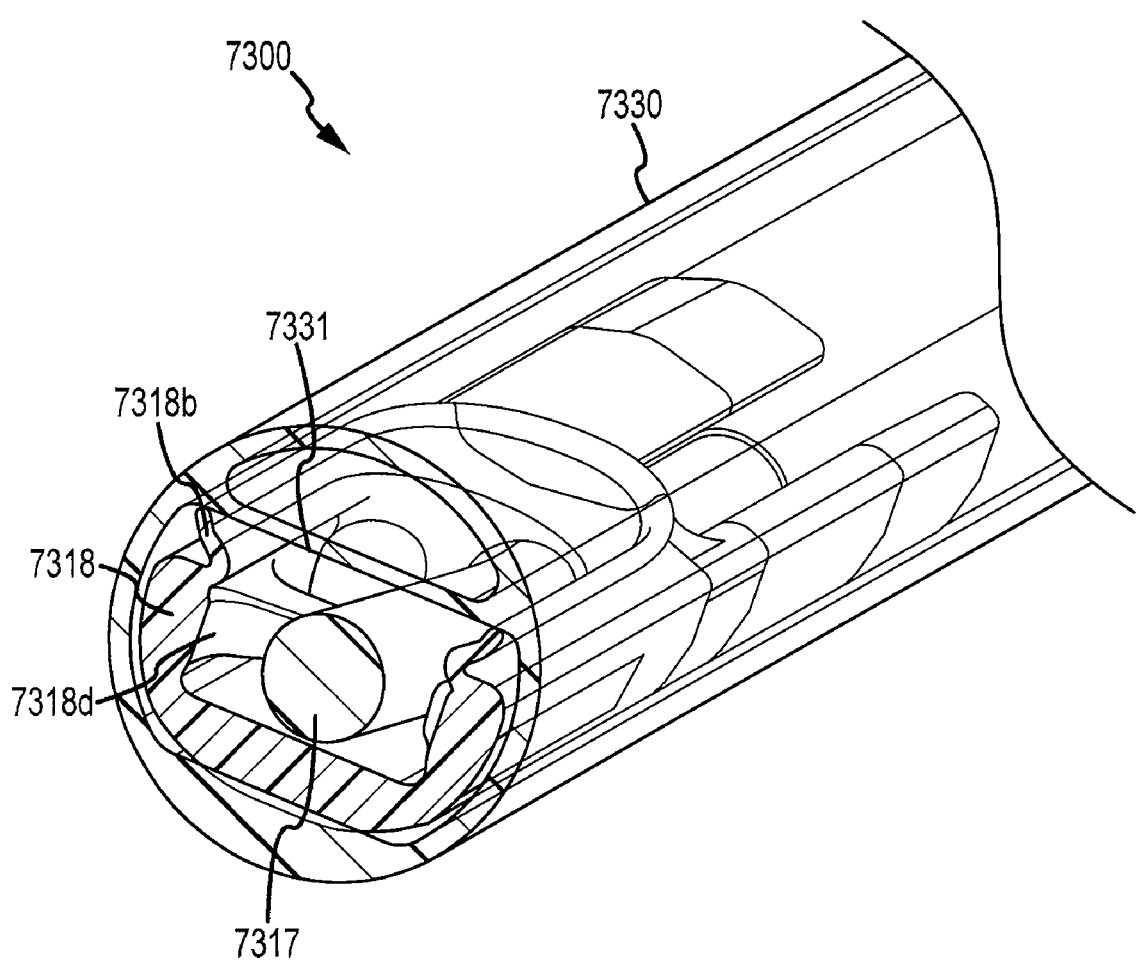
FIG. 73 shows aspects of an ablation system with a stabilizer mechanism according to embodiments of the present invention.

FIG. 72 depicts features of an exemplary treatment system 7200 according to embodiments of the present invention. Treatment system 7200 can include an ablation mechanism 7217 and a stabilizer mechanism 7218. As shown here, ablation mechanism 7217 and stabilizer mechanism 7218 are disposed at least partially within a cinching mechanism 7230 such as a trocar or push tube. Stabilizer mechanism 7218 may include a skirt 7218b configured to contact the tissue of a patient. Stabilizer mechanism 7218 may also include a coupling mechanism having coupling arms 7218d that are configured to couple with, secure, or otherwise contact the ablation mechanism. Cinching mechanism 7230 may include a seal surface 7231 that forms a seal with or otherwise contacts skirt 7218b. FIG. 73 depicts features of an exemplary treatment system 7300 according to embodiments of the present invention. Treatment system 7300 can include an ablation mechanism 7317 and a stabilizer mechanism 7318. As shown here, ablation mechanism 7317 and stabilizer mechanism 7318 are disposed at least partially within a cinching mechanism 7330 such as a trocar or push tube. Stabilizer mechanism 7318 may include a skirt 7318b configured to contact the tissue of a patient. Stabilizer mechanism 7318 may also include a coupling mechanism having coupling arms 7318d that are configured to couple with, secure, or otherwise contact the ablation mechanism. Cinching mechanism 7330 may include a seal surface 7331 that forms a seal with or otherwise contacts skirt 7318b. A suction skirt can assist in creating dependable suction against seal surface 7331 of a lumen within cinching mechanism 7330 for the portion of a suction stabilizer that remains inside the cinching mechanism tube while an ablation procedure is performed. The seal surface can allow the stabilizer mechanism to be extended to any desired length, for example when creating box or connection lesions.

Figure 74A:
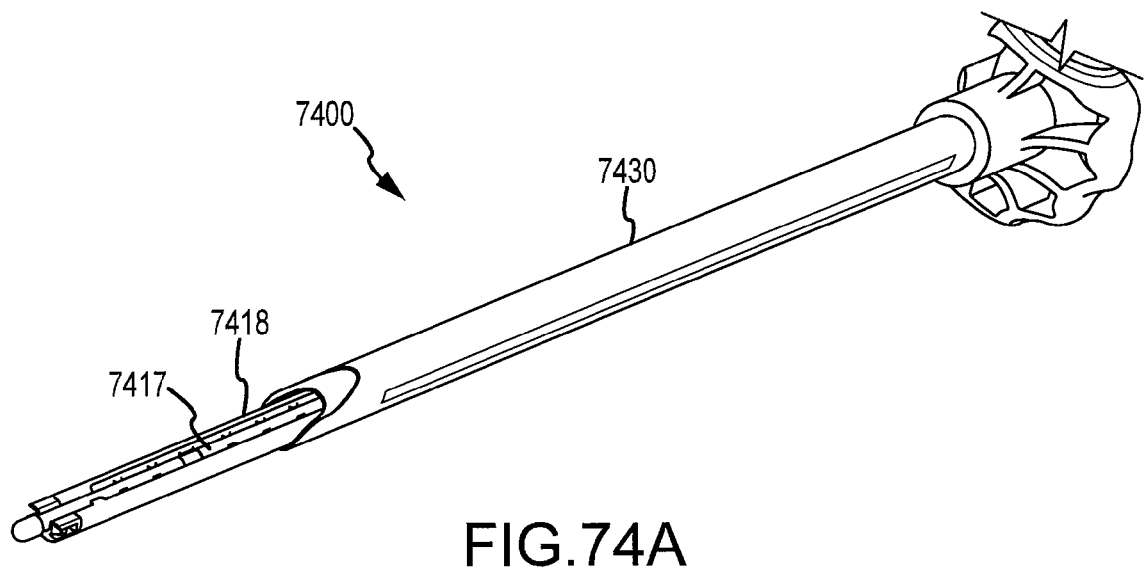
FIGS. 74A-74B show aspects of ablation systems with a stabilizer mechanism according to embodiments of the present invention.
Figure 74B:
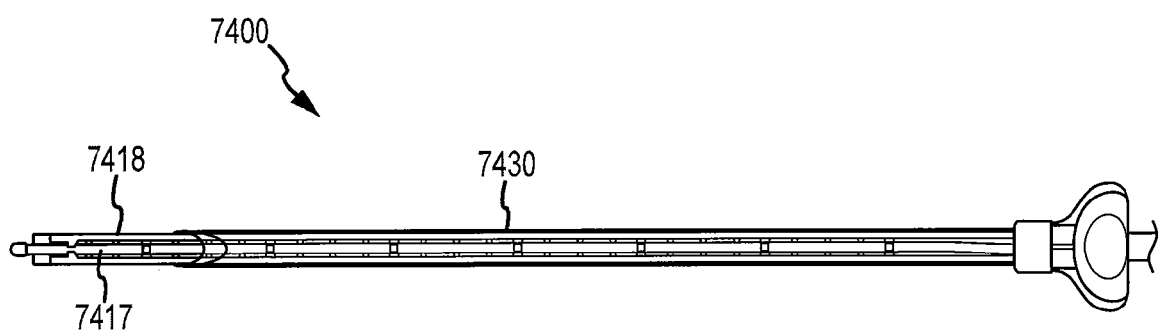
Figure 75A:
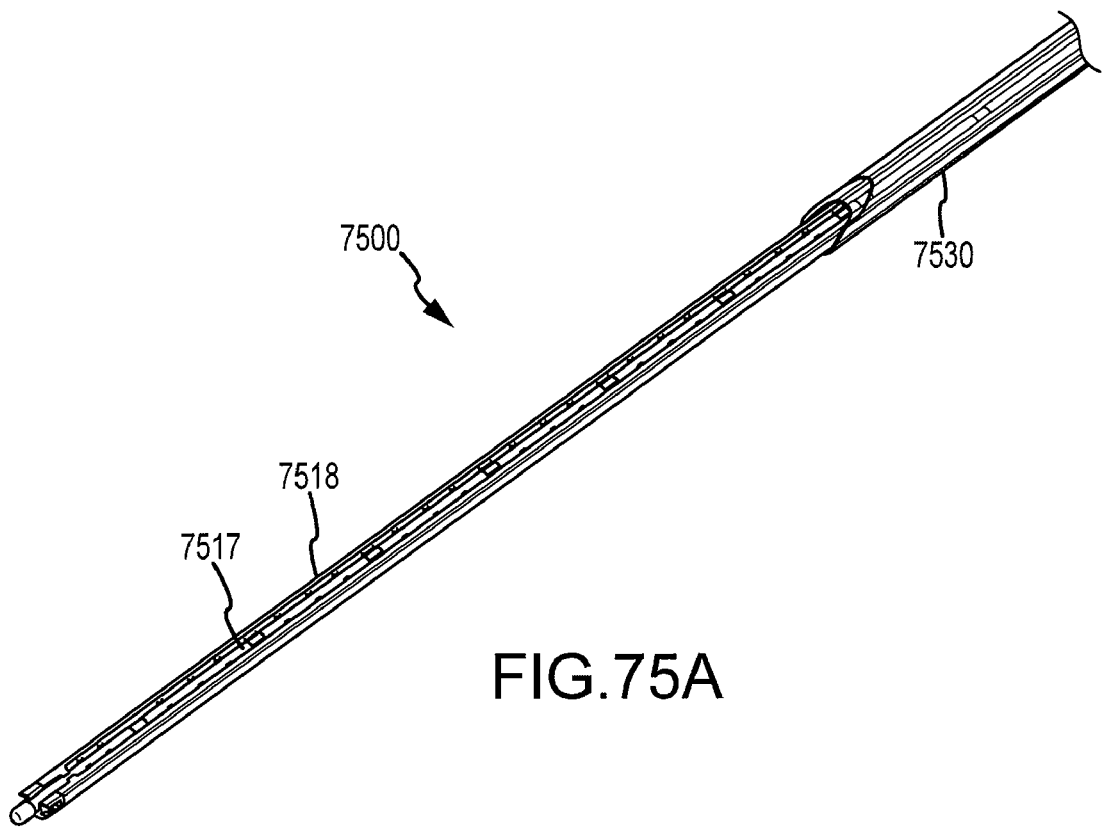
FIGS. 75A-75B show aspects of ablation systems with a stabilizer mechanism according to embodiments of the present invention.
Figure 75B:
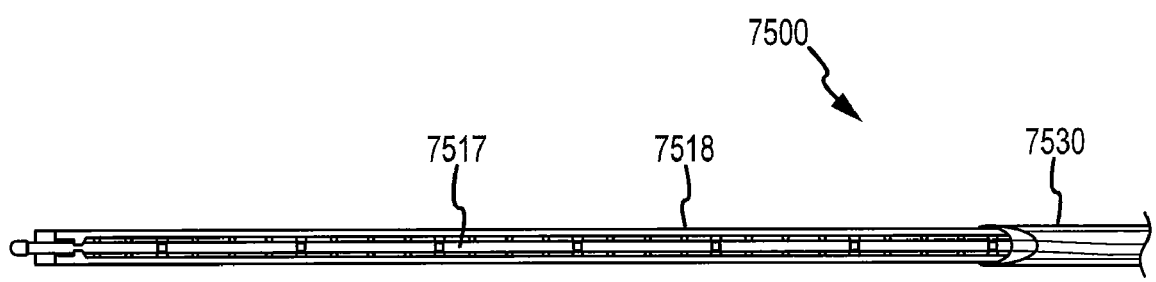

FIGS. 74A and 74B illustrate an exemplary treatment system 7400 according to embodiments of the present invention. Treatment system 7 400 includes a treatment device or ablation assembly 7410 having a flexible ablation mechanism 7417, a stabilizer mechanism 7418, and a cinching mechanism 7430 such as a trocar or push tube. As shown here, ablation mechanism 7417 and stabilizer mechanism 7418 are disposed at least partially within cinching mechanism 7430, in a retracted position. FIGS. 75A and 75B illustrate an exemplary treatment system 7 500 according to embodiments of the present invention. Treatment system 7500 includes a treatment device or ablation assembly 7510 having a flexible ablation mechanism 7517, a stabilizer mechanism 7518, and a cinching mechanism 7530 such as a trocar or push tube. As shown here, ablation mechanism 7517 and stabilizer mechanism 7518 are disposed at least partially within cinching mechanism 7530, in an extended position.

Figure 76A:
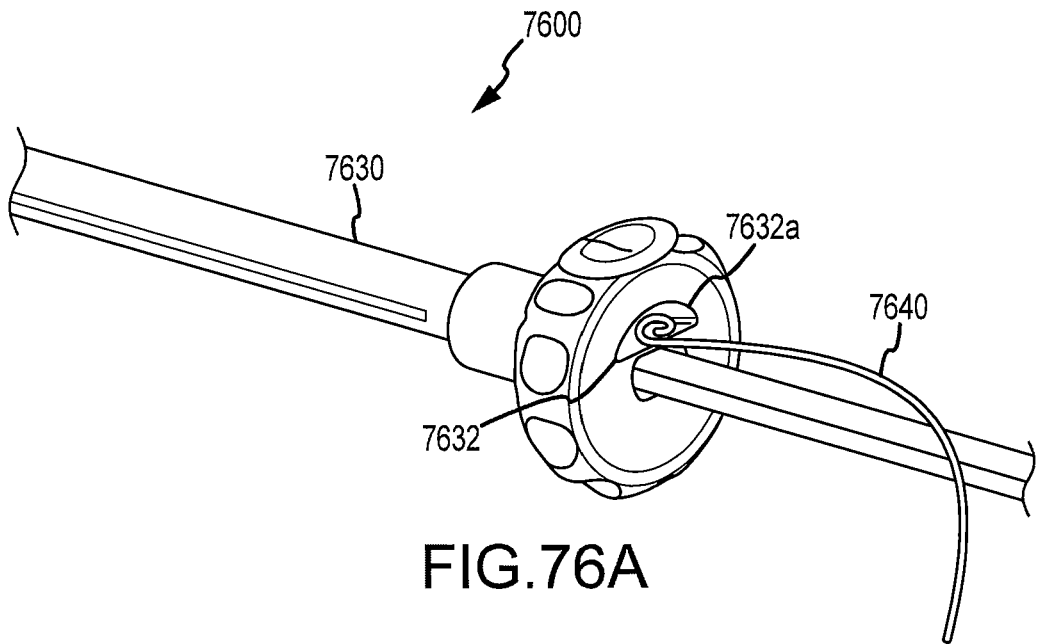
FIGS. 76A-76F show aspects of ablation systems with a coupling mechanism according to embodiments of the present invention.
Figure 76B:
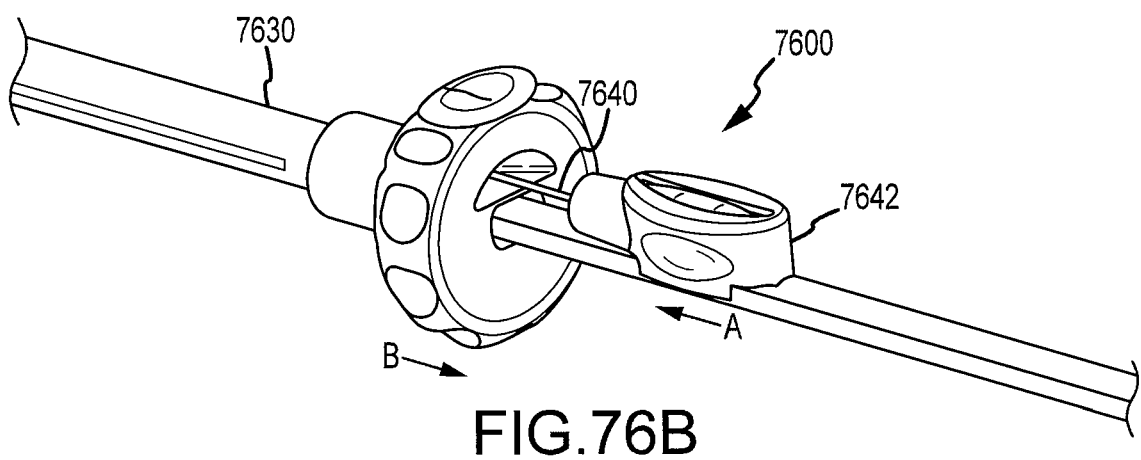
Figure 76C:
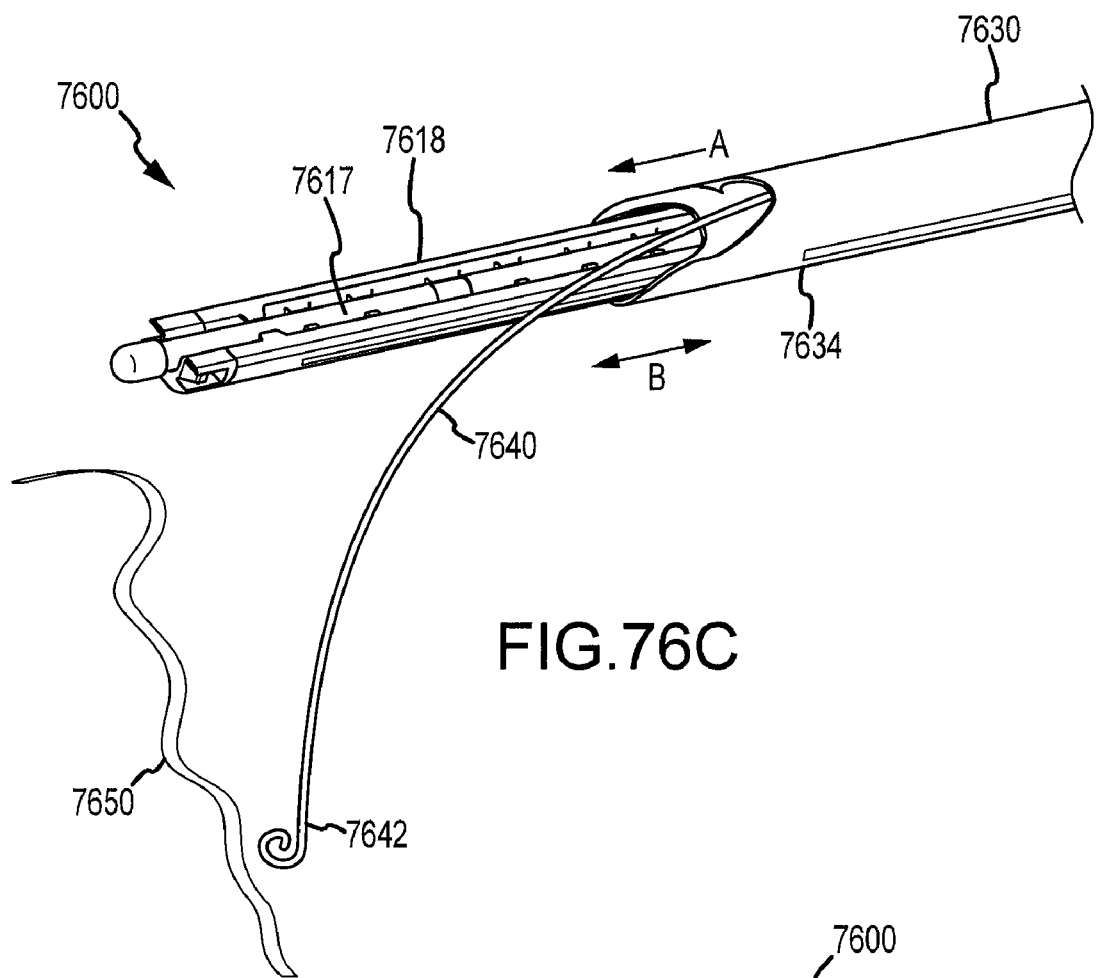
Figure 76D:
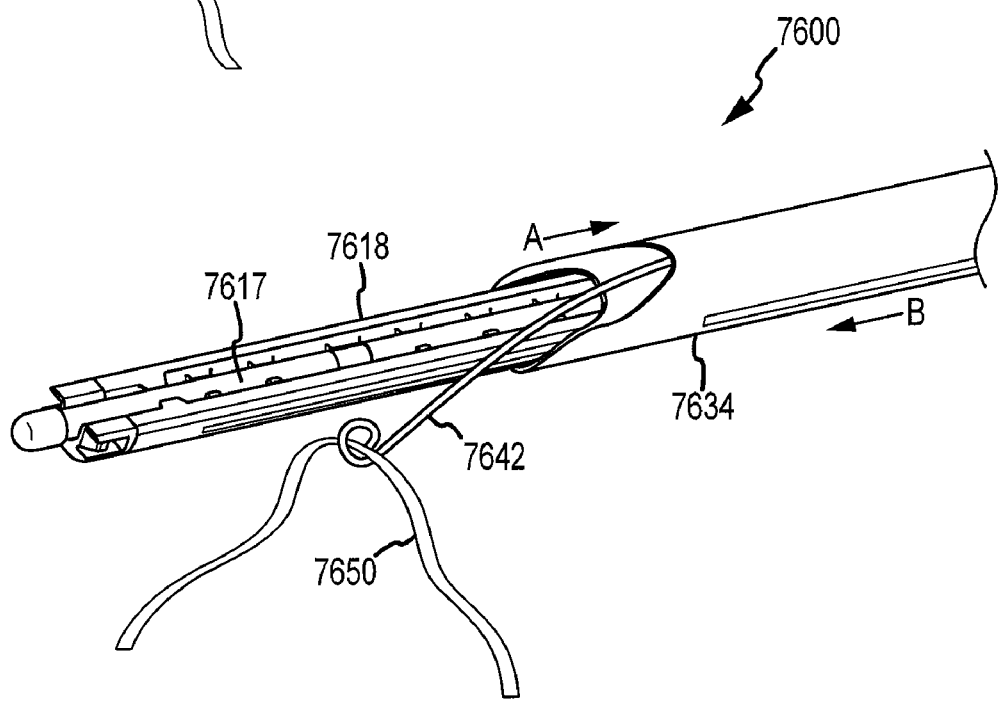
Figure 76E:
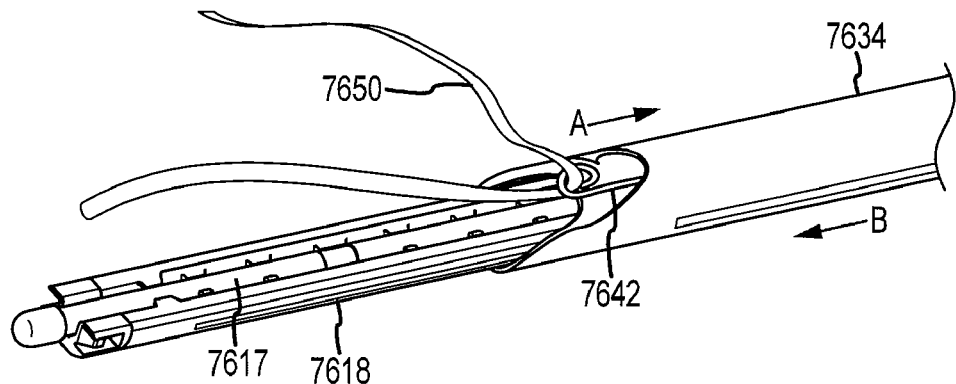
Figure 76F:
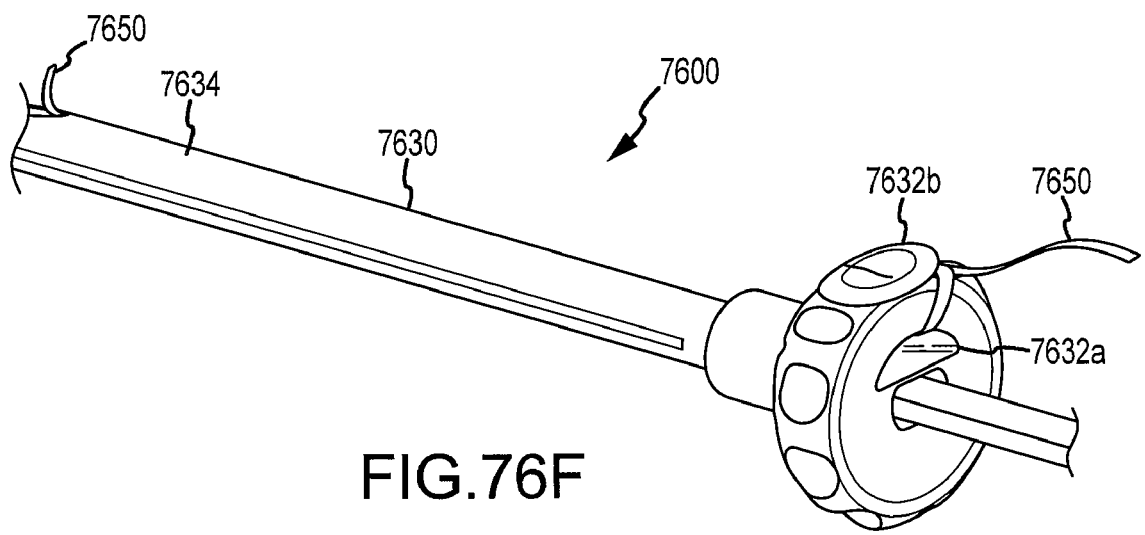
Figure 77:
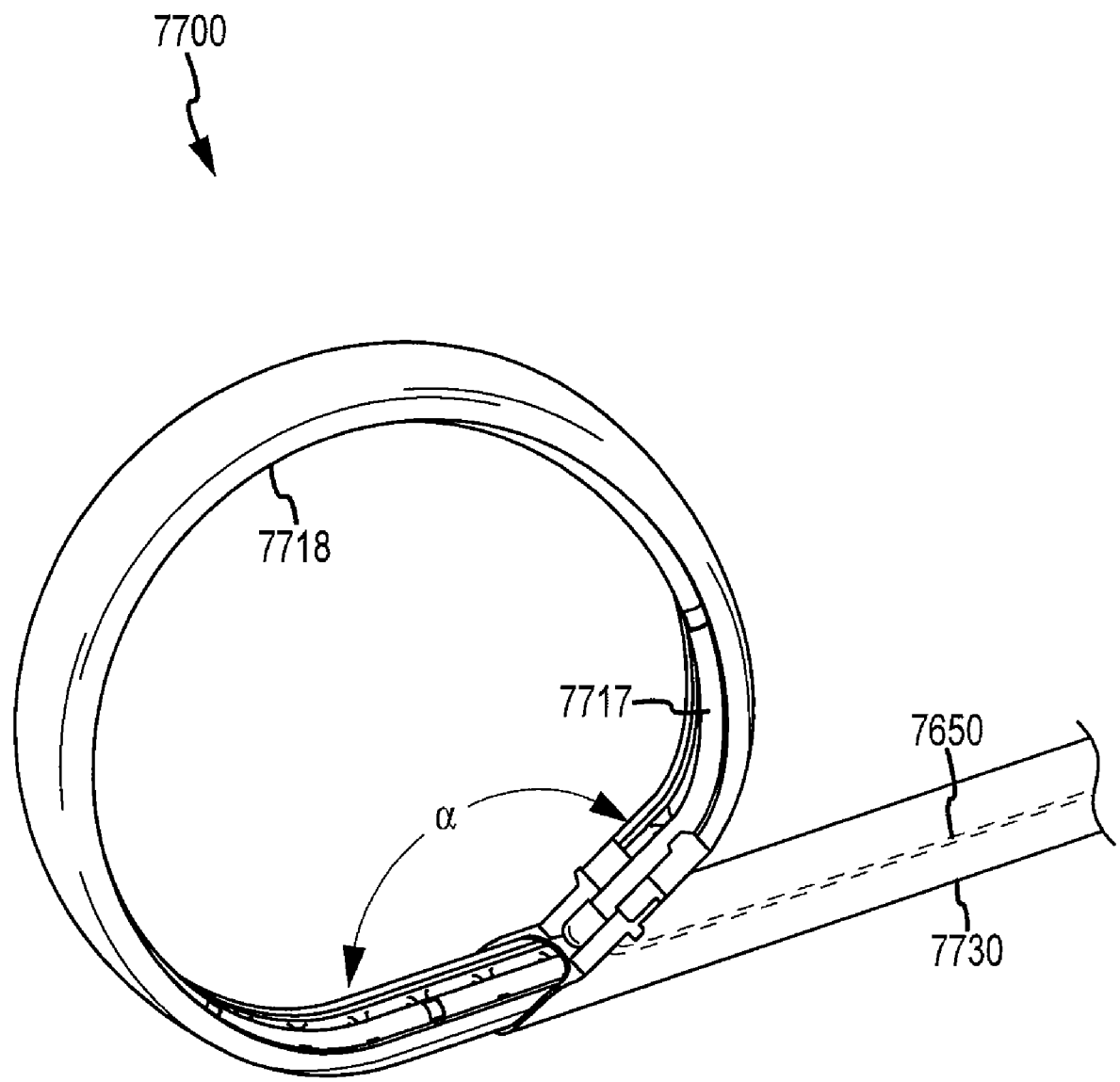
FIG. 77 shows aspects of an ablation system with an introducer according to embodiments of the present invention.

FIGS. 76A-76F show aspects of a treatment system 7600 as used in an exemplary cinching method. As depicted in FIG. 76A, methods may involve introducing a grasping or coupling mechanism through a receptacle 7632a of a proximal portion 7632 of a cinching mechanism 7630 such as a trocar or push tube. Coupling mechanism 7640 can be advanced along or through cinching mechanism 7630 as shown in FIG. 76B, for example by advancing a proximal control element 7642 of the coupling mechanism toward the cinching mechanism 7630 as indicated by arrow A. Optionally, relative translational movement between cinching mechanism 7630 and coupling mechanism 7640 can be effected by moving cinching mechanism 7630 in a proximal direction toward proximal control element 7642 as indicated by arrow B. With reference to FIG. 76C, a distal portion 7642 of coupling mechanism 7640 can be advanced distally, or extended, beyond a distal portion 7634 of cinching mechanism trocar 7630 as indicated by arrow A, and can be maneuvered so as to catch or couple with a ribbon or tape, or some other coupleable introducer mechanism or implement 7650. Optionally, the desired maneuvering of distal portion 7634 may include the inducement of translational movement of cinching mechanism 7630 along ablation mechanism 7617 and stabilizer mechanism 7618, as indicated by arrow B. As shown in FIGS. 76D and 76E, once distal portion 7642 (shown here as a loop) is coupled or engaged with introducer mechanism 7650, distal portion 7642 of coupling mechanism 7640 can be advanced proximally, or retracted, toward and into distal portion 7634 of cinching mechanism trocar 7630 as indicated by arrow A. Optionally, the desired retraction of distal portion 7634 may include the inducement of translational movement of cinching mechanism 7630 along ablation mechanism 7617 and stabilizer mechanism 7618. For example, cinching mechanism 7630 can be advanced distally relative to ablation mechanism 7617 and stabilizer mechanism 7618, as indicated by arrow B. As indicated in FIG. 76F, introducer implement 7650 can be drawn proximally through receptacle 7632a of cinching mechanism 7630, and secured or fixed with a proximal catch or clasp 7632b of the cinching mechanism. In some cases, this can involve wrapping a tape around a knob to secure the tape therewith. FIG. 77 shows an exemplary treatment system 7700, wherein introducer implement or tape 7750 is drawn proximally relative to cinching mechanism or trocar 7730, or optionally trocar 7730 is advanced distally relative to introducer tape 7750, or both, so as to form a closed or partially closed loop with ablation mechanism 7717 and stabilizer mechanism 7718. The treatment system can be configured to provide any desired angle a between the distal end of the probe, which may include the ablation mechanism, stabilizer mechanism, or both, and a more proximal section of the probe. The angle can be configured so as to provide a desired amount of contact with the tissue. In some cases, the angle can be configured so that the stabilizer mechanism can provide a desired amount of suction to the tissue. The termination of the suction bladder or stabilizer mechanism proximal to the distal end of the ablation mechanism can be configured to minimize or prevent leaks at that junction.

FIG. 78A shows a perspective view of an ablation mechanism 7817a and a stabilizer mechanism 7818a according to embodiments of the present invention. Ablation mechanism 7817a can be coupled with stabilizer mechanism 7818a at one or more locations 7819a with an adhesive material. FIG. 78B shows a perspective view of an ablation mechanism 7817b and a stabilizer mechanism 7818b according to embodiments of the present invention. By applying an adhesive material to one or more locations 7819b along ablation mechanism 7817b, or optionally by applying an adhesive material to one or more locations 7820b along stabilizer mechanism 7818b, it is possible to couple the ablation mechanism 7817b with the stabilizer mechanism 7818b. FIG. 78C shows a perspective view of an ablation mechanism 7817c and a stabilizer mechanism 7818c according to embodiments of the present invention. Ablation mechanism 7817c can be coupled with stabilizer mechanism 7818c by placing or rolling one or more 0-rings 7819c onto ablation mechanism 7817c, and coupling or bonding the o-rings with troughs 7820c of the stabilizer mechanism 7818c. FIG. 78D shows a cross section view of an ablation mechanism 7817d and a stabilizer mechanism 7818d according to embodiments of the present invention. Ablation mechanism 7817d can be coupled with stabilizer mechanism 7818d by snapping or placing the ablation mechanism into place between arms 7820d of the stabilizer mechanism, as indicated by arrow A. Optionally, the ablation mechanism can be held in place within or relative to the stabilizer mechanism by one or more loops.

Figure 79:
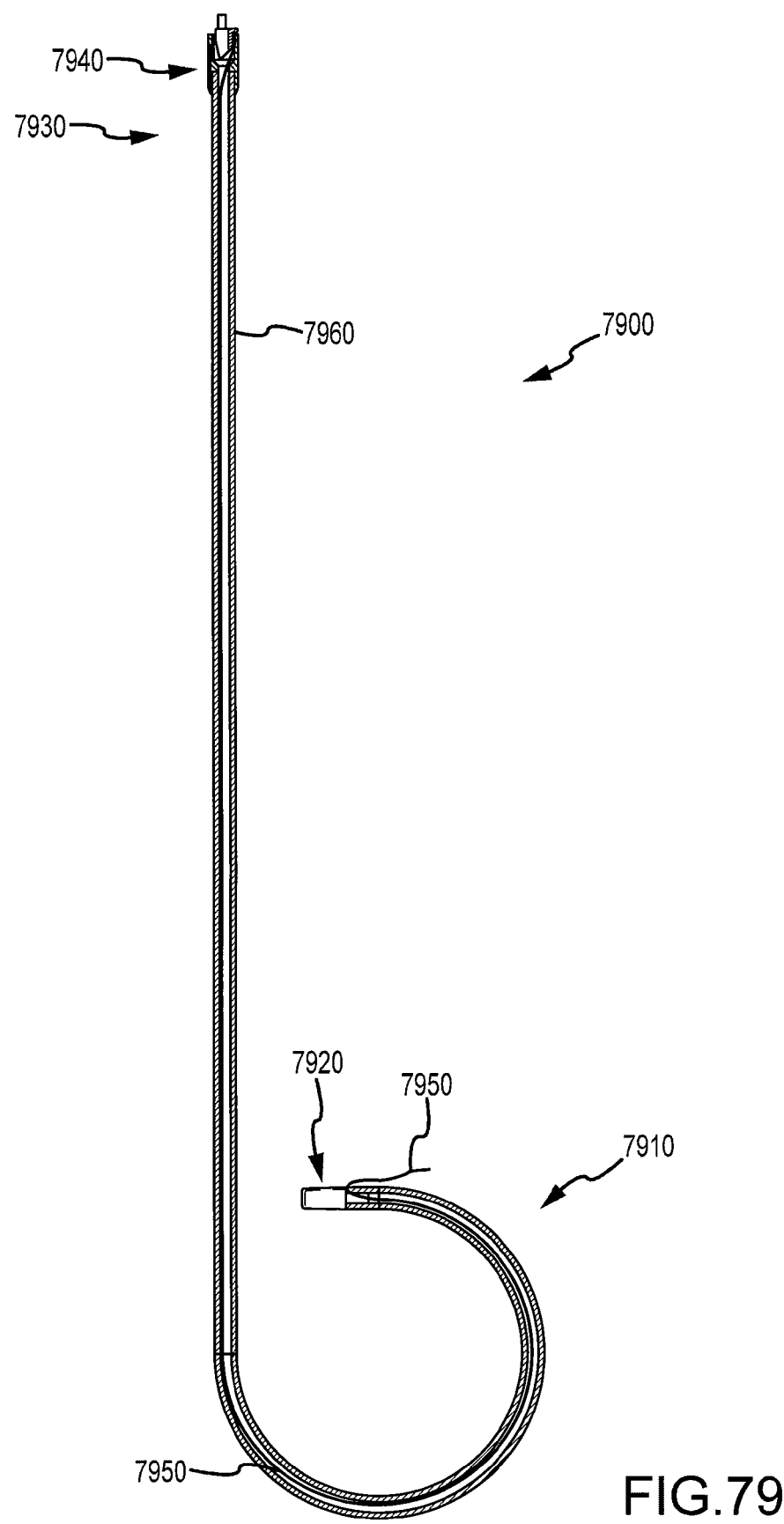
FIG. 79 shows aspects of an ablation system with a coupling mechanism according to embodiments of the present invention.

FIG. 79 illustrates an introducer assembly or mechanism 7900 according to embodiments of the present invention. Introducer assembly 7900 includes a distal portion 7910 that includes a distal coupling mechanism 7920, and a proximal portion 7930 that includes a proximal coupling mechanism 7940. Introducer assembly 7900 can also include, for example, a flexible body or tubular shaft 7960, and a ribbon, wire, or tape 7950 disposed within the body 7960. In use, introducer assembly 7900 can be positioned in a desired location within the body, for example, in a manner similar to that illustrated in FIG. 43 or FIG. 61A, or as generally described herein with reference to FIGS. 82A to 85F, or as described in previously incorporated U.S. Provisional Patent Application No. 61/015,472 filed Dec. 20, 2007. Proximal coupling mechanism 7940 can be coupled with an ablation mechanism, stabilizer mechanism, or any desired component of a treatment system, as described for example with reference to FIGS. 68A and 68B herein.

FIG. 80 illustrates an introducer assembly or mechanism 8000 according to embodiments of the present invention. Introducer assembly 8000 includes a distal portion 8010 that includes a distal coupling mechanism 8020. Introducer assembly 8000 can also include, for example, a flexible body or tubular shaft 8060, and a ribbon, wire, or tape 8050 disposed within the body 8060. In some cases, introducer assembly 8000 can be constructed by applying tension to the distal end of the tape 8050, and then gluing or fixing a cap 8022 onto the distal end of the body or tubing. As shown in FIG. 80A, a proximal portion 8022a of cap 8022 may overlap or encompass a distal portion 8060a of body 8060. FIG. 81 shows a proximal portion 8130 of an introducer assembly 8100 according to embodiments of the present invention. Proximal portion 8130 includes a coupling mechanism 8140 that can be coupled with a coupling mechanism 8170 of a treatment device having an ablation mechanism and a stabilizer mechanism. In some cases, tension on tape 8150 can operate to hold a tape anchor 8142 of coupling mechanism 8140 in place relative to the introducer assembly body 8160. Hence, the introducer assembly can be constructed such that coupling mechanism 8140 and body 8160 are otherwise freely dissociable when there is reduced tension in tape 8150. In use, after the introducer assembly 8100 has been placed in the desired position while maintaining tension on tape 8150, the operator or surgeon can sever tape at a distal end, for example by cutting the entire distal end off the introducer assembly at location A as shown in FIG. 80. Severing of tape 8150 removes the tension, and thereby allows coupling mechanism 8140 and body 8160 to separate from each other, as indicated by arrows A and B, respectively, in FIG. 81. Tape 8150 remains coupled with or attached to coupling mechanism 8140 via anchor 8142, which in turn remains coupled with or attached to coupling mechanism 8170 of an ablation and stabilizer assembly. The operator or surgeon can then reveal a length of tape 8150 by advancing body 8160 in a distal direction along introducer implement 8150, as indicated by arrow C. Hence, ribbon or tape 8150 becomes exposed, and can be engaged with a grasping mechanism, as described herein for example with reference to FIGS. 76A-76F.

Figure 82A:
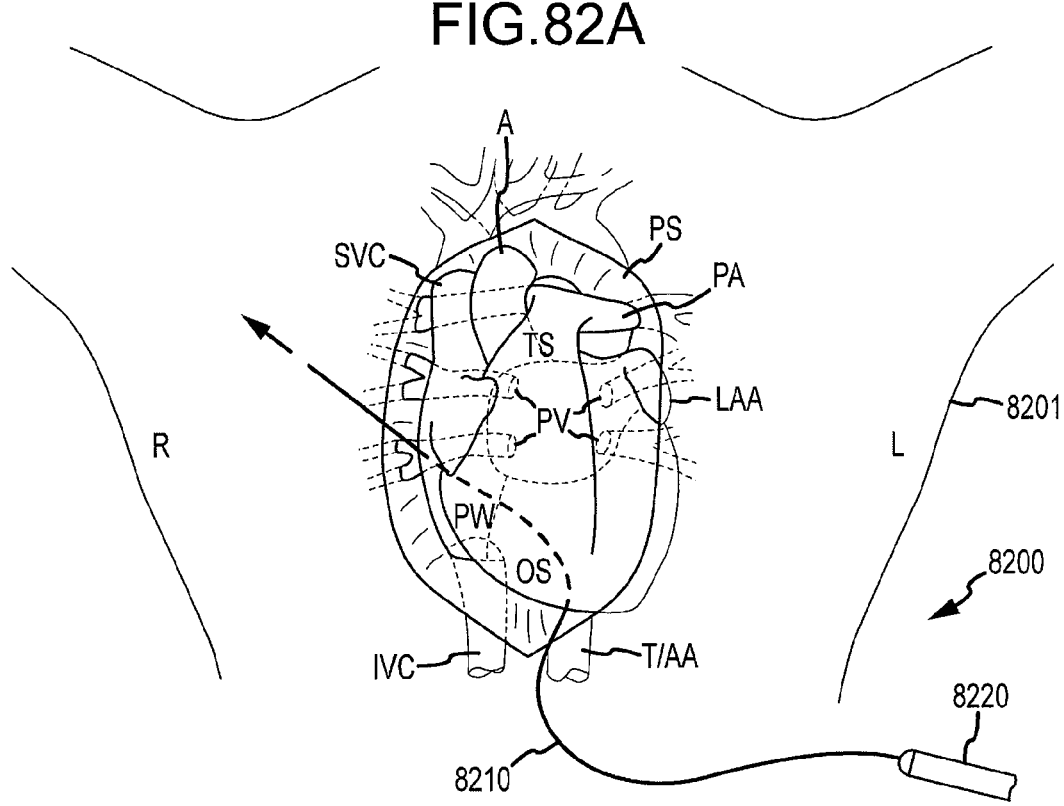
Figure 82B:
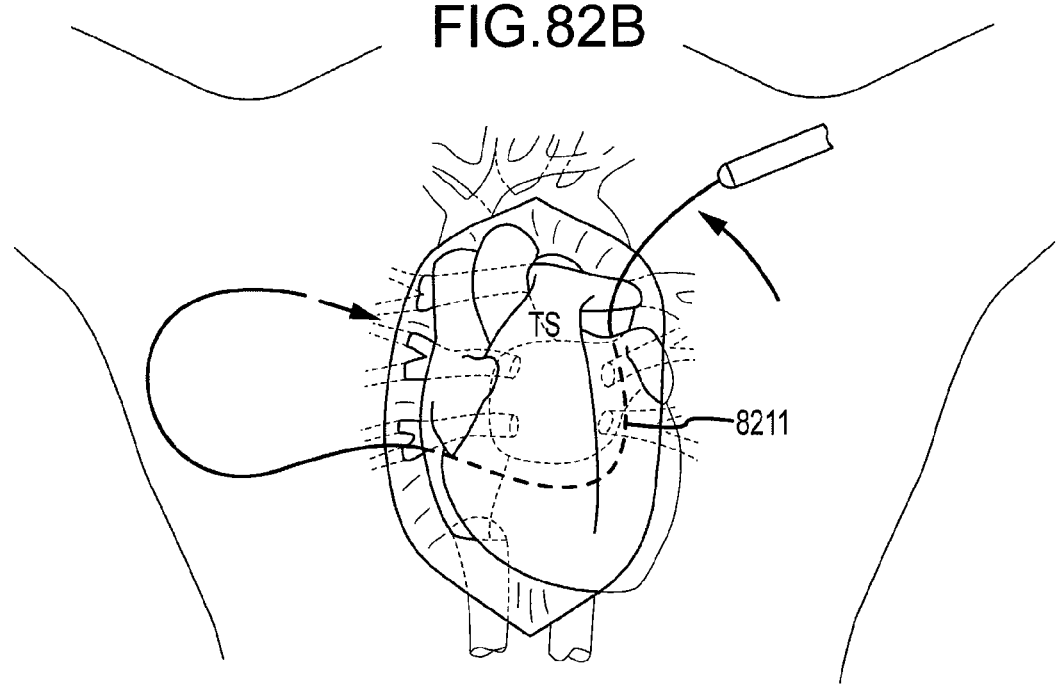
Figure 82C:
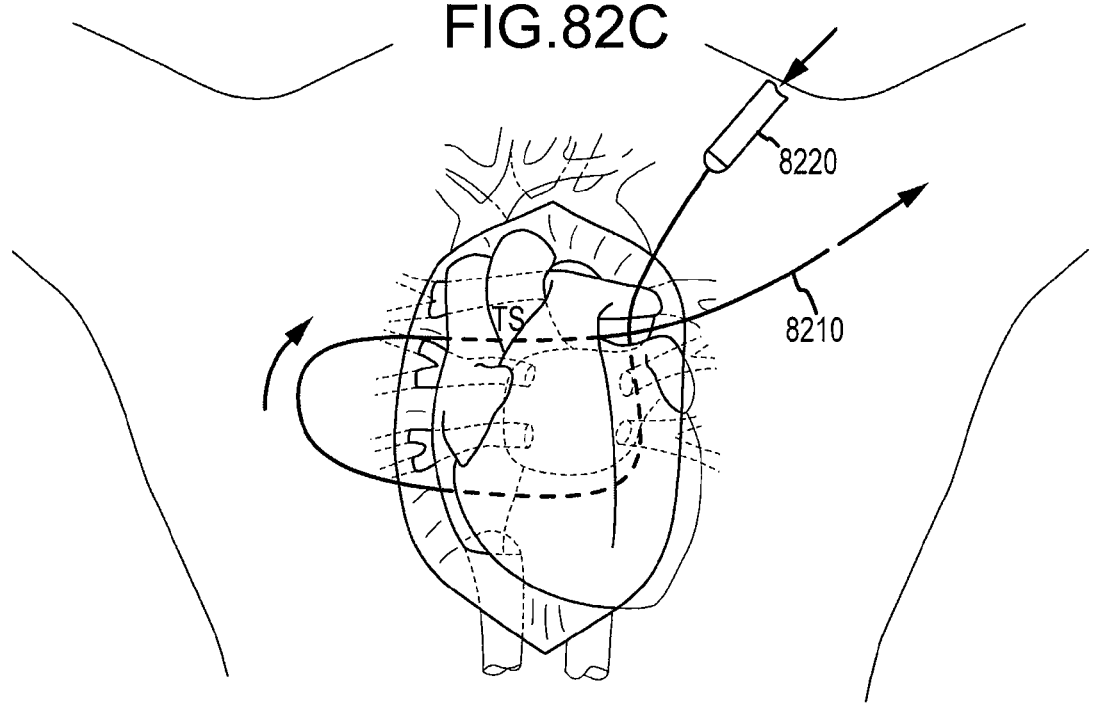
Figure 82D:
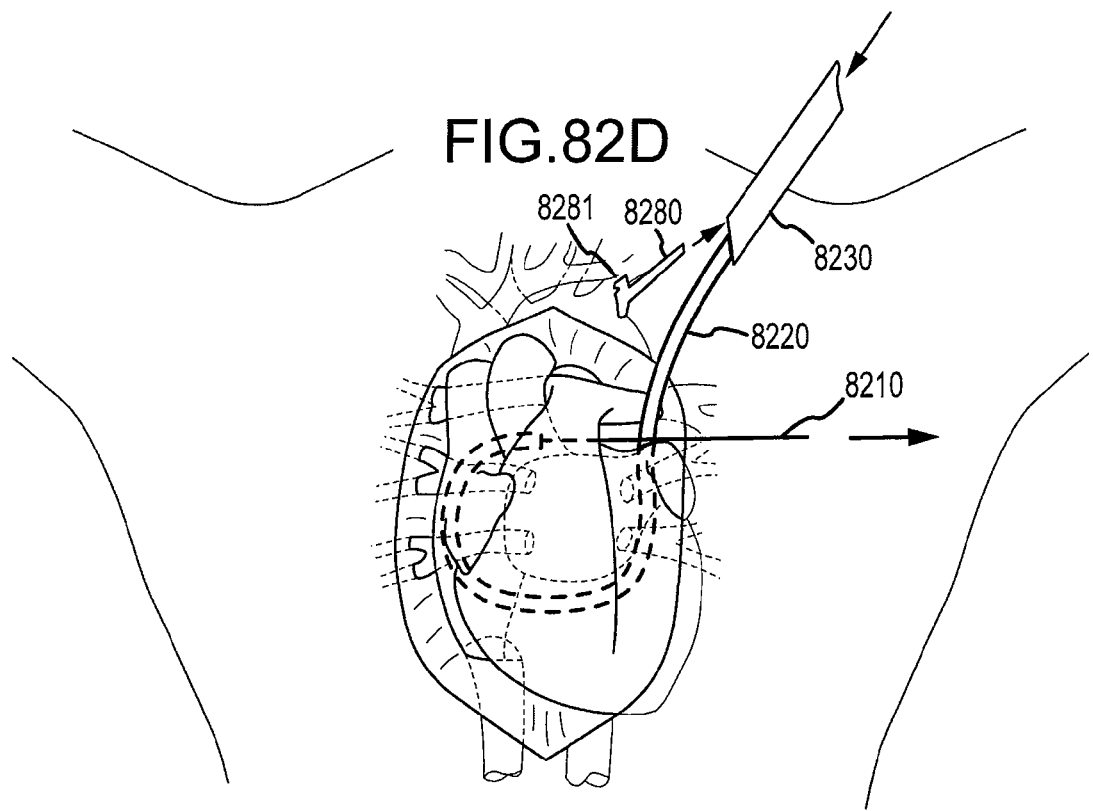

FIGS. 82A-82F show a treatment system 8200 and method of use according to embodiments of the present invention. FIG. 82A depicts a front or anterior view of a patient 8201 and an introducer system 8210 placed at a location within the body of a patient. The patient anatomy includes a superior vena cava (SVC), an aorta (A), a pericardial sac (PS) shown here in an opened configuration, a pulmonary artery (PA), a transverse sinus (TS) located posterior to the aorta, a ventricle (V), an oblique sinus (OS) located posterior the ventricle, an inferior vena cava (IVC), a left atrial appendage (LAA), pulmonary veins (PV) extending in a posterior direction from the heart, a thoracic or abdominal aorta (T/AA), and a pericardial wall (PW). In use, an operator can employ the introducer system to position the ablation and stabilizer assemblies 8220 at a desired location in the patient. As shown here, the pericardial sac has been opened by way of a sternotomy. Introducer system 8210 can be advanced through the OS, through the PW, generally passing from the left side (L) of the patient toward the right side (R) of the patient. As shown in FIGS. 82B and 82C, a proximal portion 8211 of the introducer system 8210 can be placed posterior to the LAA and against or near the roots of the left PVs, and a distal portion 8212 of the introducer system can be directed toward and passed through the TS. As shown in FIG. 82D, ablation and stabilizer assemblies 8220 are coupled with introducer system 8210, and therefore can be drawn or passed through the patient following the path taken by the introducer system. An accessory device 8280 having a catch 8281 can be inserted into the distal portion of the push tube 8230. The accessory device or sternotomy adapter 8280 can be configured to maintain a desired angle between the distal portion and a more proximal section of the ablation and stabilizer assemblies, as discussed elsewhere herein, for example with reference to FIG. 77. As depicted in FIG. 82E, tape or ribbon 8250 can be placed through catch 8281 of the accessory device, and drawn toward the proximal end of the push tube 8230 as indicated by arrow B. Cinching mechanism or push tube 8230 can be advanced distally along ablation and stabilizer assemblies 8220, as indicated by arrow A. In this way, the surgeon or operator can cinch or tighten the ablation and stabilizer assemblies 8220 about the roots of the PVs, thereby tightening a cincture encircling the PVs. One or more PVs may be encompassed by the ablation and stabilizer assemblies 8220. As shown in FIG. 82F, the tape or ribbon 8250 coupled with the distal end of the ablation and stabilizer assemblies 8220 can be drawn further taut, thereby contracting or constricting the ablation and stabilizer assemblies 8220 about the PVs. The tape or ribbon 8250 can be fixed with or wrapped around a proximal cleat or catch 8231 of the push tube or trocar 8230, so that the ablation and stabilizer assemblies 8220 remain taut around the PV roots. Thereafter, suction may be applied through a stabilizer assembly, ablation energy can be applied through an ablation assembly, and a transmural lesion can be formed.

Figure 83A:
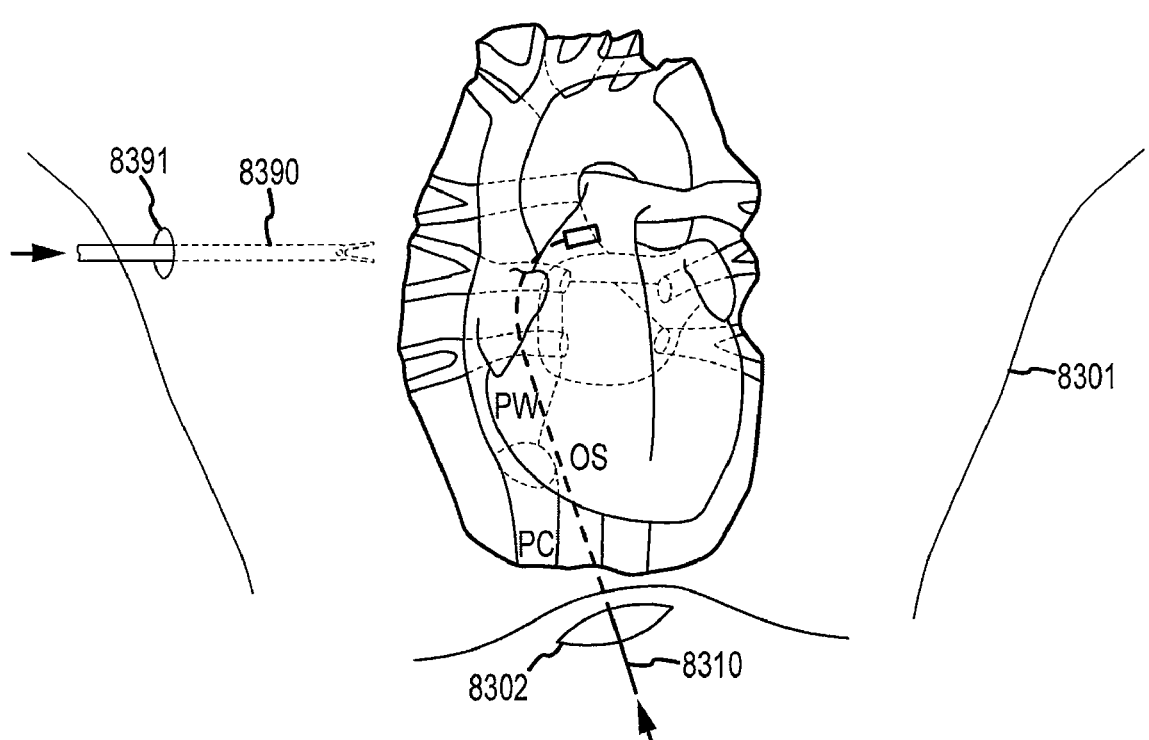
FIGS. 83A-83F show aspects of ablation systems with an introducer system according to embodiments of the present invention.
Figure 83B:
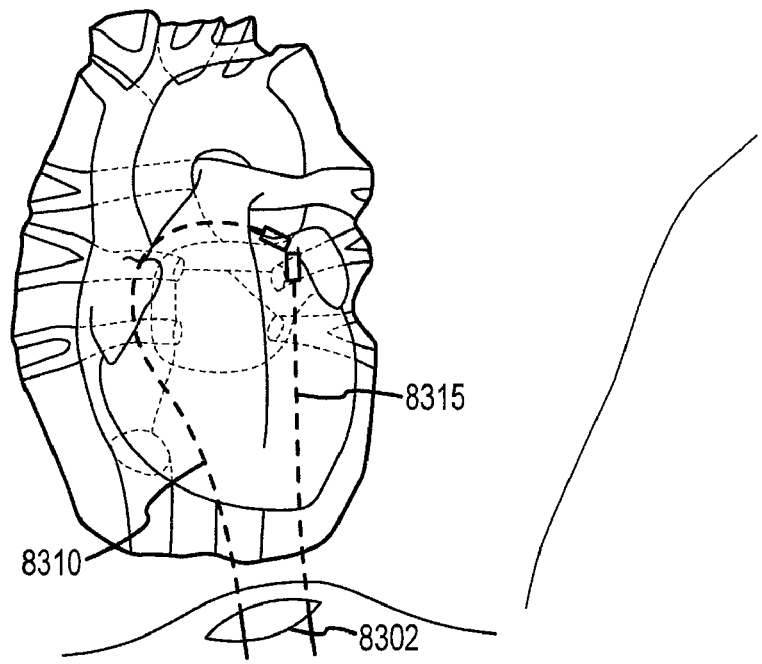
Figure 83C:
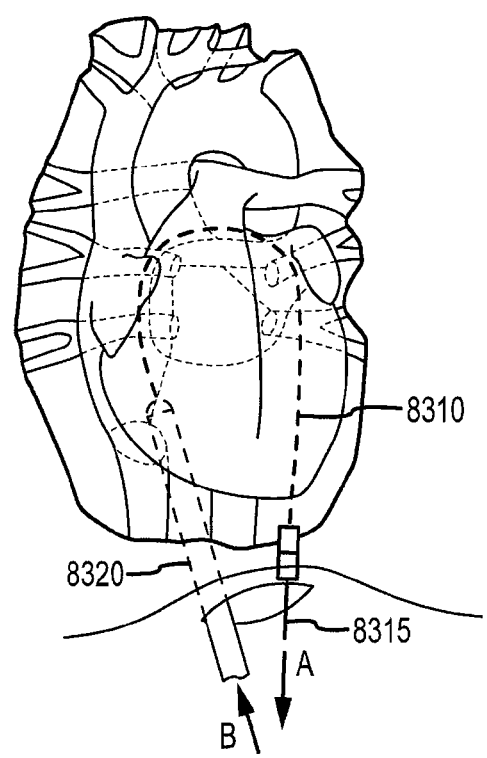
Figure 83D:
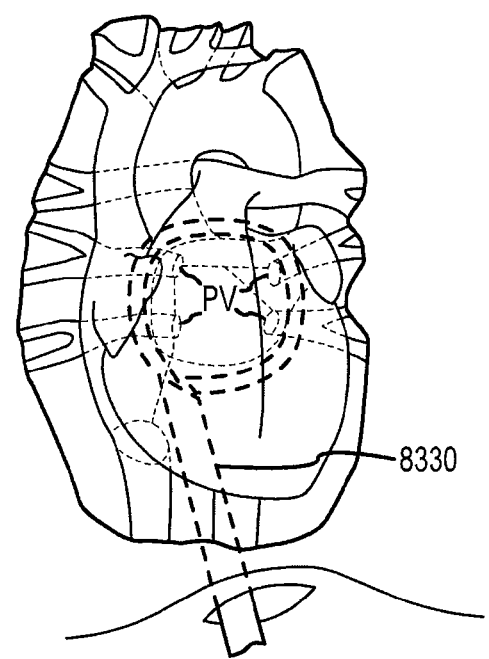
Figure 83E:
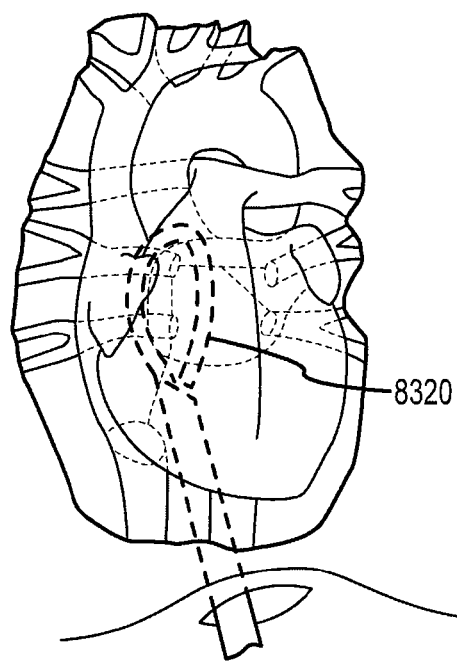
Figure 83F:
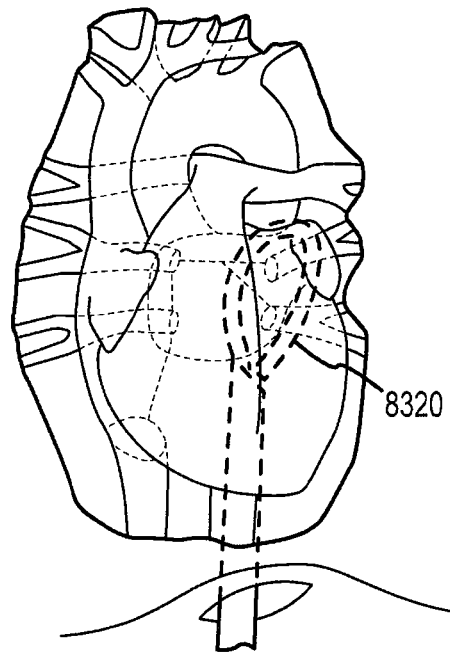

FIGS. 83A-83F show a treatment system 8300 and method of use according to embodiments of the present invention. FIG. 83A depicts a front or anterior view of a patient 8301 and an introducer system 8310 placed at a location within the body of a patient. The surgeon or operator may advance the introducer system 8310 though a subzyphoid incision 8302, through the pericardium (PC), the oblique sinus (OS), the pericardial wall (PW), and toward the transverse sinus (TS). Optionally, the surgeon or operator may place a guiding introducer 8390 through a secondary port 8391 to assist with placement of the introducer system 8310. As shown in FIG. 83B, a second introducer 8315 can be introduced into the patient, optionally through incision 8302, and coupled with the introducer system 8310. Embodiments may include any of a variety of similar introducer techniques, such as those disclosed in previously incorporated U.S. Provisional Patent Application No. 61/015,472 filed Dec. 20, 2007. For example, the operator may use stiffening stylets or obturators in conjunction with or as part of the introducers. As shown in FIG. 83C, the second or retrieving introducer 8315 can be withdrawn from the patient as indicated by arrow A, thus pulling introducer system 8310 in a desired path around the patient heart. Ablation and stabilizer assembly 8320, which is coupled with introducer system 8310, can follow the path taken by the introducer system 8310, as indicated by arrow B. As described elsewhere herein, the ablation and stabilizer assembly 8320 can be encircled about the roots of the PVs. The surgeon or operator may then advance push tube 8330 along the ablation and stabilizer assembly 8320 so as to constrict the ablation and stabilizer assembly 8320 about the PVs, as illustrated in FIG. 83D. As shown in FIG. 83E, in some cases the ablation and stabilizer assembly 8320 can be wrapped around the right PVs. As shown in FIG. 83F, in some cases the ablation and stabilizer assembly 8320 can be wrapped around the left PVs.

Figure 84A:
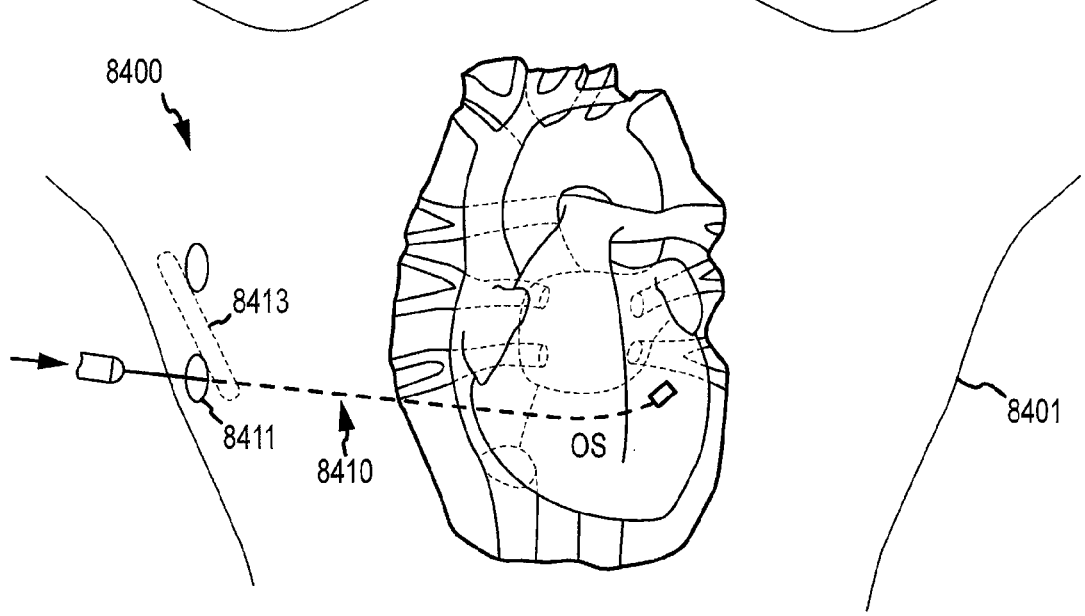
Figure 84B:
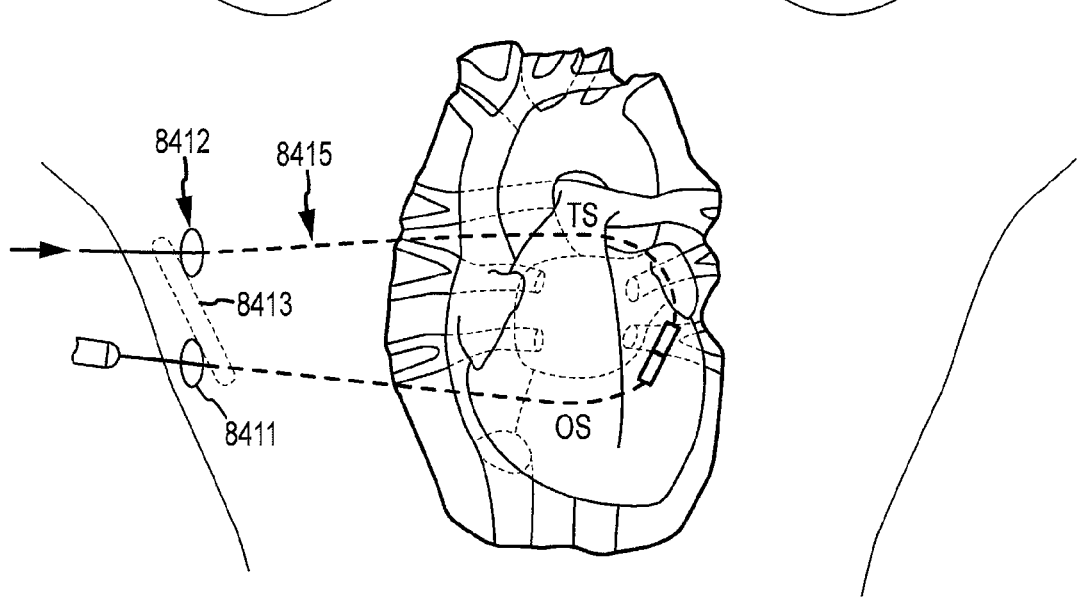

FIGS. 84A-84F show a treatment system 8400 and method of use according to embodiments of the present invention. FIG. 84A depicts a front or anterior view of a patient 8401 and an introducer system 8410 placed at a location within the body of a patient. The surgeon or operator may advance the introducer system 8410 though a first port or thoracotomy incision 8411 disposed on the patient's right side, through oblique sinus (OS). As shown in FIG. 84B, a second or retrieving introducer 8415 can be introduced into the patient, through a second port or incision

Figure 84E:
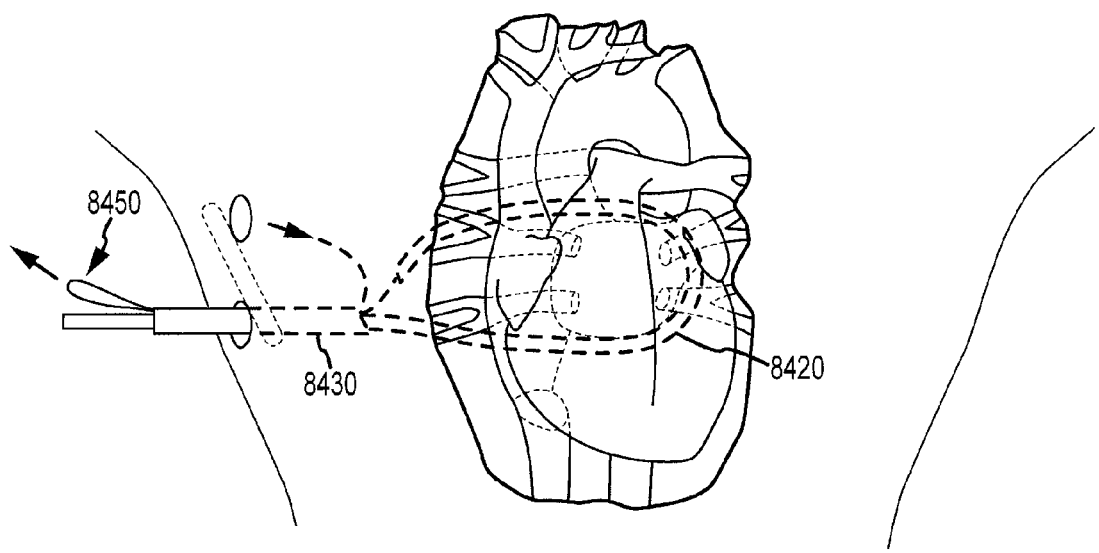
Figure 84F:
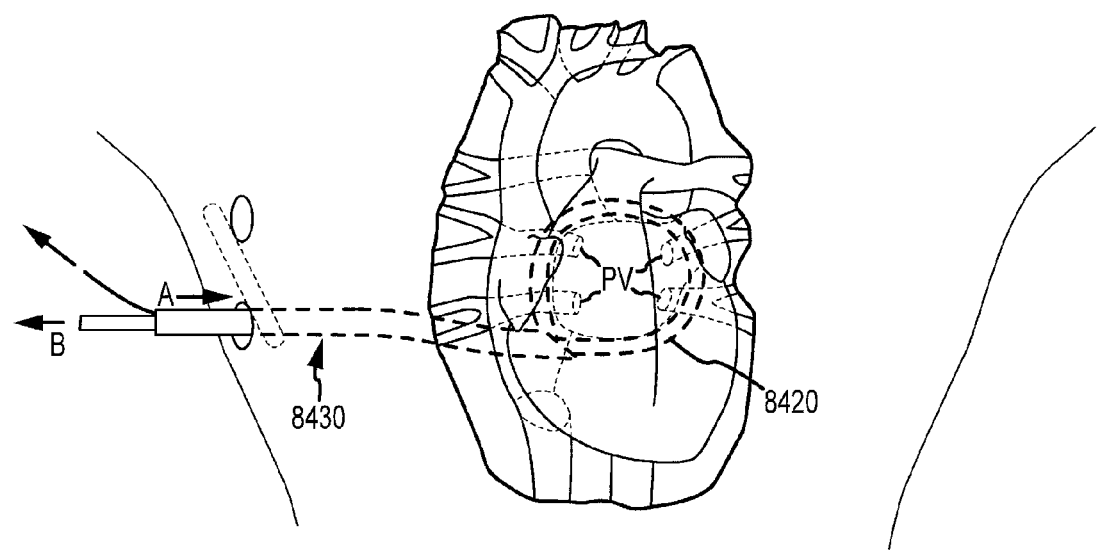

8412 and through transverse sinus (TS), and coupled with the introducer system 8410. Embodiments may include any of a variety of similar introducer techniques, such as those disclosed in previously incorporated U.S. Provisional Patent Application No. 61/015,472 filed Dec. 20, 2007. In some cases, introducer system 8410 and retrieving introducer 8415 may be inserted into the patient via a common port or incision 8413. As shown in FIG. 84C, the second or retrieving introducer 8415 can be withdrawn from the patient as indicated by arrow A, thus pulling introducer system 8410 in a desired path around the patient heart. Ablation and stabilizer assembly 8420, which is coupled with introducer system 8410, can follow the path taken by the introducer system 8410, as indicated by arrow B. As described elsewhere herein, the ablation and stabilizer assembly 8420 can be encircled about the roots of the PVs. The surgeon or operator may then remove a portion of introducer system 8410. For example, as described above with reference to FIGS. 80 and 81, a tubular body 8460 of the introducer can be removed while an exposed ribbon or tape 8450 remains attached with a distal portion of ablation and stabilizer assembly 8420. As shown in FIG. 84E, the surgeon can grasp a portion of the exposed ribbon or tape, for example as described above with reference to FIGS. 76A-76F, and withdrawn the ribbon or tape 8450 through a proximal portion of the push tube or trocar, thereby forming a looping or circular configuration with ablation and stabilizer assembly 8420. The surgeon can advance push tube 8430 along the ablation and stabilizer assembly 8420 as indicated by arrow A so as to constrict the ablation and stabilizer assembly 8420 about the PVs, as illustrated in FIG. 83F. Optionally, this cinching procedure may involve withdrawing a proximal portion of the ablation and stabilizer assembly out of push tube 8430 as indicated by arrow B. Optionally, tape or ribbon 8450 can be drawn further taut. Hence, the surgeon can contract or constrict ablation and stabilizer assembly 8420 about the PV s. The tape or ribbon 8450 can be fixed with or wrapped around a proximal cleat or catch of the push tube or trocar 8430 as described elsewhere herein, so that the ablation and stabilizer assembly 8420 remains taut around the PV roots. Thereafter, suction may be applied through a stabilizer assembly, ablation energy can be applied through an ablation assembly, and a transmural lesion can be formed.

Figure 85A:
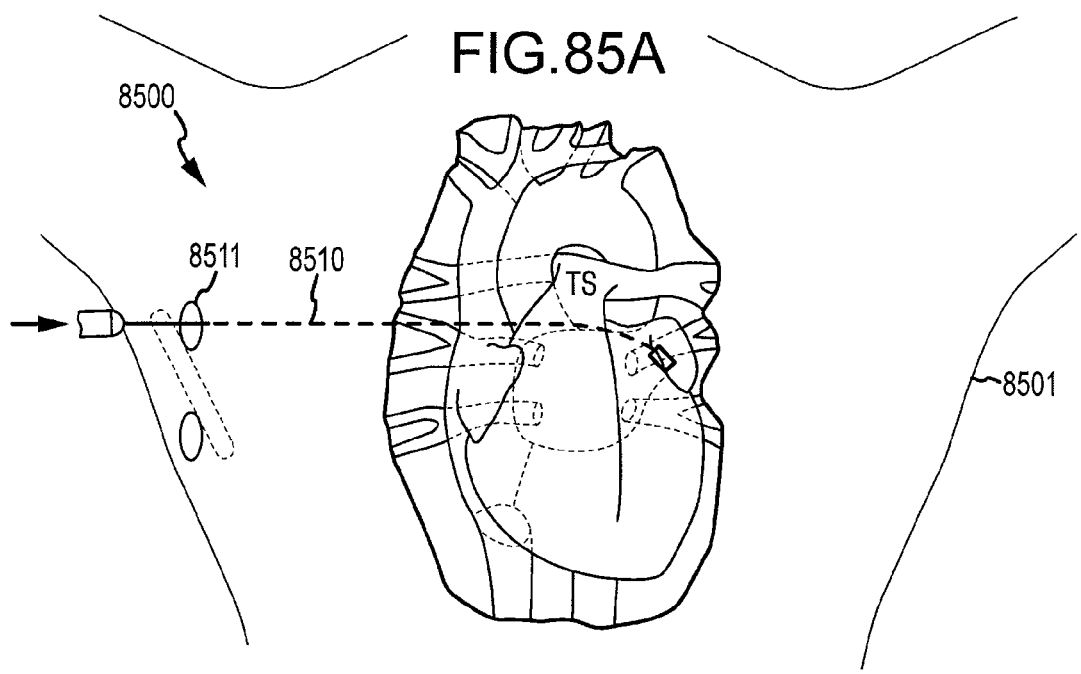
FIGS. 85A-85F show aspects of ablation systems with an introducer system according to embodiments of the present invention.
Figure 85B:
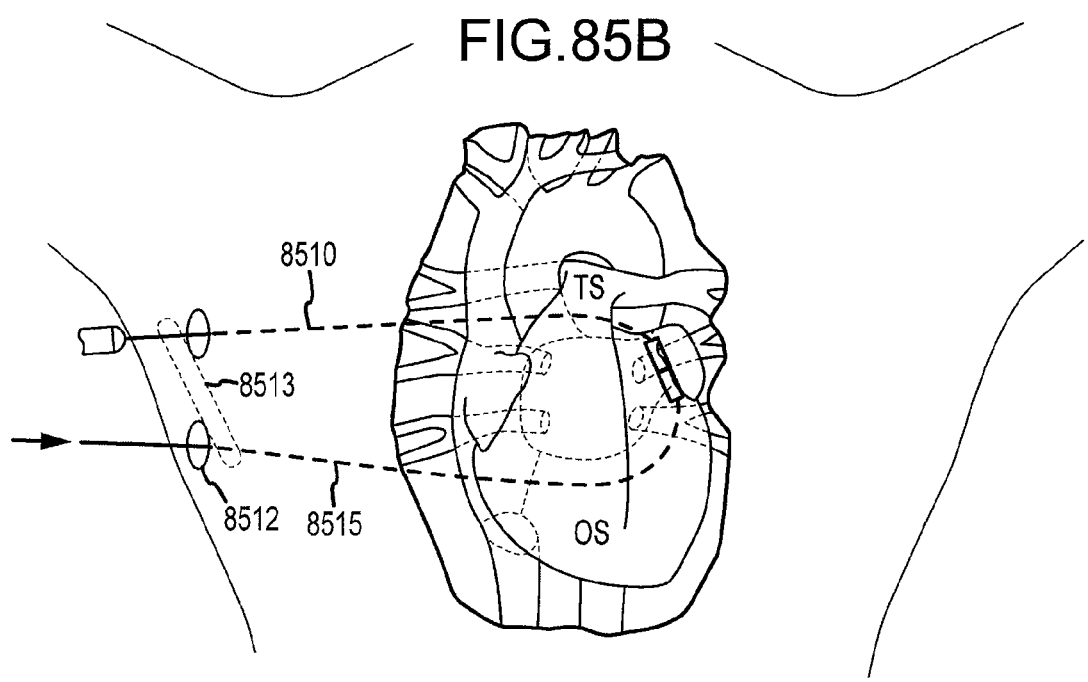
Figure 85C:
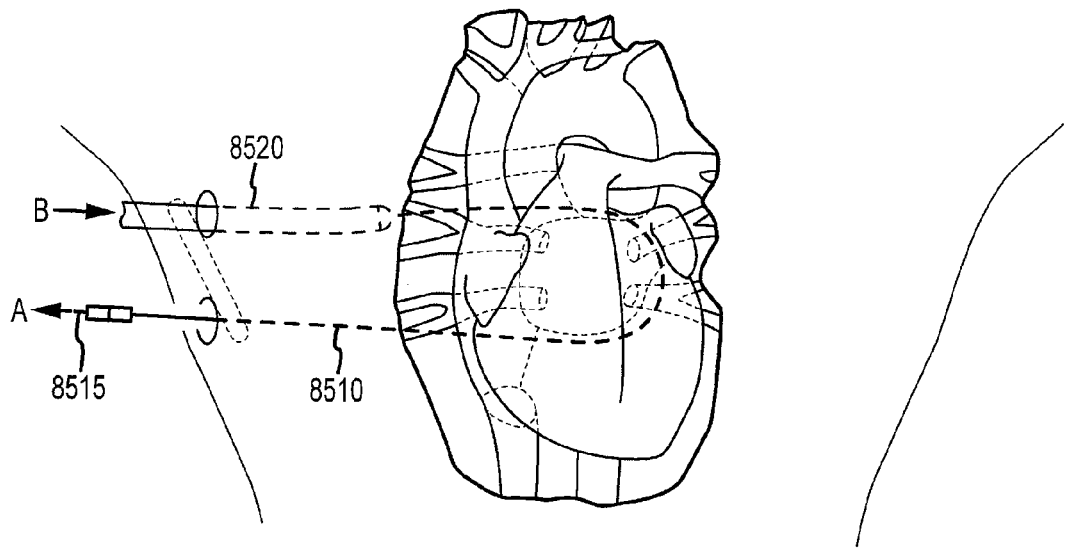
Figure 85D:
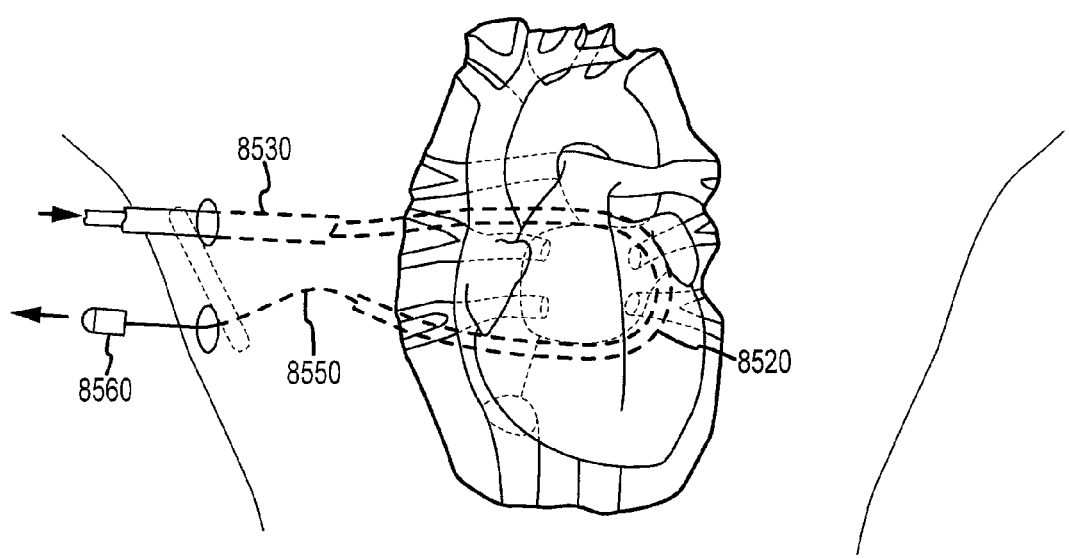
Figure 85E:
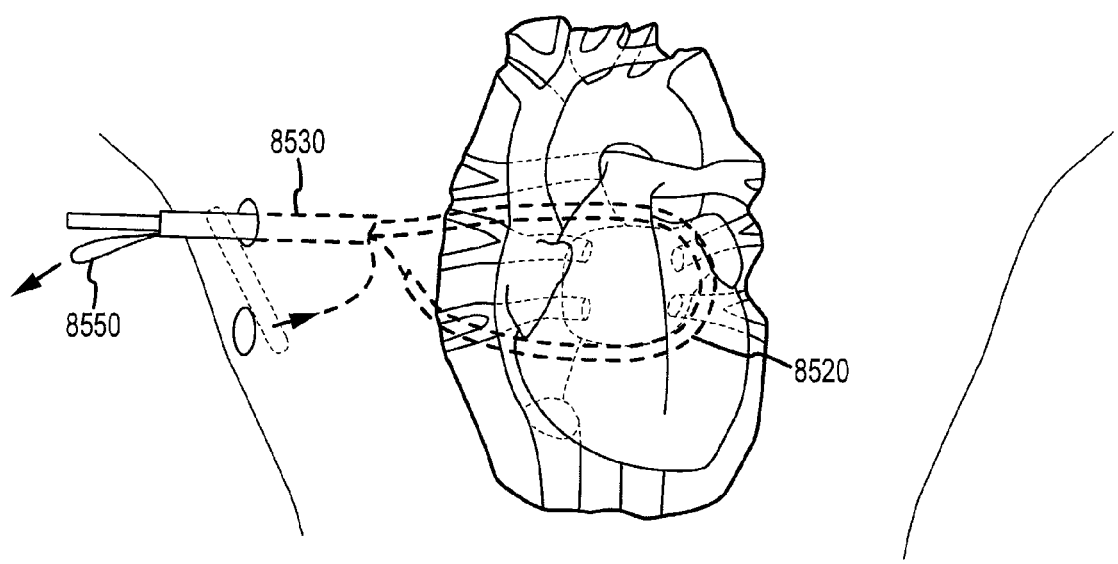
Figure 85F:
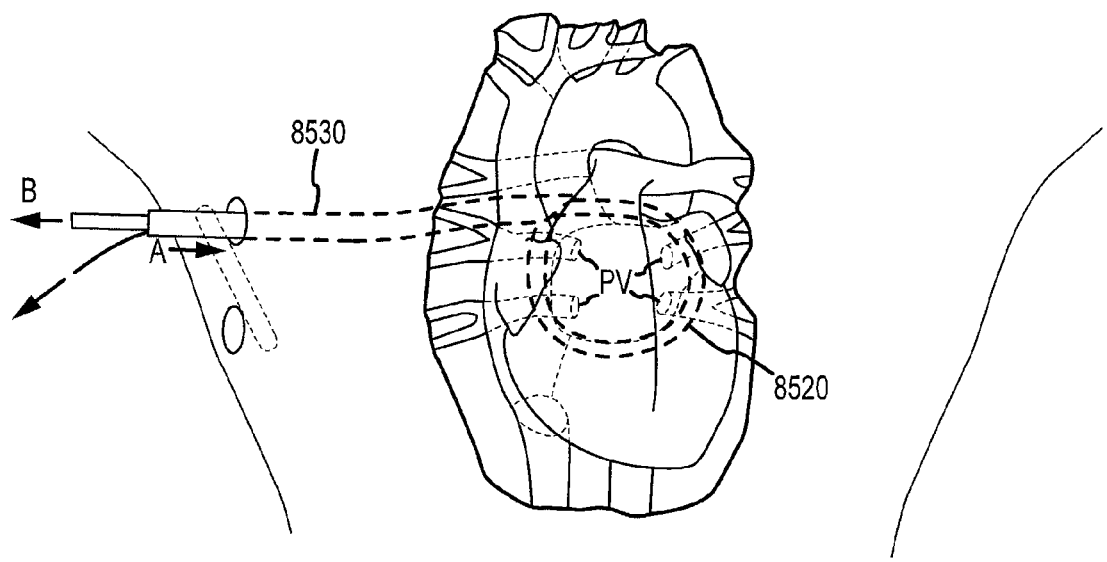

FIGS. 85A-85F show a treatment system 8500 and method of use according to embodiments of the present invention. FIG. 85A depicts a front or anterior view of a patient 8501 and an introducer system 8510 placed at a location within the body of a patient. The surgeon or operator may advance the introducer system 8510 though a first port or thoracotomy incision 8511 disposed on the patient's right side, through transverse sinus (TS). As shown in FIG. 85B, a second or retrieving introducer 8515 can be introduced into the patient, through a second port or incision 8512, and coupled with the introducer system 8510. Embodiments may include any of a variety of similar introducer techniques, such as those disclosed in previously incorporated U.S. Provisional Patent Application No. 61/015,472 filed Dec. 20, 2007. In some cases, introducer system 8510 and retrieving introducer 8515 may be inserted into the patient via a common port or incision 8513 and through. As shown in FIG. 85C, the second or retrieving introducer 8515 can be withdrawn from the patient as indicated by arrow A, thus pulling introducer system 8510 in a desired path around the patient heart. Ablation and stabilizer assembly 8520, which is coupled with introducer system 8510, can follow the path taken by the introducer system 8510, as indicated by arrow B. As described elsewhere herein, the ablation and stabilizer assembly 8520 can be encircled about the roots of the PV s. The surgeon or operator may then remove a portion of introducer system 8510. For example, as described above with reference to FIGS. 80 and 81, a tubular body 8560 of the introducer can be removed while an exposed ribbon or tape 8550 remains attached with a distal portion of ablation and stabilizer assembly 8520. As shown in FIG. 85E, the surgeon can grasp a portion of the exposed ribbon or tape, for example as described above with reference to FIGS. 76A-76F, and withdrawn the ribbon or tape 8550 through a proximal portion of the push tube or trocar 8530, thereby forming a looping or circular configuration with ablation and stabilizer assembly 8520. The surgeon can advance push tube 8530 along the ablation and stabilizer assembly 8520 as indicated by arrow A so as to constrict the ablation and stabilizer assembly 8520 about the PVs, as illustrated in FIG. 85F. Optionally, this cinching procedure may involve withdrawing a proximal portion of the ablation and stabilizer assembly out of push tube 8530 as indicated by arrow B. Optionally, tape or ribbon 8550 can be drawn further taut. Hence, the surgeon can contract or constrict ablation and stabilizer assembly 8520 about the PVs. The tape or ribbon 8550 can be fixed with or wrapped around a proximal cleat or catch of the push tube or trocar 8530 as described elsewhere herein, so that the ablation and stabilizer assembly 8520 remains taut around the PV roots. Thereafter, suction may be applied through a stabilizer assembly, ablation energy can be applied through an ablation assembly, and a transmural lesion can be formed.

Figure 86A:
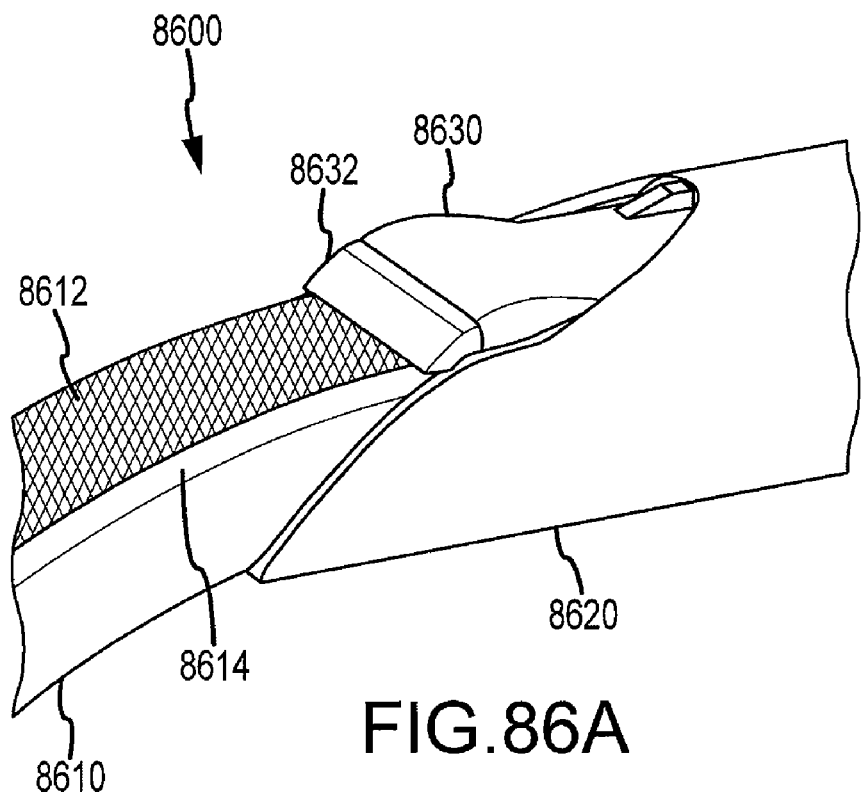
FIGS. 86A-86B show aspects of ablation systems with a stabilizer member according to embodiments of the present invention.
Figure 86B:
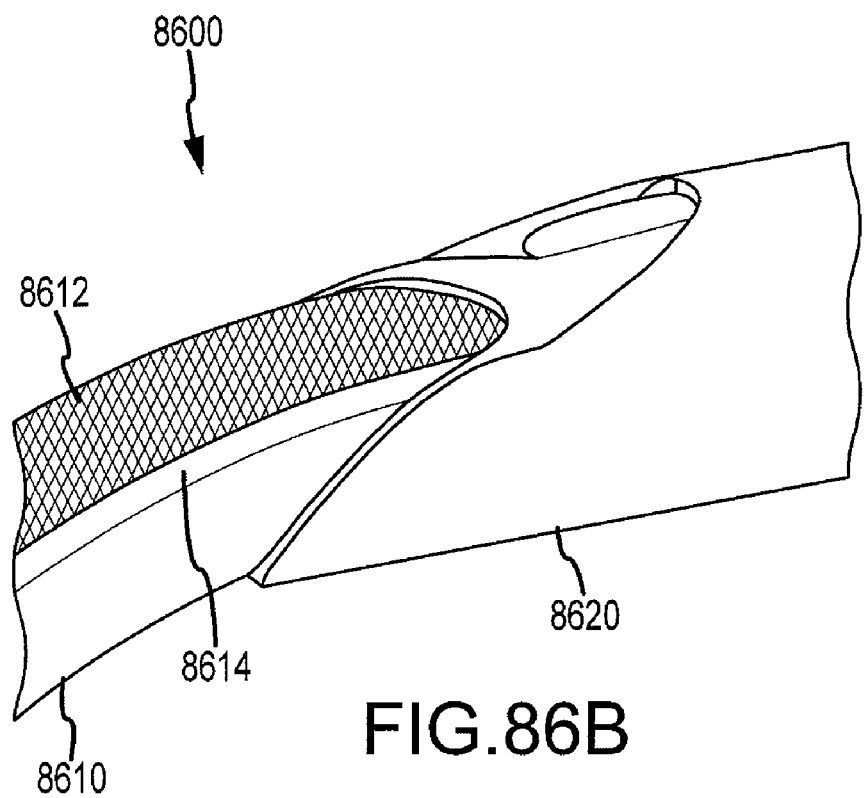

In addition to box lesions, embodiments of the present invention are well suited for use in forming connecting or linear lesions. FIG. 86A shows a portion of a treatment system that includes a stabilizer member 8610, trocar or push tube 8620, and a connecting lesion adapter 8630. The cross-hatched area of stabilizer member 8610 represents a suction zone 8612 that can be applied to and secured or sealed against a patient tissue. The stabilizer member or mechanism typically also houses an ablation member or mechanism (not shown). Connecting lesion adapter 8630 includes a distal sealing edge 8632 that, in cooperation with a sealing edge 8614 of stabilizer member 8610, can operate to form a seal against the tissue. Hence, when suction is applied via suction zone 8612, an ablation mechanism housed in stabilizer member 8610 can remain in place as desired against the patient tissue. FIG. 86B shows a treatment system without the connecting lesion adapter. As depicted in these figures, and as illustrated elsewhere herein, the treatment device can be effectively operated when the ablation and stabilizer assembly is adjusted to extend at any desired distance from the distal end of the push tube or cinching mechanism. In some embodiments, when one or more connecting lesions are being created, a cinching mechanism may not be in use. For example, a distal tape may be cut about an inch from the end of the suction stabilizer and used as an implement to hold on to by graspers to position and hold the end of the extended suction stabilizer. In some cases, about 1 to 3 inches of a suction stabilizer is exposed when creating a connecting lesion. The suction sealing features, such as distal sealing edge 8632 or sealing edge or skirt 8614, form a seal between the stabilizer mechanism and the patient tissue. In some embodiments, an ablation system may include a flexible valve at a proximal end of a push tube, for example in a handle or body of the tube, which may operate as a vacuum seal for a suction stabilizer.

Figure 87:
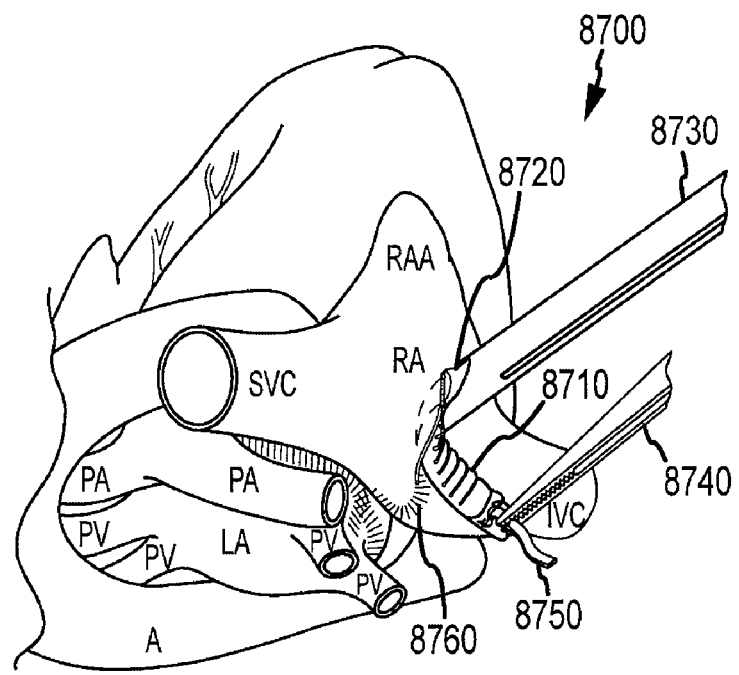
FIG. 87 shows aspects of an ablation system with a stabilizer assembly according to embodiments of the present invention.

FIG. 87 shows aspects of a treatment system 8700 and method for forming a connection lesion. As illustrated here, treatment system 8700 includes an ablation and stabilizer assembly 8710, a connecting lesion adapter 8720, and a trocar or push tube 8730. In use, the operator or surgeon can advance or extend a distal portion of ablation and stabilizer assembly 8710 out from trocar 8730 to expose a desired length of the ablation and stabilizer assembly. The surgeon can place the exposed ablation and stabilizer assembly against an area of the patient tissue, optionally with the assistance of a grasping mechanism 8740 such as forceps. As shown here, ablation and stabilizer assembly 8710 includes a distal tape or ribbon 8750 that can be grasped and maneuvered as desired by the operator. Connection lesion adapter 8720 can operate to extend a floor of push tube 8730 distally to facilitate suction. In use, the surgeon can operate treatment system 8700 to form an of a variety of epicardial connecting lesions 8760 on the patient tissue. In the embodiment shown here, the patient anatomy includes a superior vena cava (SVC), an aorta (A), a pulmonary artery (PA), an inferior vena cava (IVC), a right atrial appendage (RAA), pulmonary veins (PV), a left atrium (LA), and a right atrium (RA).

Figure 88:
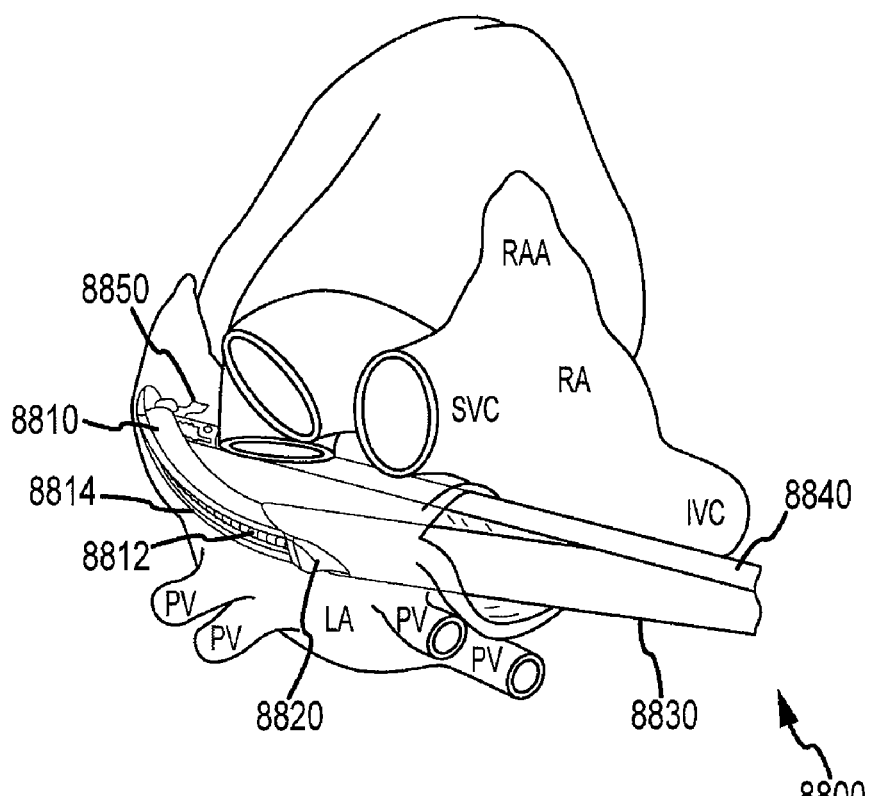
FIG. 88 shows aspects of an ablation system with a stabilizer assembly according to embodiments of the present invention.

FIG. 88 shows aspects of a treatment system 8800 and method for forming an endoablation. As illustrated here, treatment system 8800 includes an ablation and stabilizer assembly 8810, a connecting lesion adapter 8820, and a trocar or push tube 8830. Ablation and stabilizer assembly 8810 includes an ablation mechanism 8812 and a stabilizer mechanism 8814. In use, the operator or surgeon can advance or extend a distal portion of ablation and stabilizer assembly 8810 out from trocar 8830 to expose a desired length of the ablation and stabilizer assembly. The surgeon can place the exposed ablation and stabilizer assembly against an area of the patient tissue, optionally with the assistance of a grasping mechanism 8840 such as forceps. As shown here, ablation and stabilizer assembly 8810 includes a distal tape or ribbon 8850 that can be grasped and maneuvered as desired by the operator. Connection lesion adapter 8820 can operate to extend a floor of push tube 8830 distally to facilitate suction. In use, the surgeon can operate treatment system 8800 to form any of a variety of endocardial lesions on the patient tissue. As shown here, treatment system 8800 is advanced through an incision or opening in the left atrium, wherein a lesion may be formed. The wall of the left atrium (LA) is shown transparently in FIG. 88, for the sake of clarity. In the embodiment shown here, the patient anatomy includes a superior vena cava (SVC), an aorta (A), a pulmonary artery (PA), an inferior vena cava (IVC), a right atrial appendage (RAA), pulmonary veins (PV), a left atrium (LA), and a right atrium (RA).

Figure 89:
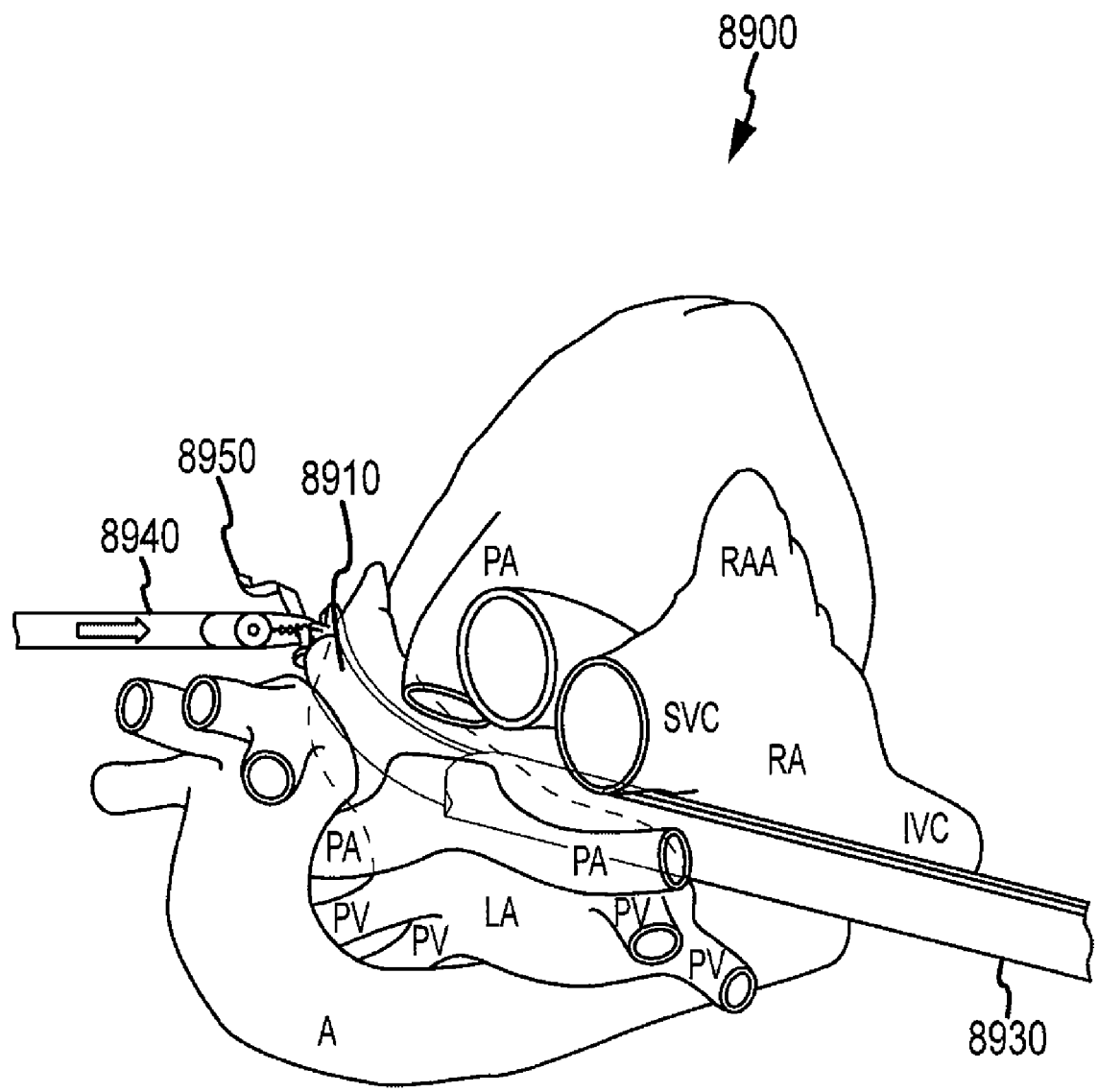
FIG. 89 shows aspects of an ablation system with a stabilizer assembly according to embodiments of the present invention.

FIG. 89 shows aspects of a treatment system 8900 and method for forming an epiablation. As illustrated here, treatment system 8900 includes an ablation and stabilizer assembly 8910 and a trocar or push tube 8830. Ablation and stabilizer assembly 8910 includes an ablation mechanism and a stabilizer mechanism. In use, the operator or surgeon can advance or extend a distal portion of ablation and stabilizer assembly 8910 out from trocar 8930 to expose a desired length of the ablation and stabilizer assembly. The surgeon can place the exposed ablation and stabilizer assembly against an area of the patient tissue, optionally with the assistance of a grasping mechanism 8940 such as forceps. As shown here, ablation and stabilizer assembly 8910 includes a distal tape or ribbon 8950 that can be grasped and maneuvered as desired by the operator. As depicted here, the ablation and stabilizer assembly is capable of forming a "forward curve" configuration where the ablation mechanism is on a concave side of the assembly. The assembly is also capable of forming a "backward curve" configuration where the ablation mechanism is on a convex side of the assembly. The assembly is also capable of twisting and side-bending, as desired. In the embodiment shown here, the patient anatomy includes a superior vena cava (SVC), an aorta (A), a pulmonary artery (PA), an inferior vena cava (IVC), a right atrial appendage (RAA), pulmonary veins (PV), a left atrium (LA), and a right atrium (RA).

Figure 90A:
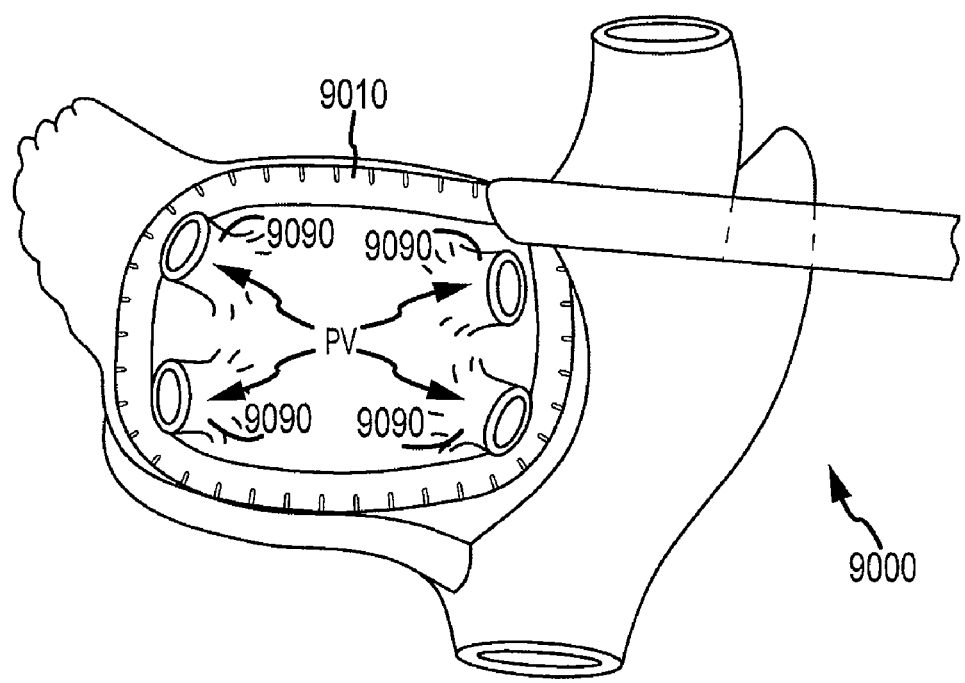
FIGS. 90A-90J show aspects of ablation systems with a stabilizer assembly according to embodiments of the present invention.
Figure 90B:
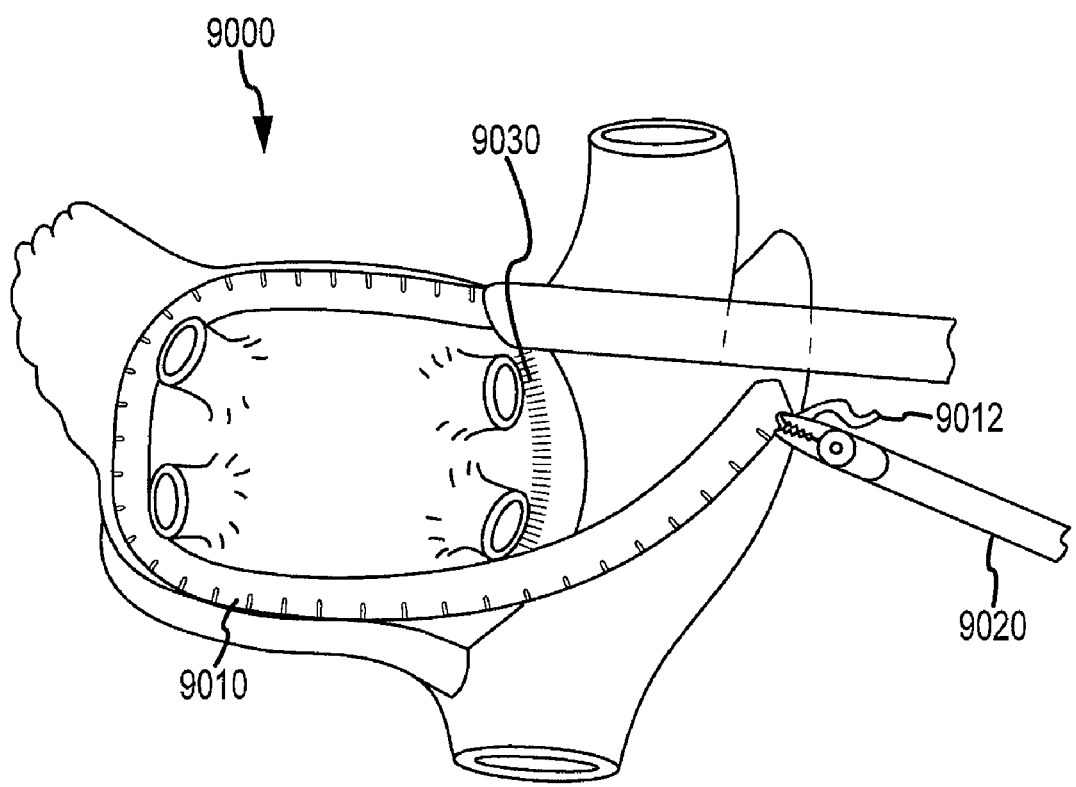
Figure 90C:
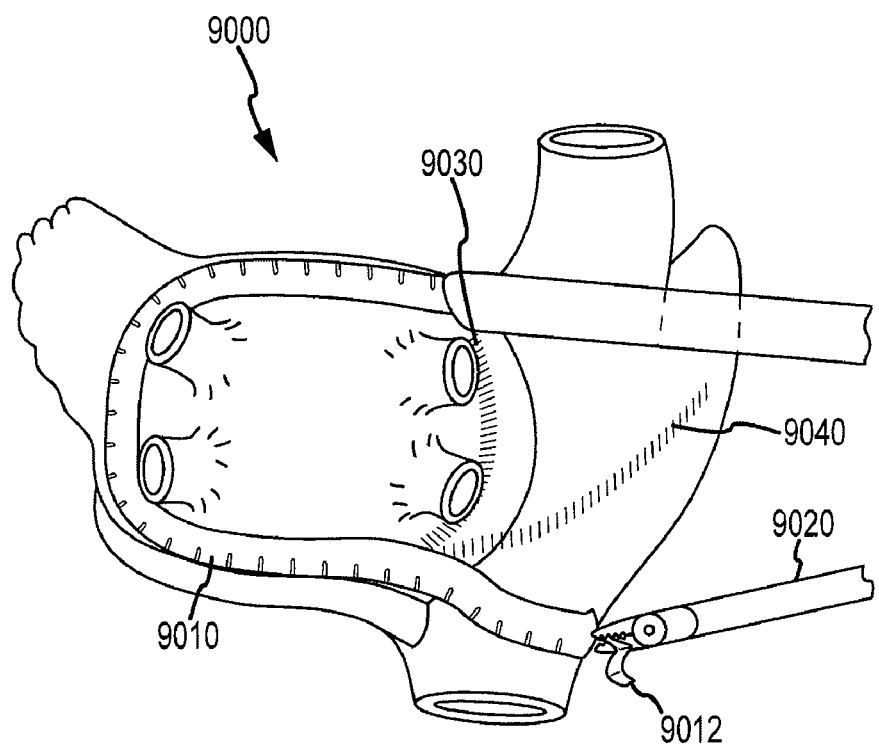
Figure 90D:
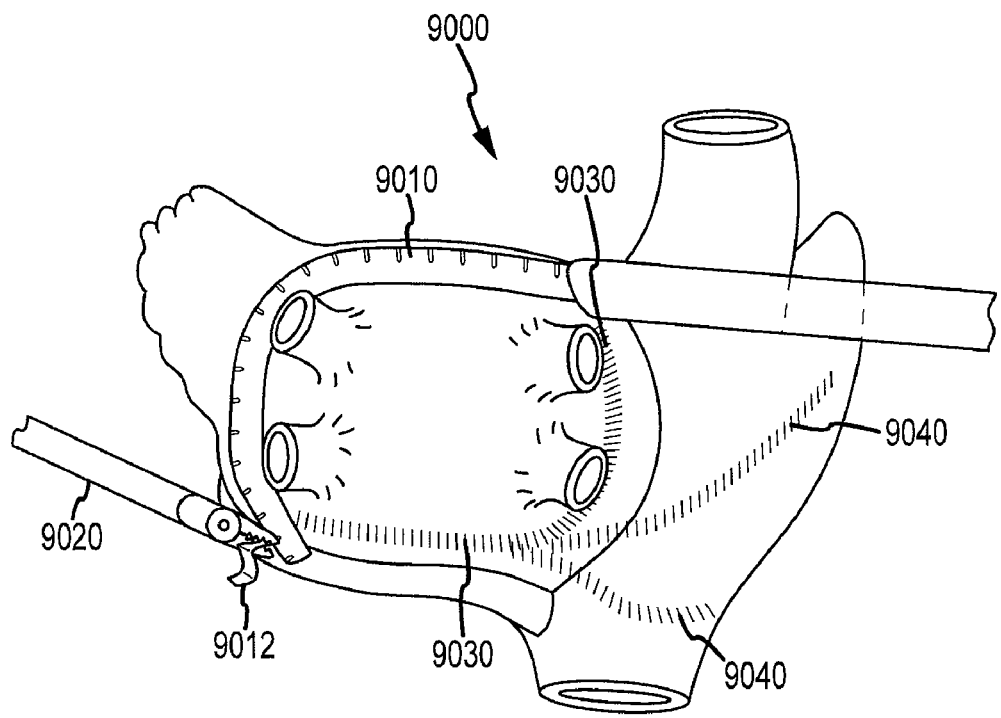
Figure 90E:
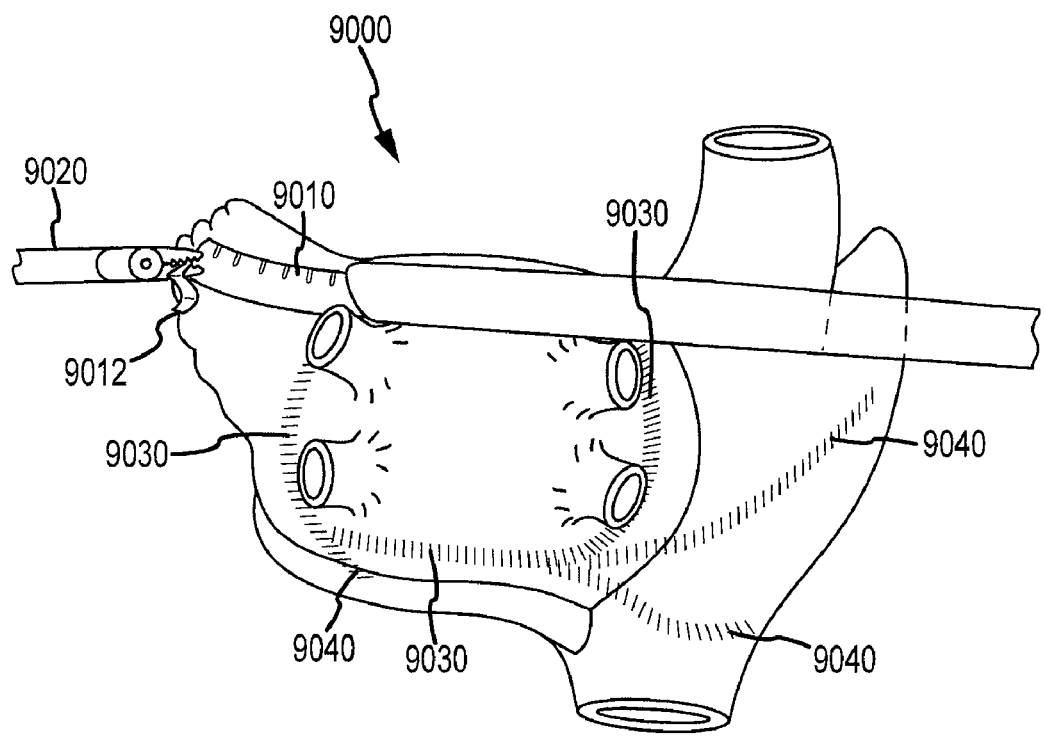
Figure 90F:
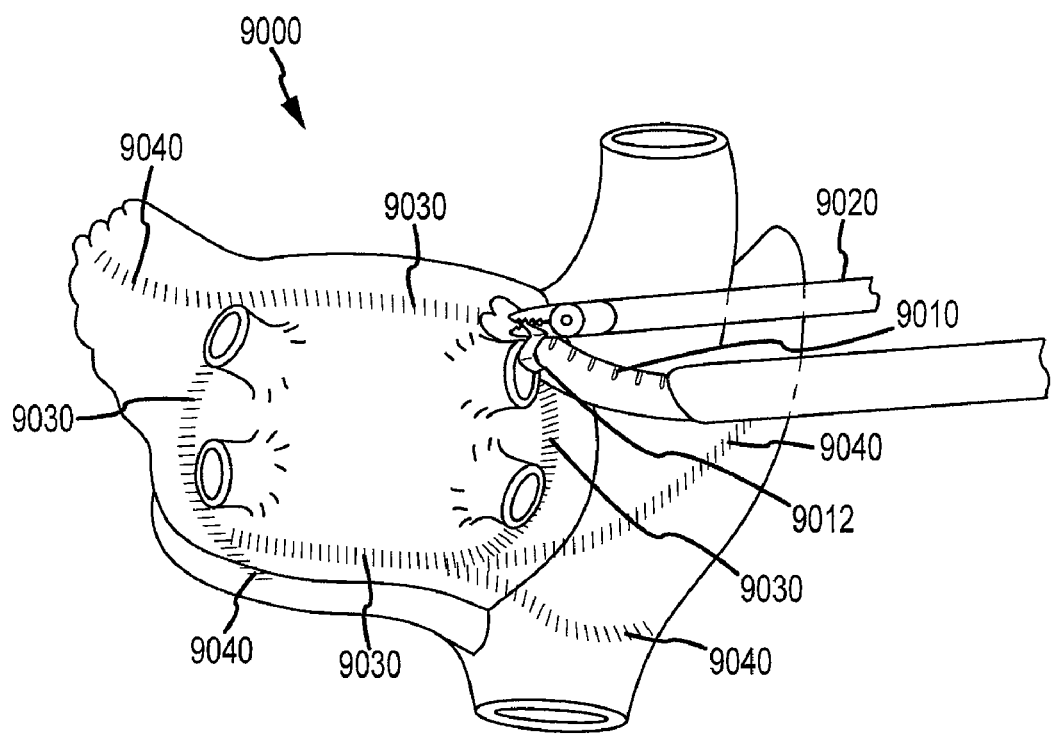
Figure 90G:
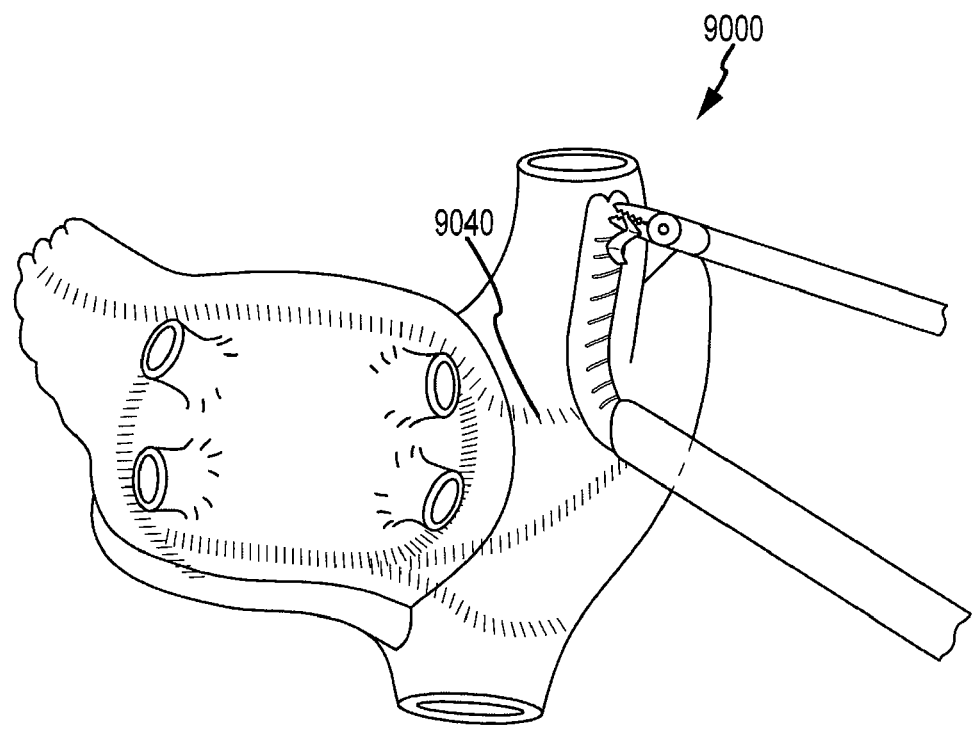
Figure 90H:
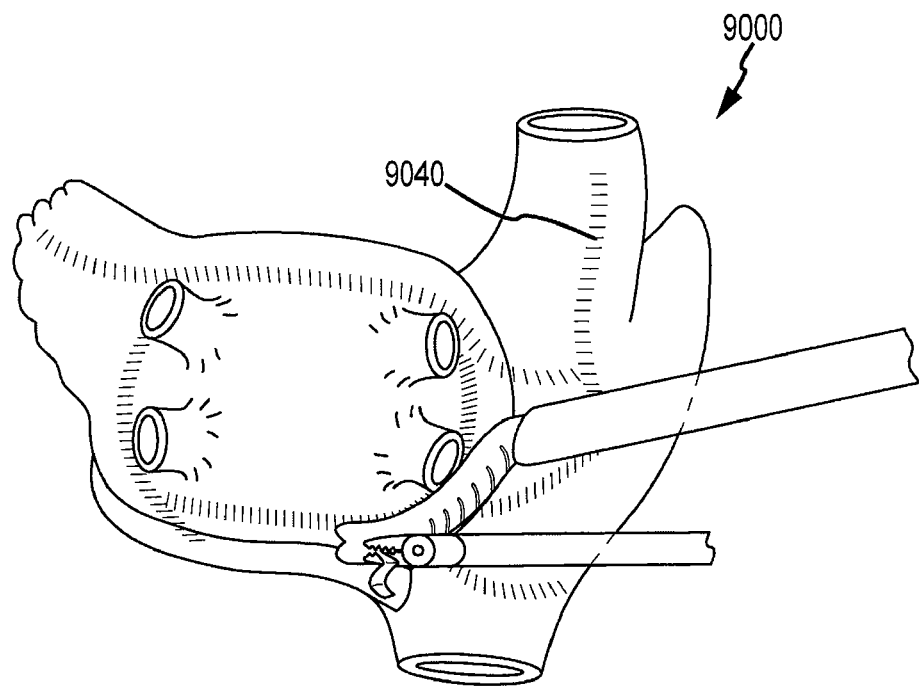
Figure 90I:
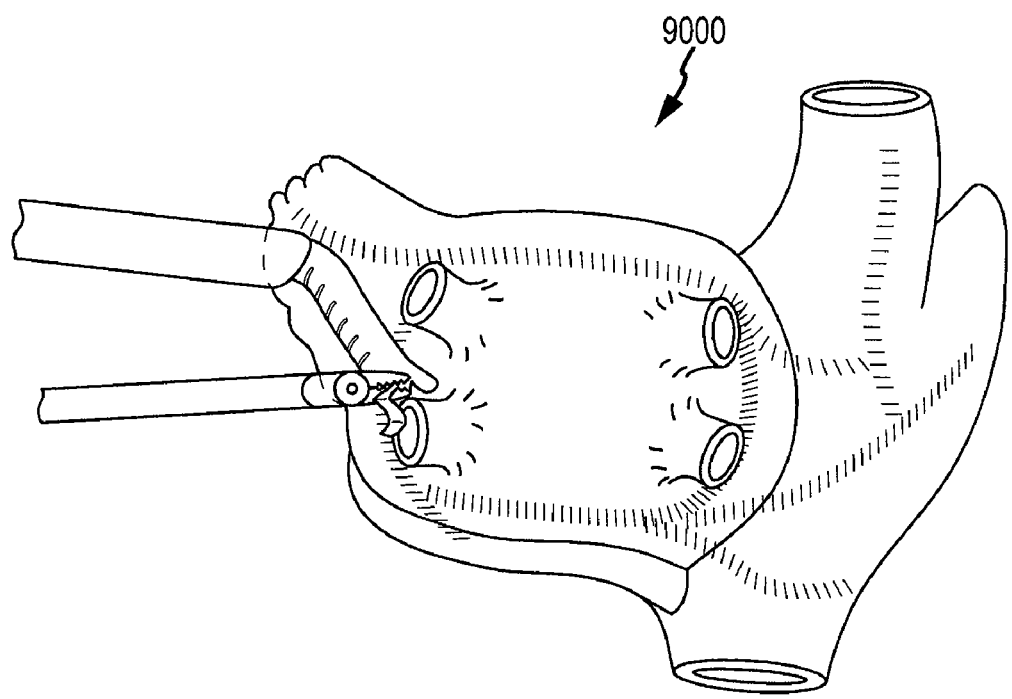
Figure 90J:
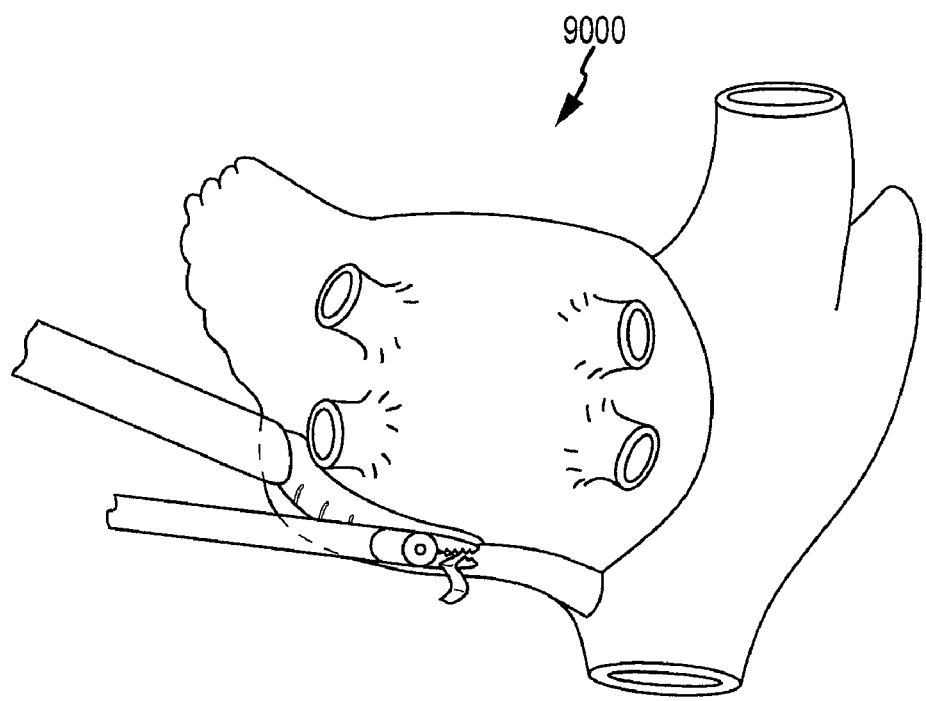

FIGS. 90A to 90J show aspects of a treatment system 9000 and methods for forming lesions on patient tissue. As illustrated in FIGS. 90A and 90B, an ablation and stabilizer assembly 9010 of the system can be wrapped about the patient tissue, so as to form a box lesion 9030 at or near the roots 9090 of the pulmonary veins (PV s), where the PV s extend from the atrium. As depicted in FIGS. 90B to 90J, ablation and stabilizer assembly 9010 may include a distal tape or implement 9012, and an operator can manipulate or position ablation and stabilizer assembly 9010 with a grasping or manipulating mechanism 9020, such as forceps, to form additional connecting lesions 9040 as desired to the patient tissue.

Figure 91:
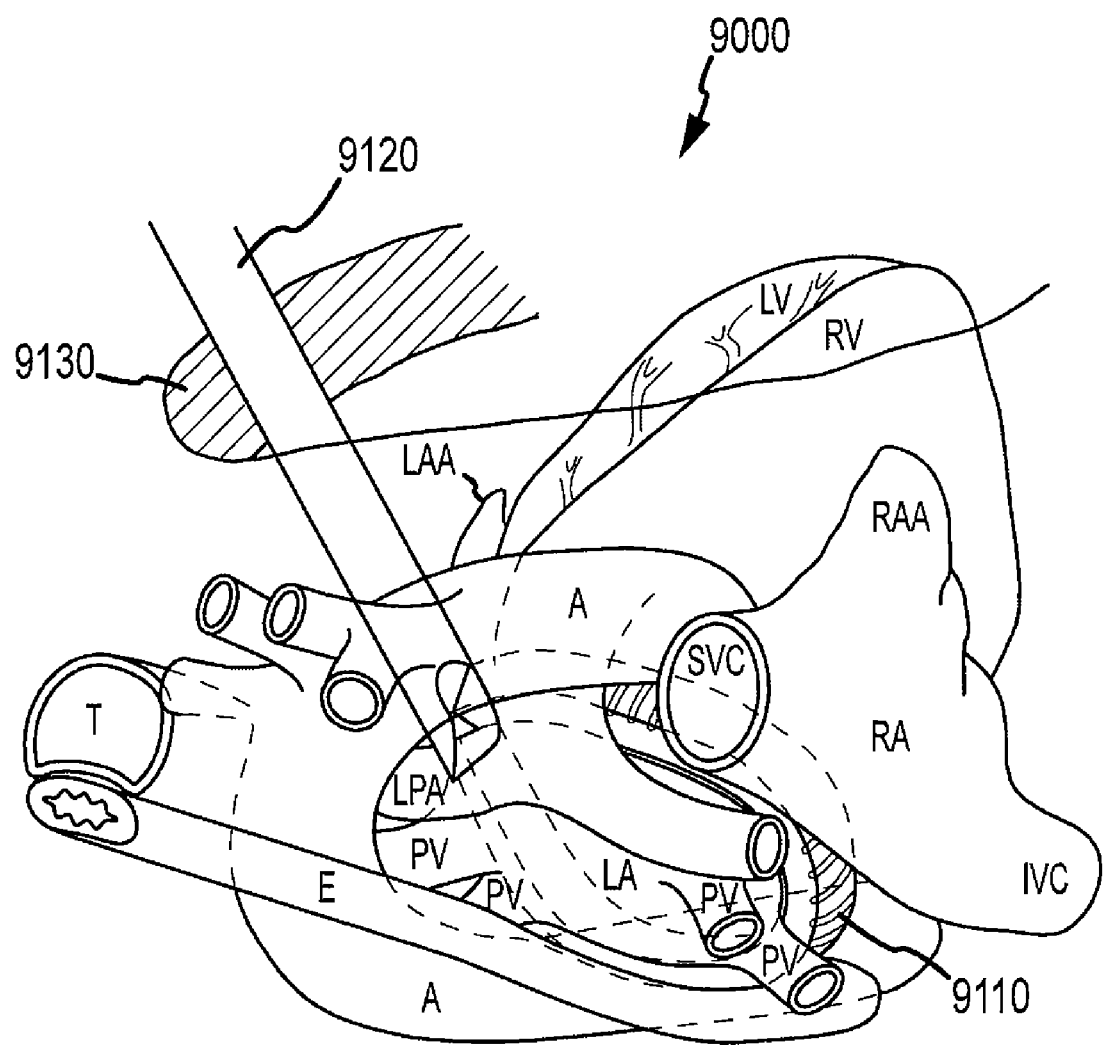
FIG. 91 shows aspects of an ablation system with a stabilizer assembly according to embodiments of the present invention.

FIG. 91 illustrates aspects of a treatment system 9100 and methods for forming a box lesion on patient tissue. Treatment system 9100 includes an ablation and stabilizer assembly 9110 and a push tube or trocar 9120. Treatment system can also include a sternotomy or sternal adapter as described herein with reference to FIGS. 82A to 82F. As depicted here, push tube 9120 extends through a chest opening 9130 at or near the patient's sternum. The push tube sternal adapter can hold the distal end of the stabilizer mechanism in the desired position, so the left atrium can be encircled from the sternal access position. In the embodiment shown here, the patient anatomy includes a superior vena cava (SVC), an aorta (A), an esophagus (E), a left pulmonary artery (LP A), a right pulmonary artery (RP A), an inferior vena cava (IVC), a right atrial appendage (RAA), a left atrial appendage (LAA), pulmonary veins (PV), a left atrium (LA), a trachea (T), a left ventricle (L V), a right ventricle (RV), and a right atrium (RA).

Figure 92A:
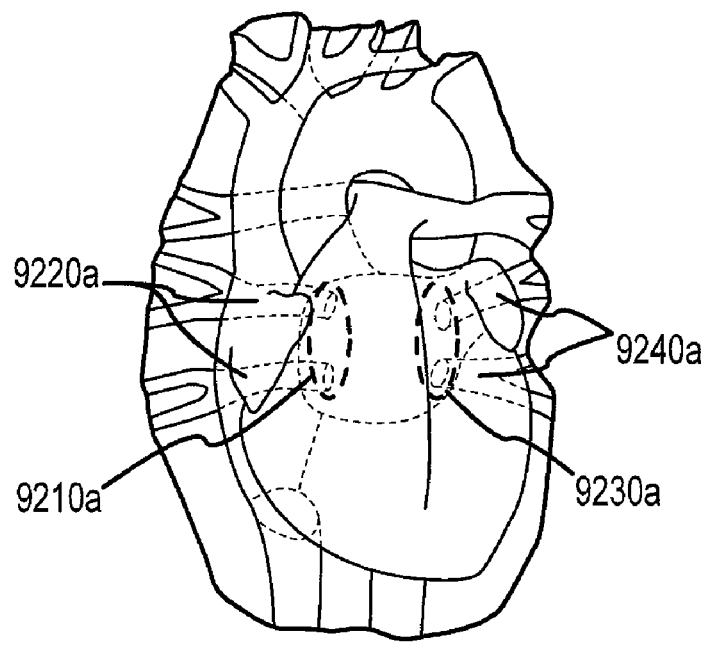
FIGS. 92A-92F show examples of various lesion subsets that can be formed by ablation systems according to embodiments of the present invention.
Figure 92B:
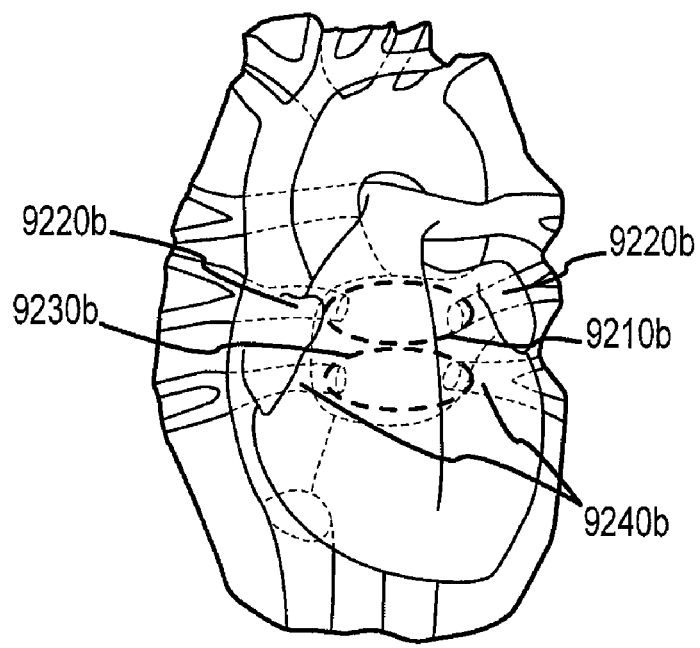
Figure 92C:
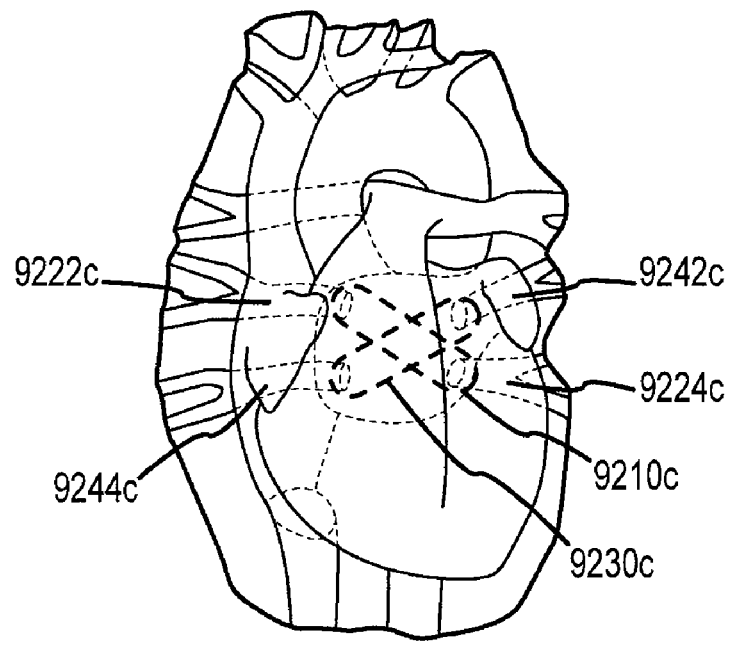
Figure 92D:
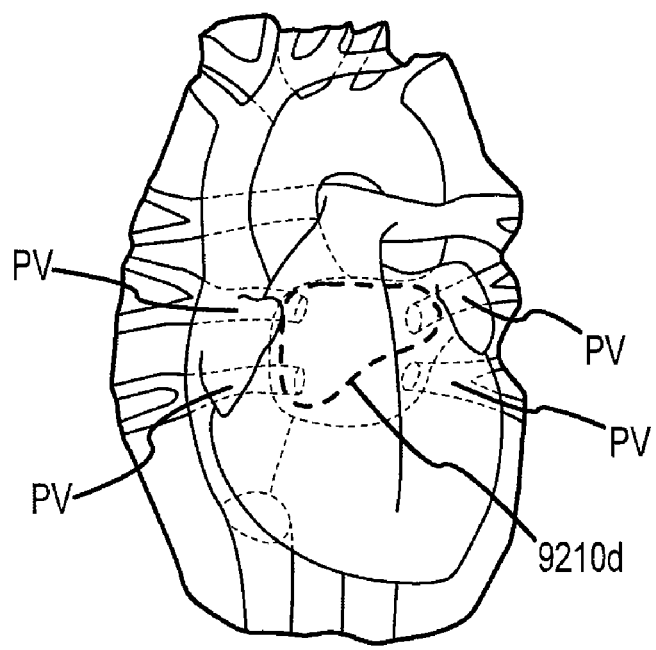
Figure 92E:
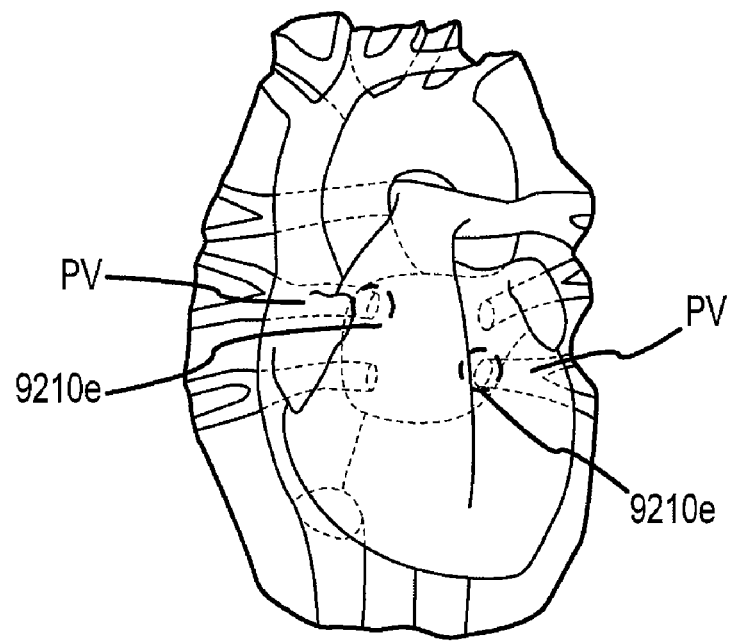
Figure 92F:
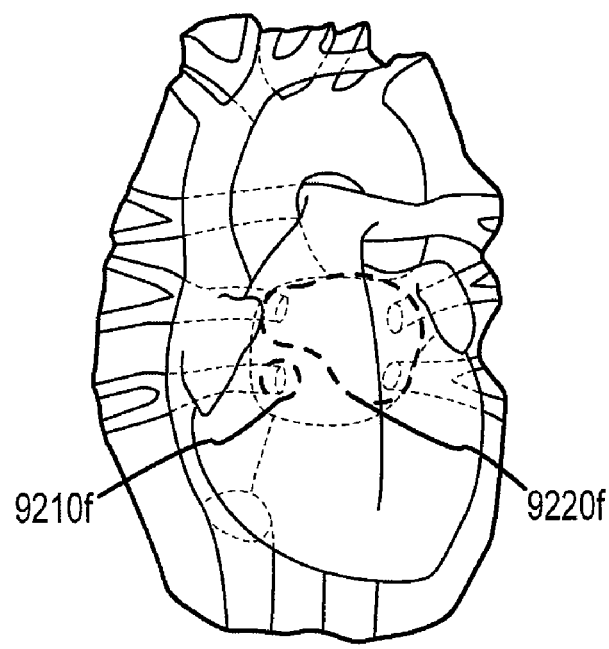

FIGS. 92A to 92F show examples of various lesion subsets that can be formed with system and method embodiments of the present invention. As depicted in FIG. 92A, systems and methods may be used to form a first lesion 9210a about the roots of a patient's right pulmonary veins 9220a, and a second lesion 9230a about the roots of a patient's left pulmonary veins 9240a. As depicted in FIG. 92B, systems and methods may be used to form a first lesion 9210b about the roots of a patient's superior pulmonary veins 9220b, and a second lesion 9230b about the roots of a patient's inferior pulmonary veins 9240b. As depicted in FIG. 92C, systems and methods may be used to form a first diagonal lesion 9210c about the roots of a patient's right superior pulmonary vein 9222c and left inferior pulmonary vein 9224c, and a second diagonal lesion 9230c about the roots of a patient's left superior pulmonary vein 9242c and right inferior pulmonary vein 9244c. In this way, the surgeon can create five small isolated areas. As depicted in FIG. 92D, systems and methods may be used to form a lesion 9210d about the roots of any three of the patient's PV s. As depicted in FIG. 92E, systems and methods may be used to form a lesion 9210e about the root of any individual PV. As shown in FIG. 92F, systems and methods may be used to form any combination of lesions or lesion subsets described herein. For example, systems and methods can be used to form a first lesion 9220f about the root of an individual PV, and a second lesion 9220f about the roots of three other PVs.

Cinching Devices and Methods of Use and Construction

Embodiments of the present invention encompass ablation devices which have cinching configurations, and methods for their use and construction. For example, a flexible ablation device can include a distal member of the device which attaches to a proximal end of the device, so as to facilitate a closed loop or a belt loop type of cinching, forming a closed or substantially closed loop. Cinching embodiments may include an attachment mechanism, such as a distal hook mechanism which can be inserted into a sliding proximal collar. An attachment mechanism can include an open distal hook mechanism into which the proximal end of the device is inserted, providing a mechanical lock. In some embodiments, the interfaces can be magnetized. An attachment mechanism can be a releasable snap or interference fit mechanism. In some cases, an attachment mechanism can be a proximal loop into which a distal end of a device inserts. In some cases, an attachment mechanism can angle an interface between a distal and a proximal end such that the resultant loop is continuous or substantially continuous.

A cinching embodiment can use suction or mechanical tension to contact tissue. An ablative member can extend to a distal extremity of a device to insure a complete and contiguous lesion. In some cases, an excess ablative member can be withdrawn through the mechanism at the proximal end to facilitate lesion continuity and provide a variable adjustment of lesion length. A flexible ablation device may have an active monopolar ablation element within a flexible trough like, energy shielding housing. An edge of a trough structure of a flexible ablation device can have at least one embedded pacing lead to function as described herein. In some cinching embodiments, one or more integrated pacing leads and connectors to an electrocardiogram (EKG) can facilitate feedback to an energy delivery generator. In some cases, it may be desirable to cease energy delivery when a pacing stimulus cannot be captured.

Introducer Devices and Methods of Use and Construction

Embodiments of the present invention encompass ablation devices which have introducer devices, and methods for their use and construction. For example, a mechanism for delivering a device in a minimally invasive surgery can include a device introducer that is steerable, flexible, malleable, rigid, or deflectable. A distal end of an introducer can encompass a magnet, and can also encompass a light, a suction lumen, or a working channel. An introducer can be used in combination with one or more like introducers such that one can magnetically attach to another in order to facilitate one pushing or pulling the other around a tissue structure from one side of the patient. A proximal end of one of the introducers can be attached to a device to be passed or advanced to a desired location. One or more of the introducers can also take the form of or include a scope with a blunted polymeric transparent cap, where the tip of the cap can house a magnet with a polarity opposite to a polarity of a magnet in a cap tip of another introducer. In this way it is possible for one introducer to seek or look for another introducer and attach. An introducer tip may include a light.

In some cases, a blunted polymeric transparent cap can be a standalone device, and can be fitted with a mechanism for sealing or preventing fluid from migrating to a lens of the scope, such as with an o-ring sealing mechanism that can fit on a variety rigid or flexible endoscopes and prevent fluids from communicating with a scope lens. An endoscope can navigate to find the introducer, contact it with opposite polarity magnets, and be retracted to lead the introducer and surgical instrument. The magnetic attachment mechanism can be replaced with or supplemented with a threaded male and female connector, a mechanical snap connector, a hook and collar connector, or a lasso connector. In some embodiments, an attachment mechanism can be advanced and retracted. In some embodiments, an attachment mechanism can include an integrated mechanism, or can include separate mechanisms. Such mechanisms can be adjacent to or within a blunted lens cap.

Convertible Ablation Devices and Methods of Use and Construction

Embodiments of the present invention encompass ablation devices which are convertible between bipolar and monopolar configurations, and methods for their use and construction. In some instances, a bipolar ablation device can be more effective than a monopolar ablation device. For example, it may be possible to creating transmural lesions with a bipolar ablation device more quickly than with a monopolar ablation device. However, when creating a complex lesion set on a beating heart, it may be desirable to use a monopolar device. Embodiments of the present invention encompass devices that can be used as either a monopolar or bipolar device.

In some cases, a convertible device includes opposing parallel jaws, with an active member and an indifferent member that can be separated. Thus, embodiments provide clamp devices having a means of detaching one jaw from another jaw, so that an active ablation element can be used independently from an indifferent element. Such configurations allow a surgeon to use the active element as a monopolar probe in conjunction with standard dispersive electrode pads, before creating bipolar lesions, after creating bipolar lesions, or both before and after creating bipolar lesions.

In some embodiments, an active jaw includes a polymeric trough structure in which a monopolar ablation device can be inserted or removed. An active jaw can be malleable or have a mechanism to change the orientation of jaw with respect to its shaft. As such, a monopolar ablation member can operate or be used as a monopolar wand or hand held device, for example when disconnected from an indifferent electrode part of a clamp. In some cases, an active ablation member or device passes through an o-ring or other sealing mechanism such that suction can be facilitated to draw tissue into the trough structure or device and in contact with the ablation member. An ablation device can be internally irrigated or the trough structure can have apertures to spray saline or other fluid in order to keep local tissue temperatures lower or otherwise modulate or control tissue temperature. Saline or other fluid can be cleared from the field via a suction mechanism or means in the device. In some embodiments, a trough structure or and edge thereof can include one or more embedded pacing leads.

System and method embodiments disclosed herein may include one or more integrated pacing leads and connectors to an electrocardiogram (EKG) which can facilitate feedback to an energy delivery generator. In some cases, it may be desirable to cease energy delivery when a pacing stimulus cannot be captured. In some cases, it may be desirable to use a device in a monopolar mode whereby the indifferent electrode only utilizes temperature sensing to provide transmurality feedback that a temperature has reach a certain level on the opposite side of a tissue from the active electrode. Embodiments also contemplate use of features disclosed herein in conjunction with a steerable scissor type clamp.

Lesion Test Systems and Methods of Use and Manufacture

Embodiments of the present invention encompass systems for testing the effectiveness of one or more cardiac ablation lesions, and methods for their use and manufacture. For example, a method of testing the effectiveness of one or more cardiac ablation lesions can insure that one or more lesions prevent or inhibit electrical excitation across a lesion. In some cases, this can be performed by a separate hand-held device after use of an ablation device. According to embodiments of the present invention, this feature can be integrated into an ablation device, in a bipolar or monopolar configuration. For example, in a bipolar embodiment, an edge of a trough structure can have at least one embedded pacing lead. The element can be oriented such that the pacing leads can lie between the ablative element and the region of tissue to be electrically isolated. After a designated period of ablation, or prior to or at the onset of ablation, the device can begin exciting the tissue. A device used to monitor the excitation of tissue, such as an electrocardiogram (EKG or ECG), can be used as a feedback tool to determine when the stimulus is no longer being captured across the ablation line, which can be an indication that one or more lesions created are effective. Such pacing can occur simultaneously with the creation of the one or more ablation lesions, or separately. An energy delivery algorithm can be controlled with a feedback loop such that energy delivery can be ceased when a pacing stimulus cannot be detected outside of the region to be electrically isolated. Embodiments of the present invention are well suited for implementing conduction block techniques such as those disclosed in U.S. Patent Application No. 61/051,975 filed May 9, 2008, the entire content of which is incorporated herein by reference for all purposes.

Embodiments of the present invention also encompass techniques for testing the effectiveness of one or more cardiac ablation lesions to insure that tissue within the area of the lesion or lesions is transmural or that cytotoxic temperatures are reached across the full thickness of the tissue. A clamp mechanism, which may be bipolar, can be used in monopolar mode, whereby an indifferent electrode element, or jaw opposite an active ablation element, utilizes temperature sensing features to provide transmurality feedback that a temperature has reach a certain level on the opposite side of tissue from the active electrode. Any of the testing techniques disclosed herein can be facilitated in various shaped clamps, included clamps in which jaws remain parallel, scissor style clamps, steerable or malleable jaw clamps, and the like.

While the exemplary embodiments have been described in some detail, by way of example and for clarity of understanding, those of skill in the art will recognize that a variety of modification, adaptations, and changes may be employed. Hence, the scope of the present invention should be limited solely by the claims.

We claim:

1. A method for ablating a cardiac tissue of a patient, comprising:
    placing an ablation assembly through a cinching mechanism and near the cardiac tissue of the patient, the ablation assembly comprising an ablation mechanism having a first magnet and a second magnet and advancing the ablation assembly with at least one roller;
    joining the first magnet to the second magnet to encircle the cardiac tissue;
    cinching the ablation assembly with the cinching mechanism so as to urge the ablation mechanism toward the cardiac tissue; and
    administering an ablation to the cardiac tissue via the ablation mechanism to create a lesion in the cardiac tissue.

2. A method as in claim 1, comprising forming a transmural lesion in the cardiac tissue.

3. A method as in claim 1, wherein the lesion is in the form of a closed path.

4. A method as in claim 1, wherein the ablation assembly is disposed at least partially within a stabilizer assembly, and the method comprises forming a seal between the stabilizer assembly and the cardiac tissue.

5. A method for treating an epicardial tissue of a patient, comprising:
    placing a treatment assembly near the epicardial tissue of the patient;
    wrapping an ablation mechanism of the treatment assembly about a portion of the epicardial tissue by joining a first magnet to a second magnet such that the ablation mechanism is disposed near at least one pulmonary vein of the patient;
    cinching the ablation mechanism toward the epicardial tissue by advancing the ablation mechanism with at least one roller; and
    delivering an ablative treatment through the ablation mechanism of the ablation assembly toward the epicardial tissue, so as to form a lesion on the epicardial tissue.

6. A method as in claim 5, comprising creating a seal between the epicardial tissue and a stabilizer mechanism of the treatment assembly.

7. A method as in claim 5, wherein placing the ablation mechanism near the epicardial tissue of the patient comprises passing the ablation mechanism through a transverse sinus of the patient, through an oblique sinus of the patient, or through both.

8. A method as in claim 5, wherein forming a lesion comprises forming a closed path lesion.

9. A method as in claim 5, comprising forming a conduction block at a junction of left atrium and the at least one pulmonary vein.

* * * * *